US007749992B2

(12) United States Patent  
Cao et al.

(10) Patent No.: US 7,749,992 B2
(45) Date of Patent: Jul. 6, 2010

(54) COMPOUNDS AND METHODS FOR TREATING DISLIPIDEMIA

(75) Inventors: Guoqing Cao, Carmel, IN (US); Ana Maria Escribano, Alcobendas-Madrid (ES); Maria Carmen Fernandez, Alcobendas-Madrid (ES); Todd Fields, Indianapolis, IN (US); Douglas Linn Gernert, Indianapolis, IN (US); Christopher Lawrence Cioffi, Troy, NY (US); Robert Jason Herr, Voorheesville, NY (US); Nathan Bryan Mantlo, Brownsburg, IN (US); Eva Maria Martin De La Nava, Alcobendas-Madrid (ES); Ana Isabel Mateo Herranz, Alcobendas-Madrid (ES); Daniel Ray Mayhugh, Carmel, IN (US); Xiaodong Wang, Carmel, IN (US)

(73) Assignee: Eli Lilly and Company, Indianapolis, IN (US)

( * ) Notice: Subject to any disclaimer, the term of this patent is extended or adjusted under 35 U.S.C. 154(b) by 994 days.

(21) Appl. No.: 10/574,649

(22) PCT Filed: Oct. 7, 2004

(86) PCT No.: PCT/US2004/030907

§ 371 (c)(1), (2), (4) Date: Mar. 30, 2006

(87) PCT Pub. No.: WO2005/037796

PCT Pub. Date: Apr. 28, 2005

(65) Prior Publication Data

US 2007/0254869 A1    Nov. 1, 2007

Related U.S. Application Data

(60) Provisional application No. 60/509,736, filed on Oct. 8, 2003.

(51) Int. Cl.
*A61P 3/06*    (2006.01)
*A61P 9/10*    (2006.01)
*A61K 31/55*    (2006.01)
*C07D 223/14*    (2006.01)
*C07D 223/16*    (2006.01)
*C07D 223/32*    (2006.01)
*C07D 225/06*    (2006.01)
*C07D 403/04*    (2006.01)
*C07D 403/12*    (2006.01)
*C07D 405/06*    (2006.01)
*C07D 405/12*    (2006.01)
*C07D 413/04*    (2006.01)
*C07D 491/04*    (2006.01)

(52) U.S. Cl. ................... 514/213.01; 540/593
(58) Field of Classification Search ............ 514/213.01; 540/593
See application file for complete search history.

(56) References Cited

U.S. PATENT DOCUMENTS 5,484,783 A    1/1996    Flynn et al.
5,602,122 A    2/1997    Flynn et al.
5,622,947 A    4/1997    Ogawa et al.
6,090,824 A    7/2000    Bernstein et al.
6,096,735 A    8/2000    Ogawa et al.
6,140,343 A    10/2000   DeNinno et al.
6,147,089 A    11/2000   DeNinno et al.
6,147,090 A    11/2000   DeNinno et al.
6,197,786 B1   3/2001    DeNinno et al.
6,235,730 B1   5/2001    Sato et al.
6,313,142 B1   11/2001   Damon et al.
6,586,448 B1   7/2003    DeNinno et al.
6,689,897 B2   2/2004    Damon et al.
6,962,931 B2   11/2005   Gumkowski et al.
2002/0072514 A1   6/2002    Brendel et al.
2002/0103225 A1   8/2002    Curatolo et al.
2003/0198674 A1   10/2003   Curatolo et al.
2004/0082609 A1   4/2004    Ghosh et al.
2004/0204450 A1   10/2004   Bechle et al.
2005/0059810 A1   3/2005    Maeda et al.
2005/0234212 A1   10/2005   Depuydt et al.
2006/0100239 A1   5/2006    Nagasaki et al.
2007/0173526 A1   7/2007    Bell et al.
2007/0208003 A1   9/2007    Bell et al.
2007/0244095 A1   10/2007   Chen et al.
2008/0269284 A1   10/2008   Escribano et al.

FOREIGN PATENT DOCUMENTS

| EP | 1125929 | 11/2000 |
|----|---------|---------|
| JP | 19972214746 A | 8/1997 |
| WO | WO 01/40190 A1 | 6/2001 |
| WO | WO 2005/033082 A2 | 4/2005 |
| WO | WO 2005/033082 A3 | 4/2005 |

OTHER PUBLICATIONS

Bisgaier et al. *J of Lipid Res.* 1993, 34, 1625-1634.

*Primary Examiner*—Brenda L Coleman
(74) *Attorney, Agent, or Firm*—James B. Myers; Francis O. Ginah

(57) ABSTRACT

Compounds of formula I

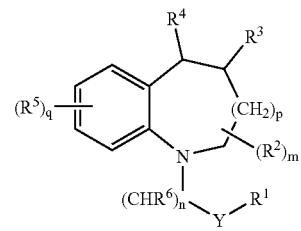

wherein n, m, p, q, y, $R^1$ $R^2$, $R^3$, $R^4$, $R^5$, and $R^6$ are as defined herein and their pharmaceutical compositions and methods of use are disclosed as useful for treating artherosclerosis and its sequelae.

14 Claims, No Drawings

COMPOUNDS AND METHODS FOR TREATING DISLIPIDEMIA

REFERENCE TO RELATED APPLICATIONS

This application is submitted as a United States national phase entry, pursuant to 35 U.S.C §371, of PCT/US2004/030907, filed on Oct. 7, 2004, which claims the benefit of U.S. provisional patent application Ser. No. 60/509,736, filed Oct. 8, 2003, which is incorporated by reference herein.

FIELD OF THE INVENTION

The current invention relates to the fields of medicinal organic chemistry, pharmacology, and medicine. Further, the current invention relates to a group of compounds that demonstrate utility for treating pathological states due to dyslipidemia

BACKGROUND OF THE INVENTION

Coronary heart disease (CHD) is one of the major causes of morbidity and mortality worldwide. Despite attempts to modify risk factors such as obesity, smoking, lack of exercise, and treatment of dyslipidemia with dietary modification or drug therapy, CHD remains the most common cause of death in the U.S. Over 50% of all CHD deaths are due to underlying atherosclerotic coronary heart disease.

Dyslipidemia is a major risk factor for CHD. Low plasma levels of high density lipoprotein (HDL) cholesterol with either normal or elevated levels of low density (LDL) cholesterol is a significant risk factor for developing atherosclerosis and associated coronary artery disease in humans. Indeed, several studies on lipoprotein profiles of CHD patients have shown that about 50% of the CHD patients have cholesterol levels that are considered to be in the normal range (<200 mg/dl). Furthermore, these studies found low HDL cholesterol in about 40% of the normo-cholesterolemic CHD patients as compared to the general population reported in the National Health and Nutrition Examination Survey. Since low levels of HDL cholesterol increase the risk of atherosclerosis, methods for elevating plasma HDL cholesterol would be therapeutically beneficial for the treatment of cardiovascular disease including, but not limited to, atherosclerosis, CHD, stroke, and peripheral vascular disease.

Cholesterol ester transfer protein (CETP) is a 74 KD glycoprotein that facilitates the exchange of cholesterol esters in HDL for triglycerides in triglyceride-rich lipoproteins (A. R. Tall et. al., (1999) 1999 George Lyman Duss Memorial Lecture: Lipid transfer proteins, HDL metabolism and atherogenesis. *Arterio. Thromb. Vasc. Biol.* 20:1185-1188.). The net result of CETP activity is a lowering of HDL cholesterol and an increase in LDL cholesterol. This effect on lipoprotein profile is believed to be proatherogenic, especially in subjects whose lipid profile constitutes an increased risk for CHD. Niacin can significantly increase HDL, but has serious toleration issues that reduce compliance. Currently marketed fibrates and HMG CoA reductase inhibitors raise HDL cholesterol only modestly (~10-12%). As a result, there is a significant unmet medical need for a well-tolerated agent which can significantly elevate plasma HDL levels, thereby reversing or slowing the progression of atherosclerosis.

CETP is expressed in multiple tissues and secreted into plasma, where it associates with HDL (X. C. Jiang et. al., (1991) Mammalian adipose tissue and muscle are major sources of lipid transfer protein mRNA. *J. Biol. Chem.* 266: 4631-4639). Humans and monkeys, which express CETP, have relatively low HDL cholesterol, whereas mice and rats do not express CETP and carry nearly all their cholesterol in HDL. Further more, transgenic expression of CETP in mice results in significantly reduced HDL cholesterol levels and developed severe atherosclerosis compared to control mice (K. R. Marotti et. al., (1993) Severe atherosclerosis in transgenic mice expressing simian cholesteryl ester transfer protein. *Nature:* 364, 73-75). Expression of human CETP in Dahl salt-sensitive hypertensive rats led to spontaneous combined hyperlipidemia, coronary heart disease and decreased survival (V. L. M. Herrera et. al., (1999) Spontaneous combined hyperlipidemia, coronary heart disease and decreased survival in Dahl salt-sensitive hypertensive rats transgenic for human cholesteryl ester transfer protein. *Nature Medicine:* 5, 1383-1389).

Antibodies either directly injected into the plasma or generated through vaccine injection can effectively inhibit CETP activity in hamsters and rabbits resulting in elevated HDL cholesterol (C. W. Rittershaus, (1999) Vaccine-induced antibodies inhibit CETP activity in vivo and reduce aortic lesions in a rabbit model of atherosclerosis. Furthermore, antibody neutralization of CETP in rabbits has been shown to be anti-atherogenic (*Arterio. Thromb. Vasc, Biol.* 20, 2106-2112; G. F. Evans et. al., (1994) Inhibition of cholesteryl ester transfer protein in normocholesterolemic and hypercholesterolemic hamsters: effects on HDL subspecies, quantity, and apolipoprotein distribution. *J. Lipid Research.* 35, 1634-1645). However, antibody and/or vaccine therapy is not currently a viable option for the treatment of large populations of patients in need of treatment for dyslipidemia and resultant or associated disease state manifestations.

Benzazepines have been reported as useful for certain therapeutic purposes. For example, Kondo et al teaches the use of certain benzazepines derivatives as potent orally active non-peptide arginine vasopressin V2 receptor antagonists, see Kondo et al., 7-chloro-5-hydroxy-1-[2-methylbenzoylamino)benzoyl]-2,3,4,5-tetrahydro-1H-1-benzazepine (OPC-41061): A potent, Orally Active Vasopressin Non-peptide Arginine Vasopressin V2 Receptor Antagonist, *Bioorganic and Medicinal Chemistry* 7 (1999) 1743-1754.

There have also been several reports of small molecule CETP inhibitors. Barrret et. al. (J. Am. Chem. Soc., 188, 7863, (1996)) and Kuo et al. (J. Am. Chem. Soc., 117, 10629, (1995)) describe cyclopropan-containing CETP inhibitors. Pietzonka et al. (Biorg. Med. Chem. Lett. 6, 1951 (1996)) describe phosphanate-containing analogs as CETP inhibitors. Coval et al. (Bioorg. Med. Chem. Lett. 5, 605, (1995)) describe Wiedendiol-A and -B related sesquiterpines as CETP inhibitors. Japanese Patent Application No. 10287662-A describes polycyclic, non-amine containing, polyhydroxylic natural compounds possessing CETP inhibition properties. Lee et al. (*J. Antibiotics,* 49, 693-96 (1996)) describe CETP inhibitors derived from an insect fungus. Busch et al. (Lipids, 25, 216-220 (1990)) describe cholesteryl acetyl bromide as a CETP inhibitor. Morton and Zillversmit (*J. Lipid Res.,* 35, 836-47 (1982)) describe that p-chloromercuriphenyl sulfonate, p-hydroxymercuribenzoate and ethyl mercurithiosalicylate inhibit CETP. Connolly et al. (*Biochem. Biophys. Res. Comm.* 223, 42-47 (1996)) describe other cysteine modification reagents as CETP inhibitors. Xia et al. Describe 1,3,5-triazines as CETP inhibitors (*Bioorg. Med. Chem. Lett.,* 6, 919-22 (1996)). Bisgaier et al. (*Lipids,* 29, 811-8 (1994) describe 4-phenyl-5-tridecyl-4H-1,2,4-triazole-thiol as a CETP inhibitor. Oomura et al. Disclose non-peptidic tetracyclic and hexacyclic phenols as CETP inhibitors in Japanese Patent Application No. 10287662.

U.S. Pat. No. 6,586,448 B1 describes 4-caboxamino-2-substituted-1,2,3,4-tetrahydroquinolines of formula I

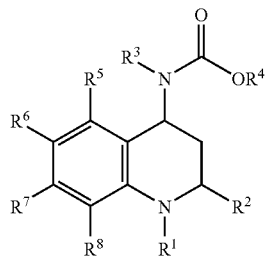

and prodrugs thereof, and pharmaceutically acceptable salts of said compounds and said prodrugs; wherein $R^1$, $R^2$, $R^3$, $R^4$, $R^5$, $R^6$, $R^7$ and $R^8$ are as defined therein. Similarly, PCT patent applications WO 03/063868A1, WO 0017164, No. 0017165, and WO 0017166, discloses variously, formulations, methods of preparation and methods of use of compounds tetrahydroquinoline compounds generally related to that of U.S. Pat. No. 6,586,448 B1 form which it derives or is a divisional application thereof.

PCT international application WO 2004/020393 A1 discloses selective and potent CETP activity inhibiting dibenzylamine compounds represented by the general formula 1

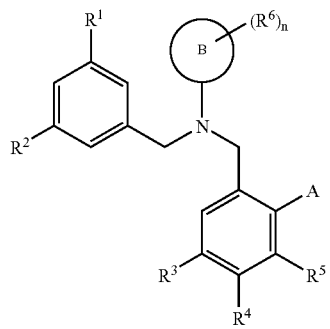

Wherein $R^1$ and $R^2$ each is optionally halogenated $C_{1-6}$ alkyl, etc.; and $R^3$, $R^4$ and $R^5$ each is a hydrogen, halogeno, etc., provided that $R^3$ and $R^4$ may form an optionally substituted homocycle or heterocycle in cooperation with the carbon atoms bonded thereto; A is —$N(R^7)(R^8)$, etc.; ring B is aryl or a heterocyclic residue; $R^6$ is hydrogen, halogeno, nitro, $C_{1-6}$ alkyl, etc.; and n is an integer of 1 to 3); a prodrug of the compound; or a pharmaceutically acceptable salt of either.

European Patent Application No. 818448 by Schmidt et al. describes tetrahydroquinoline derivatives as cholesteryl ester transfer protein inhibitors. European Patent Application No. 818197, Schmek et al. describe pyridines with fused heterocycles as cholesteryl ester transfer protein inhibitors. Brandes et al. in German Patent Application No. 19627430 describe bicyclic condensed pyridine derivatives as cholesteryl ester transfer protein inhibitors. In U.S. Pat. No. 6,207,671 Schmidt et al. describe substituted pyridine compounds as CETP inhibitors. In WO Patent Application No. 09839299, and WO Patent application No. 03028727 by Muller-gliemann et al. and Erfinder/Anmelder respectively, describe quinoline derivatives as cholesteryl ester transfer protein inhibitors.

The above disclosures notwithstanding, a great need remains for effective compounds useful to treat and/or prevent conditions caused by, associated with or exacerbated by dyslipidemia.

SUMMARY OF THE INVENTION

The present invention provides a compound of formula I

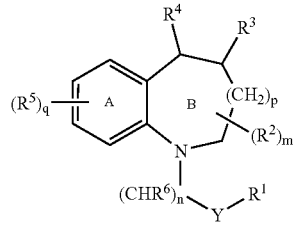

wherein n is 0, 1, 2, or 3;

m is 0, 1, 2, or 3;

p is 1 or 2;

q is 0, 1, 2, or 3;

Y is a bond, C=O, or $S(O)_t$; wherein t is 0, 1, or 2;

$R^1$ is selected from a group consisting of hydroxy, $C_1$-$C_6$ alkyl, aryl, $C_2$-$C_6$ alkenyl, $C_1$-$C_6$ haloalkyl, $C_1$-$C_6$ alkylheterocyclic, $C_3$-$C_8$ cycloalkyl, $C_1$-$C_6$ alkylcycloalkyl; $C_1$-$C_6$ alkylaryl, heterocyclyl, $C_2$-$C_6$ alkylalcohol, $C_1$-$C_6$ alkoxy, aryloxy, —$OC_2$-$C_6$ alkenyl, —$OC_1$-$C_6$ haloalkyl, —$OC_1$-$C_6$ alkylheterocyclic, —$OC_3$-$C_8$ cycloalkyl, —$OC_1$-$C_6$ alkylcycloalkyl, —$NR^7R^8$ and —$OC_1$-$C_6$ alkylaryl, —O-heterocyclic, and —$OC_1$-$C_6$ alkylheterocyclic; provided that $R^1$ is not hydroxy when Y is $S(O)_t$, CO or when n and y are both zero; and wherein each of cycloalkyl, aryl and heterocyclic group is optionally substituted with 1 to 3-groups independently selected from oxo, hydroxy, halo, $C_1$-$C_6$ alkyl, $C_2$-$C_6$ alkene, $C_2$-$C_6$ alkynyl, $C_1$-$C_6$ alkoxy, $C_1$-$C_6$ haloalkyl, $C_1$-$C_6$ alkylalcohol, $CONR^{11}R^{12}$, $NR^{11}SO_2R^{12}$, $NR^{11}COR^{12}$, $C_0$-$C_3$ alkyl$NR^{11}R^{12}$, $C_1$-$C_3$ alkyl$COR^{11}$, $C_0$-$C_6$ alkyl$COOR^{11}$, cyano, $C_1$-$C_6$ alkylcycloalkyl, phenyl, —$OC_1$-$C_6$ alkylcycloalkyl, —$OC_1$-$C_6$ alkylaryl, —$OC_1$-$C_6$ alkylheterocyclic, and $C_1$-$C_6$ alkylaryl;

$R^2$ is bound only to carbon atoms and is a group independently selected from hydrogen, hydroxy, halo, $C_1$-$C_6$ alkyl, $C_2$-$C_6$ alkene, $C_2$-$C_6$ alkynyl, $C_1$-$C_6$ alkoxy, $C_1$-$C_6$ haloalkyl, $CONR^{11}R^{12}$, $NR^{11}SO_2R^2$, $NR^{11}COR^{12}$, $C_0$-$C_6$ alkyl$NR^{11}R^{12}$, $C_0$-$C_6$ alkyl$COR^{11}$, $C_0$-$C_6$ alkyl$COOR^{11}$, cyano, nitro, $C_0$-$C_6$ alkylcycloalkyl, phenyl, and $C_0$-$C_6$ alkylaryl heterocyclyl, $C_3$-$C_8$ cycloalkyl, and $C_1$-$C_6$ haloalkyl;

$R^3$ is hydrogen;

$R^4$ is a group represented by the formula —$NR^9R^{10}$;

$R^5$ is selected from a group consisting of hydrogen, hydroxy, halogen, $C_1$-$C_6$ haloalkyl, $C_3$-$C_8$ cycloalkyl, $C_1$-$C_6$ alkylaryl, $C_1$-$C_6$ alkylheterocyclic, aryl, heterocyclic, cyano, nitro, $C_1$-$C_6$ alkyl, $C_2$-$C_6$ alkenyl $C_1$-$C_6$ alkoxy, aryloxy, —$OC_2$-$C_6$ alkenyl, —$OC_1$-$C_6$ haloalkyl, —$C_0$-$C_6$ alkyl$NR^7R^8$, $C_0$-$C_6$ alkyl$COR^7$, $C_1$-$C_6$ alkyl$CO_2R^7$, $C_0$-$C_6$ alkyl$CONR^7R^8$, $CONR^7SO_2R^1$, $NR^7SO_2R^8$, $NR^7COR^8$, N=$CR^7R^8$, $OCONR^7R^8$, $S(O)_tR^7$, $SO_2NR^7R^8$, $C_1$-$C_6$ alkylalcohol, —OC$_1$-C$_6$ alkylheterocyclic, and —OC$_1$-C$_6$ alkylaryl wherein each of the alkyl, cycloalkyl, aryl and heterocyclic groups is optionally substituted by oxo, alkyloxy, aryloxy; and wherein any two R$^5$ groups may combine to form an optionally substituted 5-7 member carbocyclic or heterocyclic, saturated or unsaturated ring fused with the A-ring to which they are attached;

R$^6$ is independently selected from a group consisting of hydrogen, C$_1$-C$_6$ alkyl, C$_2$-C$_6$ alkenyl, hydroxy, COR$^7$, C$_1$-C$_6$ alkoxy, aryloxy, —OC$_2$-C$_6$ alkenyl, —OC$_1$-C$_6$ haloalkyl, C$_1$-C$_6$ alkylNR$^{11}$R$^{12}$, C$_3$-C$_8$ cycloalkyl, heterocyclic, aryl, and C$_1$-C$_6$ alkylcycloalkyl;

each R$^7$ is independently selected from a group consisting of hydrogen, C$_1$-C$_6$ alkyl, C$_2$-C$_6$ alkenyl, C$_2$-C$_6$ alkynyl, —OC$_1$-C$_6$ alkyl, C$_1$-C$_6$ haloalkyl, —O-aryl, —OC$_3$-C$_8$ cycloalkyl, —O-heterocyclic, —NR$^{11}$R$^{12}$, —C$_1$-C$_6$ alkylcycloalkyl, —OC$_1$-C$_6$ alkylcycloalkyl, —OC$_1$-C$_6$ alkylheterocyclic, C$_1$-C$_6$ alkylheterocyclic, —O C$_1$-C$_6$ alkylaryl, C$_3$-C$_8$ cycloalkyl, heterocyclic, aryl, and C$_1$-C$_6$ alkylaryl, wherein each alkyl, cycloalkyl, heterocyclic or aryl group is optionally substituted with 1-3 groups independently selected from hydroxy, halogen, oxo, C$_1$-C$_6$ alkyl, C$_1$-C$_6$ alkoxy, SO$_2$R$^{11}$, SO2NR11R12, C$_1$-C$_6$ alkylSO$_2$NR$^{11}$R$^{12}$, COOR$^{11}$, C$_1$-C$_6$ haloalkyl, and NR$^{11}$R$^{12}$, or R$^{11}$ and R$^{12}$ combine to form a nitrogen containing heterocyclic ring having 0, 1, or 2 additional heteroatoms selected from oxygen, nitrogen and sulfur and wherein the nitrogen-containing heterocycle is optionally substituted with oxo, or C$_1$-C$_6$ alkyl;

each R$^8$ is independently selected from a group consisting of hydrogen, C$_1$-C$_6$ alkyl, C$_2$-C$_6$ alkenyl, C$_2$-C$_6$ alkynyl, —O C$_1$-C$_6$ alkyl, C$_1$-C$_6$ haloalkyl, —O-aryl, —OC$_3$-C$_8$ cycloalkyl, —O-heterocyclic, —NR$^{11}$R$^{12}$, —C$_1$-C$_6$ alkylcycloalkyl, —OC$_1$-C$_6$ alkylcycloalkyl, —OC$_1$-C$_6$ alkylheterocyclic, C$_1$-C$_6$ alkylheterocyclic, —O C$_1$-C$_6$ alkylaryl, C$_3$-C$_8$ cycloalkyl, heterocyclic, aryl, and C$_1$-C$_6$ alkylaryl, wherein each alkyl, cycloalkyl, heterocyclic or aryl group is optionally substituted with 1-3 groups independently selected from hydroxy, halogen, C$_1$-C$_6$ alkyl, C$_1$-C$_6$ alkoxy, C$_1$-C$_6$ haloalkyl, and NR$^{11}$R$^{12}$, or R$^{11}$ and R$^{12}$ combine to form a nitrogen containing heterocyclic ring having 0, 1, or 2 additional heteroatoms selected from oxygen, nitrogen and sulfur and wherein the nitrogen-containing heterocycle is optionally substituted with oxo, or C$_1$-C$_6$ alkyl;

R$^9$ is COR$^7$ or S(O)$_t$R$^7$ wherein R$^7$ is as defined above;

R$^{10}$ is selected from the group consisting of aryl, C$_1$-C$_6$ alkylaryl, C$_2$-C$_6$ alkenylaryl, C$_2$-C$_6$ alkynylaryl, C$_1$-C$_6$ alkylheterocyclic, C$_2$-C$_6$ alkenylheterocyclic, C$_1$-C$_6$ alkylcycloalkyl, C$_1$-C$_6$ alkyl-O—C$_1$-C$_6$ alkylaryl, and wherein each cycloalkyl, aryl, or heterocyclic group is optionally substituted with 1-3 groups independently selected from the group consisting of hydroxy, oxo, —SC$_1$-C$_6$ alkyl, C$_1$-C$_6$ alkyl, C$_1$-C$_6$ alkenyl, C$_1$-C$_6$ alkynyl, C$_1$-C$_6$ haloalkyl, halogen, C$_1$-C$_6$ alkoxy, aryloxy, C$_1$-C$_6$ alkenyloxy, C$_1$-C$_6$ haloalkoxyalkyl, C$_0$-C$_6$ alkylNR$^{11}$R$^{12}$, —OC$_1$-C$_6$ alkylaryl, nitro, cyano, C$_1$-C$_6$ haloalkylalcohol, and C$_1$-C$_6$ alkylalcohol;

R$^{11}$ and R$^{12}$ are independently selected from a group consisting of hydrogen, C$_1$-C$_6$ alkyl, C$_1$-C$_6$ alkenyl, C$_3$-C$_8$ cycloalkyl, heterocyclic, aryl, C$_1$-C$_6$ alkylaryl, wherein each aryl cycloalkyl and heterocyclic group is optionally substituted with 1-3 groups independently selected from halogen, C$_1$-C$_6$ alkylheterocyclic, and C$_1$-C$_6$ haloalkyl, or R$^{11}$ and R$^{12}$ combine to form a nitrogen containing heterocyclic ring which may have 0, 1, or 2 additional heteroatoms selected from oxygen, nitrogen or sulfur and is optionally substituted with oxo, C$_1$-C$_6$ alkyl, COR$^7$, and SO$_2$R$^7$;

or a pharmaceutically acceptable salt, solvate, enantiomer, racemate, diastereomer or mixture of diastereomers thereof.

The present invention also provides a method for modulating CETP activity comprising the use of a compound of formula I or a pharmaceutically acceptable salt, solvate, enantiomer, racemate, diastereomer or mixture of diastereomers thereof, for the treatment, prevention or amelioration of CETP mediated diseases.

The present invention provides a method for treating or preventing dyslipidemia comprising administering a compound of formula I, pharmaceutically acceptable salt, solvate, enantiomer, racemate, diastereomer, mixture of diastereomers, or prodrug thereof, to a patient in need thereof.

The present invention provides a method for treating or preventing Cardiovascular Disease including CHD and the sequela thereof, comprising administering a compound of formula I, pharmaceutically acceptable salt, solvate, enantiomer, racemate, diastereomer, mixture of diastereomers, or prodrug thereof, to a patient in need thereof.

The present invention provides a method for treating and/or preventing artherosclerosis comprising administering a compound of formula I, pharmaceutically acceptable salt, solvate, enantiomer, racemate diastereomer, mixture of diastereomers, or prodrug thereof, to a patient in need thereof.

The present invention provides a method for treating and/or preventing diseases related to abnormal CETP activity comprising administering a compound of formula I, pharmaceutically acceptable salt, solvate, enantiomer, racemate diastereomer, mixture of diastereomers, or prodrug thereof, to a patient in need thereof.

The present invention provides a method of raising the ratio of plasma HDL-cholesterol to plasma LDL-cholesterol in a mammal comprising administering a therapeutically effective dose of a compound of formula I, pharmaceutically acceptable salt, solvate, enantiomer, racemate, diastereomer, mixture of diastereomers, or prodrug thereof, to a patient in need thereof.

The present invention provides a method of raising the level of plasma HDL-cholesterol in a mammal comprising administering a therapeutically effective dose of a compound of formula I, pharmaceutically acceptable salt, solvate, enantiomer, racemate, diastereomer, mixture of diastereomers, or prodrug thereof, to a patient in need thereof.

The present invention provides a method of lowering the level of plasma LDL-cholesterol in a mammal comprising administering a therapeutically effective dose of a compound of formula I, pharmaceutically acceptable salt, solvate, enantiomer, racemate, diastereomer, mixture of diastereomers, or prodrug thereof, to a patient in need thereof.

The present invention also provides a pharmaceutical composition comprising a compound of formula I or a pharmaceutically acceptable salt, solvate, enantiomer, racemate, diastereomer or mixture of diastereomers thereof, and a carrier.

The present invention also provides a method of treating and/or preventing the pathological sequelae due to low levels of plasma HDL and/or high levels of LDL-cholesterol in a mammal comprising administering an effective dose of a compound of formula I, pharmaceutically acceptable salt, solvate, enantiomer, racemate, diastereomer, or mixture of diastereomers, thereof, to a patient in need thereof.

The present invention also relates to the use of a compound of formula I for the manufacture of a medicament for treating and/or preventing atherosclerosis in a mammal comprising administering an effective dose of a compound of formula I, pharmaceutically acceptable salt, solvate, enantiomer, racemate, diastereomer, mixture of diastereomers, or prodrug thereof, to a patient in need thereof.

The present invention also provides a combination therapy involving a compound of formula I and one or more other cardio protective agents such as for example, statins, leptin, and/or other LXR, CETP, ABC A1 or lipid regulating agents useful for the treatment and/or prevention of atherosclerosis.

DETAILED DESCRIPTION OF THE INVENTION

The current invention provides novel compounds of formula I useful in modulating CETP activity.

The term "modulation" would include, but not be limited to, up-regulation, down-regulation, inhibition, agonism, antagonism of the CETP receptor as appropriate to achieve HDL raising, or LDL lowering and the resulting biological sequelae from such intervention.

The phrase "diseases" or "diseases related to CETP modulation" or "diseases mediated by CETP activity" refers to pathological states where atherosclerosis and cardiovascular diseases are prone because of dyslipidemia and/or other risk factors and are therefore beneficially affected by down-regulation (modulation) of CETP activity. The phrase "diseases" as used herein also include diseases caused by, exacerbated by, or otherwise related to CETP activity. These diseases include but are not limited to hyperlipidemia and its sequelae such as atherosclerosis, CHD, elevated blood pressure, CHF, stroke, hypertension, hypertriglyceremia, diabetes, obesity, inflammatory diseases including but not limited to dermatitis, arthritis, and pain, and diseases of the central nervous system including but not limited to dementia, cognitive disorders such as Alzheimer's disease.

The term "Cardiovascular Disease" and the sequela thereof as used herein includes atherosclerosis, peripheral vascular disease, dyslipidemia, hyperlipoproteinemai (including alpha and beta), hypercholesterolemia, cardiovascular disorders, angina, ischemia, cardiac ischemia, stroke, myocardial infarction, reperfusion injury, angioplastic restenosis, hypertension, vascular complications of diabetes, obesity or endotoxemia. The use of CETP to treat Cardiovascular Diseases as enumerated above is supported by disclosures including U.S. Pat. No. 6,140,343.

The term "treatment" bears its usual meaning which includes prohibiting, inhibiting, ameliorating, halting, restraining, slowing or reversing the progression, or reducing the severity of a pathological symptom related to or resultant from the modulation of CETP activity, especially as related to raising plasma levels of HDL, or lowering LDL-cholesterol levels or raising the HDL/LDL ratio or controlling atherosclerosis, hyperlipidemia and/or hypercholesterolemia.

Generally, one of skill in the art is aware that valency must be conserved (complete) for all stable molecules. Therefore, the necessary implication that hydrogen atoms are necessary and available to complete valency in all structures including formula I unless expressly indicated otherwise, is imputed to the general knowledge of one of skill in the art.

General chemical terms used in the description of compounds herein described bear their usual meanings. For example, the term "$C_{1-6}$ alkyl," or "($C_1$-$C_6$)alkyl" or "$C_1$-$C_6$ alkyl" refers to a straight or branched aliphatic chain of 1 to 6 carbon atoms including but not limited to methyl, ethyl, propyl, iso-propyl, n-butyl, pentyl, and hexyl. Unless otherwise stated, the term "alkyl" means $C_1$-$C_6$ alkyl. Similarly, the term "$C_0$-$C_6$ alkyl" implies an alkyl group as indicated wherein when the term $C_0$ applies, the alkyl group is not present, and the remaining groups attach directly to the substrate. The present invention also contemplates that the term $C_1$-$C_6$ alkyl or $C_2$-$C_6$ alkenyl or similar terms also encompass the specified alkyl or alkenyl or similar group, which may be chiral, regio or steroisomeric. Such chiral or regio or stereoisomeric groups are also objects of the present invention.

The term alkylaryl refers to an alkyl group substituted by an aryl group. For example, $C_1$-$C_6$ alkylaryl indicates that a $C_1$-$C_6$ alkyl group is attached to the aryl group, and that the resulting $C_1$-$C_6$ alkylaryl is attached to the nucleus via the alkyl group. A most preferred alkylaryl group is benzyl.

The term "substituted phenyl" or "optionally substituted phenyl" refers to a phenyl group having one or more substituents selected from the group consisting of $C_1$-$C_6$ alkyl, $C_1$-$C_6$ alkoxy, hydroxy, —COOR$^1$, $C_0$-$C_6$ alkylNR$^{11}$R$^{12}$, nitro, chloro, fluoro, bromo, iodo, $C_1$-$C_6$haloalkyl, $C_1$-$C_6$ haloalkoxyalkyl, $C_0$-$C_6$ alkylheterocyclic.

The term "optionally substituted" as used herein unless otherwise specified means that the subject group may be substituted with one or more fragments or groups selected from $C_1$-$C_6$ alkyl, $C_1$-$C_6$ alkoxy, hydroxy, COR$^7$, —COOR$^7$, $C_0$-$C_6$ alkylNR$^7$R$^8$, nitro, oxo, chloro, fluoro, bromo, cyano, $C_3$-$C_8$ cycloalkyl, $C_1$-$C_6$ alkylcycloalkyl, $C_1$-$C_6$ haloalkyl, $C_1$-$C_6$ haloalkoxyalkyl, heterocyclic, and $C_0$-$C_6$ alkylheterocyclic.

The term "aryl" refers to a substituted or unsubstituted aromatic or heteroaromatic carbocyclic or heterocyclic radical selected from the group consisting of 2-furyl, 3-furyl, 2-thienyl 3-thienyl, 1-pyrrolyl, 2-pyrrolyl, 3-pyrrolyl, phenyl, 2-pyridyl, 3-pyridyl, 4-pyridyl, 1-naphthyl, 2-naphthyl, 2-benzofuryl, 3-benzofuryl, 4-benzofuryl, 5-benzofuryl, 6-benzofuryl, 7-benzofuryl, 2-benzothieny, 3-benzothienyl, 4-benzothienyl, 5-benzothienyl, 6-benzothienyl, 7-benzothienyl, 1-indolyl, 2-indolyl, 3-indolyl, 4-indolyl, 5-indolyl, 6-indolyl and 7-indolyl. As used herein the term aryl also encompasses the benzyl group.

The term "$C_3$-$C_8$ cycloalkyl" or similar terms refer to a saturated carbocyclic ring having from 3 to 8 carbon atoms.

The term "carbocycle" as used herein refers to a cyclic group having only carbon and an appropriate number of hydrogen atoms. The term encompasses groups such as cycloalkyl, cycloalkene, cycloalkylene, naphthyl, phenyl and the like.

The term "heterocycle", "heterocyclyl", or "heterocyclic" refers to a 5, 6 or 7 member saturated, partially unsaturated, or aromatic mono-cyclic or a benzofused bicyclic ring containing 1-5 heteroatoms selected from N, S or O, wherein said heterocycle is optionally substituted at carbon or nitrogen atom(s) unless otherwise specified. Most preferred heterocyclic groups include pyrrolidinyl, piperidinyl, hexamethyleneimmino, morpholino, benzthiophene, indolyl, quinolyl, isoquinolyl, tetrazolyl, and pyridinyl. As a corollary, the term "alkylheterocyclic" or "alkylheterocycle" is understood to mean that the alkyl group is attached to the heterocycle and the point of attachment to the molecular backbone or nucleus is the alkyl group.

The term "haloalkoxyalkyl" as used herein include for example trifluoromethoxy, pentafluoroethoxy, trifluoroethoxy (OCH$_2$CF$_3$) and the like. Similarly, the term "holaoalkyl alcohol" implies compounds such as CF$_2$CH$_2$OH and the like.

The term "Prodrugs" describes derivatives of the compounds of the invention that have chemically or metabolically cleavable groups and become by solvolysis or under physiological conditions the compounds of the invention, which are pharmaceutically active, in vivo. Derivatives of the compounds of this invention have activity in both their acid and base derivative forms, but the acid derivative form often offers advantages of solubility, tissue compatibility, or delayed release in a mammalian organism (see, Bundgard, H., *Design of Prodrugs*, pp. 7-9, 21-24, Elsevier, Amsterdam 1985). Prodrugs include acid derivatives, such as, esters prepared by reaction of the parent acidic compound with a suitable alcohol, or amides prepared by reaction of the parent acid compound with a suitable amine. Simple aliphatic esters (e.g., methyl, ethyl, propyl, isopropyl, butyl, sec-butyl, tert-butyl) or aromatic esters derived from acidic groups pendent on the compounds of this invention are preferred prodrugs. Other preferred esters include morpholinoethyloxy, diethylglycolamide and diethylaminocarbonylmethoxy. In some cases it is desirable to prepare double ester type prodrugs such as (acyloxy) alkyl esters or ((alkoxycarbonyl)oxy)alkyl esters.

As used herein, the term "protecting group" refers to a group useful for masking reactive sites in a molecule to enhance the reactivity of another group or allow reaction at another desired site or sites following which the protecting group may be removed. Protecting groups are usually used to protect or mask groups including but not limited to —OH, —NH, and —COOH. Suitable protecting groups are known to one of skill in the art and are described in Protecting groups in Organic Synthesis, 3$^{rd}$ edition, Greene, T. W.; Wuts, P.G.M. Eds., John Wiley and Sons, New York, 1999.

As used herein, the term "solvate" is a form of the compound of the invention wherein a crystal or crystals of a compound of the invention have been formed from a stoichiometric or non-stoichiometric amount of the compound of formula I and a stoichiometric or non-stoichiometric amount of a solvent. Typical solvating solvents include for example, water, methanol, ethanol, acetone and dimethylformamide.

In those instances where a compound of the invention possesses acidic or basic functional groups, various salts may be formed which are more water soluble and/or more physiologically suitable than the parent compound. Representative pharmaceutically acceptable salts, include but are not limited to, the alkali and alkaline earth salts such as lithium, sodium, potassium, calcium, magnesium, aluminum and the like. Salts are conveniently prepared from the free acid by treating the acid in solution with a base or by exposing the acid to an ion-exchange resin.

Included within the definition of pharmaceutically acceptable salts are the relatively non-toxic, inorganic and organic base or acid addition salts of compounds of the present invention. Base addition salts include for example, ammonium, quaternary ammonium, and amine cations, derived from nitrogenous bases of sufficient basicity to form salts with the compounds of this invention (see, for example, S. M. Berge, et al., "Pharmaceutical Salts," *J. Phar. Sci.*, 66: 1-19 (1977)). Moreover, the basic group(s) of the compound of the invention may be reacted with suitable organic or inorganic acids to form salts such as acetate, benzenesulfonate, benzoate, bicarbonate, bisulfate, bitartrate, borate, hydrobromide, camsylate, carbonate, clavulanate, citrate, chloride, edetate, edisylate, estolate, esylate, fluoride, fumarate, gluceptate, gluconate, glutamate, glycolylarsanilate, hexylresorcinate, hydrochloride, hydroxynaphthoate, hydroiodide, isothionate, lactate, lactobionate, laureate, maleate, mandelate, mesylate, methylbromide, methylnitrate, methylsulfate, mucate, napsylate, nitrate, oleate, oxalate, palmitate, pantothenate, phosphate, polygalacturonate, salicylate, stearate, subacetate, succinate, tannate, tartrate, tosylate, trifluoroacetate, trifluoromethane sulfonate, and valerate. Preferred salts for the purpose of the invention include the hydrochloride salt, the hydrobromide salt, the bisulfate salt, the methane sulfonic acid salt, the p-toluenesulfonic acid salt, bitartrate, the acetate and the citrate salt.

A compound of the invention as illustrated by formula I may occur as any one of its positional isomers, stereochemical isomers or regio-isomers, all of which are objects of the invention. Certain compounds of the invention may possess one or more chiral centers, and thus, may exist in optically active forms. Likewise, when the compounds contain an alkenyl or alkenylene group, there exist the possibility of cis- and trans-isomeric forms of the compounds. The R- and S-isomers and mixtures thereof, including racemic mixtures as well as mixtures of enantiomers or cis- and trans-isomers, are contemplated by this invention. Additional asymmetric carbon atoms can be present in a substituent group such as an alkyl group. All such isomers as well as the mixtures thereof are intended to be included in the invention. If a particular stereoisomer is desired, it can be prepared by methods well known in the art by using stereo-specific reactions with starting materials that contain the asymmetric centers and are already resolved. Alternatively desired stereoisomers may be prepared by methods that lead to mixtures of the stereoisomers and subsequent resolution by known methods. For example, a racemic mixture may be reacted with a single enantiomer of some other compound i.e. a chiral resolving agent. This changes the racemic form into a mixture of stereoisomers and diastereomers, because they have different melting points, different boiling points, and different solubilities and can be separated by conventional means, such as crystallization.

PREFERRED EMBODIMENTS OF THE INVENTION

Preferred n, m, p, t and q

Preferably n is 0, or 1. More preferably, n is 0.

Preferably m is 0, or 1.

Preferably p is 1, or 2.

Preferably t is 0, 1 or 2. More preferably t is 1 or 2

Preferably, q is 0, 1 or 2. More preferably q is 1 or 2. Most preferably, q is 1.

Preferred $R^1$

A preferred $R^1$ groups is selected from the group consisting of aryloxy, —$OC_1$-$C_6$ haloalkyl, —$OC_1$-$C_6$ alkylcycloalkyl, —$C_1$-$C_6$ alkylcycloalkyl, —$C_1$-$C_6$ alkylcycloalkyl$NR^7R^8$, —$OC_1$-$C_6$ alkylcycloalkyl$NR^7R^8$, $C_1$-$C_6$ alkoxy, —$OC_1$-$C_6$ alkylaryl, and —$OC_1$-$C_6$ alkylheterocyclic. More preferred is an $R^1$ group selected from $C_1$-$C_6$ alkyl, $C_1$-$C_6$ alkoxy, —$OC_1$-$C_6$ alkylaryl, and —$OC_0$-$C_6$ alkylcycloalkyl$NR^7R^8$. Most preferred is an $R^1$ group represented by $C_1$-$C_6$ alkoxy or $C_1$-$C_6$ alkylcycloalkyl, or $C_3$-$C_8$ cycloalkyl.

Preferred $R^2$

A preferred $R^2$ groups is selected from the group consisting of hydrogen, hydroxy, $C_1$-$C_6$ haloalkyl, $C_1$-$C_6$ alkyl, halo, $C_1$-$C_6$ alkylhalide, —$OC_1$-$C_6$ alkyl, —$OC_1$-$C_6$ haloalkyl, —$OC_1$-$C_5$ alkylcycloalkyl, $C_0$-$C_6$ alkyl$NR^7R^8$, —$OC_1$-$C_6$ alkylaryl, and —$OC_1$-$C_6$ alkylheterocyclic. More preferred is an $R^2$ group selected from hydroxy, $C_1$-$C_6$ alkyl, halo $C_1$-$C_6$ alkylhalide and $C_1$-$C_6$ alkoxyalkyl. Most preferred is an $R^2$ group represented by hydrogen or $C_1$-$C_6$ alkyl.

Preferred $R^3$ $R^3$ is hydrogen.

Preferred $R^4$

Preferred $R^4$ is the group —$NR^9R^{10}$. The group —$NR^9R^{10}$ is preferably represented by a group selected from the group consisting of:

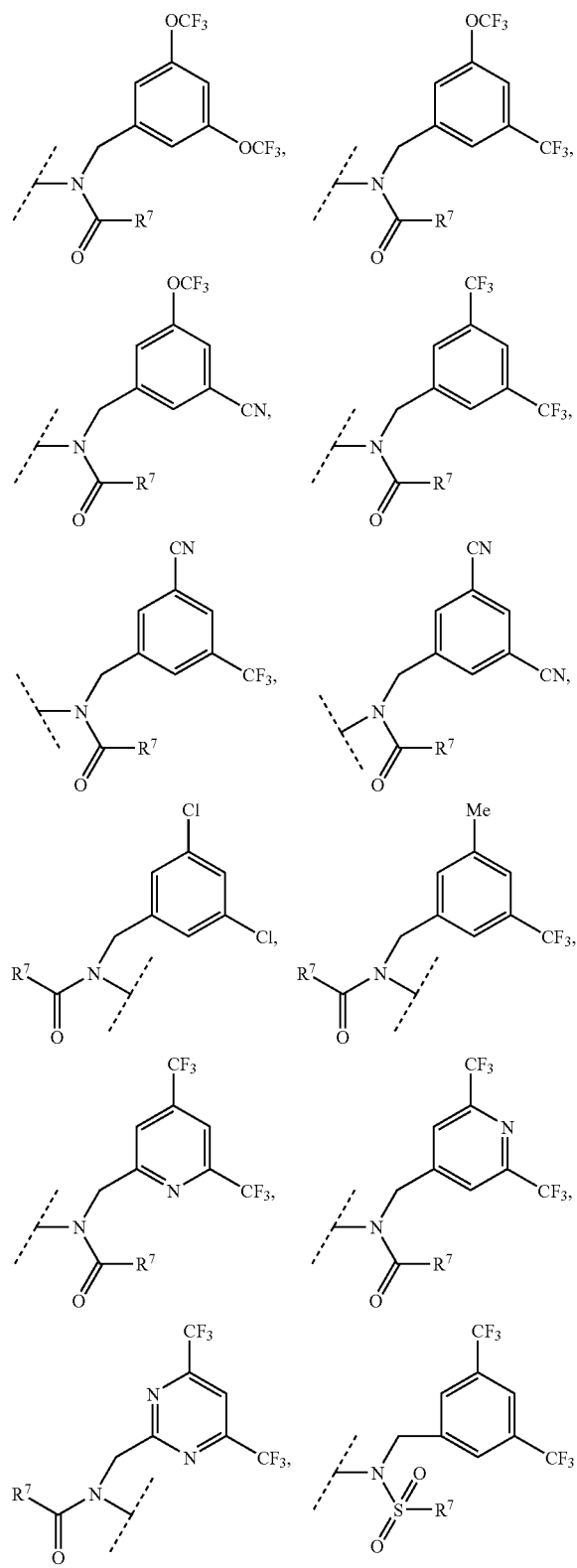

Preferred $R^5$ $R^5$ is preferably selected from a group consisting of hydrogen, hydroxy, $C_1$-$C_6$ alkyl, $C_2$-$C_6$ alkenyl, halo, heterocyclic, aryl, $C_1$-$C_6$ haloalkyl, $C_1$-$C_6$ alkoxy, aryloxy, —$OC_2$-$C_6$ alkenyl, —$OC_1$-$C_6$ haloalkyl, —$CH_2NR^7R^8$, —$NH_2$, —CN, —COOH, benzyl, and $NO_2$;

Preferred $R^6$ $R^6$ is at each occurrence independently selected preferably from a group consisting of hydrogen, $C_1$-$C_6$ alkyl, and $C_1$-$C_6$ alkoxy, $C_1$-$C_6$ cycloalkyl, $C_1$-$C_6$ alkylaryl, $C_1$-$C_6$ alkylheterocyclic, and aryloxy.

Preferred $R^7$

Preferred $R^7$ is a group selected from the group consisting of $C_1$-$C_6$ alkyl, $C_2$-$C_6$ alkenyl, $C_1$-$C_6$ alkylaryl, $C_1$-$C_6$ alkylcycloalkyl, $C_3$-$C_8$ cycloalkyl, phenyl, heterocyclic, and $C_1$-$C_6$alkylheterocyclic, $OC_1$-$C_6$ alkyl, $OC_2$-$C_6$ alkenyl, $OC_1$-$C_6$ alkylaryl, Oaryl, $C_1$-$C_6$ alkylcycloalkyl, Oheterocyclic, and $OC_1$-$C_6$alkylheterocyclic wherein each aryl or heterocyclic group is optionally substituted with 1-3 groups independently selected from $C_1$-$C_6$ alkyl, halo, and $C_1$-$C_6$ haloalkyl. More preferably, $R^7$ is selected from the group consisting of $C_1$-$C_6$ alkyl, $C_2$-$C_6$ alkenyl, $C_1$-$C_6$ alkylaryl, and phenyl.

Preferred $R^8$

Preferred $R^8$ is a group selected from the group consisting of $C_1$-$C_6$ alkyl, $C_2$-$C_6$ alkenyl, $C_1$-$C_6$ alkylaryl, phenyl, heterocyclic, and $C_1$-$C_6$alkylheterocyclic, wherein each aryl or heterocyclic group is optionally substituted with 1-3 groups independently selected from $C_1$-$C_6$ alkyl, halo, and $C_1$-$C_6$ haloalkyl. More preferably, $R^8$ is selected from the group consisting of $C_1$-$C_6$ alkyl, $C_2$-$C_6$ alkenyl, $C_1$-$C_6$ alkylaryl, and phenyl.

Preferred $R^9$

A preferred $R^9$ is the group $COR^7$ wherein $R^7$ is selected from the group consisting of $C_1$-$C_6$ alkyl, $C_2$-$C_6$ alkenyl, $C_1$-$C_6$ alkylaryl, $C_1$-$C_6$ alkylcycloalkyl, $C_3$-$C_8$ cycloalkyl, phenyl, heterocyclic, and $C_1$-$C_6$alkylheterocyclic, $OC_1$-$C_6$ alkyl, $OC_2$-$C_6$ alkenyl, $OC_1$-$C_6$ alkylaryl, Oaryl, $C_1$-$C_6$ alkylcycloalkyl, Oheterocyclic, and $OC_1$-$C_6$alkylheterocyclic wherein each aryl or heterocyclic group is optionally substituted with 1-3 groups independently selected from $C_1$-$C_6$ alkyl, halo, and $C_1$-$C_6$ haloalkyl.

Preferred $R^{10}$ $R^{10}$ is preferably the group optionally substituted aryl, alkylaryl, heterocyclic or alkylheterocyclic. More preferred is an optionally substituted aryl or alkylaryl.

Preferred $R^{11}$ and $R^{12}$

Preferred $R^{11}$ and $R^{12}$ are independently selected from a group consisting of $C_1$-$C_6$ alkyl, $C_2$-$C_6$ alkenyl, $C_1$-$C_6$ alkylaryl, and $C_1$-$C_6$alkylheterocyclic, wherein each aryl group is optionally substituted with 1-3 groups independently selected from $C_1$-$C_6$ alkyl, halo, and $C_1$-$C_6$ haloalkyl.

A preferred compound of the invention is a compound selected from the group consisting of:

5-[Acetyl-(3,5-bis-trifluoromethyl-benzyl)-amino]-7-trifluoromethyl-2,3,4,5-tetrahydro-benzo[b]azepine-1-carboxylic acid isopropyl ester, 5-[(3,5-Bis-trifluoromethyl-benzyl)-methoxycarbonyl-amino]-7-trifluoromethyl-2,3,4,5-tetrahydro-benzo[b]azepine-1-carboxylic acid isopropyl ester, 5-[(3,5-Bis-trifluoromethyl-benzyl)-methoxycarbonyl-amino]-7-trifluoromethyl-2,3,4,5-tetrahydro-benzo[b]azepine-1-carboxylic acid ethyl ester, 5-[Acetyl-(3,5-bis-trifluoromethyl-benzyl)-amino]-7-trifluoromethyl-2,3,4,5-tetrahydro-benzo[b]azepine-1-carboxylic acid ethyl ester, 5-[Acetyl-(3,5-bis-trifluoromethyl-benzyl)-amino]-2,3,4,5-tetrahydro-benzo[b]azepine-1-carboxylic acid isopropyl ester,
5-[(3,5-Bis-trifluoromethyl-benzyl)-methoxycarbonyl-amino]-2,3,4,5-tetrahydro-benzo[b]azepine-1-carboxylic acid isopropyl ester,
5-[(3,5-Bis-trifluoromethyl-benzyl)-methoxycarbonyl-amino]-7-bromo-2,3,4,5-tetrahydro-benzo[b]azepine-1-carboxylic acid isopropyl ester,
5-[(3,5-Bis-trifluoromethyl-benzyl)-methoxycarbonyl-amino]-7-bromo-2,3,4,5-tetrahydro-benzo[b]azepine-1-carboxylic acid ethyl ester,
5-[Acetyl-(3,5-bis-trifluoromethyl-benzyl)-amino]-7-bromo-2,3,4,5-tetrahydro-benzo[b]azepine-1-carboxylic acid ethyl ester,
5-[Acetyl-(3,5-bis-trifluoromethyl-benzyl)-amino]-7-methoxy-2,3,4,5-tetrahydro-benzo[b]azepine-1-carboxylic acid ethyl ester,
5-[Acetyl-(3,5-bis-trifluoromethyl-benzyl)-amino]-8-trifluoromethyl-2,3,4,5-tetrahydro-benzo[b]azepine-1-carboxylic acid isopropyl ester,
5-[Acetyl-(3,5-bis-trifluoromethyl-benzyl)-amino]-8-fluoro-7-trifluoromethyl-2,3,4,5-tetrahydro-benzo[b]azepine-1-carboxylic acid isopropyl ester,
5-[Acetyl-(3,5-bis-trifluoromethyl-benzyl)-amino]-2-methyl-7-trifluoromethyl-2,3,4,5-tetrahydro-benzo[b]azepine-1-carboxylic acid isopropyl ester,
5-[Acetyl-(3,5-bis-trifluoromethyl-benzyl)-amino]-4,4-dimethyl-7-trifluoromethyl-2,3,4,5-tetrahydro-benzo[b]azepine-1-carboxylic acid isopropyl ester,
6-[Acetyl-(3,5-bis-trifluoromethyl-benzyl)-amino]-8-trifluoromethyl-3,4,5,6-tetrahydro-2H-benzo[b]azocine-1-carboxylic acid isopropyl ester,
6-[Acetyl-(3,5-bis-trifluoromethyl-benzyl)-amino]-9-trifluoromethyl-3,4,5,6-tetrahydro-2H-benzo[b]azocine-1-carboxylic acid isopropyl ester,
5-[Acetyl-(3,5-bis-trifluoromethyl-benzyl)-amino]-9-trifluoromethyl-3,4,5,6-tetrahydro-2H-benzo[b]azocine-1-carboxylic acid isopropyl ester,
4-[Acetyl-(3,5-bis-trifluoromethyl-benzyl)-amino]-7-trifluoromethyl-2,3,4,5-tetrahydro-benzo[b]azepine-1-carboxylic acid isopropyl ester,
5-[Acetyl-(3,5-bis-trifluoromethyl-benzyl)-amino]-8-chloro-2,3,4,5-tetrahydro-benzo[b]azepine-1-carboxylic acid isopropyl ester,
5-[(3,5-Bis-trifluoromethyl-benzyl)-methoxycarbonyl-amino]-8-chloro-2,3,4,5-tetrahydro-benzo[b]azepine-1-carboxylic acid isopropyl ester, or a pharmaceutically acceptable salt, solvate enantiomer or diastereomer or mixture thereof.

The geometric isomers associated with the asymmetric carbon atoms of compounds of formula I are also within the scope of the current invention as useful for the treatment of diseases related to CETP modulation.

Synthesis of Compounds of the Invention

Intermediates and compounds of the instant invention can be synthesized as illustrated in the following schemes. Anthranilate intermediates of Formula 1 can be chemically prepared, for example, by following the synthetic routes set forth in the schemes below. However, the following discussion is not intended to be limiting to the scope of the present invention in any way. The reagents and starting materials are readily available commercially or by derivation from other available starting materials to one of ordinary skill in the art. Other necessary reagents and starting materials may be made by procedures which are selected from standard techniques of organic and heterocyclic chemistry, techniques which are analogous to the syntheses of known structurally similar intermediates, and in the procedures described in the preparations and examples below, including any novel procedures. This includes, but is not limited to, esterification of a carboxylic acid, hydrolysis of a nitrile to a carboxylic acid, and subsequent esterification. In addition, one of ordinary skill in the art will appreciate that many of the necessary reagents or starting materials can be readily obtained from commercial suppliers. The R, R1, R2, R3, R4, R5, R6, etc, used within this section for the purpose of illustrating the various methods of synthesizing compounds of the invention are not necessarily synonymous in scope or meaning with similar groups used in the generic structure for compounds of formula I. However, groups in similar positions for final compounds (compounds of the invention) of the schemes are co-extensive in scope and meaning compared to groups occupying similar positions as defined for the generic structure of compounds of formula I.

Intermedaite compounds of formula 1 or 4 useful for preparing compounds of the invention may be prepared as shown in Scheme 1.

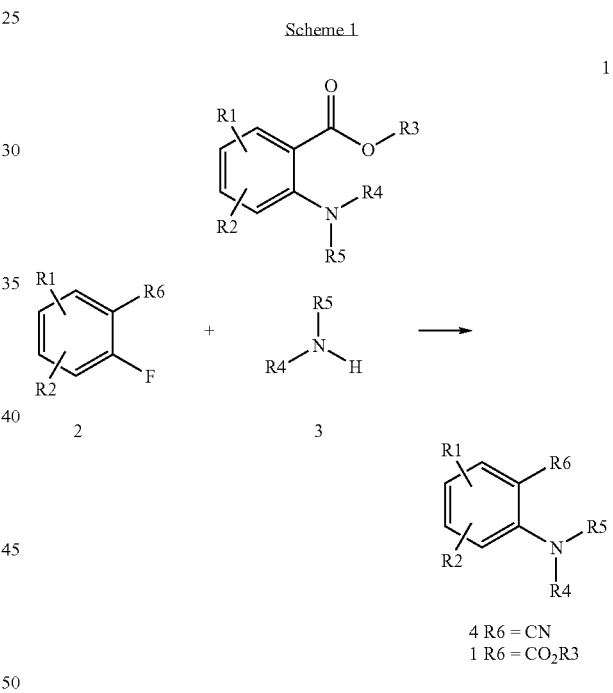

According to Scheme 1, the nucleophilic aromatic substitution occurs by methods known in the art, (Wells, K. M. et al. Tetrahedron Letters, 1996, 37(36), 6439-6442). The appropriately substituted amine is dissolved in a suitable solvent, such as DMF or DMSO, with a base, such as cesium carbonate, and the appropriately substituted fluoro benzoate or benzonitrile (R6=CN or $CO_2R3$). The reaction proceeds at 0° C. to elevated temperatures in anywhere from ten minutes to several days depending on the stability of the starting materials. The product of structure 4 (R6=CN) or 1 (R6=$CO_2R^3$) can then be isolated by a standard aqueous workup, followed by normal phase chromatographic methods or recrystallization techniques commonly employed in the art.

Intermedaite compounds of formula 1 or 4 useful for preparing compounds of the invention may also be prepared as shown in Scheme 2.

Scheme 2

In Scheme 2, the N-Aryl coupling occurs by methods known in the art, (Hartwig, J. F. et al. Angew. Chem., Int. Ed. Engl. 1998, 37, 2046-2067). The appropriately substituted amine is dissolved in a suitable solvent, such as DMF, with a base, such as cesium carbonate or sodium tert-butoxide, the appropriately substituted halogenated benzoate or benzonitrile (R6=CN or CO$_2$R3), and a suitable catalyst complex, such as palladium acetate and diphenyl phospino ferrocene. The reaction proceeds at 0° C. to elevated temperatures in anywhere from ten minutes to several days depending on the stability of the starting materials. The product of structure 4 (R6=CN) or 1 (R6=CO$_2$R3) can then be isolated by a standard aqueous workup, followed by normal phase chromatographic methods or recrystallization techniques commonly employed in the art.

Intermediate compounds of formula 1 or 4 useful for preparing compounds of the invention may also be prepared as shown in Scheme 3.

Scheme 3

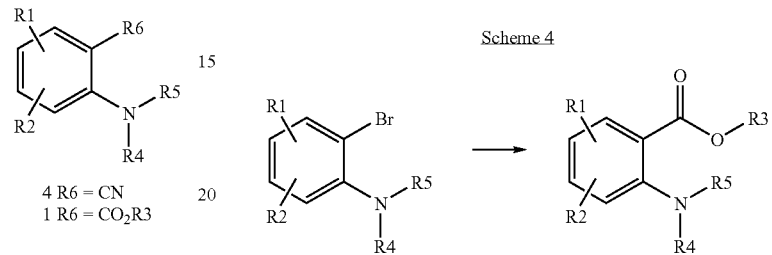

In Scheme 3, the carbonylation occurs by methods known in the art, (Heck, *Palladium Reagents in Organic Synthesis*; Academic Press: New York, 1985, p. 348-358). The appropriately substituted aryl bromide is dissolved in a suitable solvent, such as DMF, with a base, such as cesium carbonate or sodium tert-butoxide, and a suitable catalyst complex, such as palladium acetate and diphenyl phospino ferrocene, appropriate alcohol (R3-OH) and saturated with carbon monoxide. The reaction proceeds at 0° C. to elevated temperatures in anywhere from ten minutes to several days depending on the stability of the starting materials. The product of structure 1 may then be isolated by a standard aqueous workup, optionally followed by normal phase chromatographic methods or recrystallization techniques commonly employed in the art.

Intermedaite compounds of formula 1 or 4 useful for preparing compounds of the invention may also be prepared as shown in Scheme 4.

Scheme 4

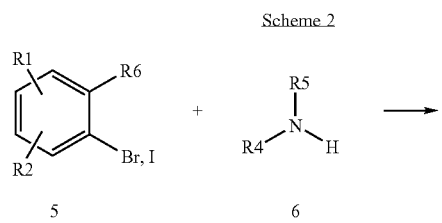

In Scheme 4, the aromatic carboxylation occurs by methods known in the art, (Boger, D. L. et al, Journal of Organic Chemistry, 1994, 59(17), 4943-4949, Volpin et al, *Organomet. Reactions,* 1975, 5, 313-386). The appropriately substituted aryl bromide is dissolved in a suitable solvent, such as diethyl ether or tetrahydrofuran, with an alkyl lithium, such as n-butyl lithium or ter-butyl lithium or magnesium turnings. The resulting anion is quenched with a suitable carbon dioxide source, such as dry ice, or dimethyl carbonate. The reaction proceeds at −78° C. to room temperature in anywhere from about five minutes to several hours depending on the stability of the starting materials. The product of structure 1 can then be isolated by a standard aqueous workup, followed by normal phase chromatographic methods or recrystallization techniques commonly employed in the art.

Synthetic Scheme 5 shows preparation of the benzazepine intermediates for compounds of the invention depicted by Formula 1.

Scheme 5

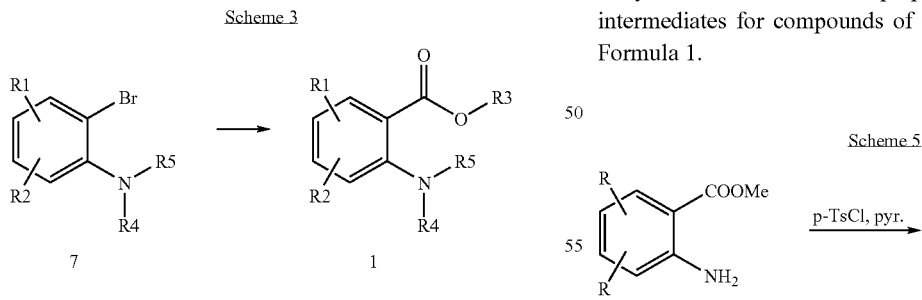

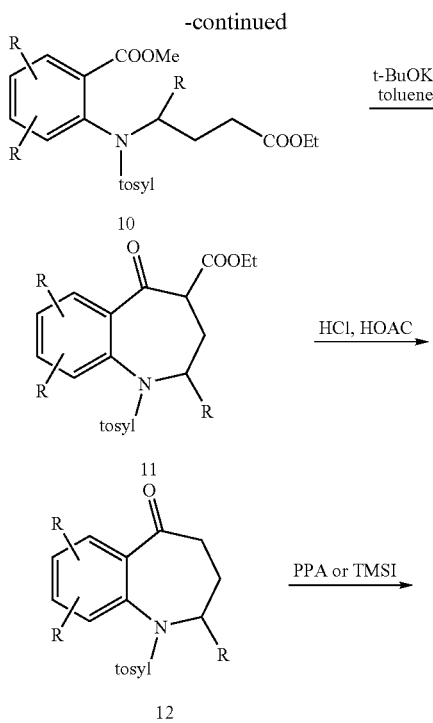

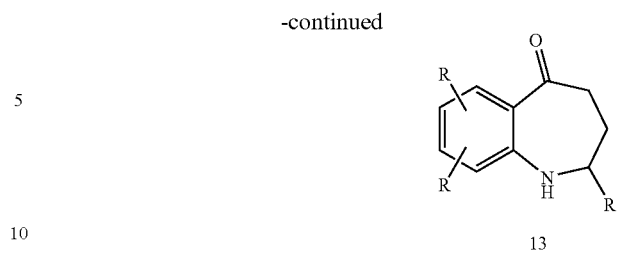

For example, substituted anthranilic esters 1 that are either commercially available or prepared as set forth in the literature or in schemes 1-4, can be N-sulfonylated to provide 8, which in turn may be alkylated with appropriately substituted, or unsubstituted 3-bromopropanoic acid esters 9 thus affording 10. Dieckmann condensation/cyclization of intermediate 10 yields N-tosyl benzazepine 11, which is subjected to acid hydrolysis and de-carboxylation to give benzodiazepin-5-one derivatives 12. Removal of tosyl group with either acid (e.g. PPA (polyphosphoric acid)) or TMSI (trimethylsilyliodide) provides intermediate benzazepin-5-one 13.

Benzazepine-5-ones of general structure 13 are converted to compounds of formula I utilizing the steps outlined in Scheme 6.

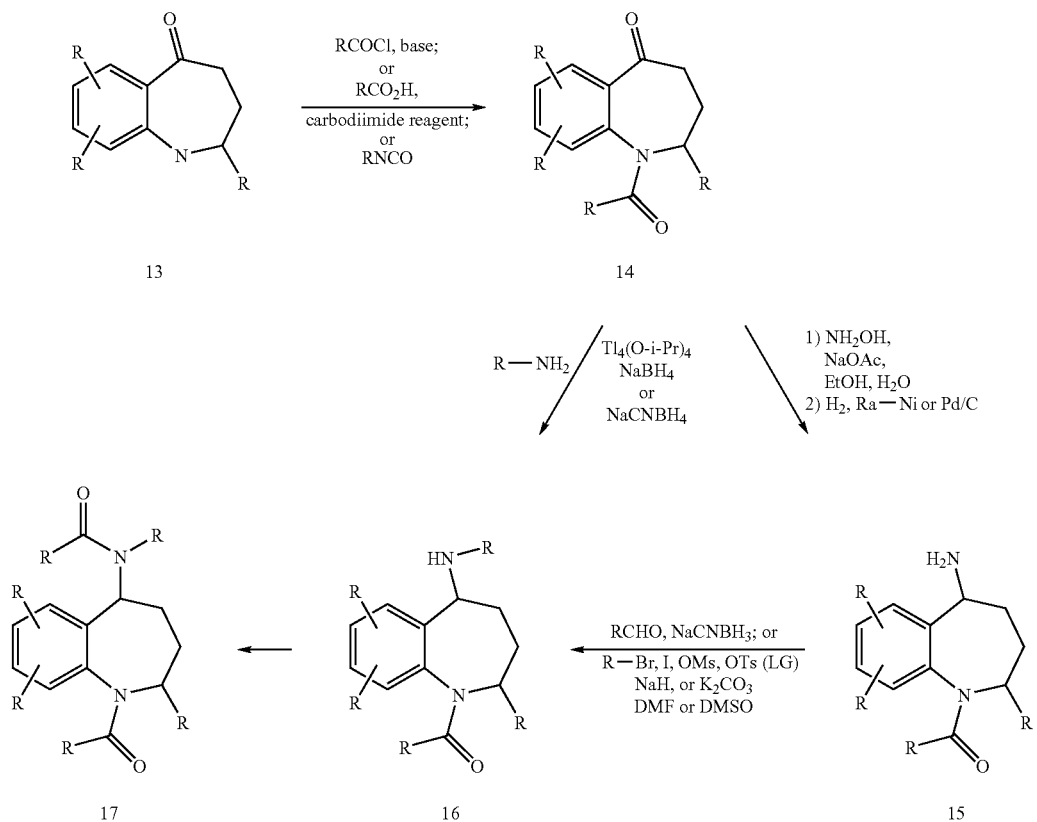

N-acylation of 13 to afford carbamates of structure 14 is accomplished by treatment with an appropriately substituted aryl or alkyl chloroformate in the presence of an organic base such as pyridine. Alternatively, treatment with an acid chloride or an appropriate activated ester, such as those generated in-situ from the reaction of an appropriately substituted aryl or alkyl carboxylic acid Generation of urea derivatives from 13 is accomplished by treatment with a carbamoyl chloride in the presence of base such as pyridine and DMAP (dimethylamino pyridine) or an alternative base such as NaH in DMF. Alternatively treatment with phosgene, or carbodiimide (CDI) reagent such as cyclohexylcarbodiimide or analog thereof, followed by the addition of an appropriately di-substituted amine will afford ureas of structure 14. Formation of sulfonamide derivatives from 13 can be accomplished by reaction with appropriately substituted sulfonyl chlorides in the presence of base. Conversion of ketone 14 to 17 may be performed either through direct reductive amination with an appropriately substituted alkyl or aryl amine to directly afford 16, or alternatively through formation of the amine derivate 15 by reduction of an intermediate oxime, followed by alkylation with an appropriately substituted benzylic halide, mesylate or tosylate, or reductive alkylation with the appropriate aldehyde or ketone in the presence of a reducing reagent such as NaCNBH$_3$. 16 is converted to 17 (a compound of the invention) by acylation with an appropriately substituted symmetrical anhydride or acid halides to afford amides, or chloroformates to afford carbamates, or isocyanates, carbamoyl chlorides, etc. to form ureas, or appropriately substituted sulfonyl chlorides to afford sulfonamides.

Scheme 7 shows, for example, the synthesis of intermediates used for the preparation of 1-benzazacines of Formula I.

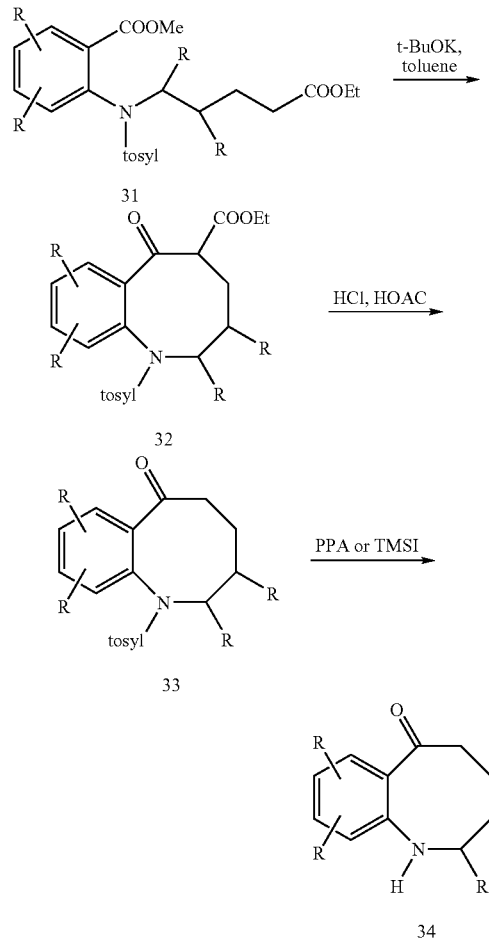

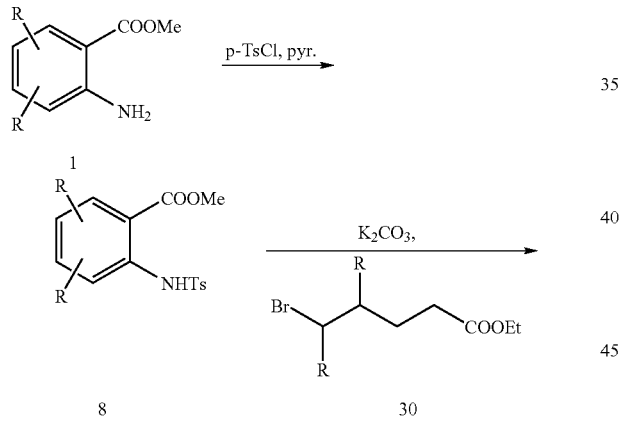

For example, tosylation of 1 to give 8, followed by alkylation with 30 provides 31. Deickmann cyclization (Leonard, et al.: *J. Org. Chem.*, 1969, 34, 1066) of 31 provides 1-benzazacin-6-one 32, which is further elaborated to 34 after decarboxylation and tosylate removal.

1-Benzazacin-6-one compounds of general structure 34 are converted to compounds of formula I (38) utilizing the steps outlined in Scheme 8.

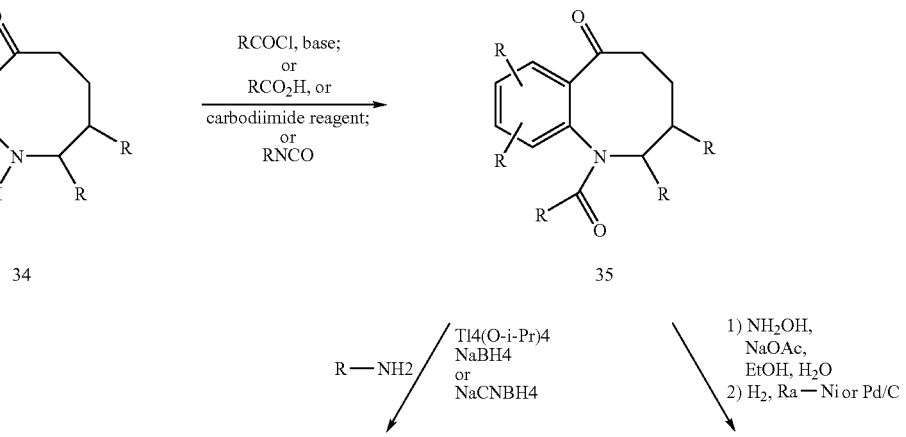

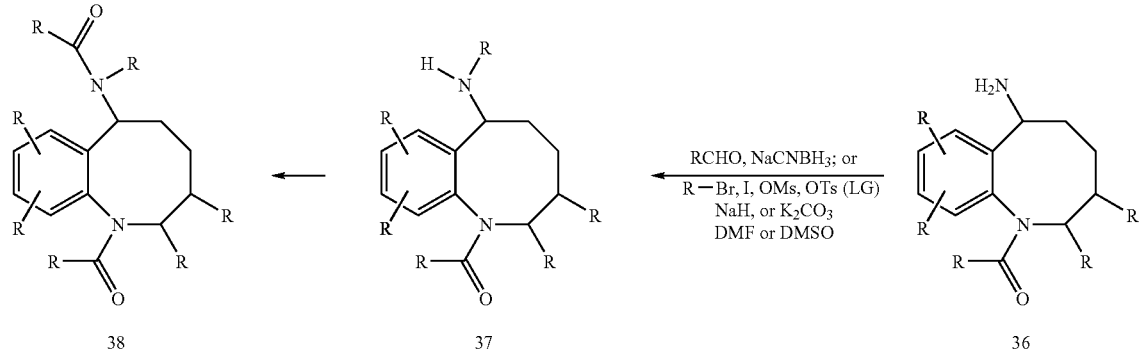

-continued

N-acylation of 34 to afford carbamates of structure 35 is accomplished by treatment with an appropriately substituted aryl or alkyl chloroformate in the presence of an organic base such as pyridine. Alternatively, treatment with an acid chloride or an appropriate activated ester, such as those generated in situ from the reaction of an appropriately substituted aryl or alkyl carboxylic acid Generation of urea derivatives from 34 is accomplished by treatment with a carbamoyl chloride in the presence of base such as pyridine and DMAP or an alternative base such as NaH in DMF. Alternatively treatment with phosgene, or CDI, or an analog thereof, followed by the addition of an appropriately di-substituted amine will afford ureas of structure 35. Formation of sulfonamide derivatives from 34 can be accomplished by reaction with appropriately substituted sulfonyl chlorides in the presence of base. Conversion of ketone 35 to 38 can be performed either through direct reductive amination with an appropriately substituted alkyl or aryl amine to directly afford 37, or alternatively through formation of the amine derivate 36 by reduction of an intermediate oxime, followed by alkylation with an appropriately substituted benzylic halide, mesylate or tosylate, or reductive alkylation with the appropriate aldehyde or ketone in the presence of a reducing reagent such as NaCNBH$_3$. 37 is converted to 38 (a compound of the invention) by acylation with and appropriately substituted symmetrical anhydride or acid halides to afford amides, or chloroformates to afford carbamates, or isocyanates, carbamoyl chlorides, etc. to form ureas, or appropriately substituted sulfonyl chlorides to afford sulfonamides. Compounds of formula I wherein two R$^5$ groups combine to form a cyclopentane or other cycloalkyl ring may be prepared according to the following scheme 9 or known variations thereof.

Scheme 9

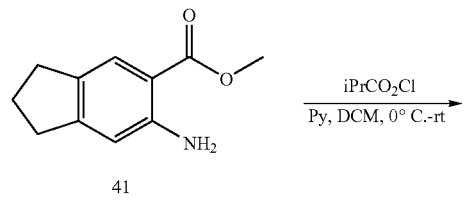

41

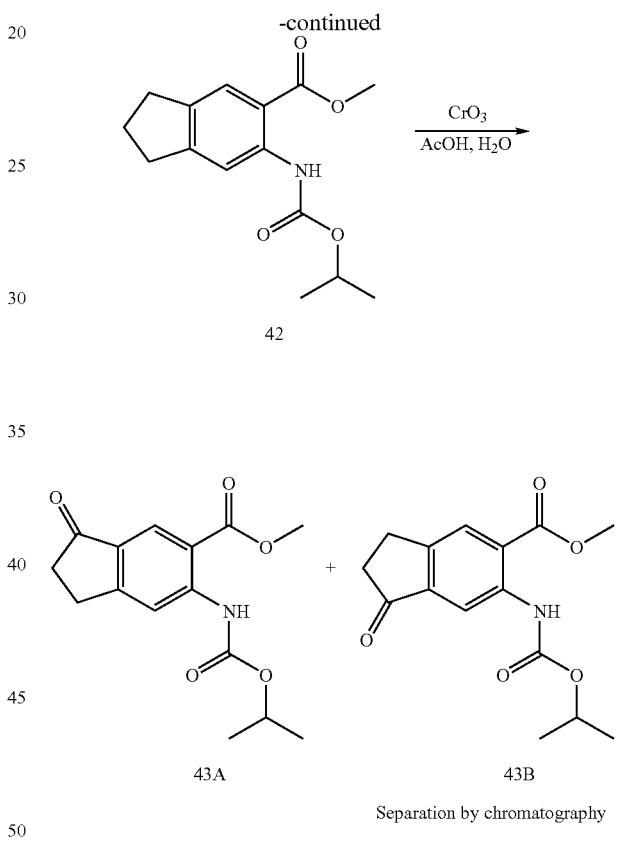

Separation by chromatography

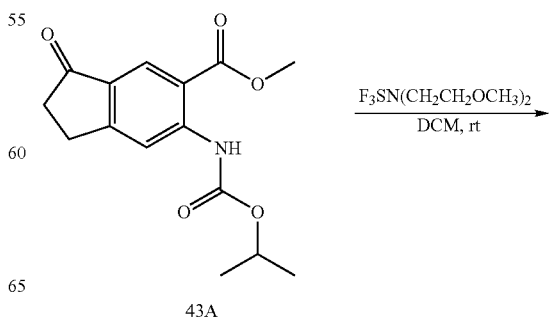

43A

-continued

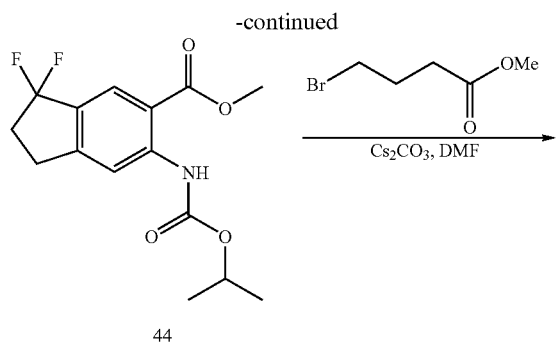

44

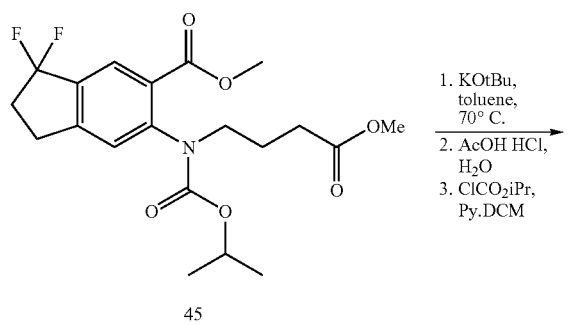

45

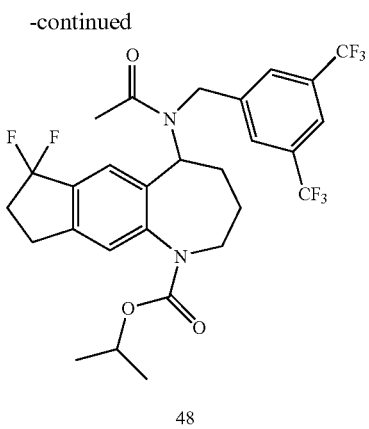

48

According to Scheme 9, 6-aminoindane-5-carboxylic acid methylester (42) is N-protected by reacting with isopropylchloroformate to afford compound 42. Compound 42 is oxidized at the benzylic carbon atoms to afford the indanone mixtures 43A and 43B. The mixture may be separated by chromatography or other techniques known to one of skill in the art. The compound 43A is reacted with Deoxo-Fluor® (registered trademark of Aldrich Chemical company) available from Aldrich Chemical Company, Milwaukee Wis., USA, 2004-2005 catalog of fine chemicals, number 49, 411-9. The fluorination reaction is performed in the presence of a suitable solvent such as dichloromethane to afford the difluorinated compound 44. Compound 44 is N-alkylated with 4-bromobutyl methyl ester in the presence of a mild base such as cesium carbonate to afford the diester 45. The diester is cyclized by decarboxylation in the presence of a strong protic base such as for example potassium t-butoxide. The reaction is worked up using aqueous extraction conditions followed by isolation of the intermediate keto azepine as the salt, preferably the hydrochloride salt. The intermediate ketoazepine is protected as the isopropylcarbamate 46 by reaction with isopropylchloroformate in the presence of a base such as, for example, pyridine in a suitable solvent such as dichloromethane. The carbamate 46 is then reductively aminated with the desired substituent such as for example an optionally substituted benzylamine (e.g. 3,5-bistrifluoromethyl benzylamine shown) or other desired substituent. Amine 47 may be acylated, or sulfonylated as shown, for example, by the treatment of an appropriate reagent such as acetic anhydride to provide 48.

Scheme 10 shows the conversion of the other indene isomer to a compound of formula I (for example, compounds 54).

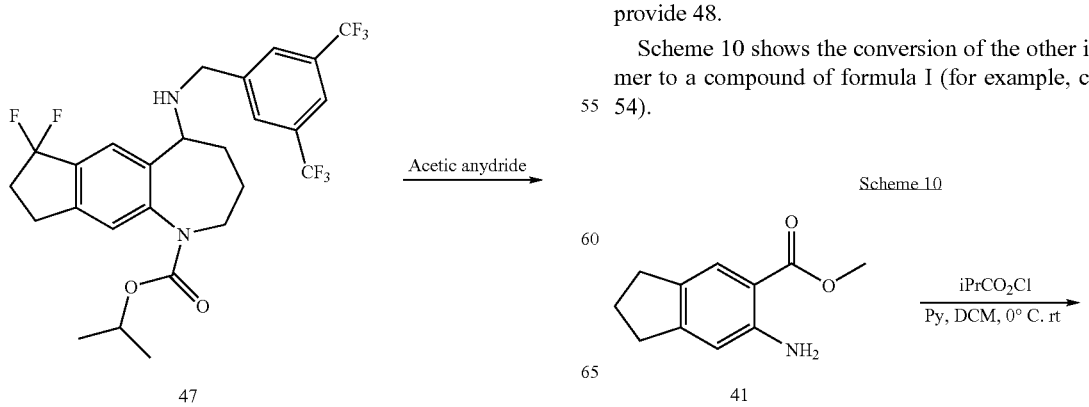

Scheme 10

-continued
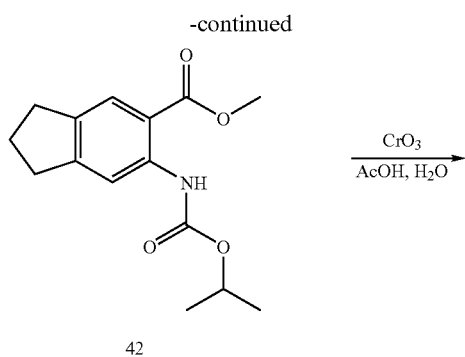
42
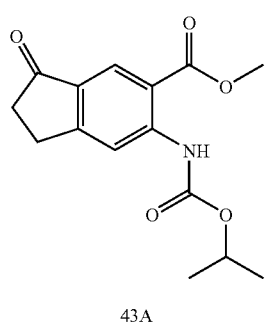
43A
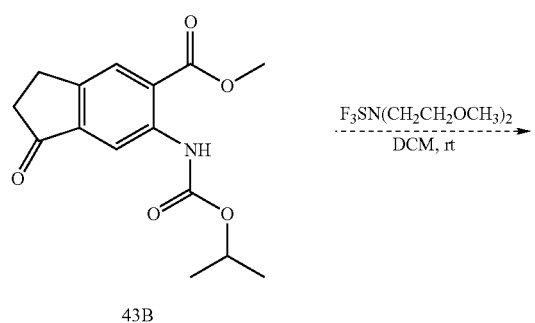
43B
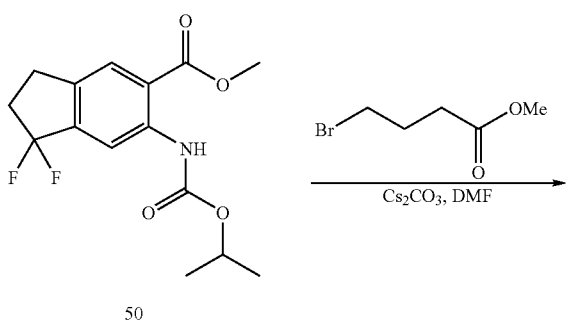
50
-continued
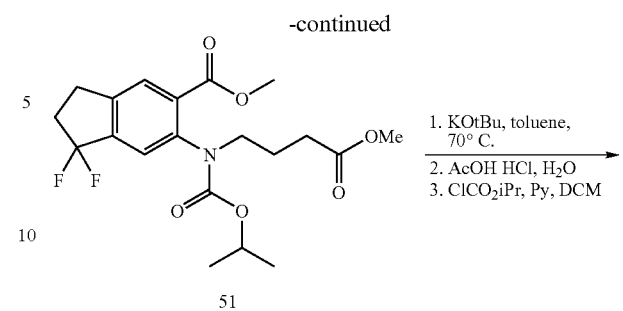
51
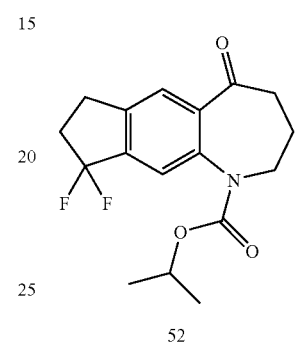
52
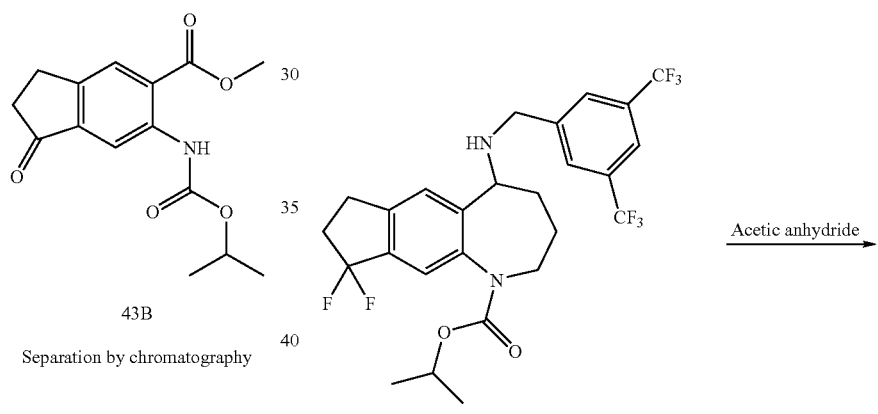
53
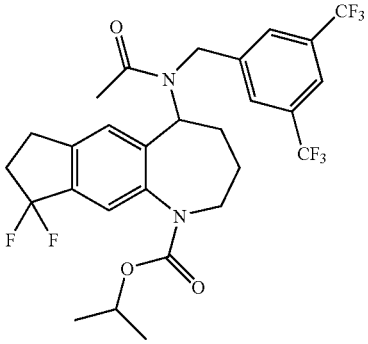
54
According to Scheme 10, the other difluoro isomer 43B may be converted to a compound of formula I using procedures analogous to those described for Scheme 9.
N-acyl analogs of compound of formula 55 and 49 may be prepared as shown in scheme 11 for preparing an analog of compound 55.

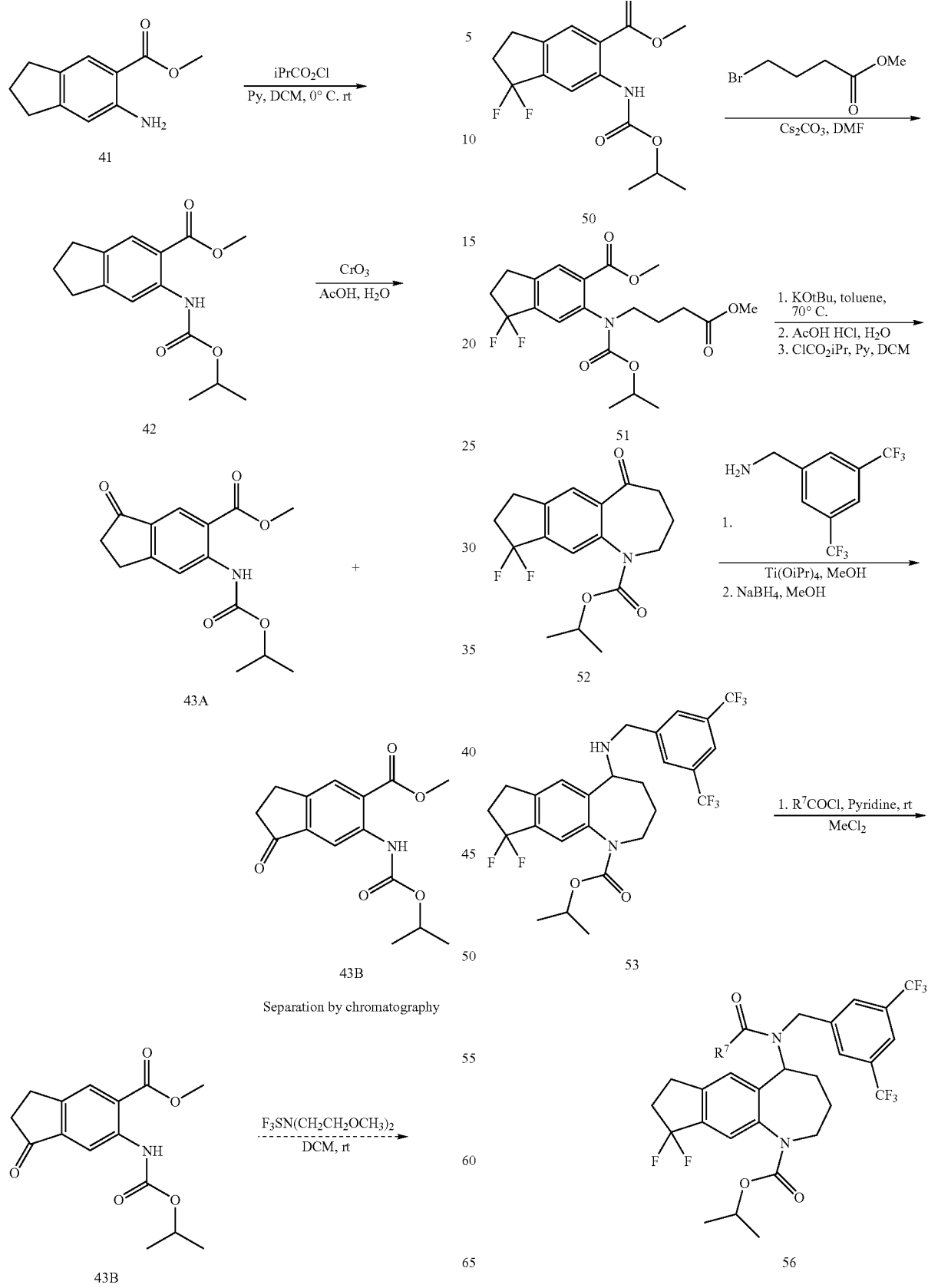

Assay

The following assay protocols and result(s) thereof demonstrating the utility and efficacy of the compounds and/or methods of the current invention are given for the purpose of illustration and are not meant to be limiting in any way.

In Vitro CETP Inhibitor Assay:Spa Assay

An in vitro scintillation proximity assay (SPA) has been used to test the ability of compounds of this invention to inhibit the transfer of radiolabeled cholesterol esters between HDL and LDL. This assay monitors the inhibition of the transfer of [$^3$H]cholesterol esters from HDL (Amersham) to biotinylated LDL (Amersham) by a CETP source. CETP produced by AV-12 cells that have been created to express human CETP has been used to mediate the transfer. After a 30-minute incubation at 37 C in which the radiolabeled cholesterol ester is transferred in a HEPES-NaCl based buffer, the reaction is stopped and the biotinylated LDL is bound to streptavidin/scintillant coated SPA beads (Amersham). Then the radioactive signal is measured in a Packard 96-well scintillation TopCounter with window settings fully open. Compounds of this invention can be added to the reaction mixture in an appropriate solvent to assess their ability to inhibit the transfer of the radiolabeled cholesterol esters by CETP, represented by a decrease in radioactive signal. The activity transferred in the reaction mixtures with control solvents is rated as 100% transfer. The compound concentration at which the activity is midway between 100% and the lowest recorded activity is indicated as the IC50 value. A three-parameter fixed top logistic curve-fitting algorithm is used to generate the IC50 value.

Examine of IC50 values determined by these methods are summarized in Table 1.

TABLE 1

Inhibition of CETP Activity (SPA assay)

| Compound of example No. | IC50 nM |
|---|---|
| 1 | 293 |
| 117 | 65 |
| 111 | 68 |
| 119 | 42 |
| 129 | 54 |
| 182 | 191 |

Alternatively, additional CETP sources can be used to mediate the transfer of radiolabeled cholesterol ester in this assay. Endogenous CETP from human plasma, CETP from mice made to express human CETP, endogenous CETP from hamsters, and CETP from additional mammalian species can be used as the CETP source in this assay.

Alternatively, other sources may be used as the buffer. In addition to the HEPES-NaCl based buffer that has been used in this assay, human plasma, mouse plasma or a Tris-buffer that may be high in albumin may be used as the buffer in which the transfer of radiolabeled cholesterol esters from HDL to LDL may occur.

Alternatively, other sources of radioactivity and or acceptors may be used to track the CETP activity in this assay.

Alternatively, radiolabeled-LDL may be used in this assay. One of skill in the art is able to practice the different assay methodologies disclosed herein with minimal experimentation.

Assay of CETP Activity In Vivo

A strain of transgenic mice that express both human CETP and human apolipoprotein A-1 (Taconic, Germantown, N.Y.) is used to test compounds of this invention. Test compounds are administered once orally or IV in selected aqueous or oil based vehicles. At various times after dosing, ranging from 4 h to 24 h, blood is obtained. Blood is allowed to clot and serum is obtained by centrifugation. CETP activity is determined by a method similar to that described for the in vitro CETP activity assay, except that plasma from treated animals is used as the CETP source in the assay.

The efficacy of compounds of the invention in vivo may also be determined utilizing Syrian Golden Hamsters, which express endogenous CETP. Test compounds are administered orally in selected aqueous or oil based vehicles for up to one week. At various times after dosing, ranging from 4 h to 24, blood is obtained. Blood is allowed to clot and serum is obtained by centrifugation. CETP activity is determined by a method similar to that described for the in vitro CETP activity assay, except that serum from treated animals is used as the CETP source in the assay.

Alternatively, a strain of transgenic mice that express human CETP (Taconic, Germantown, N.Y.) is used to test compounds of this invention. Test compounds are administered once orally or IV in selected aqueous or oil based vehicles. At various times after dosing, ranging from 4 h to 24 h, blood is obtained. Blood is allowed to clot and serum is obtained by centrifugation. CETP activity is determined by a method similar to that described for the in vitro CETP activity assay, except that serum from treated animals is used as the CETP source in the assay.

Assay of Plasma Lipids In Vivo

Activity of compounds of this invention in vivo can be determined by the level of elevation of HDL cholesterol relative to control by a given amount of compound in a CETP-containing animal species. A strain of transgenic mice that express both human CETP and human apolipoprotein A-1 (Taconic, Germantown, N.Y.) is used to test compounds of this invention. Test compounds are administered once orally in selected aqueous or oil based vehicles. At various times after dosing, ranging from 4 h to 24 h, blood is obtained. Blood is allowed to clot and serum is obtained by centrifugation. HDL cholesterol levels in the serum is determined by HDL-C plus reagents (Roche/Hitachi, Indianapolis, Ind.) with a clinical chemistry analyzer (Roche/Hitachi, Indianapolis, Ind.). Additional serum lipids can be analyzed by enzymatic methods. Lipids in the VLDL, LDL and HDL fractions are analyzed by enzymatic methods after precipitation or size exclusion chromatography. An example of the elevation of HDL cholesterol levels at 8 hr are summarized in table 2

TABLE 2

Elevation of HDL cholesterol levels at 8 hr by example 98 of the invention

| Compound of Example No. | Single Oral Dose (mg/kg) | % HDL cholesterol increase |
|---|---|---|
| 119 | 30 | 123 |

The efficacy of compounds of the invention in vivo may also be determined utilizing Syrian Golden Hamsters. The compounds can be tested in hamsters made hypercholesterolemic by feeding a high fat high cholesterol diet for a minimum of two weeks or in non-hypercholesterolemic hamsters fed normal chow for two weeks. Test compounds can be administered orally in selected aqueous or oil based vehicles for up to 1 week. Serum can be obtained and lipids can be analyzed by enzymatic methods. Lipids in the VLDL, LDL and HDL fractions are analyzed by enzymatic methods after precipitation or size exclusion chromatography.

Alternatively, a strain of transgenic mice that express human CETP (Taconic, Germantown, N.Y.) is used to test the efficacy of the compounds of this invention. The hCETP mice can be made hypercholesterolemic by feeding a high fat chow diet such as TD 88051, as described by Nishina et al. (J Lipid Res., 31, 859-869 (1990)) for at least two weeks before the start of the study. Test compounds can be administered orally in selected aqueous or oil based vehicles for up to 1 week. Serum can be obtained and lipids can be analyzed by enzymatic methods. Lipids in the VLDL, LDL and HDL fractions are analyzed by enzymatic methods after precipitation or size exclusion chromatography.

Method of Treatment

As used herein, the term "effective amount" means an amount of compound of the present invention, i.e., formula I, which is capable of alleviating the symptoms of the various pathological conditions herein described. The specific dose of a compound administered according to this invention will, of course, be determined by the particular circumstances surrounding the case including, for example, the compound administered, the route of administration, the state of being of the patient, and the pathological condition being treated. A typical daily dose will contain a nontoxic dosage level of from about 0.01 mg to about 100 mg/day of a compound of the present invention. Preferred daily doses generally will be from about 1 mg to about 250 mg/day.

The compounds of this invention can be administered by a variety of routes including oral, rectal, transdermal, subcutaneous, intravenous, intramuscular, and intranasal. These compounds preferably are formulated prior to administration, the selection of which will be decided by the attending physician. Thus, another aspect of the present invention is a pharmaceutical composition comprising an effective amount of a compound of Formula I, or a pharmaceutically acceptable salt thereof, solvate, prodrug, enantiomer or prodrug thereof, and a pharmaceutically acceptable carrier, diluent, or excipient.

The total active ingredients in such formulations comprises from 0.1% to 99.9% by weight of the formulation. By "pharmaceutically acceptable" it is meant the carrier, diluent, excipients and salt must be compatible with the other ingredients of the formulation, and not deleterious to the recipient thereof.

Pharmaceutical formulations of the present invention can be prepared by procedures known in the art using well-known and readily available ingredients. For example, the compounds of formula I can be formulated with common excipients, diluents, or carriers, and formed into tablets, capsules, suspensions, powders, and the like. Examples of excipients, diluents, and carriers that are suitable for such formulations include the following: fillers and extenders such as starch, sugars, mannitol, and silicic derivatives; binding agents such as carboxymethyl cellulose and other cellulose derivatives, alginates, gelatin, and polyvinyl-pyrrolidone; moisturizing agents such as glycerol; disintegrating agents such as calcium carbonate and sodium bicarbonate; agents for retarding dissolution such as paraffin; resorption accelerators such as quaternary ammonium compounds; surface active agents such as cetyl alcohol, glycerol monostearate; adsorptive carriers such as kaolin and bentonite; and lubricants such as talc, calcium and magnesium stearate, and solid polyethyl glycols.

The compounds also can be formulated as elixirs or solutions for convenient oral administration or as solutions appropriate for parenteral administration, for example, by intramuscular, subcutaneous or intravenous routes. Additionally, the compounds may be formulated as sustained release dosage forms and the like. The formulations can be so constituted that they release the active ingredient only or preferably in a particular physiological location, possibly over a period of time. The coatings, envelopes, and protective matrices may be made, for example, from polymeric substances or waxes.

Compounds of formula I, generally, will be administered in a convenient formulation as determined by the attending physician. The following formulation examples are only illustrative and are not intended to limit the scope of the present invention.

Formulations

In the formulations which follow, "Active Ingredient" means a compound of formula I, a salt, solvate, racemate, enantiomer diastereomer or mixture of diastereomers, or prodrug thereof, or a combination of a compound of formula I and other effective agent for the treatment or prevention of dyslipidemia or atherosclerosis.

Formulation 1: Gelatin Capsules
Hard gelatin capsules are prepared using the following:

| Ingredient | Quantity (mg/capsule) |
|---|---|
| Active ingredient | 0.1-1000 |
| Starch, NF | 0-650 |
| Starch flowable powder | 0-650 |
| Silicone fluid 350 centistokes | 0-15 |

The formulation above may be changed in compliance with the reasonable variations provided.

A tablet formulation is prepared using the ingredients below:

Formulation 2: Tablets

| Ingredient | Quantity (mg/tablet) |
|---|---|
| Active ingredient | 2.5-1000 |
| Cellulose, microcrystalline | 200-650 |
| Silicon dioxide, fumed | 10-650 |
| Stearate acid | 5-15 |

The components are blended and compressed to form tablets.

Alternatively, tablets each containing 2.5-1000 mg of active ingredient are made up as follows:

Formulation 3: Tablets

| Ingredient | Quantity (mg/tablet) |
|---|---|
| Active ingredient | 25-1000 |
| Starch | 45 |
| Cellulose, microcrystalline | 35 |
| Polyvinylpyrrolidone (as 10% solution in water) | 4 |
| Sodium carboxymethyl cellulose | 4.5 |
| Magnesium stearate | 0.5 |
| Talc | 1 |

The active ingredient, starch, and cellulose are passed through a No. 45 mesh U.S. sieve and mixed thoroughly. The solution of polyvinylpyrrolidone is mixed with the resultant powders that are then passed through a No. 14 mesh U.S. sieve. The granules so produced are dried at 50°-60° C. and passed through a No. 18 mesh U.S. sieve. The sodium carboxymethyl starch, magnesium stearate, and talc, previously passed through a No. 60 U.S. sieve, are then added to the granules, which after mixing, are compressed on a tablet machine to yield tablets.

Suspensions each containing 0.1-1000 mg of medicament per 5 ml dose are made as follows:

| Formulation 4: Suspensions | |
| --- | --- |
| Ingredient | Quantity (mg/5 ml) |
| Active ingredient | 0.1-1000 mg |
| Sodium carboxymethyl cellulose | 50 mg |
| Syrup | 1.25 mg |
| Benzoic acid solution | 0.10 mL |
| Flavor | q.v. |
| Color | q.v. |
| Purified water to | 5 mL |

The medicament is passed through a No. 45 mesh U.S. sieve and mixed with the sodium carboxymethyl cellulose and syrup to form a smooth paste. The benzoic acid solution, flavor, and color are diluted with some of the water and added, with stirring. Sufficient water is then added to produce the required volume.

An aerosol solution is prepared containing the following ingredients:

| Formulation 5: Aerosol | |
| --- | --- |
| Ingredient | Quantity (% by weight) |
| Active ingredient | 0.25 |
| Ethanol | 25.75 |
| Propellant 22 (Chlorodifluoromethane) | 70.00 |

The active ingredient is mixed with ethanol and the mixture added to a portion of the propellant 22, cooled to 30° C., and transferred to a filling device. The required amount is then fed to a stainless steel container and diluted with the remaining propellant. The valve units are then fitted to the container.

| Formulation 6: Intravenous Solution | |
| --- | --- |
| Ingredient | Quantity |
| Active ingredient | 50 mg |
| Isotonic saline | 1,000 mL |

The solution of the above ingredients is intravenously administered to a patient at a rate of about 1 mL per minute.

EXAMPLES

The following examples include actual and prophetic examples. The examples herein are not all-inclusive and are not intended to limit the scope of the invention but to provide an illustration of the breadth and scope of the compounds falling within the scope of the invention. In general, commercially available reagents have been used. Every attempt has been made to teach processes and/or procedures for preparing non-commercial reagents. Where a procedure for making a reagent is not taught it is presumed that such reagent may be made by one of skill in the art following procedures to make analogous reagents taught in the available literature and standard reference texts and/or procedures involving minimal experimentation known to one of skill in the art.

Example 1

Synthesis of 5-[Acetyl-(3,5-bis-trifluoromethyl-benzyl)-amino]-2,3,4,5-tetrahydro-benzo[b]azepine-1-carboxylic acid isopropyl ester Step 1. Preparation of 2-(Toluene-4-sulfonylamino)-benzoic acid methyl ester To a mixture of 2-Amino-benzoic acid methyl ester (900 g, 6 mol) in pyridine (6 L) was added p-Toluenesulfonyl chloride (1500 g, 7.5 mol). The mixture was stirred overnight at room temperature. The mixture was poured into ice water, and the resultant precipitates were collected by filtration. The filtrates were dissolved in $CH_2Cl_2$, and the solution washed with diluted HCl, $H_2O$, and dried over $MgSO_4$. The residue thus obtained was crystallized from ethanol to give 2-(Toluene-4-sulfonylamino)-benzoic acid methyl ester (1454 g, 80%).

Step 2. Preparation of 2-[(3-Ethoxycarbonyl-propyl)-(toluene-4-sulfonyl)-amino]-benzoic acid methyl ester A mixture of 2-(Toluene-4-sulfonylamino)-benzoic acid methyl ester (1000 g, 3.27 mol), ethyl 4-bromobutyrate (639 g, 3.45 mol) in 2-butanone (5.6 L) was heated at reflux for 24 hours. After the reaction was completed, the mixture was poured into ice-water, and the resultant precipitates were collected by filtration. The filtrates were washed with ethyl acetate to give 2-[(3-Ethoxycarbonyl-propyl)-(toluene-4-sulfonyl)-amino]-benzoic acid methyl ester (890 g, 65%).

Step 3. Preparation of 5-Oxo-1-(toluene-4-sulfonyl)-2,3,4,5-tetrahydro-1H-benzo[b]azepine-4-carboxylic acid ethyl ester To a heated mixture of potassium t-butoxide (371 g, 3.58 mol) in toluene (4 l) at 70° C. was added 2-[(3-Ethoxycarbonyl-propyl)-(toluene-4-sulfonyl)-amino]-benzoic acid methyl ester (750 g, 1.79 mol). After the addition was completed, the mixture was cooled to room temperature then poured into ice water. The extraction with $CH_2Cl_2$ was successively done, and organic layer was dried over $MgSO_4$ and concentrated under reduced pressure to afford crude compound 5-Oxo-1-(toluene-4-sulfonyl)-2,3,4,5-tetrahydro-1H-benzo[b]azepine-4-carboxylic acid ethyl ester (450 g) as a mixture of Me and Et esters.

Step 4. Preparation of 1-(Toluene-4-sulfonyl)-1,2,3,4-tetrahydro-benzo[b]azepin-5-one To the mixture of 5-Oxo-1-(toluene-4-sulfonyl)-2,3,4,5-tetrahydro-1H-benzo[b]azepine-4-carboxylic acid ethyl ester thus obtained, were added AcOH (2.4 l), conc.HCl (800 ml) and $H_2O$ (240 ml). The mixture was heated at reflux for 5 h and poured into ice water. The pH was adjusted to about 7-8 by adding diluted aqueous NaOH. The mixture was extracted with $CH_2Cl_2$. The organic layer was separated, dried over $MgSO_4$, concentrated, and the residue was crystallized from the mixture (4:1 n-hexane:AcOEt) to give 1-(Toluene-4-sulfonyl)-1,2,3,4-tetrahydro-benzo[b]azepin-5-one (278 g, 60%) as a white powder.

Step 5. Preparation of 1,2,3,4-Tetrahydro-benzo[b]azepin-5-one

To preheated polyphosphoric acid (PPA, 220 g) at 70-80° C. was added 1-(Toluene-4-sulfonyl)-1,2,3,4-tetrahydro-benzo[b]azepin-5-one (50.0 g, 0.16 mol). The mixture was stirred for 3.0 h at the same temperature and then poured into ice water. After the pH was adjusted to about 8-9 by adding aq NaOH, the mixture was extracted with ethyl acetate. The organic layer was separated, dried over MgSO$_4$, and concentrated. The residue was purified by silica gel column chromatography (eluent, 3:1 n-hexanes:ethyl acetate) to give 1,2,3,4-Tetrahydro-benzo[b]azepin-5-one (22 g).

Step 6. Preparation of 5-Oxo-2,3,4,5-tetrahydro-benzo[b]azepine-1-carboxylic acid isopropyl ester To a cooled (0° C.) solution of 1,2,3,4-Tetrahydro-benzo[b]azepin-5-one (1.5 g, 9.3 mmol) and pyridine (2.26 ml, 27.9 mmol) in dichloromethane (30 ml) was added 1M isopropylchloroformate (solution in toluene) dropwise over 10 minutes. After addition was completed, the mixture was removed from the cold bath and stirred for 18 hours at room temperature. The mixture was cooled to 0° C., then treated with aqueous 1N NaOH and stirred for 30 minutes. After layer separation, the aqueous layer was extracted with dichloromethane. The combined organic phases were washed with 1N HCl, saturated aqueous NaHCO$_3$, brine, then dried (Na$_2$SO$_4$) and concentrated to an oil. Purification by silica gel chromatography (eluent, 3:1 n-hexanes:ethyl acetate) provided 5-Oxo-2,3,4,5-tetrahydro-benzo[b]azepine-1-carboxylic acid isopropyl ester (1.91 g).

Step 7. Preparation of 5-(3,5-Bis-trifluoromethyl-benzylamino)-2,3,4,5-tetrahydro-benzo[b]azepine-1-carboxylic acid isopropyl ester A mixture of 5-Oxo-2,3,4,5-tetrahydro-benzo[b]azepine-1-carboxylic acid isopropyl ester (283 mg, 1.14 mmol), 3,5-Bis(trifluoromethyl)benzylamine (304 mg, 1.25 mmol) and titanium(IV) isopropoxide (0.43 ml, 1.43 mmol) was stirred at room temperature for 6 hours. The mixture was diluted with methanol (5 ml) and treated with sodium borohydride (65 mg, 1.71 mmol), then stirred at room temperature for 18 hours. The mixture was treated with 0.1N NaOH (25 ml) and stirred for 10 minutes, then filtered through Celite. The filtered residue washed successively with diethyl ether and dichloromethane. The filtrate was transferred to a separatory funnel and the organic layer was separated, dried (Na$_2$SO$_4$) and concentrated to provide crude 5-(3,5-Bis-trifluoromethyl-benzylamino)-2,3,4,5-tetrahydro-benzo[b]azepine-1-carboxylic acid isopropyl ester, which was elaborated without purification.

Step 8. Preparation of 5-[Acetyl-(3,5-bis-trifluoromethyl-benzyl)-amino]-2,3,4,5-tetrahydro-benzo[b]azepine-1-carboxylic acid isopropyl ester A solution of crude 5-(3,5-Bis-trifluoromethyl-benzylamino)-2,3,4,5-tetrahydro-benzo[b]azepine-1-carboxylic acid isopropyl ester (200 mg, 0.42 mmol) and pyridine (0.85 ml, 10.5 mmol) in dichloromethane (2 ml) at room temperature was treated with acetic anhydride (0.79 ml, 8.4 mmol) via dropwise addition over 4 minutes. The mixture was stirred at room temperature for 20 hours. The mixture was cooled (0° C.) and treated with 1N NaOH and stirred for 30 minutes. The aqueous layer was extracted with dichloromethane. The combined organic phases were washed with 1N HCl, dried (Na$_2$SO$_4$) and concentrated to an oil. Purification by silica gel chromatography (eluent, 2:1 n-hexanes:ethyl acetate) provided 5-[Acetyl-(3,5-bis-trifluoromethyl-benzyl)-amino]-2,3,4,5-tetrahydro-benzo[b]azepine-1-carboxylic acid isopropyl ester (144 mg).

Additional compounds were prepared utilizing this same methodology in which R1 is variable and is introduced by replacement of acetic anhydride with alternative reagents following the procedure of Example 1, Step 8 for the synthesis of 5-[Acetyl-(3,5-bis-trifluoromethyl-benzyl)-amino]-2,3,4,5-tetrahydro-benzo[b]azepine-1-carboxylic acid isopropyl ester.

| Example # | Reagent | R$^1$ | MS (ES+) |
|---|---|---|---|
| Example 2 | methylchloroformate | methoxycarbonyl | 533 (M + H) |

Example 3

5-[Acetyl-(3,5-bis-trifluoromethyl-benzyl)-amino]-8-chloro-2,3,4,5-tetrahydro-benzo[b]azepine-1-carboxylic acid isopropyl ester

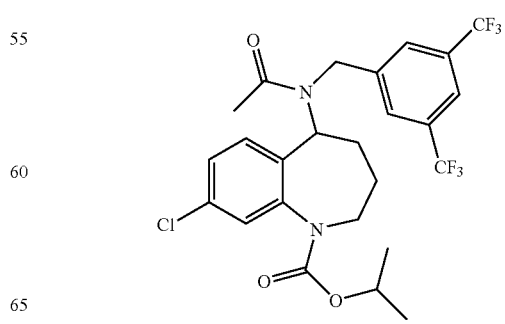

The titled compounds was prepared following the procedures described in Example 1 by replacing 2-Amino-benzoic acid methyl ester with 2-Amino-4-chloro-benzoic acid methyl ester in Example 1, step 1. MS (ES+): 551 (M+H).

Example 4

5-[(3,5-Bis-trifluoromethyl-benzyl)-methoxycarbonyl-amino]-8-chloro-2,3,4,5-tetrahydro-benzo[b]azepine-1-carboxylic acid isopropyl ester

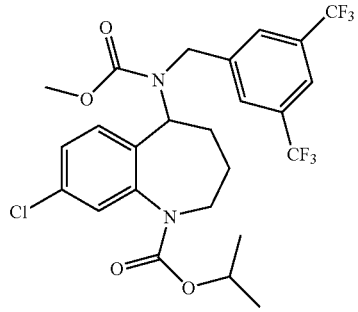

The titled compounds was prepared following the procedures described in Example 1 by replacing 2-Amino-benzoic acid methyl ester with 2-Amino-4-chloro-benzoic acid methyl ester in Example 1, step 1 as well as replacing acetic anhydride with methyl chloroformate in Example 1, Step 8. MS (ES+): 567 (M+H).

The following Examples were prepared utilizing the same methodology described in Example 1 wherein R1 is a variable and is introduced by replacement of 2-amino-benzoic acid methyl ester with alternative reagents following the procedure of Example 1, Steps 1-8 for the synthesis of 5-[acetyl-(3,5-bistrifluoromethylbenzyl)amino]-2,3,4,5-tetrahydrobenzo[b]azepine-1-carboxylic acid isopropyl ester.

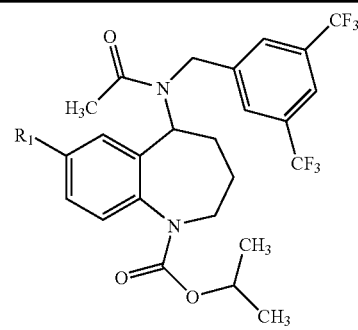

| Example # | Reagent | R1 | MS (ES+) |
|---|---|---|---|
| Example 4A | 2-amino-5-bromobenzoic acid methyl ester | bromo | 595 (M + H) |
| Example 4B | 2-amino-5-trifluoromethoxybenzoic acid methyl ester | trifluoromethoxy | 601 (M + H) |

Example 5

Isopropyl 5-[acetyl-(3,5-bistrifluoromethylbenzyl)amino]-7-methyl-2,3,4,5-tetrahydrobenzo[b]azepine-1-carboxylate

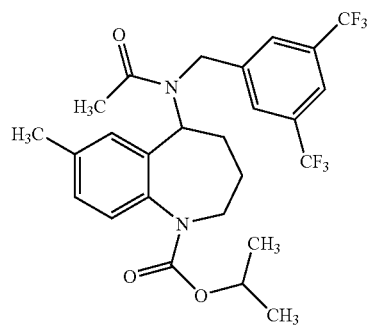

Purge a mixture of isopropyl-5-[acetyl-(3,5-bistrifluoromethylbenzyl)amino]-7-bromo-2,3,4,5-tetrahydrobenzo[b]azepine-1-carboxylate (0.400 g, 0.672 mmol), trimethylboroxine (0.084 g, 0.672 mmol), and potassium carbonate (0.279 g, 2.02 mmol) in anhydrous tetrahydrofuran (5 mL) with nitrogen, then add tetrakis(triphenylphosphine)palladium (0) (0.077 g, 0.067 mmol) and stir at reflux for 1 h. Cool the mixture to room temperature and dilute with ethyl acetate (30 mL) and wash with water and brine (10 mL each). Dry the organic layer over anhydrous sodium sulfate, filter and remove the solvent under reduced pressure. Chromatograph the residue over silica gel, eluting with hexanes/ethyl acetate (20:1 to 3:1), to provide the title compound as a white solid (0.156 g, 44%): ESI MS 531 (M+H).

The following Examples were prepared utilizing the same methodology described in Example 5 wherein R1 is a variable and is introduced by replacement of trimethylboroxine with alternative reagents following the procedure of Example 5 for the synthesis of Isopropyl 5-[acetyl-(3,5-bistrifluoromethylbenzyl)amino]-7-methyl-2,3,4,5-tetrahydrobenzo[b]azepine-1-carboxylate.

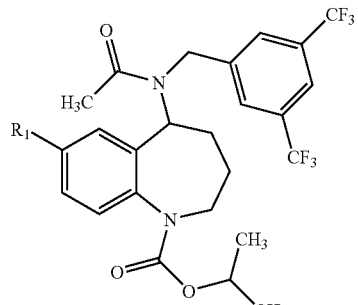

| Example # | Reagent | R1 | MS (ES+) |
|---|---|---|---|
| Example 5a | 4-methylphenylboronic acid | 4-methylphenyl | 607 (M + H) |
| Example 5b | 4-chlorophenylboronic acid | 4-chlorophenyl | 627 (M + H) |
| Example 5c | 4-methoxyphenylboronic acid | 4-methoxyphenyl | 624 (M + H) |

-continued

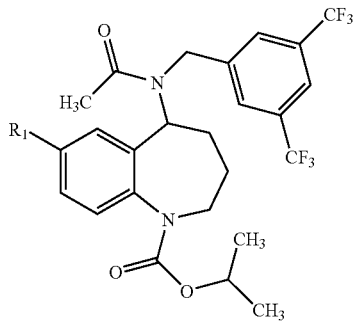

| Example # | Reagent | R1 | MS (ES+) |
|---|---|---|---|
| Example 5d | 4-fluorophenylboronic acid | 4-fluorophenyl | 611 (M + H) |
| Example 5e | 2-fluorophenylboronic acid | 2-fluorophenyl | 611 (M + H) |
| Example 5f | 2-trifluoromethylphenyl-bornonic acid | 2-trifluoro-methylphenyl | 662 (M + H) |
| Example 5g | 2-methylphenylboronic acid | 2-methylphenyl | 607 (M + H) |
| Example 5h | phenylboronic acid | Phenyl | 593 (M + H) |
| Example 5i | 4-(trifluoromethyl)phenyl-boronic acid | 4-(trifluoro-methyl)phenyl | 661 (M + H) |

Example 6

Isopropyl 5-[acetyl-(3,5-bistrifluoromethylbenzyl)amino]-7-morpholino-2,3,4,5-tetrahydrobenzo[b]azepine-1-carboxylate

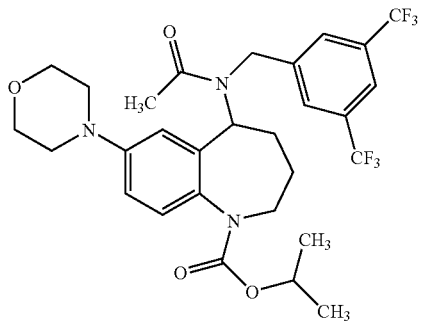

Combine tris(dibenzylideneacetone)dipalladium (0) (0.031 g, 0.034 mmol), racemic-2,2'-bis(diphenylphosphino)-1,1'-binaphyl (0.064 g, 0.102 mmol) and sodium t-butoxide (0.045 g, 0.470 mmol) in toluene (2 mL) and purge this suspension with nitrogen at room temperature for 5 min. Add morpholine (0.033 mL, 0.369 mmol) followed by isopropyl-5-[acetyl-(3,5-bistrifluoromethylbenzyl)amino]-7-bromo-2,3,4,5-tetrahydrobenzo[b]azepine-1-carboxylate (0.200 g, 0.336 mmol) and heat this mixture at 80° C. under nitrogen for 1 h. Cool the reaction mixture to room temperature, dilute the mixture with dichloromethane, filter through Celite, and concentrate under reduced pressure. Chromatograph the residue over silica gel, eluting with hexanes/ethyl acetate (20:1 to 1:2), to provide the title compound as an off-white solid (0.130 g, 64%): APCI MS 603 (M+H).

The following Examples were prepared utilizing the same methodology described in Example 6 wherein $R^1$ is a variable and is introduced by replacement of morpholine with alternative reagents following the procedure of Example 6 for the synthesis of Isopropyl 5-[acetyl-(3,5-bistrifluoromethylbenzyl)amino]-7-morpholino-2,3,4,5-tetrahydrobenzo[b]azepine-1-carboxylate.

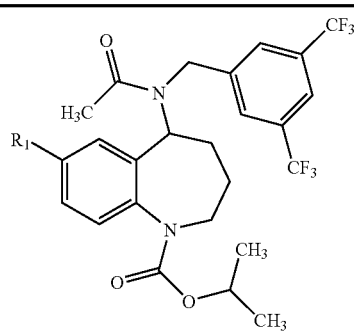

| Example # | Reagent | R1 | MS (ES+) |
|---|---|---|---|
| Example 6a | 4-methylpiperazine | N-methylpiperazinyl | 615 (M + H) |
| Example 6b | benzophenoneimine | benzhydrylideneamino | 696 (M + H) |
| Example 6c | Aniline | phenylamino | 609 (M+) |
| Example 6d | Pyrrolidine | pyrrolidin-1-yl | 586 (M + H) |
| Example 6e | azetidin-2-one | 2-oxo-azetidin-1-yl | 586 (M + H) |
| Example 7 | pyrrolidin-2-one | 2-oxo-pyrrolidin-1-yl | 600 (M + H) |
| Example 8 | Azetidine | azetidin-1-yl | 572 (M + H) |
| Example 9 | Methanol | Methoxy | 547 (M + H) |

Example 10

Isopropyl 5-[acetyl-(3,5-bistrifluoromethylbenzyl)amino]-7-amino-2,3,4,5-tetrahydrobenzo[b]azepine-1-carboxylate

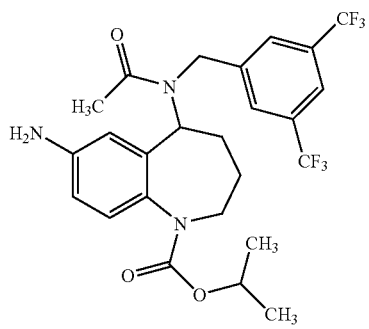

Add 2 N hydrochloric acid (2 mL) to a solution of isopropyl 5-[acetyl-(3,5-bistrifluoromethylbenzyl)amino]-7-(benzhydrylideneamino)-2,3,4,5-tetrahydrobenzo[b]azepine-1-carboxylate (example 6b) (0.920 g, 1.32 mmol) in tetrahydrofuran (10 mL) at room temperature and stir for 15 min. Dilute the mixture with ethyl acetate (20 mL) and wash with saturated sodium hydrogen carbonate solution and brine (10 mL each). Dry the organic layer over anhydrous sodium sulfate, filter and remove the solvent under reduced pressure. Chromatograph the residue over silica gel, eluting with hexanes/ ethyl acetate (1:1), to provide the title compound as an off-white solid (0.526 g, 75%); APCI MS 531 (M+H).

Example 11

Isopropyl 5-[acetyl-(3,5-bistrifluoromethylbenzyl)amino]-7-dimethylamino-2,3,4,5-tetrahydrobenzo[b]azepine-1-carboxylate

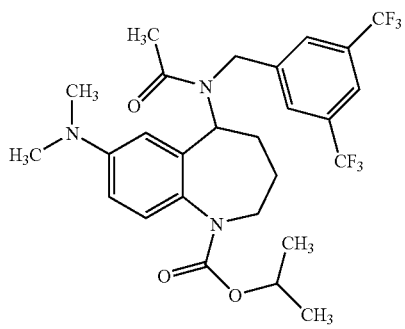

Add sodium cyanoborohydride (0.035 g, 0.564 mmol) in one portion to a solution of isopropyl-5-[(acetyl-(3,5-bistrifluoromethylbenzyl)amino]-7-amino-2,3,4,5-tetrahydrobenzo[b]azepine-1-carboxylate (0.100 g, 0.188 mmol) and 37% aqueous formaldehyde (0.020 mL, 0.621 mmol) in acetonitrile (6 mL) at room temperature. Add acetic acid over 40 min to the resulting clear solution and stir for 2 h. Dilute the reaction with ethyl acetate (30 mL) and wash with 2 N sodium hydroxide (10 mL) and brine (20 mL). Dry the organic layer over anhydrous sodium sulfate, filter and remove solvent under reduced pressure. Chromatograph the residue over silica gel, eluting with hexanes/ethyl acetate (20:1 to 3:1), to provide the title compound as a colorless gum (0.059 g, 56%), APCI MS 560 (M+H).

Example 12

Isopropyl 5-[acetyl-(3,5-bistrifluoromethylbenzyl)amino]-7-methanesulfonylamino-2,3,4,5-tetrahydrobenzo[b]azepine-1-carboxylate

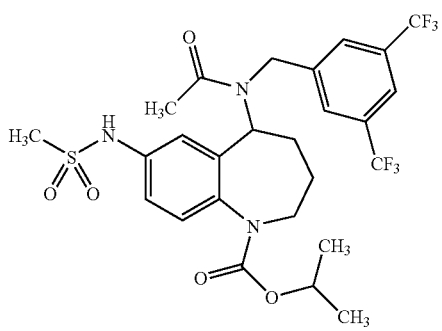

Add methanesulfonyl chloride (8 µl, 0.103 mmol) dropwise to a suspension of isopropyl-5-[acetyl-(3,5-bistrifluoromethylbenzyl)amino]-7-amino-2,3,4,5-tetrahydrobenzo[b]azepine-1-carboxylate (0.050 g, 0.094 mmol) and pyridine (8 µl, 0.103 mmol) in dichloromethane (2 mL) at 0° C. under atmosphere of nitrogen. Stir the suspension for 30 min, then remove the cooling bath and warm to room temperature while stirring overnight. Dilute the mixture with dichloromethane (30 mL) and wash with 2 N hydrochloric acid, water, and brine (10 mL each). Dry the organic layer over anhydrous sodium sulfate, filter and remove the solvent under reduced pressure. Chromatograph the residue over silica gel, eluting with ethyl acetate/hexanes (10:1 to 1:2), to provide the title compound as a white solid (0.037 g, 65%): ESI MS 610 (M+H).

The following Examples were prepared utilizing the same methodology described in Example 12 wherein R1 is a variable and is introduced by replacement of methanesulfonyl chloride with alternative reagents following the procedure of Example 19 for the synthesis of Isopropyl 5-[acetyl-(3,5-bistrifluoromethylbenzyl)amino]-7-dimethylamino-2,3,4,5-tetrahydrobenzo[b]azepine-1-carboxylate.

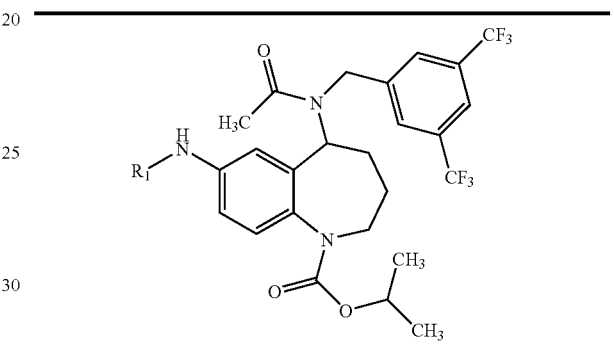

| Example # | Reagent | R1 | MS (ES+) |
|---|---|---|---|
| Example 13 | acetic anhydride | Acetyl | 574 (M + H) |
| Example 14 | benzenesulfonyl chloride | benzenesulfonyl | 672 (M + H) |
| Example 15 | benzoyl chloride | Benzoyl | 636 (M + H) |

The following Examples were prepared utilizing the same methodology described in Example 5 wherein R1 is a variable and is introduced by replacement of trimethylboroxine with alternative reagents following the procedure of Example 5 for the synthesis of Isopropyl 5-[acetyl-(3,5-bistrifluoromethylbenzyl)amino]-7-methyl-2,3,4,5-tetrahydrobenzo[b]azepine-1-carboxylate.

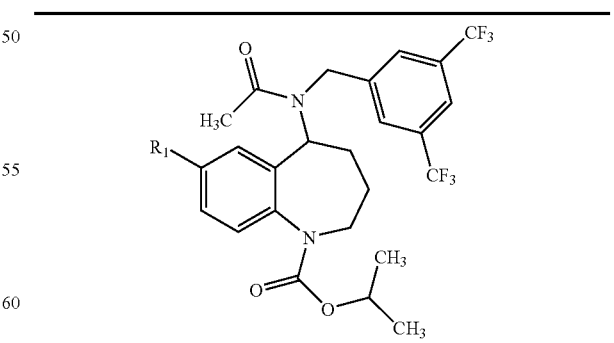

| Example # | Reagent | R1 | MS (ES+) |
|---|---|---|---|
| Example 16 | tributyl(vinyl)tin | Vinyl | 543 (M + H) |
| Example 17 | tributyl(1-methoxyvinyl)tin | 7-acetyl | 559 |

Example 18

Isopropyl 5-[acetyl-(3,5-bistrifluoromethylbenzyl)amino]-7-methylcarboxylate-2,3,4,5-tetrahydrobenzo[b]azepine-1-carboxylate

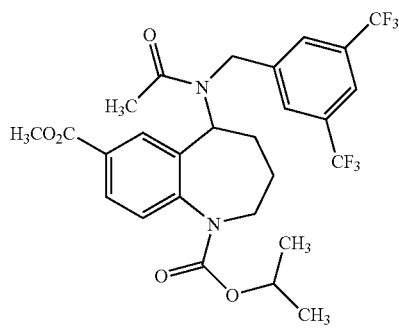

Purge with a suspension of isopropyl-5-[acetyl-(3,5-bistrifluoromethylbenzyl)amino]-7-bromo-2,3,4,5-tetrahydrobenzo[b]azepine-1-carboxylate (0.400 g, 0.671 mmol), triethylamine (0.20 mL, 1.48 mmol), and tetrakis(triphenylphosphine)palladium (0) (0.080 g, 0.070 mmol) in acetonitrile (3 mL) and methanol (1 mL) with carbon monoxide gas at room temperature in a high pressure vessel for 5 min. Pressurize the vessel with carbon monoxide gas to 20 psi and heat the mixture at 60° C. for 16 h. Cool the mixture to room temperature and dilute with ethyl acetate (30 mL) and wash with water (3×10 mL) and brine (25 mL). Dry the organic layer over anhydrous sodium sulfate, filter and remove the solvent under reduced pressure. Chromatograph the residue over silica gel, eluting with hexanes/ethyl acetate (20:1 to 3:1), to provide the title compound as a white solid (0.320 g, 83%): APCI MS 575 (M+H).

Example 19

Isopropyl 5-[acetyl-(3,5-bistrifluoromethylbenzyl)amino]-7-formyl-2,3,4,5-tetrahydrobenzo[b]azepine-1-carboxylate

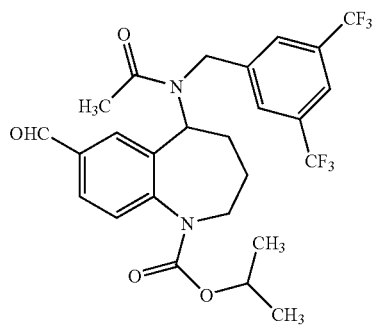

This compound was prepared utilizing the same methodology described in Example 18 wherein replacement of methanol with triethylsilane following the procedure of Example 18 for the synthesis of Isopropyl 5-[acetyl-(3,5-bistrifluoromethylbenzyl)amino]-7-methylcarboxylate-2,3,4,5-tetrahydrobenzo[b]azepine-1-carboxylate.
ESI MS m/z 545 $[C_{26}H_{26}F_6N_2O_4+H]^+$

Example 20

Isopropyl 5-[acetyl-(3,5-bistrifluoromethylbenzyl)amino]-7-carboxy-2,3,4,5-tetrahydrobenzo[b]azepine-1-carboxylate

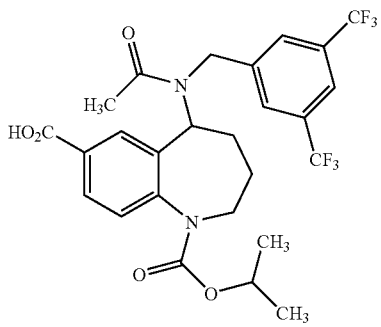

Add 2 N sodium hydroxide solution (2 mL) to a solution of isopropyl-5-[acetyl-(3,5-bistrifluoromethylbenzyl)amino]-7-bromo-2,3,4,5-tetrahydrobenzo[b]azepine-1-carboxylate (0.100 g, 0.174 mmol) in methanol (5 mL) at 0° C. and allow to stir for 30 min. Acidify to pH 4 with 2 N hydrochloric acid solution and extract the aqueous mixture with ethyl acetate (3×10 mL). Wash the organic layer with water and brine (10 mL each). Dry the organic layer over anhydrous sodium sulfate, filter and remove the solvent under reduced pressure. Purify the residue by triturating with water, to provide the title compound as a white solid (0.091 g, 96%): APCI MS 561 (M+H).

The following Example was prepared utilizing the same methodology described in Example 1 wherein R1 is a variable and is introduced by replacement of 2-amino-benzoic acid methyl ester with alternative reagents following the procedure of Example 1, Steps 1-8 for the synthesis of 5-[acetyl-(3,5-bistrifluoromethylbenzyl)amino]-2,3,4,5-tetrahydrobenzo[b]azepine-1-carboxylic acid isopropyl ester.

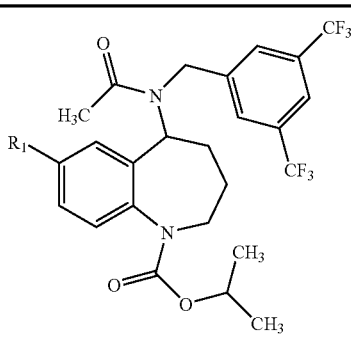

| Example # | Reagent | R1 | MS (ES+) |
| --- | --- | --- | --- |
| Example 21 | 2-amino-5-fluorobenzoic acid methyl ester | Fluoro | 535 (M + H) |

Example 22

Isopropyl 5-[Acetyl-(3,5-bistrifluoromethylbenzyl)amino]-8-bromo-2,3,4,5-tetrahydrobenzo[b]azepine-1-carboxylate

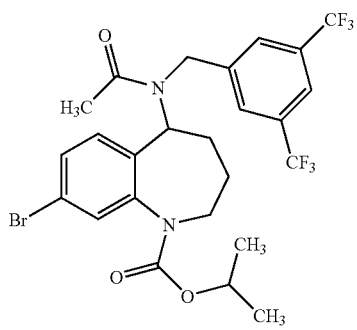

Step 1. Preparation of Methyl 4-bromo-2-nitrobenzoate

Add concentrated sulfuric acid (7 mL) to a solution of commercially available 4-bromo-2-nitrobenzoic acid (25.0 g, 102 mmol) in methanol (150 mL), and heat at reflux for 16 hours. Cool the reaction to room temperature and pour into water (500 mL) and adjust the pH of the suspension to 9 with solid sodium carbonate. Extract the solution with ethyl acetate (2×250 mL), then combine the organic extracts and wash with brine (100 mL), dry over sodium sulfate, filter and remove the solvent under reduced pressure to afford the title compound as a pale amber oil, which crystallizes upon standing (20.5 g, 78%)

Step 2. Preparation of Methyl 2-amino-4-bromobenzoate

Add tin(II) chloride (65.9 g, 292 mmol) to a suspension of methyl 4-bromo-2-nitrobenzoate (15.2 g, 58.4 mmol) in concentrated hydrochloric acid (120 mL) at room temperature and stir for 24 h. Slowly pour the mixture into water (700 mL) and adjust the pH to 9 with solid potassium hydroxide. Filter the white suspension through Celite, then stir the filter cake with ethyl acetate and filter that suspension. Separate the filtrate and extract the aqueous layer with ethyl acetate (200 mL). Combine the organic layers, dry over sodium sulfate, filter and remove the solvent under reduced pressure to afford the title compound as an off-white solid (11.3 g, 84%)

Step 3. Preparation of Methyl 4-bromo-2-isopropoxycarbonylaminobenzoate

Add isopropyl chloroformate (104 mL, 104 mmol, 1.0 M in toluene) dropwise to a solution of methyl 2-amino-4-bromobenzoate (14.5 g, 63.0 mmol) and pyridine (10.3 mL, 126.0 mmol) in dichloromethane (210 mL) at room temperature under nitrogen and stir for 5.5 h. Pour the reaction into water (500 mL) and separate the layers. Extract the aqueous layer with dichloromethane (2×100 mL) and combine the organic extracts and wash with 2 N HCl, saturated sodium bicarbonate and brine (100 mL each), then dry over sodium sulfate, filter and remove the solvent under reduced pressure to afford the title compound as a pale orange solid (19.2 g, 96%)

Step 4. Preparation of Methyl 4-bromo-2-[isopropoxycarbonyl-(3-methoxycarbonylpropyl)amino]benzoate Heat a suspension of methyl 4-bromo-2-isopropoxycarbonylaminobenzoate (19.2 g, 60.7 mmol), methyl 4-iodobutyrate (16.4 mL, 121 mmol) and cesium carbonate (39.6 g, 121 mmol) in N,N-dimethylformamide (240 mL) under nitrogen at 80° C. for 24 h. Cool the mixture to room temperature and pour into a saturated ammonium chloride solution (500 mL) and extract with ethyl acetate (3×200 mL). Combine the organic extracts and wash with water (2×400 mL), brine (100 mL), then dry the solution over sodium sulfate, filter and remove the solvent under reduced pressure. Purify the residue using chromatography on silica gel, eluting with hexanes/ethyl acetate (60:40), to provide the title compound as an orange oil (15.9 g, 63%): APCI MS 416 (M+H

Step 5. Preparation of Isopropyl 8-bromo-5-oxo-2,3,4,5-tetrahydrobenzo[b]azepine-1-carboxylate Add a solution of methyl 4-bromo-2-[isopropoxycarbonyl-(3-methoxycarbonylpropyl)amino]benzoate (15.9 g, 38.2 mmol) in toluene (500 mL) over 0.5 h to a suspension of potassium t-butoxide (8.57 g, 76.4 mmol) in toluene (1800 mL) at 70° C. under nitrogen. After 7 h, cool the mixture to room temperature and pour the suspension into ice water (2000 mL) and adjust the pH of the solution to 3 with 2 N HCl (25 mL) and separate the layers. Extract the aqueous layer with ethyl acetate (3×200 mL), then combine the organic extracts, dry the solution over sodium sulfate, filter and remove the solvent under reduced pressure to provide 1-isopropyl-4-methyl-8-bromo-5-oxo-2,3,4,5-tetrahydrobenzo[b]azepine-1,4-dicarboxylate as an orange semi-solid (11.8 g, 80%). Dissolve 1-isopropyl-4-methyl-8-bromo-5-oxo-2,3,4,5-tetrahydrobenzo[b]azepine-1,4-dicarboxylate (11.8 g, 30.7 mmol) in glacial acetic acid (72 mL) and add water (6.5 mL) followed by concentrated hydrochloric acid (22.6 mL) and heat the resulting solution at reflux for 45 min. Cool the mixture to room temperature and pour the solution into ice water (500 mL) and adjust the pH to 8 with potassium hydroxide (85 g) in water (200 µL). Extract this mixture with ethyl acetate (3×150 mL) and combine the organic extracts and dry them over sodium sulfate, filter and remove the solvent under reduced pressure. The crude material is purified using chromatography on silica gel eluting with hexanes/ethyl acetate (60:40), to afford the title compound as a yellow solid (5.24 g, 52%): ESI MS 326 (M+H).

Step 6. Preparation of Isopropyl 5-[acetyl-(3,5-bistrifluoromethylbenzyl)amino]-8-bromo-2,3,4,5-tetrahydrobenzo[b]azepine-1-carboxylate Add 3,5-bis(trifluoromethyl)benzylamine (5.47 g, 22.5 mmol) followed by titanium isopropoxide (5.98 mL, 20.1 mmol) to a solution of isopropyl 8-bromo-5-oxo-2,3,4,5-tetrahydro benzo[b]azepine-1-carboxylate (5.24 g, 16.1 mmol) in tetrahydrofuran (20 mL) at room temperature under nitrogen was and stir the solution for 4 h. Dilute the reaction with methanol (40 mL) and slowly add sodium borohydride (0.912 g, 24.1 mmol) over 15 min to the reaction and stir at room temperature for 3.5 h. Quench the reaction with addition of 2 N NaOH (56 mL) and water (50 mL) and stir for 0.5 h. Filter the mixture and wash the solids with ethyl acetate/ethanol (4:1, 3×100 mL). Separate the filtrate and wash the organic layer with 2 N NaOH, 2 N HCl, and brine (50 mL each), then dry the solution over sodium sulfate, filter and remove the solvent under reduced pressure to afford isopropyl-5-(3,5-bistrifluoromethylbenzylamino)-8-bromo-2,3,4,5-tetrahydrobenzo[b]azepine-1-carboxylate as a white solid. Add acetic anhydride (22.6 mL, 241 mmol) dropwise to a suspension of isopropyl 5-(3,5-bistrifluoromethylbenzylamino)-8-bromo-2,3,4,5-tetrahydrobenzo[b]azepine-1-carboxylate (8.89 g, 16.1 mmol) and pyridine (19.6 mL g, 241 mmol) in dichloromethane (64 mL) under nitrogen cooled to 0° C. After the addition is complete, remove the cooling bath and warm the reaction to room temperature and stir for 12 h. Dilute the mixture with dichloromethane (100 mL) and wash with 2 N hydrochloric acid (2×50 mL), saturated aqueous sodium bicarbonate (50 mL) and brine (50 mL). Dry the organic layer over sodium sulfate, filter and remove the solvent under reduced pressure. Purify the residue using chromatography on silica gel, eluting with hexanes/ethyl acetate (60:40), to afford the title compound as a white solid (7.60 g, 79%, 2 steps): ESI MS 595 (M+H).

Example 23

Isopropyl 5-[acetyl-(3,5-bistrifluoromethylbenzyl)amino]-8-fluoro-2,3,4,5-tetrahydrobenzo[b]azepine-1-carboxylate

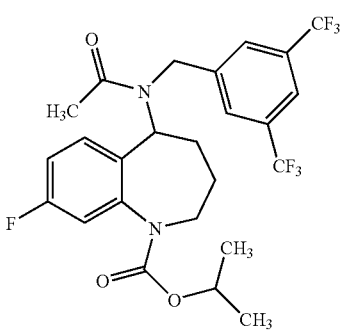

This compound was prepared utilizing the same methodology described in Example 22 by replacement of methyl 2-amino-4-bromobenzoate with 2-amino-4-fluorobenzoate following the procedure of Example 22, Steps 1-6 for the synthesis of isopropyl 5-[acetyl-(3,5-bistrifluoromethylbenzyl)amino]-8-bromo-2,3,4,5-tetrahydrobenzo[b]azepine-1-carboxylate. EI MS 535 (M+H).

Example 24

Synthesis of Isopropyl 5-[acetyl-(3,5-bistrifluoromethylbenzyl)amino]-8-phenyl-2,3,4,5-tetrahydrobenzo[b]azepine-1-carboxylate

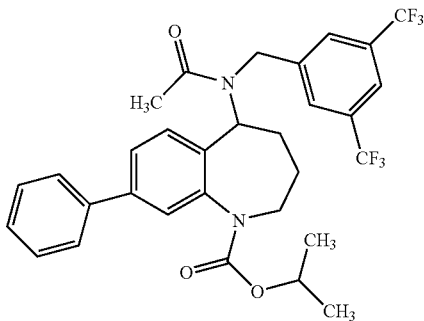

Add a solution of isopropyl-5-[acetyl-(3,5-bistrifluoromethylbenzyl)amino]-8-bromo-2,3,4,5-tetrahydrobenzo[b]azepine-1-carboxylate (0.080 g, 0.134 mmol) in tetrahydrofuran (1 mL) to phenylboronic acid (0.024 g, 0.202 mmol), palladium acetate (0.0015 g, 0.0067 mmol), 2-(dicyclohexylphosphino)biphenyl (0.0047 g, 0.013 mmol) and potassium fluoride (0.023 g, 0.403 mmol) and purge with nitrogen and stir for 2 h at room temperature, then at 50° C. for 12 h. After this initial period, additional phenylboronic acid (0.024 g, 0.202 mol), palladium acetate (0.0015 g, 0.0067 mmol), 2-(dicyclohexylphosphino)biphenyl (0.0047 g, 0.013 mmol) and potassium fluoride (0.023 g, 0.403 mmol) is added and the reaction is heated at 50° C. for 1 h. Cool the reaction to room temperature and dilute with ethyl acetate (30 mL) and wash with 2 N sodium hydroxide and brine (10 mL each). Dry the organic layer over sodium sulfate, filter and remove the solvent under reduced pressure. Purify the residue using chromatography on silica gel, eluting with hexanes/ethyl acetate (60:40), to provide the title compound as a white solid (0.058 g, 72%): ESI MS 593 (M+H).

Example 25

Synthesis of Isopropyl 5-[acetyl-(3,5-bistrifluoromethylbenzyl)amino]-8-cyano-2,3,4,5-tetrahydrobenzo[b]azepine-1-carboxylate

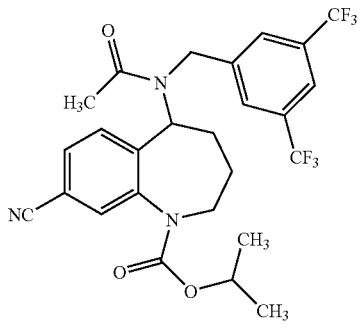

Purge with nitrogen, a solution of isopropyl-5-[acetyl-(3,5-bistrifluoromethylbenzyl)amino]-8-bromo-2,3,4,5-tetrahydrobenzo[b]azepine-1-carboxylate (0.074 g, 0.124 mmol) and zinc cyamide (0.014 g, 0.124 mmol) in N,N-dimethylformamide (2 mL) in a 10 mL microwave vial. Add tetrakis(triphenylphosphine)palladium (0) (0.0043 g, 0.0037 mmol) and irradiate the mixture at 175° C. for 0.5 h (60-80 Watts). Add a second portion of zinc cyamide (0.014 g, 0.124 mmol) and tetrakis(triphenylphosphine) palladium (0) (0.0043 g, 0.0037 mmol) and continue irradiating for 8 min. Cool the mixture to room temperature and dilute with ethyl acetate (35 mL) and wash with water (3×25 mL) and brine (25 mL each), then dry the organic layer over sodium sulfate, filter and remove the solvent under reduced pressure. Purify the residue using chromatography on silica gel, eluting with hexanes/ethyl acetate (60:40), to provide the title compound as a crushable white foam (0.034 g, 51%): ESI MS 542 (M+H).

Example 26

Isopropyl 5-[acetyl-(3,5-bistrifluoromethylbenzyl)amino]-8-amino-2,3,4,5-tetrahydrobenzo[b]azepine-1-carboxylate

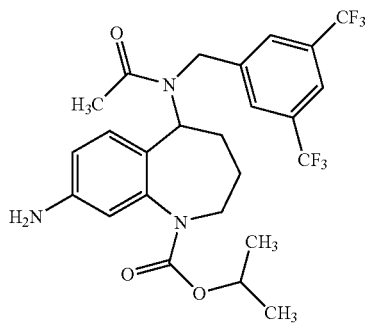

Step 1. Preparation of Isopropyl 5-[acetyl-(3,5-bistrifluoromethylbenzyl)amino]-8-(benzhydrylideneamino)-2,3,4,5-tetrahydrobenzo[b]azepine-1-carboxylate Combine tris(dibenzylideneacetone)dipalladium (0) (0.077 g, 0.084 mmol), 2,2'-bis(diphenylphosphino)-1,1'-binaphyl (0.157 g, 0.252 mmol) and sodium t-butoxide (0.113 g, 1.18 mmol) in toluene (5 mL) and purge this suspension with nitrogen at room temperature for 5 min. Add benzophenoneimine (0.155 mL, 0.924 mmol) followed by isopropyl-5-[acetyl-(3,5-bistrifluoromethylbenzyl)amino]-8-bromo-2,3,4,5-tetrahydrobenzo[b]azepine-1-carboxylate (0.500 g, 0.840 mmol) and heat this mixture at 80° C. under nitrogen for 1 h. Cool the mixture to room temperature, dilute with dichloromethane and filter through Celite. Remove the filtrate solvent under reduced pressure and purify the residue using chromatography on silica gel, eluting with hexanes/ethyl acetate (60:40), to provide the title compound as an orange oil (0.520 g, 89%): APCI MS 696 (M+H).

Step 2. Preparation of Isopropyl 5-[acetyl-(3,5-bistrifluoromethylbenzyl)amino]-8-amino-2,3,4,5-tetrahydrobenzo[b]azepine-1-carboxylate Add 2 N hydrochloric acid (0.19 mL) to a solution of isopropyl 5-[acetyl-(3,5-bistrifluoromethylbenzyl)amino]-8-(benzhydrylideneamino)-2,3,4,5-tetrahydrobenzo[b]azepine-1-carboxylate (0.520 g, 0.747 mmol) in tetrahydrofuran (5 mL) at room temperature and stir for 3 h. Dilute the mixture with ethyl acetate (20 mL) and wash with saturated sodium bicarbonate solution and brine (10 mL each), then dry the organic layer over sodium sulfate, filter and remove the solvent under reduced pressure. Purify the residue using chromatography on silica gel, eluting with hexanes/ethyl acetate (1:1), to provide the title compound as an off-white solid (0.297 g, 75%): 530 (M−H).

Example 27

Isopropyl 5-[acetyl-(3,5-bistrifluoromethylbenzyl)amino]-8-methanesulfonylamino-2,3,4,5-tetrahydrobenzo[b]azepine-1-carboxylate

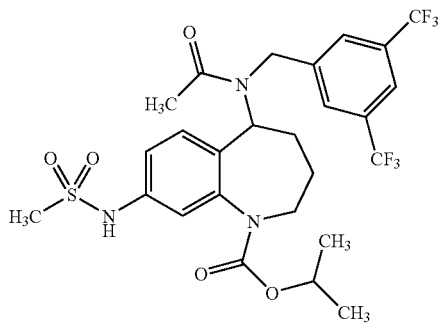

Add methanesulfonyl chloride (13 µl, 0.170 mmol) dropwise to a suspension of isopropyl-5-[acetyl-(3,5-bistrifluoromethylbenzyl)amino]-8-amino-2,3,4,5-tetrahydrobenzo[b]azepine-1-carboxylate (0.082 g, 0.154 mmol) and pyridine (15 µl, 0.185 mmol) in dichloromethane (2 mL) at 0° C. under nitrogen. Stir the orange suspension for 0.5 h, then remove the cooling bath and warm the mixture to room temperature and stir overnight. Dilute the mixture with dichloromethane (30 mL) and wash with 2 N HCl, water and brine (10 mL each), then dry the organic layer over sodium sulfate, filter and remove the solvent under reduced pressure. Purify the residue using chromatography on silica gel, eluting with ethyl acetate/hexanes (70:30), to provide the title compound as a white solid (0.055 g, 58%): ESI MS 610 (M+H).

The following Examples were prepared utilizing the same methodology described in Example 27 wherein R1 is a variable and is introduced by replacement of methanesulfonyl chloride with alternative reagents following the procedure of Example 27 for the synthesis of Isopropyl 5-[acetyl-(3,5-bistrifluoromethylbenzyl)amino]-8-methanesulfonylamino-2,3,4,5-tetrahydrobenzo[b]azepine-1-carboxylate.

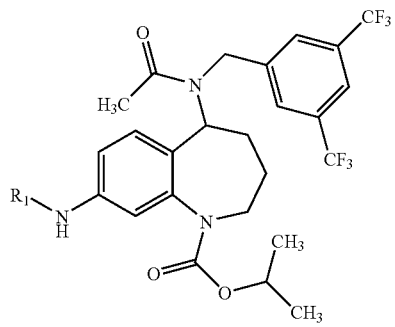

| Example # | Reagent | R1 | MS (ES+) |
|---|---|---|---|
| Example 28 | acetic anhydride | Acetyl | 574 (M + H) |
| Example 29 | benzenesulfonyl chloride | benzenesulfonyl | 670 (M + H) |
| Example 30 | benzoyl chloride | Benzoyl | 636 (M + H) |

Example 31

Isopropyl 5-[acetyl-(3,5-bistrifluoromethylbenzyl)amino]-8-methyl-2,3,4,5-tetrahydrobenzo[b]azepine-1-carboxylate

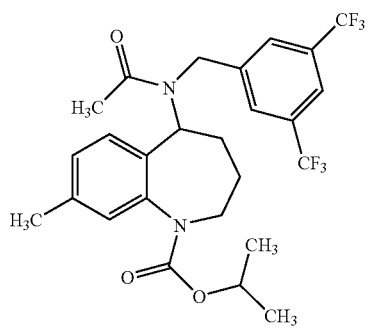

Purge with nitrogen, a suspension of isopropyl-5-[acetyl-(3,5-bistrifluoromethylbenzyl)amino]-8-bromo-2,3,4,5-tetrahydrobenzo[b]azepine-1-carboxylate (0.153 g, 0.257 mmol), trimethylboroxine (36 μl, 0.257 mmol), and potassium carbonate (0.106 g, 0.771 mmol) in N,N-dimethylformamide (2 mL) in a 10 mL microwave vessel. Add tetrakis(triphenylphosphine)palladium (0) (0.030 g, 0.026 mmol) and irradiate the mixture at 150° C. for 20 min (50 W). Dilute the mixture with ethyl acetate (20 mL), wash with water and brine (10 mL each), then dry the organic layer over sodium sulfate, filter and remove the solvent under reduced pressure. Purify the residue first using chromatography on silica gel, eluting with hexanes/ethyl acetate (60:40), to provide the title compound as a white solid (0.056 g, 41%): 531 (M+H).

The following Examples were prepared utilizing the same methodology described in Example 31 wherein R1 is a variable and is introduced by replacement of trimethylboroxine with alternative reagents following the procedure of Example 31 for the synthesis of Isopropyl 5-[acetyl-(3,5-bistrifluoromethylbenzyl)amino]-8-methyl-2,3,4,5-tetrahydrobenzo[b]azepine-1-carboxylate.

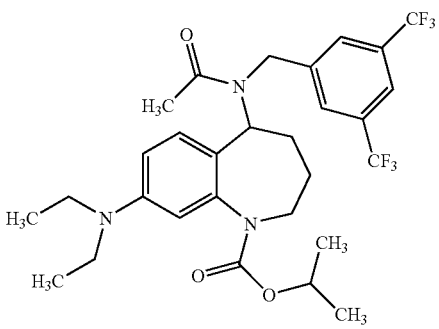

| Example # | Reagent | R1 | MS (ES+) |
| --- | --- | --- | --- |
| Example 32 | tributyl(vinyl)tin | Vinyl | 543 (M + H) |
| Example 33 | ethylboronic acid | Ethyl | 545 (M + H) |

Example 34

Isopropyl 5-[acetyl-(3,5-bistrifluoromethylbenzyl)amino]-8-dimethylamino-2,3,4,5-tetrahydrobenzo[b]azepine-1-carboxylate

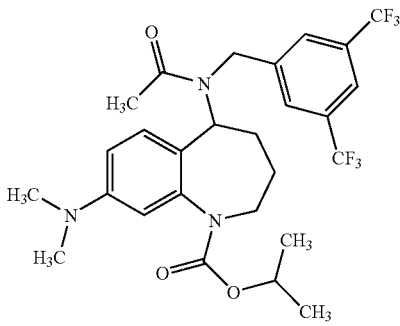

Add sodium cyanoborohydride (0.011 g, 0.175 mmol) in one portion to a solution of isopropyl-5-[acetyl-(3,5-bistrifluoromethylbenzyl)amino]-8-amino-2,3,4,5-tetrahydrobenzo[b]azepine-1-carboxylate (0.031 g, 0.058 mmol) and 37% aqueous formaldehyde (0.014 mL, 0.192 mmol) in acetonitrile (3.2 mL) at room temperature. Add acetic acid over 40 min to the resulting clear solution and stir for 2 h. Dilute the reaction with methylene chloride (30 mL) and wash with 2 N NaOH (10 mL) and brine (20 mL), then dry over sodium sulfate, filter and remove solvent under reduced pressure. Purify the residue using chromatography on silica gel, eluting with hexanes/ethyl acetate (60:40), to provide the title compound as a white solid (0.021 g, 64%): ESI MS 560 (M+H).

Example 35

Isopropyl 5-[acetyl-(3,5-bistrifluoromethylbenzyl)amino]-8-diethylamino-2,3,4,5-tetrahydrobenzo[b]azepine-1-carboxylate This compound was prepared utilizing the same methodology described in Example 34 wherein replacement of formaldehyde with acetaldehyde following the procedure of Example 34 for the synthesis of Isopropyl 5-[acetyl-(3,5-bistrifluoromethylbenzyl)amino]-8-dimethylamino-2,3,4,5-tetrahydrobenzo[b]azepine-1-carboxylate.

Example 36

Synthesis of (+/−)-Isopropyl 5-[acetyl-(3,5-bistrifluoromethylbenzyl)amino]-8-hydroxymethyl-2,3,4,5-tetrahydrobenzo[b]azepine-1-carboxylate

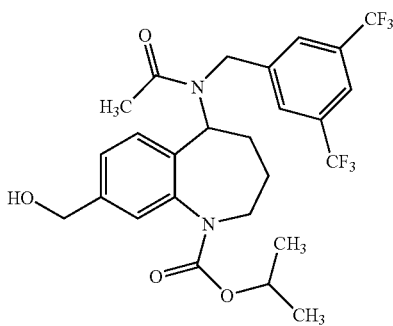

Add butyl lithium (0.157 mL, 0.252 mmol, 1.6 M in hexanes) dropwise to a solution of isopropyl-5-[acetyl-(3,5-bistrifluoromethylbenzyl)amino]-8-bromo-2,3,4,5-tetrahydrobenzo[b]azepine-1-carboxylate (0.100 g, 0.168 mmol) in tetrahydrofuran (2 mL) under nitrogen at −78° C. and stir for 1 h. Add N,N-dimethylformamide (0.052 mL, 0.672 mmol) dropwise to the cold solution and stir for 40 min at −78° C. then warm to room temperature. Quench the reaction with saturated aqueous ammonium chloride (10 mL) and dilute with ethyl acetate (20 mL). Separate the layers and wash the organic layer with water (2×30 mL) and brine (30 mL), then dry over sodium sulfate, filter and remove solvent under reduced pressure to provide the crude aldehyde. Dissolve the crude aldehyde (0.091 g, 0.167 mmol) in methanol (3 mL) and add sodium borohydride (0.019 g, 0.501 mmol) in one portion at room temperature. After stirring for 3 h, dilute the reaction with ethyl acetate (25 mL) and wash with brine (40 mL), then dry the organic layer over sodium sulfate, filter and remove the solvent under reduced pressure. Purify the crude material by chromatography on silica gel, eluting with acetonitrile to provide the title compound as an off-white solid (0.008 g, 8%): ESI MS 547 (M+H).

Example 37

Isopropyl 5-[acetyl-(3,5-bistrifluoromethylbenzyl)amino]-8-morpholin-4-yl-2,3,4,5-tetrahydrobenzo[b]azepine-1-carboxylate

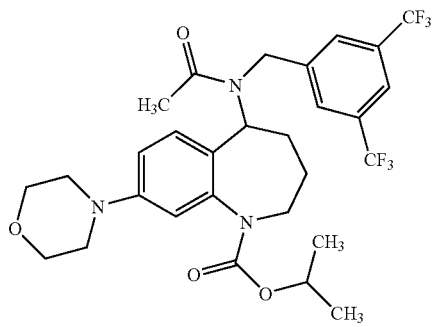

Combine tris(dibenzylideneacetone)dipalladium (0) (0.015 g, 0.017 mmol), 2,2'-bis(diphenylphosphino)-1,1'-binaphyl (0.031 g, 0.050 mmol) and sodium t-butoxide (0.023 g, 0.235 mmol) in toluene (3 mL) in a 10 mL microwave vessel and purge this suspension with nitrogen at room temperature for 5 min. Add morpholine (0.016 mL, 0.185 mmol) followed by isopropyl-5-[acetyl-(3,5-bistrifluoromethylbenzyl)amino]-8-bromo-2,3,4,5-tetrahydrobenzo[b]azepine-1-carboxylate (0.100 g, 0.168 mmol) and irradiate this mixture at 110° C. for 15 min. Dilute the cooled mixture with dichloromethane and filter through Celite. Remove the filtrate solvent under reduced pressure and purify the residue using chromatography on silica gel, eluting with hexanes/ethyl acetate (60:40), to provide the title compound a yellow solid (0.041 g, 40%): ESI MS 602 (M+H)

The following Examples were prepared utilizing the same methodology described in Example 37 wherein R1 is a variable and is introduced by replacement of morpholine with alternative reagents following the procedure of Example 37 for the synthesis of Isopropyl 5-[acetyl-(3,5-bistrifluoromethylbenzyl)amino]-8-morpholin-4-yl-2,3,4,5-tetrahydrobenzo[b]azepine-1-carboxylate.

| Example # | Reagent | R1 | MS (ES+) |
|---|---|---|---|
| Example 38 | Pyrrolidine | pyrrolidin-1-yl | 586 (M + H) |
| Example 39 | Ethylamine | ethylamino | |
| Example 40 | Azetidine | azetidin-1-yl | 572 (M + H) |

Example 41

Isopropyl 5-[acetyl-(3,5-bistrifluoromethylbenzyl)amino]-8-methoxy-2,3,4,5-tetrahydrobenzo[b]azepine-1-carboxylate

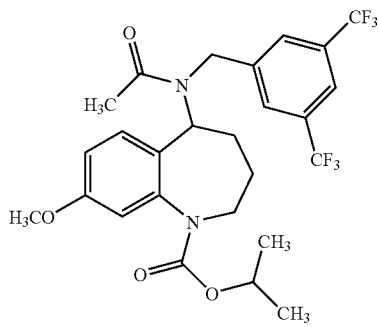

Combine isopropyl-5-[acetyl-(3,5-bistrifluoromethylbenzyl)amino]-8-bromo-2,3,4,5-tetrahydrobenzo[b]azepine-1-carboxylate (0.100 g, 0.168 mmol), palladium acetate (0.001 g, 0.0033 mmol), 2-di-tert-butylphosphino-2',4',6'-triisopropylbiphenyl (0.002 g, 0.0041 mmol), cesium carbonate (0.082 g, 0.252 mmol), and methanol (0.03 mL, 0.67 mmol) in toluene (1 mL) in a 10 mL microwave vessel and irradiate the mixture at 110° C. for 30 min (45 W). Dilute the mixture with ethyl acetate (20 mL), filter through Celite® and remove the solvent under reduced pressure. Purify the residue using chromatography on silica gel, eluting with hexanes/ethyl acetate (60:40), to provide the title compound as a white solid (0.028 g, 30%): ESI MS 547 (M+H)

Example 42

Isopropyl 5-[acetyl-(3,5-bistrifluoromethylbenzyl)amino]-8-thiomethyl-2,3,4,5-tetrahydrobenzo[b]azepine-1-carboxylate

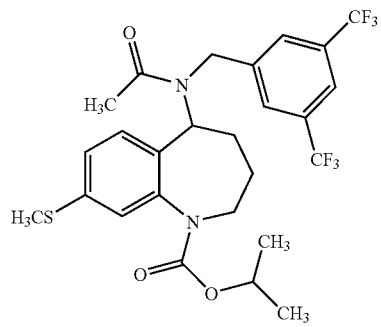

Combine isopropyl-5-[acetyl-(3,5-bistrifluoromethylbenzyl)amino]-8-bromo-2,3,4,5-tetrahydrobenzo[b]azepine-1-carboxylate (0.100 g, 0.168 mmol) and sodium thiomethoxide (0.018 g, 0.252 mmol) in N,N-dimethylformamide (0.34 mL) in a 10 mL microwave vessel and irradiate at 100° C. for 40 min (50 W). Dilute the mixture with ethyl acetate (20 mL) and wash with water (2×25 mL) and brine (25 mL). Dry the organic layer over sodium sulfate, filter and remove the solvent under reduced pressure. Purify the crude material using chromatography on silica gel, eluting with hexanes/ethyl:acetate (60:40), to provide the title compound as a white solid (0.033 g, 35%). ESI MS 563 (M+H).

Example 43

Isopropyl 5-[acetyl-(3,5-bistrifluoromethylbenzyl)amino]-8-methanesulfonyl-2,3,4,5-tetrahydrobenzo[b]azepine-1-carboxylate

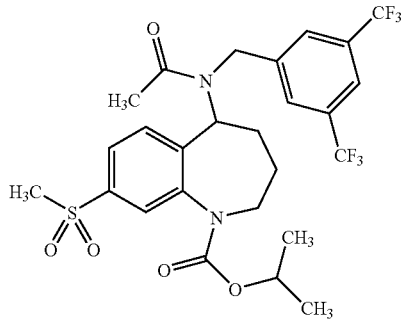

Add a solution of oxone (0.111 g, 0.181 mmol) in water (1 mL) dropwise to a solution of isopropyl 5-[acetyl-(3,5-bistrifluoromethylbenzyl)amino]-8-thiomethyl-2,3,4,5-tetrahydrobenzo[b]azepine-1-carboxylate (0.034 g, 0.060 mmol) in methanol (2 mL) at 0° C. Warm the white suspension to room temperature and stir for 1 h. Dilute the reaction with water (25 mL) and extract with ethyl acetate (2×10 mL). Dry the combined organic extracts over sodium sulfate, filter and remove the solvent under reduced pressure. Purify the residue using chromatography on silica gel, eluting with ethyl acetate/hexanes (70:30), to provide the title compound as a white solid (0.016 g, 44%): ESI MS 595 (M+H).

Example 44

Isopropyl 5-[acetyl-(3,5-bistrifluoromethylbenzyl)amino]-8-benzyloxy-2,3,4,5-tetrahydrobenzo[b]azepine-1-carboxylate

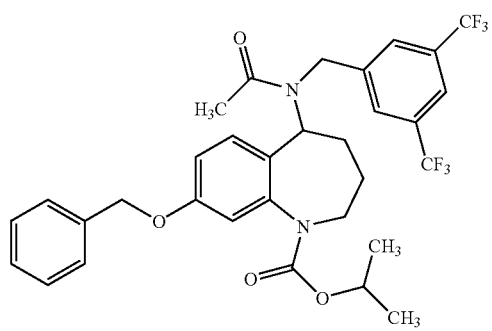

Combine isopropyl-5-[acetyl-(3,5-bistrifluoromethylbenzyl)amino]-8-bromo-2,3,4,5-tetrahydrobenzo[b]azepine-1-carboxylate (0.100 g, 0.168 mmol), tris(dibenzylideneacetone)dipalladium (0) (0.0031 g, 0.0033 mmol), 2-di-tert-butylphosphino-2',4',6'-triisopropylbiphenyl (0.0043 g, 0.010 mmol), cesium carbonate (0.082 g, 0.252 mmol) and benzyl alcohol (0.035 mL, 0.336 mmol) in toluene (0.67 mL) in a sealed tube and heat at 110° C. for 20 h. Dilute the cooled mixture with dichloromethane (50 mL) and filter through Celite. Remove the filtrate solvent under reduced pressure and first purify the residue using chromatography on silica gel, eluting with hexanes/ethyl acetate (60:40), to provide the title compound as a white solid (0.054 g, 52%): ESI MS 623 (M+H).

Example 45

Isopropyl 5-[acetyl-(3,5'-bistrifluoromethylbenzyl)amino]-8-hydroxy-2,3,4,5-tetrahydrobenzo[b]azepine-1-carboxylate

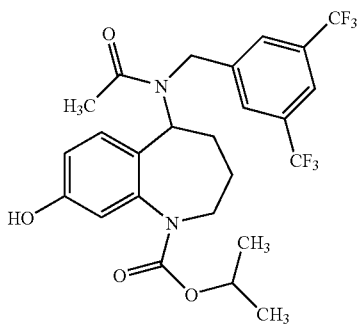

Combine isopropyl-5-[acetyl-(3,5-bistrifluoromethylbenzyl)amino]-8-benzyloxy-2,3,4,5-tetrahydrobenzo[b]azepine-1-carboxylate (0.050 g, 0.080 mmol) and 10% palladium on carbon (50% wet, 10 mg) in ethanol (3 mL) and stir at room temperature under an atmosphere of hydrogen (1 atm) for 19 h. Filter the reaction through Celite, rinse the filter cake with ethyl acetate and remove the filtrate solvent under reduced pressure. Purify the crude material using chromatography on silica gel, eluting with hexanes/ethyl acetate (60:40), to provide the title compound as a white solid (0.054 g, 52%): ESI MS 533 (M+H).

Example 46 tert-Butyl-5-[acetyl-(3,5-bistrifluoromethylbenzyl)amino]-8-bromo-2,3,4,5-tetrahydrobenzo[b]azepine-1-carboxylate

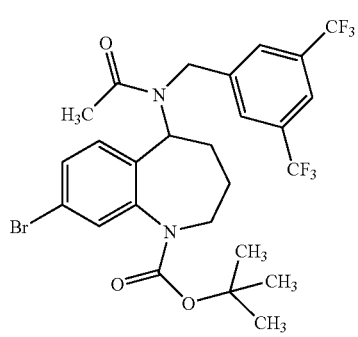

Step 1. Preparation of 8-Bromo-1,2,3,4-tetrahydrobenzo[b]azepin-5-one

Dissolve 1-isopropyl-4-methyl-8-bromo-5-oxo-2,3,4,5-tetrahydrobenzo[b]azepine-1,4-dicarboxylate (4.47 g, 11.6 mmol) in glacial acetic acid (32 mL). Add water (2.9 mL) followed by concentrated HCl (9.9 mL) and heat the orange solution at reflux for 24 h. Cool the mixture to room temperature and remove the solvents under reduced pressure. Add 2 N NaOH to the residue and extract this mixture with ethyl acetate (3×100 mL), then combine the organic extracts, dry the solution over sodium sulfate, filter and remove the solvent under reduced pressure. Purify the crude material using chromatography on silica gel eluting with hexanes/ethyl acetate (60:40), to provide 8-bromo-1,2,3,4-tetrahydrobenzo[b]azepin-5-one as an orange solid (1.39 g, 50%).

Step 2. Preparation of tert-Butyl 8-bromo-5-oxo-2,3,4,5-tetrahydrobenzo[b]azepine-1-carboxylate Add di-tert-butyl-dicarbonate (0.189 g, 0.866 mmol) to a solution of 8-bromo-1,2,3,4-tetrahydrobenzo[b]azepin-5-one (0.104 g, 0.433 mmol), N,N-diisopropylethylamine (0.15 mL, 0.866 mmol) and 4-(dimethylamino)pyridine (0.010 g, 0.087 mmol) in dichloromethane (1 mL) at 0° C. and slowly warm to room temperature. After 6 h add more di-tert-butyl-dicarbonate (0.189 g, 0.866 mmol) and N,N-diisopropylethylamine (0.15 mL, 0.866 mmol) and stir at room temperature for 15 h. Remove the solvent under reduced pressure and purify the crude material using chromatography on silica gel, eluting with hexanes/ethyl acetate (60:40), to afford tert-butyl 8-bromo-5-oxo-2,3,4,5-tetrahydrobenzo[b]azepine-1-carboxylate as an off-white solid (0.097 g, 66%).

Step 3. Preparation of tert-Butyl 5-[acetyl-(3,5-bistrifluoromethylbenzyl)amino]-8-bromo-2,3,4,5-tetrahydrobenzo[b]azepine-1-carboxylate Add 3,5-bis(trifluoromethyl)benzylamine (1.49 g, 6.13 mmol) followed by titanium isopropoxide (1.60 mL, 5.47 mmol) to a solution of tert-butyl 8-bromo-5-oxo-2,3,4,5-tetrahydro benzo[b]azepine-1-carboxylate (1.49 g, 4.38 mmol) in tetrahydrofuran (17.5 mL) at room temperature under nitrogen and stir the solution for 14 h. Dilute the reaction with methanol (35 mL) and slowly add sodium borohydride (0.248 g, 6.57 mmol) to the reaction and stir at room temperature for 3 h. Add 2 N NaOH (20 mL) and water (20 mL) to the reaction and stir for 0.5 h. Filter the mixture and wash the solids with ethyl acetate (3×75 mL). Separate the filtrate and wash the organic layer with brine (25 mL), then dry the solution over sodium sulfate, filter and remove the solvent under reduced pressure to afford tert-butyl 5-(3,5-bistrifluoromethylbenzylamino)-8-bromo-2,3,4,5-tetrahydrobenzo[b]azepine-1-carboxylate as a white solid. Add acetic anhydride (6.0 mL, 64.0 mmol) dropwise to a suspension of tert-butyl 5-(3,5-bistrifluoromethylbenzylamino)-8-bromo-2,3,4,5-tetrahydrobenzo[b]azepine-1-carboxylate (2.42 g, 4.26 mmol) and pyridine (5.2 mL, 64.0 mmol) in dichloromethane (17 mL) under nitrogen cooled to 0° C. After the addition is complete, remove the cooling bath and warm the reaction to room temperature and stir for 12 h. Dilute the mixture with dichloromethane (25 mL) and wash with 2 M potassium hydrogen sulfate and saturated aqueous sodium bicarbonate (25 mL each). Dry the organic layer over sodium sulfate, filter and remove the solvent under reduced pressure. Purify the residue using chromatography on silica gel, eluting with hexanes/ethyl acetate (60:40), to afford the title compound as a white solid.

Example 47 tert-Butyl-5-[acetyl-(3,5-bistrifluoromethylbenzyl)amino]-8-methyl-2,3,4,5-tetrahydrobenzo[b]azepine-1-carboxylate

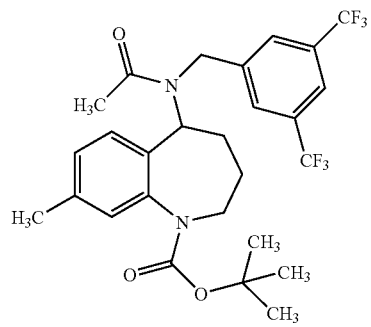

Combine tert-butyl-5-[acetyl-(3,5-bistrifluoromethylbenzyl)amino]-8-bromo-2,3,4,5-tetrahydrobenzo[b]azepine-1-carboxylate (0.438 g, 0.719 mmol), methylboronic acid (0.086 g, 1.44 mmol), [1,1'-bis(diphenylphosphino)ferrocene]dichloropalladium(II), complex with dichloromethane (1:1) (0.059 g, 0.072 mmol) and cesium fluoride (0.328 g, 2.16 mmol) in dioxane (2.5 mL) in a 10 mL microwave vessel and irradiate this mixture at 110° C. for 80 min. Dilute the cooled mixture with dichloromethane and filter through Celite®. Remove the filtrate solvent under reduced pressure and purify the residue first using chromatography on silica gel, eluting with hexanes/ethyl acetate (60:40), to afford the title compound as a white solid (0.116 g, 30%).

Example 48

Isopropyl 5-[acetyl-(3,5-bistrifluoromethylbenzyl)amino]-8-chloro-7-cyano-2,3,4,5-tetrahydrobenzo[b]azepine-1-carboxylate

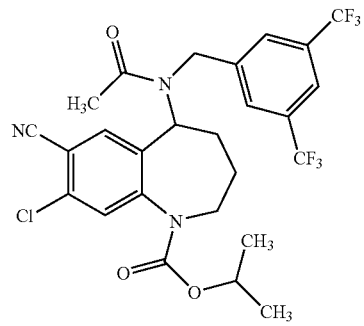

Purge with nitrogen a suspension of isopropyl-5-[acetyl-(3,5-bistrifluoromethylbenzyl)amino]-7-bromo-8-chloro-2,3,4,5-tetraydrobenzo[b]azepine-1-carboxylate (0.100 g, 0.159 mmol) and zinc cyamide (0.023 g, 0.198 mmol) in N,N-dimethylformamide (3 mL) at room temperature in a 10 mL microwave vessel. Add tetrakis(triphenylphosphine)palladium (0) (0.006 g, 0.0047 mmol) and irradiate the mixture at 175° C. for 5 min (50-75 W). Cool the mixture to room temperature and dilute with ethyl acetate (30 mL) and wash with water (3×10 mL) and brine (25 mL), then dry the organic layer over sodium sulfate, filter and remove the solvent under reduced pressure. Purify the residue using chromatography on silica gel, eluting with hexanes/ethyl acetate (60:40), to provide the title compound as a white solid (0.051 g, 56%): ESI MS 576 (M+H).

Example 49

Isopropyl 5-[acetyl-(3,5-bistrifluoromethylbenzyl)amino]-7,8-dichloro-2,3,4,5-tetrahydrobenzo[b]azepine-1-carboxylate

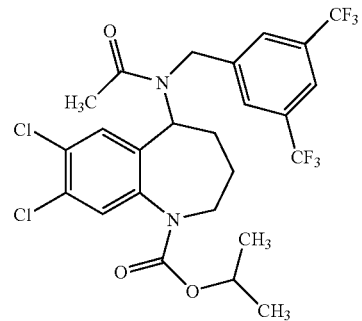

Irradiate a suspension of isopropyl-5-[acetyl-(3,5-bistrifluoromethylbenzyl)amino]-7-bromo-8-chloro-2,3,4,5-tetrahydrobenzo[b]azepine-1-carboxylate (0.100 g, 0.159 mmol) and copper(I) chloride (0.017 g, 0.175 mmol) in N,N-dimethylformamide (1.5 mL) in a 10 mL microwave vessel at 160° C. for 60 min (170 W). Cool the mixture to room temperature and dilute with ethyl acetate (30 mL) and wash with water (2×30 mL) and brine (30 mL), then dry the organic layer over sodium sulfate, filter and remove the solvent under reduced pressure. Purify the mixture using chromatography on silica gel, eluting with hexanes/ethyl acetate (60:40), ESI MS 585 (M+H).

Example 50

Isopropyl 5-[acetyl-(3,5-bistrifluoromethylbenzyl)amino]-8-chloro-7-dimethylamino-2,3,4,5-tetrahydrobenzo[b]azepine-1-carboxylate

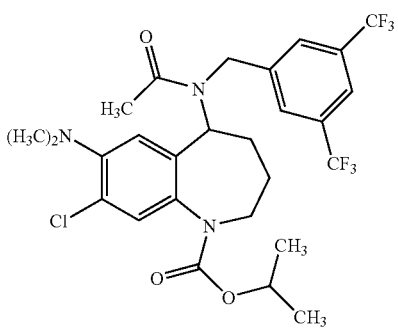

Combine isopropyl-5-[acetyl-(3,5-bistrifluoromethylbenzyl)amino]-7-bromo-8-chloro-2,3,4,5-tetrahydrobenzo[b]azepine-1-carboxylate (0.075 g, 0.119 mmol), tris(dibenzylideneacetone)dipalladium (0) (0.003 g, 0.0029 mmol), 2-dicyclohexylphosphino-2',4',6'-triisopropylbiphenyl (0.006 g, 0.012 mmol), sodium tert-butoxide (0.029 g, 0.298 mmol) and dimethylamine (0.071 mL, 0.143 mmol, 2.0 M in THF) in toluene (0.5 mL) in a 10 mL microwave vessel and irradiate at 110° C. for 20 min (50 W). Add a large excess of dimethylamine (2 mL, 4 mmol, 2.0 M in THF) and irradiate at 110° C. for 20 min. Dilute the cooled mixture with ethyl acetate (25 mL) and filter through Celite. Remove the filtrate solvent under reduced pressure and purify the residue using chromatography on silica gel, eluting with hexanes/ethyl acetate (60:40), to provide the title compound as an off-white solid (0.037 g, 52%): ESI MS 594 (M+H).

Example 51

Isopropyl 5-[acetyl-(3,5-bistrifluoromethylbenzyl)amino]-8-chloro-7-methoxy-2,3,4,5-tetrahydrobenzo[b]azepine-1-carboxylate

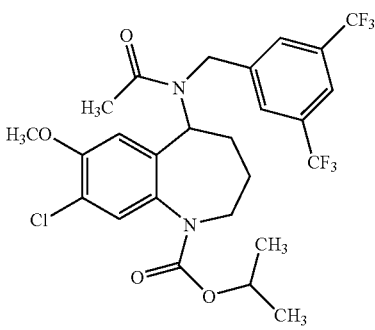

Combine isopropyl-5-[acetyl-(3,5-bistrifluoromethylbenzyl)amino]-7-bromo-8-chloro-2,3,4,5-tetrahydrobenzo[b]azepine-1-carboxylate (0.050 g, 0.079 mmol), tris(dibenzylideneacetone)dipalladium (0) (0.0014 g, 0.0015 mmol), 2-di-tert-butylphosphino-2',4',6'-triisopropylbiphenyl (0.002 g, 0.0047 mmol), cesium carbonate (0.039 g, 0.119 mmol) and methanol (0.016 mL, 0.397 mmol) in toluene (1 mL) in a sealed tube and heat at 110° C. for 24 h. Dilute the cooled mixture with ethyl acetate (25 mL) and filter through Celite. Remove the filtrate solvent under reduced pressure and first purify the residue using chromatography on silica gel, eluting with hexanes/ethyl acetate (60:40), to provide the title compound as a white solid (0.017 g, 37%): ESI MS 581 (M+H).

Example 52

Isopropyl-5-[acetyl-(3,5-bistrifluoromethylbenzyl) amino]-7-bromo-8-methyl-2,3,4,5-tetrahydrobenzo [b]azepine-1-carboxylate

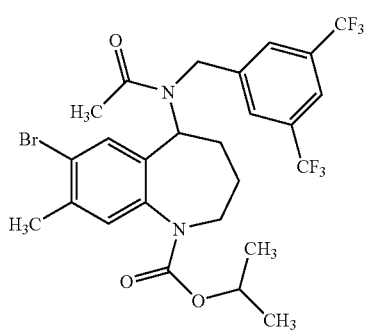

Add bromine (0.016 mL, 0.303 mmol) dropwise to a solution of isopropyl-5-[acetyl-(3,5-bistrifluoromethylbenzyl) amino]-8-methyl-2,3,4,5-tetrahydrobenzo[b]azepine-1-carboxylate (0.153 g, 0.288 mmol) in glacial acetic acid (2.8 mL) and heat at 50° C. under nitrogen for 18 h. Cool the mixture to room temperature, dilute with ethyl acetate (50 mL) and wash with saturated sodium bicarbonate (2×50 mL) and 10% aqueous sodium thiosulfate (50 mL), then dry the organic layer over sodium sulfate, filter and remove the solvent under reduced pressure to provide the title compound as a white solid (0.176 g, >99%): ESI MS 609 (M+H).

Example 53

Isopropyl-5-[acetyl-(3,5-bistrifluoromethylbenzyl) amino]-7-chloro-8-methyl-2,3,4,5-tetrahydrobenzo [b]azepine-1-carboxylate

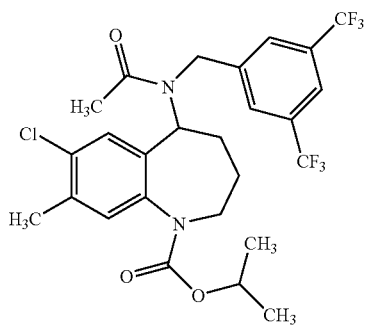

Irradiate a suspension of isopropyl-5-[acetyl-(3,5-bistrifluoromethylbenzyl)amino]-7-bromo-8-methyl-2,3,4,5-tet-rahydrobenzo[b]azepine-1-carboxylate (0.053 g, 0.087 mmol) and copper(I) chloride (0.013 g, 0.130 mmol) in N,N-dimethylformamide (0.35 mL) in a 10 mL microwave vessel at 160° C. for 20 min (110 W). Cool the mixture to room temperature and dilute with ethyl acetate (30 mL) and wash with water (2×40 mL) and brine (25 mL), then dry the organic layer over sodium sulfate, filter and remove the solvent under reduced pressure. The crude material was first purified using chromatography on silica gel, eluting with hexanes/ethyl acetate (60:40), to provide the title compound as a white solid (0.014 g, 29%): ESI MS 565 (M+H).

Example 54

Isopropyl 5-[Acetyl-(3,5-bis-trifluoromethyl-benzyl)-amino]-7-amino-8-methyl-2,3,4,5-tetrahydrobenzo[b]azepine-1-carboxylate

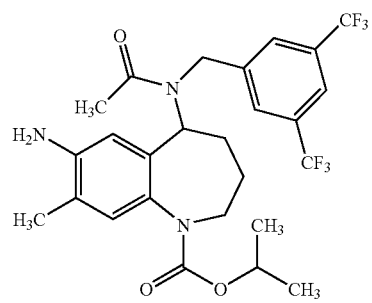

This compound was prepared utilizing the same methodology described in Example 26 wherein replacement of isopropyl-5-[acetyl-(3,5-bistrifluoromethylbenzyl)amino]-8-bromo-2,3,4,5-tetrahydrobenzo[b]azepine-1-carboxylate with isopropyl-5-[acetyl-(3,5-bistrifluoromethylbenzyl) amino]-7-bromo-8-methyl-2,3,4,5-tetrahydrobenzo[b] azepine-1-carboxylate following the procedure of Example 26, Steps 1-2 for the synthesis of isopropyl 5-[acetyl-(3,5-bistrifluoromethylbenzyl)amino]-8-amino-2,3,4,5-tetrahydrobenzo[b]azepine 1-carboxylate. CI MS 546 (M+H).

Example 55

Isopropyl-5-[acetyl-(3,5-bistrifluoromethylbenzyl) amino]-7-dimethylamino-8-methyl-2,3,4,5-tetrahydrobenzo[b]azepine-1-carboxylate

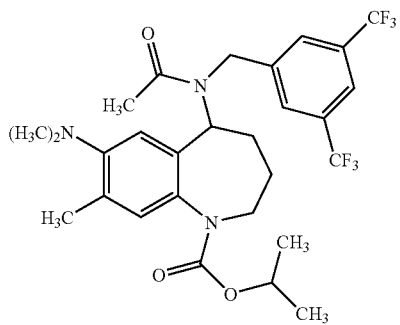

This compound was prepared utilizing the same methodology described in Example 50 wherein replacement of isopropyl-5-[acetyl-(3,5-bistrifluoromethylbenzyl)amino]-7-bromo-8-chloro-2,3,4,5-tetrahydrobenzo[b]azepine-1-carboxylate with isopropyl-5-[acetyl-(3,5-bistrifluoromethylbenzyl)amino]-7-bromo-8-methyl-2,3,4,5-tetrahydrobenzo[b]azepine-1-carboxylate the procedure of Example 50 for the synthesis of isopropyl 5-[acetyl-(3,5-bistrifluoromethylbenzyl)amino]-8-chloro-7-dimethylamino-2,3,4,5-tetrahydrobenzo[b]azepine-1-carboxylate. ESI MS m/z 574 (M+H).

Example 56

Isopropyl-5-[acetyl-(3,5-bistrifluoromethylbenzyl)amino]-7,8-dimethyl-2,3,4,5-tetrahydrobenzo[b]azepine-1-carboxylate

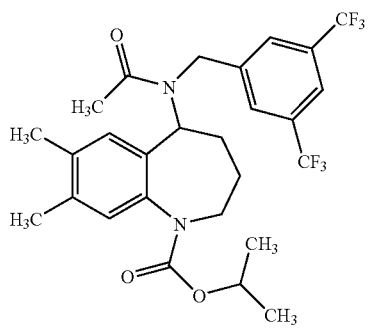

Combine isopropyl-5-[acetyl-(3,5-bistrifluoromethylbenzyl)amino]-7-bromo-8-methyl-2,3,4,5-tetrahydrobenzo[b]azepine-1-carboxylate (0.058 g, 0.095 mmol), methylboronic acid (0.011 g, 0.190 mmol), palladium acetate (0.0009 g, 0.004 mmol), 2-dicyclohexylphosphino-2',6'-dimethoxybiphenyl (0.0036 g, 0.0087 mmol) and potassium phosphate monohydrate (0.044 g, 0.190 mmol) in toluene (2 mL) and heat in a sealed tube at 100° C. for 24 h. Dilute the cooled mixture with ethyl acetate (30 mL) and filter through Celite. Remove the filtrate solvent under reduced pressure and purify the residue using chromatography on silica gel, eluting with hexanes/ethyl acetate (60:40), to provide the title compound as a white solid (0.020 g, 38%): ESI MS 545 (M+H).

Example 57

Isopropyl-5-[acetyl-(3,5-bistrifluoromethylbenzyl)amino]-7-bromo-8-fluoro-2,3,4,5-tetrahydrobenzo[b]azepine-1-carboxylate

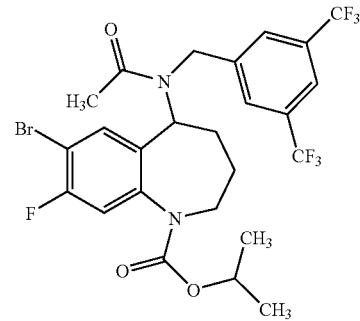

This compound was prepared utilizing the same methodology described in Example 56 wherein replacement of isopropyl-5-[acetyl-(3,5-bistrifluoromethylbenzyl)amino]-8-methyl-2,3,4,5-tetrahydrobenzo[b]azepine-1-carboxylate with isopropyl-5-[acetyl-(3,5-bistrifluoromethylbenzyl)amino]-8-fluoro-2,3,4,5-tetrahydrobenzo[b]azepine-1-carboxylate following the procedure of Example 56 for the synthesis of isopropyl-5-[acetyl-(3,5-bistrifluoromethylbenzyl)amino]-7-bromo-8-methyl-2,3,4,5-tetrahydrobenzo[b]azepine-1-carboxylate. ESI MS 613 (M+H).

Example 58

Isopropyl 5-[Acetyl-(3,5-bis-trifluoromethyl-benzyl)-amino]-8-fluoro-7-methyl-2,3,4,5-tetrahydrobenzo[b]azepine-1-carboxylate

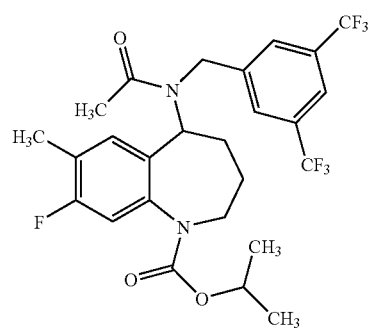

This compound was prepared utilizing the same methodology described in Example 56 wherein replacement of isopropyl-5-[acetyl-(3,5-bistrifluoromethylbenzyl)amino]-7-bromo-8-methyl-2,3,4,5-tetrahydrobenzo[b]azepine-1-carboxylate with isopropyl-5-[acetyl-(3,5-bistrifluoromethylbenzyl)amino]-7-bromo-8-fluoro-2,3,4,5-tetrahydrobenzo[b]azepine-1-carboxylate following the procedure of Example 56 for the synthesis of isopropyl 5-[acetyl-(3,5-bistrifluoromethylbenzyl)amino]-7,8-dimethyl-2,3,4,5-tetrahydrobenzo[b]azepine-1-carboxylate. ESI MS 549 (M+H).

Example 59

Isopropyl 5-[acetyl-(3,5-bistrifluoromethylbenzyl)amino]-7,8-dimethoxy-2,3,4,5-tetrahydrobenzo[b]azepine-1-carboxylate

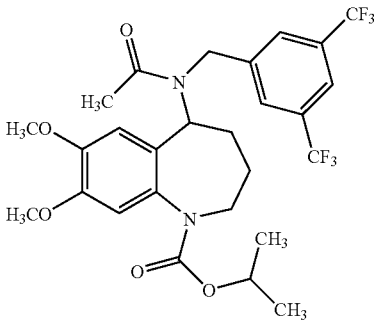

This compound was prepared utilizing the same methodology described in Example 1 wherein replacement of 2-amino-benzoic acid methyl ester with methyl 2-amino-4,5-dimethoxybenzoate following the procedure of Example 1, Steps 1-8 for the synthesis of 5-[acetyl-(3,5-bistrifluoromethylbenzyl)amino]-2,3,4,5-tetrahydrobenzo[b]azepine-1-carboxylic acid isopropyl ester. CI MS 577 (M+H).

Example 60

Isopropyl 5-[Acetyl-(3,5-bis-trifluoromethyl-benzyl)-amino]-2,3,4,5-tetrahydro-naphtho[2,3-b]azepine-1-carboxylate

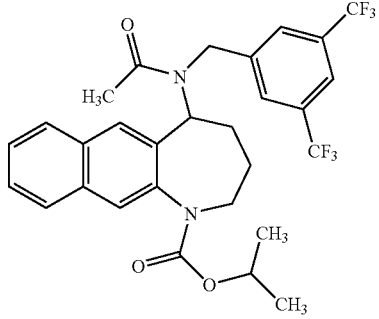

This compound was prepared utilizing the same methodology described in Example 1 wherein replacement of 2-amino-benzoic acid methyl ester with methyl 3-aminonaphthalene-2-carboxylate following the procedure of Example 1, Steps 1-8 for the synthesis of 5-[acetyl-(3,5-bistrifluoromethylbenzyl)amino]-2,3,4,5-tetrahydrobenzo[b]azepine-1-carboxylic acid isopropyl ester. CI MS 567 (M+H).

Example 61

Isopropyl 5-[acetyl-(3,5-bistrifluoromethylbenzyl)amino]-9-methyl-2,3,4,5-tetrahydrobenzo[b]azepine-1-carboxylate

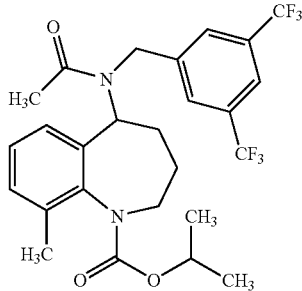

This compound was prepared utilizing the same methodology described in Example 1 wherein replacement of 2-amino-benzoic acid methyl ester with methyl 2-amino-3-methylbenzoate following the procedure of Example 1, Steps 1-8 for the synthesis of 5-[acetyl-(3,5-bistrifluoromethylbenzyl)amino]-2,3,4,5-tetrahydrobenzo[b]azepine-1-carboxylic acid isopropyl ester. CI MS 531 (M+H).

Example 62

Isopropyl 5-[acetyl-(3,5-bistrifluoromethylbenzyl)amino]-9-methoxy-2,3,4,5-tetrahydrobenzo[b]azepine-1-carboxylate

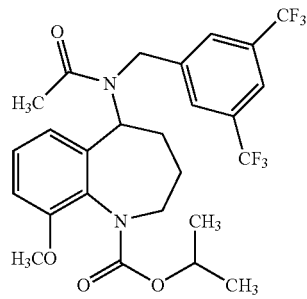

This compound was prepared utilizing the same methodology described in Example 1 wherein replacement of 2-amino-benzoic acid methyl ester with methyl 2-amino-3-methoxybenzoate following the procedure of Example 1, Steps 1-8 for the synthesis of 5-[acetyl-(3,5-bistrifluoromethylbenzyl)amino]-2,3,4,5-tetrahydrobenzo[b]azepine-1-carboxylic acid isopropyl ester. CI MS 547 (M+H).

Example 63

Isopropyl 5-[acetyl-(3,5-bistrifluoromethylbenzyl)amino]-9-chloro-2,3,4,5-tetrahydrobenzo[b]azepine-1-carboxylate

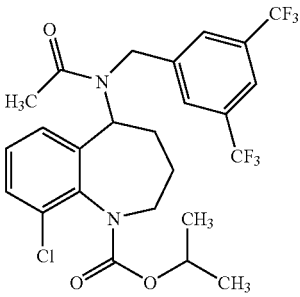

This compound was prepared utilizing the same methodology described in Example 1 wherein replacement of 2-amino-benzoic acid methyl ester with methyl 2-amino-3-chlorobenzoate following the procedure of Example 1, Steps 1-8 for the synthesis of 5-[acetyl-(3,5-bistrifluoromethylbenzyl)amino]-2,3,4,5-tetrahydrobenzo[b]azepine-1-carboxylic acid isopropyl ester. CI MS 551 (M+H).

Example 64

Isopropyl 5-[acetyl-(3,5-bistrifluoromethylbenzyl)amino]-9-bromo-2,3,4,5-tetrahydrobenzo[b]azepine-1-carboxylate

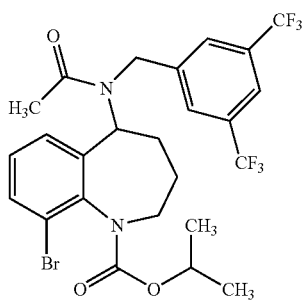

This compound was prepared utilizing the same methodology described in Example 1 wherein replacement of 2-amino-benzoic acid methyl ester with methyl 2-amino-3-bromobenzoate following the procedure of Example 1, Steps 1-8 for the synthesis of 5-[acetyl-(3,5-bistrifluoromethylbenzyl)amino]-2,3,4,5-tetrahydrobenzo[b]azepine-1-carboxylic acid isopropyl ester. CI MS 595 (M+H).

Example 65

Isopropyl 5-[acetyl-(3,5-bistrifluoromethylbenzyl)amino]-9-trifluoromethoxy-2,3,4,5-tetrahydrobenzo[b]azepine-1-carboxylate

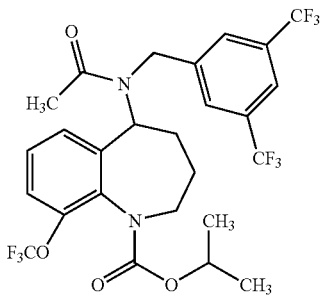

This compound was prepared utilizing the same methodology described in Example 1 wherein replacement of 2-amino-benzoic acid methyl ester with methyl 2-amino-3-trifluoromethoxybenzoate following the procedure of Example 1, Steps 1-8 for the synthesis of 5-[acetyl-(3,5-bistrifluoromethylbenzyl)amino]-2,3,4,5-tetrahydrobenzo[b]azepine-1-carboxylic acid isopropyl ester. CI MS 601 (M+H).

Example 66

Isopropyl 5-[Acetyl-(3,5-bis-trifluoromethyl-benzyl)-amino]-9-amino-2,3,4,5-tetrahydro-benzo[b]azepine-1-carboxylate

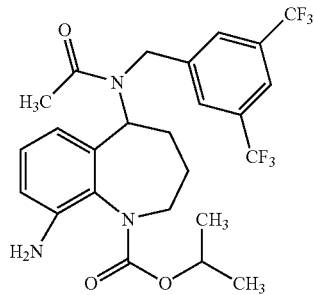

This compound was prepared utilizing the same methodology described in Example 26 wherein replacement of isopropyl-5-[acetyl-(3,5-bistrifluoromethylbenzyl)amino]-8-bromo-2,3,4,5-tetrahydrobenzo[b]azepine-1-carboxylate with isopropyl 5-[acetyl-(3,5-bistrifluoromethylbenzyl)amino]-9-bromo-2,3,4,5-tetrahydrobenzo[b]azepine-1-carboxylate following the procedure of Example 26, Steps 1-2 for the synthesis of isopropyl 5-[acetyl-(3,5-bistrifluoromethylbenzyl)amino]-8-amino-2,3,4,5-tetrahydrobenzo[b]azepine-1-carboxylate. CI MS 532 (M+H).

Example 67

Isopropyl 5-[Acetyl-(3,5-bis-trifluoromethyl-benzyl)-amino]-9-dimethylamino-2,3,4,5-tetrahydrobenzo[b]azepine-1-carboxylate

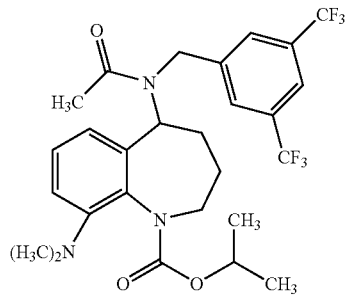

This compound prepared utilizing the same methodology described in Example 50 wherein replacement of isopropyl-5-[acetyl-(3,5-bistrifluoromethylbenzyl)amino]-7-bromo-8-chloro-2,3,4,5-tetrahydrobenzo[b]azepine-1-carboxylate with isopropyl 5-[acetyl-(3,5-bistrifluoromethylbenzyl)amino]-9-bromo-2,3,4,5-tetrahydrobenzo[b]azepine-1-carboxylate following the procedure of Example 50 for the synthesis of isopropyl 5-[acetyl-(3,5-bistrifluoromethylbenzyl)amino]-8-chloro-7-dimethylamino-2,3,4,5-tetrahydrobenzo[b]azepine-1-carboxylate. CI MS 560 (M+H).

Example 68

Isopropyl 5-[Acetyl-(3,5-bis-trifluoromethyl-benzyl)-amino]-9-bromo-7-methyl-2,3,4,5-tetrahydro-benzo[b]azepine-1-carboxylate

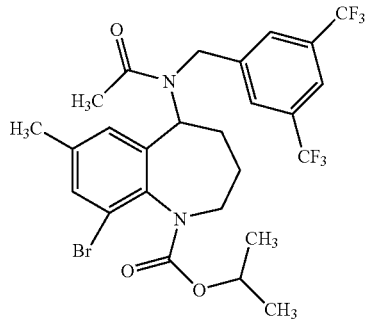

This compound prepared utilizing the same methodology described in Example 1 wherein replacement of 2-aminobenzoic acid methyl ester with methyl 2-amino-3-bromo-5-methylbenzoate following the procedure of Example 1, Steps 1-8 for the synthesis of 5-[acetyl-(3,5-bistrifluoromethylbenzyl)amino]-2,3,4,5-tetrahydrobenzo[b]azepine-1-carboxylic acid isopropyl ester. ESI MS 609 (M+H).

Example 69

Isopropyl 5-[Acetyl-(3,5-bis-trifluoromethyl-benzyl)-amino]-9-amino-7-methyl-2,3,4,5-tetrahydro-benzo[b]azepine-1-carboxylate

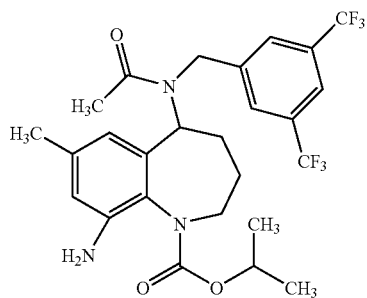

This compound prepared utilizing the same methodology described in Example 26 wherein replacement of isopropyl-5-[acetyl-(3,5-bistrifluoromethylbenzyl)amino]-8-bromo-2,3,4,5-tetrahydrobenzo[b]azepine-1-carboxylate with isopropyl 5-[acetyl-(3,5-bis-trifluoromethyl-benzyl)-amino]-9-bromo-7-methyl-2,3,4,5-tetrahydro-benzo[b]azepine-1-carboxylate following the procedure of Example 26, Steps 1-2 for the synthesis of isopropyl 5-[acetyl-(3,5-bistrifluoromethylbenzyl)amino]-8-amino-2,3,4,5-tetrahydrobenzo[b]azepine-1-carboxylate. CI MS 546 (M+H).

Example 70

Isopropyl 5-[Acetyl-(3,5-bis-trifluoromethyl-benzyl)-amino]-9-dimethylamino-7-methyl-2,3,4,5-tetrahydro-benzo[b]azepine-1-carboxylate

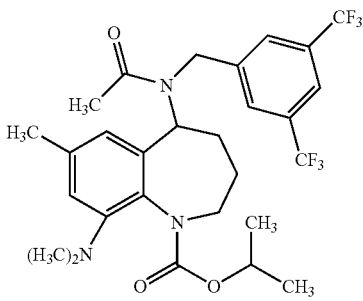

This compound prepared utilizing the same methodology described in Example 51 wherein replacement of isopropyl-5-[acetyl-(3,5-bistrifluoromethylbenzyl)amino]-7-bromo-8-chloro-2,3,4,5-tetrahydrobenzo[b]azepine-1-carboxylate with isopropyl 5-[acetyl-(3,5-bis-trifluoromethyl-benzyl)-amino]-9-bromo-7-methyl-2,3,4,5-tetrahydro-benzo[b]azepine-1-carboxylate following the procedure of Example 51 for the synthesis of isopropyl 5-[acetyl-(3,5-bistrifluoromethylbenzyl)amino]-8-chloro-7-dimethylamino-2,3,4,5-tetrahydrobenzo[b]azepine-1-carboxylate. CI MS 574 (M+H).

Example 71

Isopropyl 5-[Acetyl-(3,5-bis-trifluoromethyl-benzyl)-amino]-7,9-dimethyl-2,3,4,5-tetrahydro-benzo[b]azepine-1-carboxylate

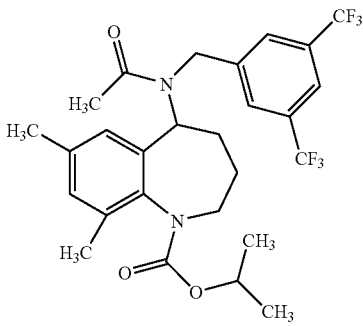

This compound prepared utilizing the same methodology described in Example 56 wherein replacement of isopropyl-5-[acetyl-(3,5-bistrifluoromethylbenzyl)amino]-7-bromo-8-methyl-2,3,4,5-tetrahydrobenzo[b]azepine-1-carboxylate with isopropyl 5-[acetyl-(3,5-bis-trifluoromethyl-benzyl)-amino]-9-bromo-7-methyl-2,3,4,5-tetrahydro-benzo[b]azepine-1-carboxylate following the procedure of Example 56 for the synthesis of isopropyl 5-[acetyl-(3,5-bistrifluoromethylbenzyl)amino]-7,8-dimethyl-2,3,4,5-tetrahydrobenzo[b]azepine-1-carboxylate. ESI MS 545 (M+H).

Example 72

(S)-5-[Acetyl-(3,5-bis-trifluoromethyl-benzyl)-amino]-8-chloro-2,3,4,5-tetrahydro-benzo[b]azepine-1-carboxylic acid isopropyl ester(isomer 1)

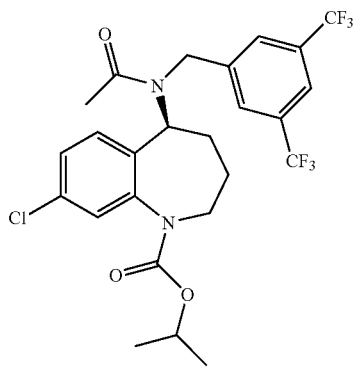

The title compound was obtained by chiral resolution of Example 3 on a Chiralpak AD-H (0.46×150 mm), flow rate: 1.0 ml/min, solvents: 40% propan-2-ol in heptane, $R_t$=2.72 min, wavelength: 225 nm. EE=100%. MS (ES+): 551 (M+H).

Example 73

(R)-5-[Acetyl-(3,5-bis-trifluoromethyl-benzyl)-amino]-8-chloro-2,3,4,5-tetrahydro-benzo[b]azepine-1-carboxylic acid isopropyl ester

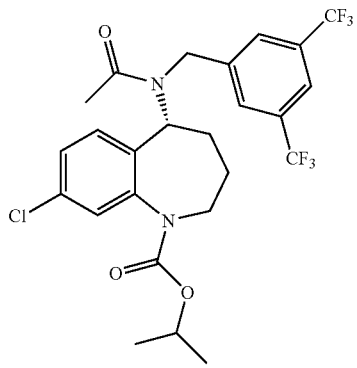

The title compound was obtained by chiral resolution of Example 3 on a Chiralpak AD-H (0.46×150 mm), flow rate: 1.0 ml/min, solvents: 40% propan-2-ol in heptane, $R_t$=3.74 ml, wavelength: 225 nm. EE=100%. MS (ES+): 551 (M+H).

Example 74

5-[Acetyl-(3,5-bis-trifluoromethyl-benzyl)-amino]-8-trifluoromethyl-2,3,4,5-tetrahydro-benzo[b]azepine-1-carboxylic acid isopropyl ester

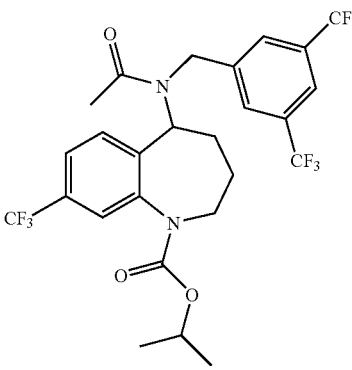

The titled compounds was prepared following the procedures described in Example 1 by replacing 2-Amino-benzoic acid methyl ester with 2-Amino-4-trifluoromethyl-benzoic acid methyl ester in Example 1, step 1. MS (ES+): 585 (M+H). Preparation of 2-Aminos-trifluoromethyl-benzoic acid methyl ester A solution of 2-amino-4-trifluoromethyl-benzoic acid (9.15 g, 44.6 mmol) in THF/MeOH (300 ml/75.0 ml) was treated with trimethylsilyldiazonium methane (2.00 M in hexane, 23.0 ml) and stirred at room temperature for an hour. The reaction was quenched by acetic acid (3.00 ml). The solvent was evaporated in vacuo and the residue was purified by silica gel chromatography eluting with 0-10% ethyl acetate in hexane to provide 8.55 g (88%) white crystalline of the titled compound. The structure was confirmed by $^1$H-NMR.

Example 75

5-[(3,5-Bis-trifluoromethyl-benzyl)-methoxycarbonyl-amino]-8-trifluoromethyl-2,3,4,5-tetrahydro-benzo[b]azepine-1-carboxylic acid isopropyl ester

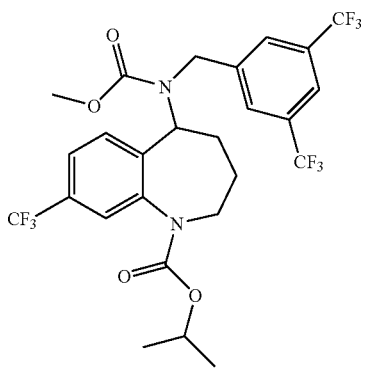

The titled compounds was prepared following the procedures described in Example 1 by replacing 2-Amino-benzoic acid methyl ester with 2-Amino-4-trifluoromethyl-benzoic acid methyl ester in Example 1, step 1 as well as replacing acetic anhydride with methyl chloroformate in Example 1, Step 8. MS (ES+): 601 (M+H).

Example 76

5-[Acetyl-(3,5-bis-trifluoromethyl-benzyl)-amino]-8-trifluoromethyl-2,3,4,5-tetrahydro-benzo[b]azepine-1-carboxylic acid ethyl ester

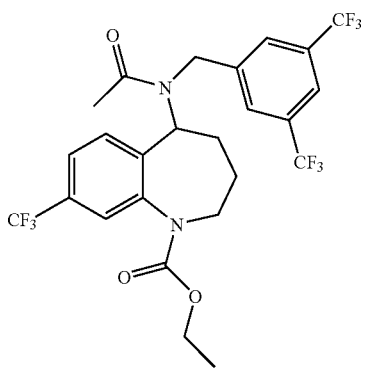

The titled compounds was prepared following the procedures described in Example 1 by replacing 2-Amino-benzoic acid methyl ester with 2-Amino-4-trifluoromethyl-benzoic acid methyl ester in Example 1, step 1 as well as replacing isopropylchloroformate with ethyl chloroformate in Example 1, Step 6. MS (ES+): 571 (M+H).

Example 77

5-[(3,5-Bis-trifluoromethyl-benzyl)-methoxycarbonyl-amino]-8-trifluoromethyl-2,3,4,5-tetrahydro-benzo[b]azepine-1-carboxylic acid ethyl ester

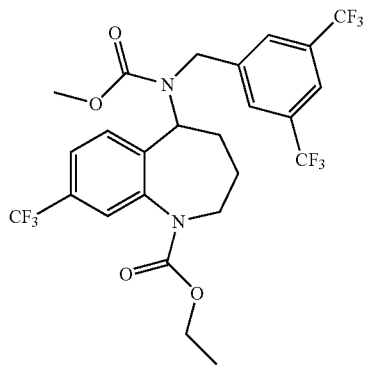

The titled compounds was prepared following the procedures described in Example 1 by replacing 2-Amino-benzoic acid methyl ester with 2-Amino-4-trifluoromethyl-benzoic acid methyl ester in Example 1, step 1; replacing isopropyl-chloroformate with ethyl chloroformate in Example 1, Step 6; as well as replacing acetic anhydride with methyl chloroformate in Example 1, Step 8. MS (ES+): 587 (M+H).

The following Examples 78-82 were prepared utilizing the same methodology described in Example 1 wherein R1 is variable and is introduced by replacement of acetic anhydride with alternative reagents following the procedure of Example 1, Step 8 for the synthesis of 5-[Acetyl-(3,5-bis-trifluoromethyl-benzyl)-amino]-2,3,4,5-tetrahydro-benzo[b]azepine-1-carboxylic acid isopropyl ester

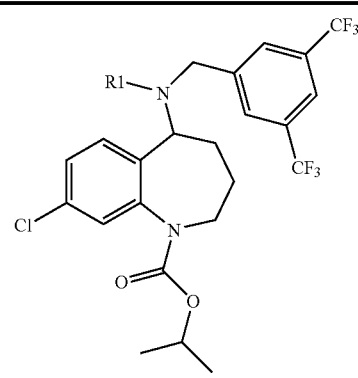

| Example # | Reagent | R1 | MS (ES+) |
|---|---|---|---|
| Example 78 | Propionyl chloride | propionyl | 565 (M + H) |
| Example 79 | Trifluoroacetic anhydride | 2,2,2-trifluoro-acetyl | 605 (M + H) |

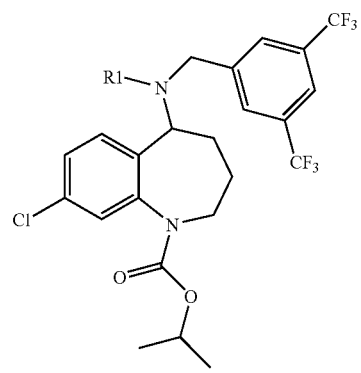

| Example # | Reagent | R1 | MS (ES+) |
|---|---|---|---|
| Example 80 | Ethyl chloroformate | ethoxycarbonyl | 581 (M + H) |
| Example 81 | Isopropyl chloroformate | isopropoxycarbonyl | 595 (M + H) |
| Example 82 | Ethyl isocyanate | 3-ethyl-ureido | 580 (M + H) |

Example 83

5-[Acetyl-(4-fluoro-benzyl)-amino]-8-chloro-2,3,4,5-tetrahydro-benzo[b]azepine-1-carboxylic acid isopropyl ester

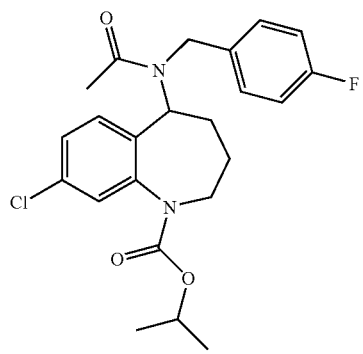

Step 1. Preparation of 8-Chloro-5-oxo-2,3,4,5-tetrahydro-benzo[b]azepine-1-carboxylic acid isopropyl ester The titled compound was prepared following the procedures described in Example 1 from step 1 to step 6 by replacing 2-Amino-benzoic acid methyl ester with 2-Amino-4-chloro-benzoic acid methyl ester in Example 1, step 1. MS (ES+): 282 (M+H).

Step 2. Preparation of 8-Chloro-5-hydroxyimino-2,3,4,5-tetrahydro-benzo[b]azepine-1-carboxylic acid isopropyl ester To a solution of 8-Chloro-5-oxo-2,3,4,5-tetrahydro-benzo[b]azepine-1-carboxylic acid isopropyl ester (3.40 g, 12.1 mmole) in EtOH/H₂O (96.0 ml/24.0 ml) was added hydroxylamine hydrochloride (8.39 g, 121 mmole) followed by sodium acetate (9.93 g, 121 mmole). The reaction was heated under 60° C. for 3 hours. The mixture was partitioned between ethyl acetate (100 ml) and 1.00N HCl (100 ml). After separated the two layers, the aqueous layer was extracted with more acetate (2×100 ml). The combined organics washed with NaHCO₃ (aq) and followed by brine (2×200 ml). Dried over Na₂SO₄, filtered and concentrated to provide the crude product (3.45 g, 96%), which was used directly for the next step without further purification. MS (ES+): 297 (M+H).

Step 3. Preparation of 5-Amino-8-chloro-2,3,4,5-tetrahydro-benzo[b]azepine-1-carboxylic acid isopropyl ester To a mixture of 8-chloro-5-hydroxyimino-2,3,4,5-tetrahydro-benzo[b]azepine-1-carboxylic acid isopropyl ester (3.33 g, 11.2 mmole) and MoO₃ (2.45 g, 17.0 μmmole) in MeOH (50.0 ml) was added a solution of sodium borohydride (2.13 g, 56.2 mmole) in DMF (50.0 ml). The reaction was stirred at room temperature overnight. To the reaction mixture was added 2.0N NaOH (aq) (100 ml). The precipitate was removed by filtration, and the filtrate was extracted with ethyl acetate (5×100 ml). The combined organics was washed with brine (3×500 ml). Dried over Na₂SO₄, filtered and concentrated to 100 ml, which was then treated with 4.0N HCl in dioxane (3.50 ml). Removal of solvents in vacuo gave a white solid, which washed with ethyl ether and dried under vacuum to provide the titled compound as hydrochloride salt (2.87 g, 80%). MS (ES+): 283 (M+H).

Step 4. Preparation of 8-Chloro-5-(4-fluoro-benzylamino)-2,3,4,5-tetrahydro-benzo[b]azepine-1-carboxylic acid isopropyl ester To a solution of 5-Amino-8-chloro-2,3,4,5-tetrahydro-benzo[b]azepine-1-carboxylic acid isopropyl ester hydrochloride (0.100 g, 0.313 mmole) in DMF/HOAc (3.00 ml/0.300 ml) was added 4-fluoro-benzaldehyde (0.0388 g, 0.313 mmole). The mixture was stirred at room temperature for an hour. To it was added sodium triacetoxyborohydride (0.265 g, 1.25 mmole) in one portion and the reaction was continued at room temperature overnight. The mixture was partitioned between ethyl acetate (10.0 ml) and saturated Na₂CO₃ (aq) (10 ml). The organic layer was separated and washed with brine (3×10.0 ml). Dried over Na₂SO₄, filtered and concentrated to provide the crude product (0.147 g, 100%), which was used directly for the next step without further purification. MS (ES+): 391 (M+H).

Step 5. Preparation of 5-[Acetyl-(4-fluoro-benzyl)-amino]-8-chloro-2,3,4,5-tetrahydro-benzo[b]azepine-1-carboxylic acid isopropyl ester The titled compound was prepared following the procedures described in Example 1 Step 8. MS (ES+): 433 (M+H).

The following Examples 83-100 were prepared utilizing this same methodology described in Example 61, in which R2 is variable and is introduced by replacement of 4-fluorobenzaldehyde with alternative reagents following the procedure of Example 61, Step 4 for the synthesis of 5-[Acetyl-(4-fluoro-benzyl)-amino]-8-chloro-2,3,4,5-tetrahydro-benzo[b]azepine-1-carboxylic acid isopropyl ester.

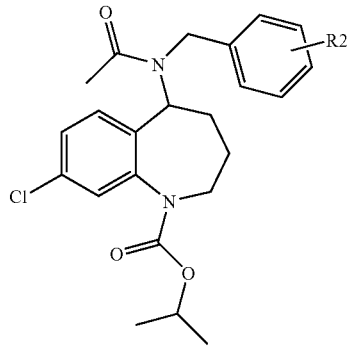

| Example # | Reagent | R2 | MS (ES+) |
|---|---|---|---|
| Example 83 | 4-trifluoromethyl-benzaldehyde | 4-trifluoromethyl-benzyl | 483 (M + H) |
| Example 84 | 4-trifluoromethoxy-benzaldehyde | 4-trifluoromethoxy-benzyl | 499 (M + H) |
| Example 85 | 3-trifluoromethyl-benzaldehyde | 3-trifluoromethyl-benzyl | 483 (M + H) |
| Example 86 | 3,5-dimethoxy-benzaldehyde | 3,5-dimethoxy-benzyl | 475 (M + H) |
| Example 87 | 3,5-dibromo-benzaldehyde | 3,5-dibromo-benzyl | 571, 573 (M + H) |
| Example 88 | 3,5-dimethyl-benzaldehyde | 3,5-dimethyl-benzyl | 443 (M + H) |
| Example 89 | 3,5-dichloro-benzaldehyde | 3,5-dichloro-benzyl | 483, 485 (M + H) |
| Example 90 ) | 3,5-difluoro-benzaldehyde | 3,5-difluoro-benzyl | 451 (M + H) |
| Example 91 | 3-fluoro-5-trifluoromethyl-benzaldehyde | 3-fluoro-5-trifluoromethyl-benzyl | 501 (M + H) |
| Example 92 | 2,4-bis-trifluoromethyl-benzaldehyde | 2,4-bis-trifluoromethyl-benzyl | 550 (M + H) |
| Example 93 | 4-fluoro-2-trifluoromethyl-benzaldehyde | 4-fluoro-2-trifluoromethyl-benzyl | 501 (M + H) |
| Example 94 | 2-fluoro-4-trifluoromethyl-benzaldehyde | 2-fluoro-4-trifluoromethyl-benzyl | 501 (M + H) |
| Example 95 | 4-fluoro-3-trifluoromethyl-benzaldehyde | 4-fluoro-3-trifluoromethyl-benzyl | 501 (M + H) |
| Example 96 | 3-fluoro-4-trifluoromethyl-benzaldehyde | 3-fluoro-4-trifluoromethyl-benzyl | 501 (M + H) |
| Example 97 | 4-chloro-3-trifluoromethyl-benzaldehyde | 4-chloro-3-trifluoromethyl-benzyl | 517, 519 (M + H) |
| Example 98 | 2-chloro-5-trifluoromethyl-benzaldehyde | 2-chloro-5-trifluoromethyl-benzyl | 517, 519 (M + H) |
| Example 99 | 2-fluoro-5-trifluoromethyl-benzaldehyde | 2-fluoro-5-trifluoromethyl-benzyl | 501 (M + H) |
| Example 100 | 5-fluoro-2-trifluoromethyl-benzaldehyde | 5-fluoro-2-trifluoromethyl-benzyl | 501 (M + H) |

Example 101

5-[Acetyl-(3,5-bis-trifluoromethyl-benzyl)-amino]-8-chloro-2,3,4,5-tetrahydro-benzo[b]azepine-1-carboxylic acid benzyl ester

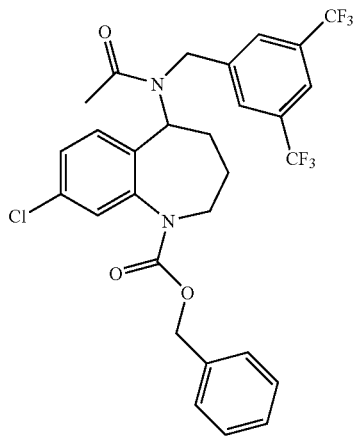

The titled compound was prepared following the procedures described in Example 1 by replacing 2-Amino-benzoic acid methyl ester with 2-Amino-4-chloro-benzoic acid methyl ester in Example 1, step 1 as well as replacing isopropyl chloroformate with benzyl chloroformate in Example 1, Step 6. MS (ES+): 599 (M+H).

Example 102

5-[Acetyl-(3,5-bis-trifluoromethyl-benzyl)-amino]-7-bromo-8-chloro-2,3,4,5-tetrahydro-benzo[b]azepine-1-carboxylic acid isopropyl ester

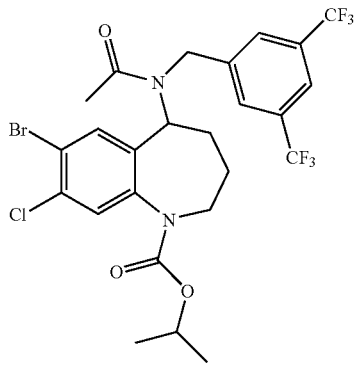

Step 1. Preparation of 2-Amino-5-bromo-4-chloro-benzoic acid methyl ester

To a solution of 2-Amino-4-chloro-benzoic acid methyl ester (1.85 g, 10.0 mmole) in HOAc (20.0 ml) was injected bromine (0.512 ml, 10.0 mmole) dropwise. The reaction was stirred at room temperature for an hour. The mixture was diluted with ethyl ether (200 ml) and then the solvents were decanted. The residue was partitioned between ethyl acetate (200 ml) and 0.100N NaOH(aq) (200 ml). After separated the two layers, the organic layer was dried over $Na_2SO_4$, filtered and concentrated to provide the crude product (2.08 g, 78%), which was used directly for the next step without further purification. MS (ES+): 264, 266 (M+H).

Step 2. Preparation of 5-Bromo-4-chloro-2-isopropoxycarbonylamino-benzoic acid methyl ester To a solution of 2-Amino-5-bromo-4-chloro-benzoic acid methyl ester (2.08 g, 7.86 mmol) and pyridine (1.91 ml, 23.6 mmol) in dichloromethane (75.0 ml) was added 1.00N isopropylchloroformate in toluene dropwise. The mixture was stirred for 16 hours at room temperature. The mixture washed with 0.500N HCl(aq) (100 ml), and brine (3×100 ml), then dried ($Na_2SO_4$) and concentrated to an oil. Purification by silica gel chromatography (gradient eluent, 0-10% ethyl acetate in hexane) provided 5-Bromo-4-chloro-2-isopropoxycarbonylamino-benzoic acid methyl ester (2.53 g, 92%) as a white crystalline material. MS (ES+): 350, 352 (M+H).

Step 3. Preparation of 5-Bromo-4-chloro-2-[isopropoxycarbonyl-(3-methoxycarbonyl-propyl)-amino]-benzoic acid methyl ester To a mixture of 5-Bromo-4-chloro-2-isopropoxycarbonylamino-benzoic acid methyl ester (2.52 g, 7.19 mmol) and cesium carbonate (4.68 g, 14.4 mmol) in DMF (35 ml) under nitrogen was added methyl 4-bromobutyrate (2.60 g, 14.4 mmol) dropwise. The reaction mixture was heated to 60° C. for 4 hours and then cooled to room temperature. The mixture was diluted with ethyl acetate (100 ml), and then washed with 0.1N HCl(aq) (100 ml) and brine (3×100 ml). The organic layer was dried over $Na_2SO_4$ and concentrated under reduced pressure. Purification by silica gel chromatography (gradient eluent, 0-20% ethyl acetate in hexane) provided 5-Bromo-4-chloro-2-[isopropoxycarbonyl-(3-methoxycarbonyl-propyl)-amino]-benzoic acid methyl ester (2.78 g, 86%) as oil. MS (ES+): 450, 452 (M+H).

Step 4. Preparation of 7-Bromo-8-chloro-5-oxo-2,3,4,5-tetrahydro-benzo[b]azepine-1,4-dicarboxylic acid 1-isopropyl ester 4-methyl ester To a heated mixture of potassium t-butoxide (1.27 g, 11.3 mmol) in toluene (50 ml) at 70° C. was added a solution of 5-Bromo-4-chloro-2-[isopropoxycarbonyl-(3-methoxycarbonyl-propyl)-amino]-benzoic acid methyl ester (2.55 g, 5.66 mmol) in toluene (50.0 ml) over 30 minutes. After the addition was completed, the mixture was cooled to room temperature and diluted with ethyl acetate (100 ml), and then washed with 1.00N HCl(aq) (120 ml) and brine (3×120 ml). The organic layer was dried over $Na_2SO_4$ and concentrated under reduced pressure. Purification by silica gel chromatography (gradient eluent, 0-15% ethyl acetate in hexane) provided 7-Bromo-8-chloro-5-oxo-2,3,4,5-tetrahydro-benzo[b]azepine-1,4-dicarboxylic acid 1-isopropyl ester 4-methyl ester (1.46 g, 62%) as oil. MS (ES+): 418, 420 (M+H).

Step 5. Preparation of 7-Bromo-8-chloro-5-oxo-2,3,4,5-tetrahydro-benzo[b]azepine-1-carboxylic acid isopropyl ester A mixture of 7-Bromo-8-chloro-5-oxo-2,3,4,5-tetrahydro-benzo[b]azepine-1,4-dicarboxylic acid 1-isopropyl ester 4-methyl ester (1.43 g, 3.42 mmol) in HOAc (30.0 ml), concentrated HCl (9.00 ml) and water (3.00 ml) was heated at 100° C. for 4 hours and then cooled down to room temperature overnight. The solvents were evaporated under reduced pressure, and the residue was partitioned between ethyl acetate (100 ml) and saturated $NaHCO_3$ (aq) (100 ml). The aqueous layer was extracted with more ethyl acetate (20.0 ml). The combined organics washed with brine (3×120 ml), dried over $Na_2SO_4$, filtered and concentrated. The material obtained was subjected to the conditions described in step 2 to provide 7-Bromo-8-chloro-5-oxo-2,3,4,5-tetrahydro-benzo[b]azepine-1-carboxylic acid isopropyl ester (0.990 g, 80%) as white solid. MS (ES+): 360, 362 (M+H).

Step 6. Preparation of 5-(3,5-Bis-trifluoromethyl-benzylamino)-7-bromo-8-chloro-2,3,4,5-tetrahydro-benzo[b]azepine-1-carboxylic acid isopropyl ester A mixture of 7-Bromo-8-chloro-5-oxo-2,3,4,5-tetrahydro-benzo[b]azepine-1-carboxylic acid isopropyl ester (0.98 g, 2.72 mmole), 3,5-bistrifluoromethyl benzyl amine (0.682 g, 2.72 mmol) and titanium(IV) isopropoxide (1.00 ml, 3.26 mmol) was stirred at room temperature overnight. To it was added sodium cyanoborohydride (0.684 g, 10.9 mmole) in MeOH (20.0 ml) and the reaction was continued at room temperature for 6 hours. The mixture was partitioned between ethyl acetate (50.0 ml) and water (50.0 ml). The precipitate was removed by filtration. The aqueous layer was extracted with more ethyl acetate (2×50.0 ml). The combined organics washed with brine (3×150 ml). Dried over $Na_2SO_4$, filtered and concentrated to provide the crude product (1.47 g, 88%), which was used directly for the next step without further purification. MS (ES+): 587, 589 (M+H).

Step 7. Preparation of 5-[Acetyl-(3,5-bis-trifluoromethyl-benzyl)-amino]-7-bromo-8-chloro-2,3,4,5-tetrahydro-benzo[b]azepine-1-carboxylic acid isopropyl ester (2312873)

A mixture of crude 5-(3,5-Bis-trifluoromethyl-benzylamino)-7-bromo-8-chloro-2,3,4,5-tetrahydro-benzo[b]azepine-1-carboxylic acid isopropyl ester (1.40 g, 2.38 mmol) and pyridine (5.00 ml) was treated with acetic anhydride (5.00 ml) via dropwise addition. The mixture was stirred at room temperature overnight and then diluted with ethyl acetate (50.0 ml), washed with 1.00N HCl (2×50.0 ml) and brine (3×150 ml). Dried over $Na_2SO_4$, filtered and concentrated. Purification by silica gel chromatography (gradient eluent, 0-40% ethyl acetate in hexane) provided the titled compound (1.28 g, 85%) as white foamy solid. MS (ES+): 629, 631 (M+H).

Example 103

5-[Acetyl-(3,5-bis-trifluoromethyl-benzyl)-amino]-8-chloro-7-methyl-2,3,4,5-tetrahydro-benzo[b]azepine-1-carboxylic acid isopropyl ester

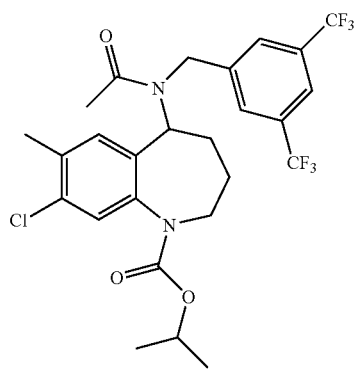

A mixture of 5-[Acetyl-(3,5-bis-trifluoromethyl-benzyl)-amino]-7-bromo-8-chloro-2,3,4,5-tetrahydro-benzo[b]azepine-1-carboxylic acid isopropyl ester (0.118 g, 0.187 mmol), methyl boronic acid (0.0340 g, 0.561 mmol) and cesium fluoride (0.0990 mg, 0.655 mmol) in dioxane (2.00 ml) was purged with nitrogen for 10 minutes. To it was added $PdCl_2(dppf)$ (0.0240 g) in one portion. The mixture was heated at 100° C. overnight. The solid was removed by filtration, washed with ethyl acetate (30.0 ml) and the filtrate was concentrated in vacuo. Purification by silica gel chromatography (gradient eluent, 0-35% ethyl acetate in hexane) provided the titled compound (0.0820 g, 77%) as white foamy solid. MS (ES+): 565 (M+H).

Example 104

(R)-5-[Acetyl-(3,5-bis-trifluoromethyl-benzyl)-amino]-8-chloro-7-methyl-2,3,4,5-tetrahydro-benzo[b]azepine-1-carboxylic acid isopropyl ester)

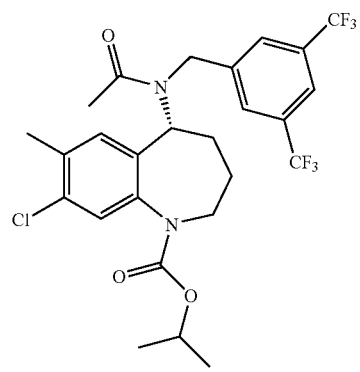

The title compound was obtained by chiral resolution of Example 103 on a Chiralcel OD-H (0.46×250 mm), flow rate: 1.0 ml/min, solvents: 5% 3A alcohol in heptane, $R_f$=6.54 min, wavelength: 220 nm. EE=98.0%. MS (ES+): 564 (M+H).

Example 105

(S)-5-[Acetyl-(3,5-bis-trifluoromethyl-benzyl)-amino]-8-chloro-7-methyl-2,3,4,5-tetrahydro-benzo[b]azepine-1-carboxylic acid isopropyl ester

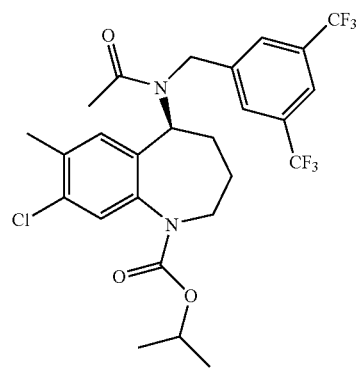

The title compound was obtained by chiral resolution of Example 103 on a Chiralcel OD-H (0.46×250 mm), flow rate:

Example 106

5-[Acetyl-(3,5-bis-trifluoromethyl-benzyl)-amino]-8-chloro-7-trifluoromethyl-2,3,4,5-tetrahydro-benzo[b]azepine-1-carboxylic acid isopropyl ester

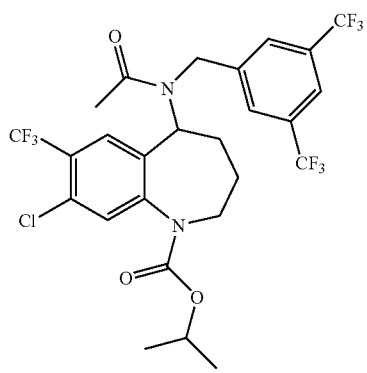

To a heated mixture of 5-[Acetyl-(3,5-bis-trifluoromethyl-benzyl)-amino]-7-bromo-8-chloro-2,3,4,5-tetrahydro-benzo[b]azepine-1-carboxylic acid isopropyl ester (Example 48) (0.335 g, 0.532 mmol) and CuI (0.101 mg, 0.532 mmol) in DMF (5.00 ml)/HMPA (1.00 ml) at 80° C., was added methyl fluorosulphonyl difluoroacetate (0.410 ml, 3.19 mmol). The reaction was continued at 80° C. for an hour. The mixture was partitioned between ethyl acetate (50.0 ml) and brine (50.0 ml). The organic layer was washed with brine (2×150 ml). Dried over Na$_2$SO$_4$, filtered and concentrated. Purification by silica gel chromatography (gradient eluent, 0-35% ethyl acetate in hexane) provided the titled compound (0.00520 g, 1.6%) as white solid. MS (ES+): 619 (M+H).

Example 107

5-[Acetyl-(3,5-bis-trifluoromethyl-benzyl)-amino]-7-bromo-8-trifluoromethyl-2,3,4,5-tetrahydro-benzo[b]azepine-1-carboxylic acid isopropyl ester

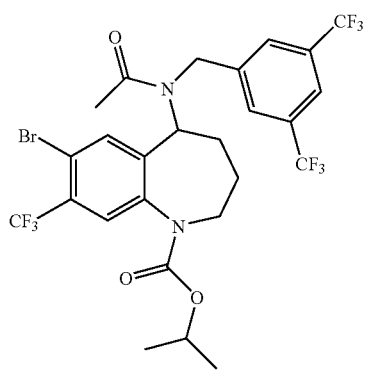

The titled compounds was prepared following the procedures described in Example 102 by replacing 2-amino-4-chloro-benzoic acid methyl ester with 2-amino-4-trifluoromethyl-benzoic acid methyl ester. MS (ES+): 663, 665 (M+H).

Example 108

5-[Acetyl-(3,5-bis-trifluoromethyl-benzyl)-amino]-7-chloro-8-trifluoromethyl-2,3,4,5-tetrahydro-benzo[b]azepine-1-carboxylic acid isopropyl ester

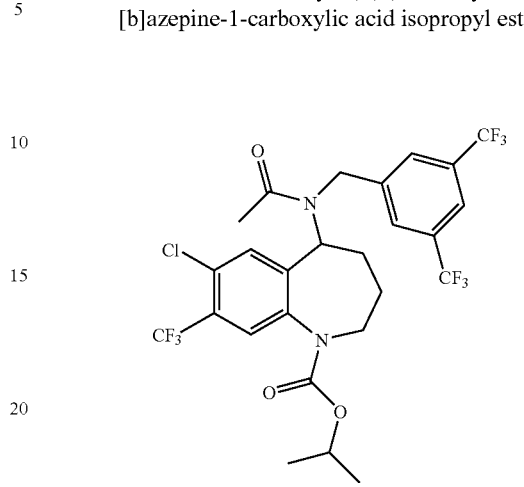

The titled compound was prepared following the procedures described in Example 102 by replacing 5-[acetyl-(3,5-bis-trifluoromethyl-benzyl)-amino]-7-bromo-8-chloro-2,3,4,5-tetrahydro-benzo[b]azepine-1-carboxylic acid isopropyl ester with 5-[acetyl-(3,5-bis-trifluoromethyl-benzyl)-amino]-7-bromo-8-trifluoromethyl-2,3,4,5-tetrahydro-benzo[b]azepine-1-carboxylic acid isopropyl ester. MS (ES+): 619 (M+H).

Example 109

5-[Acetyl-(3,5-bis-trifluoromethyl-benzyl)-amino]-7-methyl-8-trifluoromethyl-2,3,4,5-tetrahydro-benzo[b]azepine-1-carboxylic acid isopropyl ester

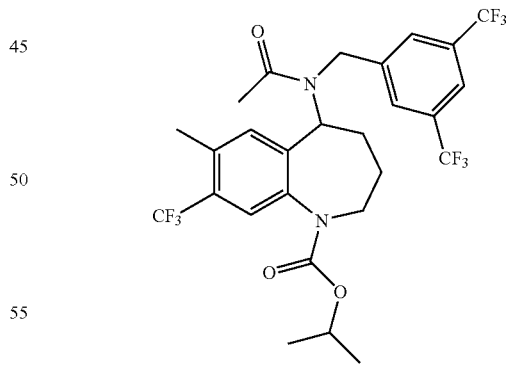

The titled compound was prepared following the procedures described in Example 103 by replacing 5-[Acetyl-(3,5-bis-trifluoromethyl-benzyl)-amino]-7-bromo-8-chloro-2,3,4,5-tetrahydro-benzo[b]azepine-1-carboxylic acid isopropyl ester (Example 103) with 5-[Acetyl-(3,5-bis-trifluoromethyl-benzyl)-amino]-7-bromo-8-trifluoromethyl-2,3,4,5-tetrahydro-benzo[b]azepine-1-carboxylic acid isopropyl ester. MS (ES+): 599 (M+H).

Example 110

(R)-5-[Acetyl-(3,5-bis-trifluoromethyl-benzyl)-amino]-7-methyl-8-trifluoromethyl-2,3,4,5-tetrahydro-benzo[b]azepine-1-carboxylic acid isopropyl ester

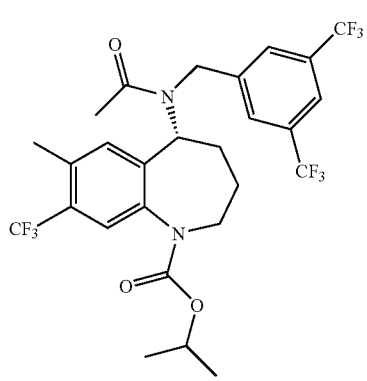

The title compound was obtained by chiral resolution of Example 109 on a Chiralpak AD-H (0.46×150 mm), flow rate: 1.0 ml/min, solvents: 10% propan-2-ol in heptane, $R_f$=2.88 min, wavelength: 225 nm. EE=100%. MS (ES+): 599 (M+H).

Example 111

(S)-5-[Acetyl-(3,5-bis-trifluoromethyl-benzyl)-amino]-7-methyl-8-trifluoromethyl-2,3,4,5-tetrahydro-benzo[b]azepine-1-carboxylic acid isopropyl ester

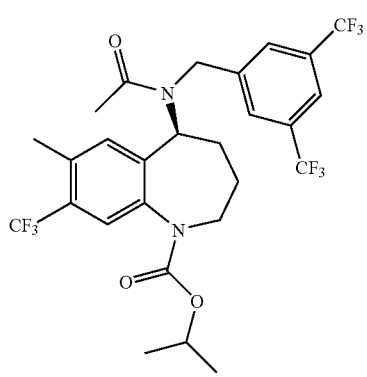

The title compound was obtained by chiral resolution of Example 109 on a Chiralpak AD-H (0.46×150 mm), flow rate: 1.0 ml/min, solvents: 10% propan-2-ol in heptane, $R_f$=4.37 min, wavelength: 225 nm. EE=100%. MS (ES+): 599 (M+H).

Example 112

5-[Acetyl-(3,5-bis-trifluoromethyl-benzyl)-amino]-7-amino-8-trifluoromethyl-2,3,4,5-tetrahydro-benzo[b]azepine-1-carboxylic acid isopropyl ester

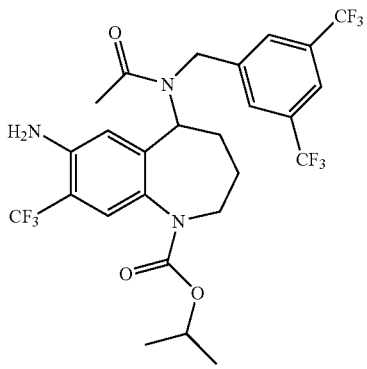

The titled compound was prepared following the procedures described in Example 26 by replacing 5-[acetyl-(3,5-bis-trifluoromethyl-benzyl)-amino]-8-bromo-2,3,4,5-tetrahydro-benzo[b]azepine-1-carboxylic acid isopropyl ester with 5-[(acetyl-(3,5-bis-trifluoromethyl-benzyl)-amino]-7-bromo-8-trifluoromethyl-2,3,4,5-tetrahydro-benzo[b]azepine-1-carboxylic acid isopropyl ester. MS (ES+): 600 (M+H).

Example 113

5-[Acetyl-(3,5-bis-trifluoromethyl-benzyl)-amino]-7-dimethylamino-8-trifluoromethyl-2,3,4,5-tetrahydro-benzo[b]azepine-1-carboxylic acid isopropyl ester

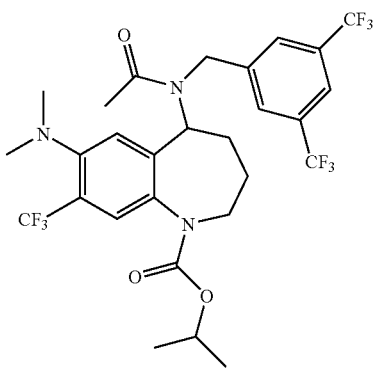

The titled compound was prepared following the procedures described in Example 34 by replacing 5-[Acetyl-(3,5-bis-trifluoromethyl-benzyl)-amino]-8-amino-2,3,4,5-tetrahydro-benzo[b]azepine-1-carboxylic acid isopropyl ester with 5-[Acetyl-(3,5-bis-trifluoromethyl-benzyl)-amino]-7-amino-8-trifluoromethyl-2,3,4,5-tetrahydro-benzo[b]azepine-1-carboxylic acid isopropyl ester. MS (ES+): 628 (M+H).

Example 114

5-[Acetyl-(3,5-bis-trifluoromethyl-benzyl)-amino]-8-trifluoromethyl-7-vinyl-2,3,4,5-tetrahydro-benzo[b]azepine-1-carboxylic acid isopropyl ester

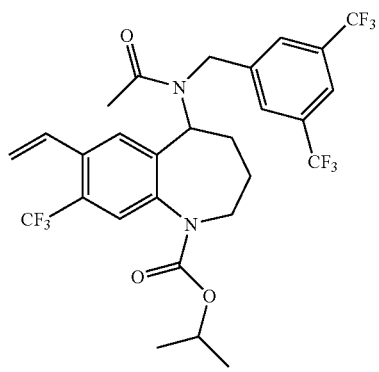

The titled compound was prepared following the procedures described in Example 32 by replacing 5-[Acetyl-(3,5-bis-trifluoromethyl-benzyl)-amino]-8-bromo-2,3,4,5-tetrahydro-benzo[b]azepine-1-carboxylic acid isopropyl ester with 5-[Acetyl-(3,5-bis-trifluoromethyl-benzyl)-amino]-7-bromo-8-trifluoromethyl-2,3,4,5-tetrahydro-benzo[b]azepine-1-carboxylic acid isopropyl ester (Example 107). MS (ES+): 611 (M+H).

Example 115

5-[Acetyl-(3,5-bis-trifluoromethyl-benzyl)-amino]-7-ethyl-8-trifluoromethyl-2,3,4,5-tetrahydro-benzo[b]azepine-1-carboxylic acid isopropyl ester

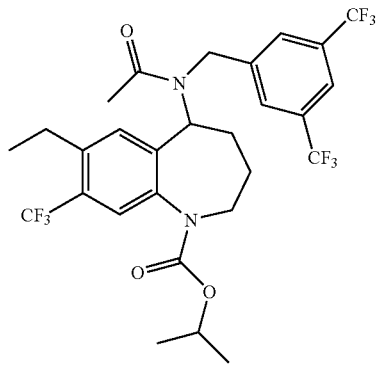

The titled compound was prepared following the procedures described in Example 33 by replacing 5-[Acetyl-(3,5-bis-trifluoromethyl-benzyl)-amino]-8-vinyl-2,3,4,5-tetrahydro-benzo[b]azepine-1-carboxylic acid isopropyl ester with 5-[Acetyl-(3,5-bis-trifluoromethyl-benzyl)-amino]-8-trifluoromethyl-7-vinyl-2,3,4,5-tetrahydro-benzo[b]azepine-1-carboxylic acid isopropyl ester. MS (ES+): 613 (M+H).

Example 116

5-[Acetyl-(3,5-bis-trifluoromethyl-benzyl)-amino]-7-bromo-8-trifluoromethyl-2,3,4,5-tetrahydro-benzo[b]azepine-1-carboxylic acid tert-butyl ester

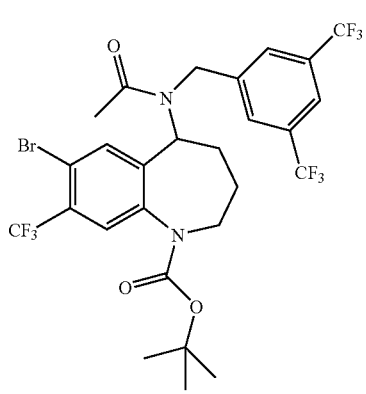

The titled compound was prepared following the procedures described Example 1 by replacing 2-Amino-4-trifluoromethyl-benzoic acid methyl ester with 2-Amino-5-bromo-4-trifluoromethyl-benzoic acid methyl ester in step 1. MS (ES+): 677, 679 (M+H).

Example 117

5-[Acetyl-(3,5-bis-trifluoromethyl-benzyl)-amino]-7-methyl-8-trifluoromethyl-2,3,4,5-tetrahydro-benzo[b]azepine-1-carboxylic acid tert-butyl ester

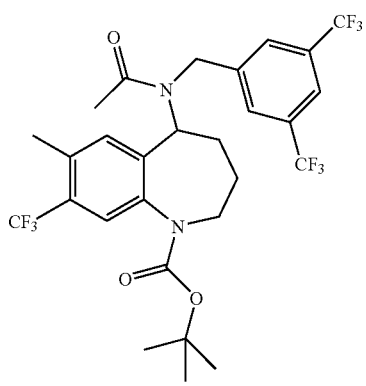

The titled compound was prepared following the procedures described in Example 109 by replacing 5-[Acetyl-(3,5-bis-trifluoromethyl-benzyl)-amino]-7-bromo-8-trifluoromethyl-2,3,4,5-tetrahydro-benzo[b]azepine-1-carboxylic acid isopropyl ester with 5-[Acetyl-(3,5-bis-trifluoromethyl-benzyl)-amino]-7-bromo-8-trifluoromethyl-2,3,4,5-tetrahydro-benzo[b]azepine-1-carboxylic acid tert-butyl ester. MS (ES−): 611 (M−H).

Example 118

(R)-5-[Acetyl-(3,5-bis-trifluoromethyl-benzyl)-amino]-7-methyl-8-trifluoromethyl-2,3,4,5-tetrahydro-benzo[b]azepine-1-carboxylic acid tert-butyl ester

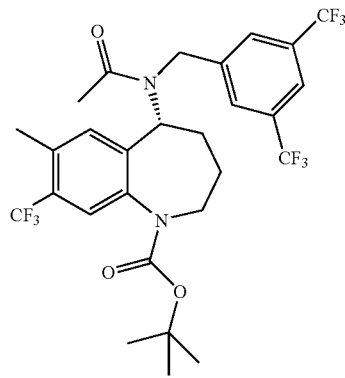

The title compound was obtained by chiral resolution of Example 117 on a Chiralpak AD-H (0.46×150 mm), flow rate: 1.0 ml/min, solvents: 10% propan-2-ol in heptane, $R_f$=2.54 min, wavelength: 225 nm. EE=100%. MS (ES−): 611 (M−H).

Example 119

(S)-5-[Acetyl-(3,5-bis-trifluoromethyl-benzyl)-amino]-7-methyl-8-trifluoromethyl-2,3,4,5-tetrahydro-benzo[b]azepine-1-carboxylic acid tert-butyl ester

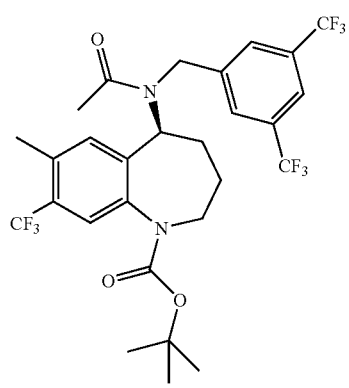

The title compound was obtained by chiral resolution of Example 117 on a Chiralpak AD-H (0.46×150 mm), flow rate: 1.0 ml/min, solvents: 10% propan-2-ol in heptane, $R_f$=3.24 min, wavelength: 225 nm. EE=100%. MS (ES−): 611 (M−H).

Example 120

(S)-5-[Acetyl-(3,5-bis-trifluoromethyl-benzyl)-amino]-7-methyl-8-trifluoromethyl-2,3,4,5-tetrahydro-benzo[b]azepine-1-carboxylic acid tetrahydro-pyran-4-yl ester

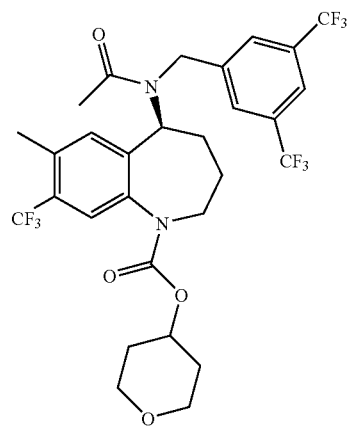

Step 1. Preparation of N-(3,5-Bis-trifluoromethyl-benzyl)-N-(7-methyl-8-trifluoromethyl-2,3,4,5-tetrahydro-1H-benzo[b]azepin-5-yl)-acetamide

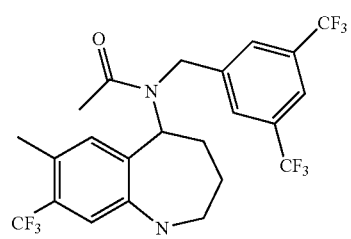

A solution of (S)-5-[Acetyl-(3,5-bis-trifluoromethyl-benzyl)-amino]-7-methyl-8-trifluoromethyl-2,3,4,5-tetrahydro-benzo[b]azepine-1-carboxylic acid tert-butyl ester (0.920 g, 1.50 mmol) (Example 110) in 1:1 TFA/DCM (10.0 ml) was stirred at room temperature for 2 hours. The solvents were evaporated on a (rotary evaporation). Purification by silica gel chromatography (gradient eluent, 0-30% ethyl acetate in hexane) provided the titled compound (0.736 g, 96%) as white solid. MS (ES+): 513 (M+H).

Step 2. Preparation of (S)-5-[Acetyl-(3,5-bis-trifluoromethyl-benzyl)-amino]-7-methyl-8-trifluoromethyl-2,3,4,5-tetrahydro-benzo[b]azepine-1-carboxylic acid tetrahydro-pyran-4-yl ester To a mixture of tetrahydro-pyran-4-ol (0.0830 ml, 0.876 mmol) and di-isopropyl ethyl amine (0.153 ml, 0.876 mmol) in DCM (2.00 ml) at 0° C., was added a solution of phosgene in toluene (0.384 ml, 0.730). The reaction mixture was stirred for 2 hours. To it was added N-(3,5-Bis-trifluoromethyl-benzyl)-N-(7-methyl-8-trifluoromethyl-2,3,4,5-tetrahydro-1H- benzo[b]azepin-5-yl)-acetamide (Step 1) followed by pyridine (0.059 ml, 0.730 mmol) and then warmed up to room temperature overnight. The reaction mixture washed with water (3×2.00 ml), dried over Na$_2$SO$_4$ and concentrated followed by purification by silica gel chromatography. MS (ES+): 641 (M+H).

The following Examples were prepared utilizing this same methodology described in Example 120 wherein R30 is variable and is introduced by replacement of tetrahydro-pyran-4-ol (Example 120, Step 2) with corresponding alcohol.

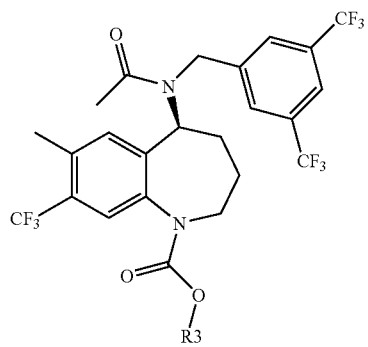

| Example # | Reagent | R30 | MS (ES+) |
| --- | --- | --- | --- |
| Example 121 | Cyclobutanol | Cyclobutyl | 627 (M + H) |
| Example 122 | Cyclopentanol | Cyclopentyl | 627 (M + H) |

Example 123

5-[Acetyl-(3,5-bis-trifluoromethyl-benzyl)-amino]-9-methyl-7-trifluoromethyl-2,3,4,5-tetrahydro-benzo[b]azepine-1 carboxylic acid isopropyl ester

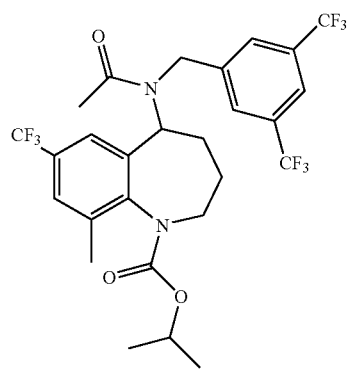

Step 1. Preparation of N-(3,5-Bis-trifluoromethyl-benzyl)-N-(7-trifluoromethyl-2,3,4,5-tetrahydro-1H-benzo[b]azepin-5-yl)-acetamide

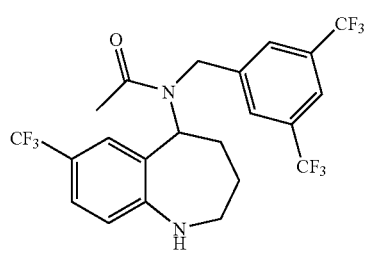

5-[Acetyl-(3,5-bis-trifluoromethyl-benzyl)-amino]-7-trifluoromethyl-2,3,4,5-tetrahydro-benzo[b]azepine-1-carboxylic acid tert-butyl ester (0.118 g, 0.197 mmol) was treated with 1:1 TFA/DCM (2.00 ml) at room temperature. Evaporation of solvents provided the titled compound, which was used directly for the next step without further purification. MS (ES+): 499 (M+H).

Step 2. Preparation of N-(3,5-Bis-trifluoromethyl-benzyl)-N-(9-bromo-7-trifluoromethyl-2,3,4,5-tetrahydro-1H-benzo[b]azepin-5-yl)-acetamide

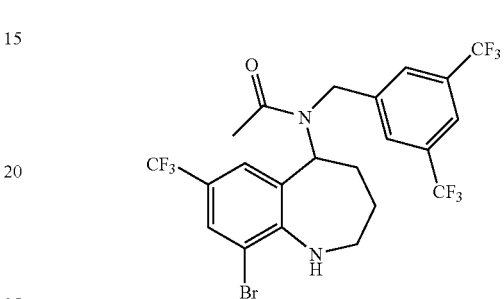

To a solution of crude N-(3,5-Bis-trifluoromethyl-benzyl)-N-(7-trifluoromethyl-2,3,4,5-tetrahydro-1H-benzo[b]azepin-5-yl)-acetamide (0.0980 mg, 0.197 mmol) in HOAc (2.00 ml), was added bromine (0.0106 ml, 0.207 mmol) dropwise. The reaction mixture was stirred at room temperature overnight. Remove the solvent on a rotary evaporator. Purification by silica gel chromatography (eluent, 0-40% ethyl acetate in hexane) provided the titled compound (0.0850 mg, 75%). MS (ES+): 577, 579 (M+H).

Step 3. Preparation of N-(3,5-Bis-trifluoromethyl-benzyl)-N-(9-methyl-7-trifluoromethyl-2,3,4,5-tetrahydro-1H-benzo[b]azepin-5-yl)-acetamide

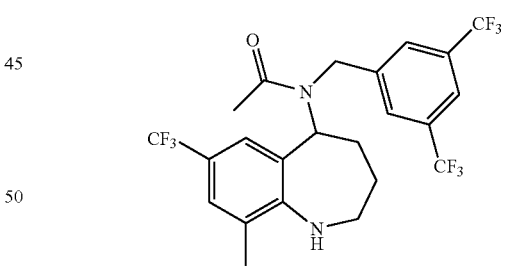

A mixture of N-(3,5-Bis-trifluoromethyl-benzyl)-N-(9-bromo-7-trifluoromethyl-2,3,4,5-tetrahydro-1H-benzo[b]azepin-5-yl)-acetamide (0.0830 g, 0.144 mmol), methyl boronic acid (0.0260 g, 0.432 mmol) and cesium fluoride (0.0770 mg, 0.504 mmol) in dioxane (2.00 ml) was purged with nitrogen for 10 minutes. To it was added PdCl$_2$(dppf) (0.0170 g) in one portion. The mixture was heated at 80° C. overnight. The solid was removed by filtration, washed with ethyl acetate (30.0 ml) and the filtrate was concentrated in vacuo. Purification by silica gel chromatography (gradient eluent, 0-40% ethyl acetate in hexane) provided the titled compound (0.0460 g, 63%) as white solid. MS (ES+): 513 (M+H).

Step 4. Preparation of 5-[Acetyl-(3,5-bis-trifluoromethyl-benzyl)-amino]-9-methyl-7-trifluoromethyl-2,3,4,5-tetrahydro-benzo[b]azepine-1-carboxylic acid isopropyl ester To a solution of N-(3,5-Bis-trifluoromethyl-benzyl)-N-(9-methyl-7-trifluoromethyl-2,3,4,5-tetrahydro-1H-benzo[b]azepin-5-yl)-acetamide (0.0210 g, 0.0410 mmol) and pyridine (0.0100 ml, 0.123 mmol) in dichloromethane (1.00 ml) was added 1M isopropylchloroformate (solution in toluene) (0.120 ml), 0.123 mmol) dropwise. The mixture was stirred at room temperature overnight. The solvents were evaporated on a rotavapor (rotary evaporator). Purification by silica gel chromatography (gradient eluent, 0-30% ethyl acetate in hexane) provided the titled compound (0.0180 g, 72%) as white crystalline. MS (ES+): 599 (M+H).

Example 124

5-[Acetyl-(3,5-bis-trifluoromethyl-benzyl)-amino]-7,9-dimethyl-8-trifluoromethyl-2,3,4,5-tetrahydro-benzo[b]azepine-1-carboxylic acid isopropyl ester

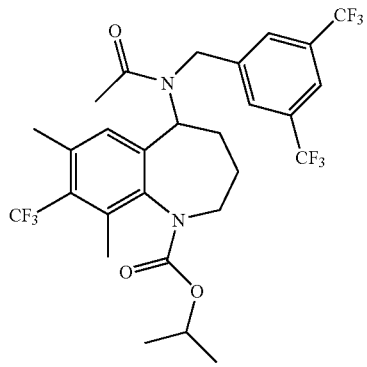

The titled compound was prepared using the method described in Example 123 by replacing 5-[Acetyl-(3,5-bis-trifluoromethyl-benzyl)-amino]-7-trifluoromethyl-2,3,4,5-tetrahydro-benzo[b]azepine-1-carboxylic acid tert-butyl ester with 5-[Acetyl-(3,5-bis-trifluoromethyl-benzyl)-amino]-7-methyl-8-trifluoromethyl-2,3,4,5-tetrahydro-benzo[b]azepine-1-carboxylic acid tert-butyl ester in Example 117, step 1.

Example 125

Synthesis of (+/−)-5-[Acetyl-(3,5-bis-trifluoromethyl-benzyl)-amino]-6-fluoro-7-methyl-2,3,4,5-tetrahydro-benzo[b]azepine-1-carboxylic acid isopropyl ester

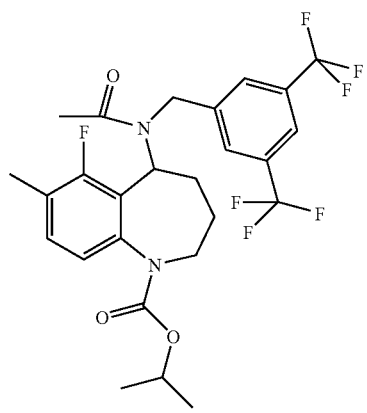

Step 1. Preparation of N-(3-Fluoro-4-methyl-phenyl)-2-hydroxyimino-acetamide

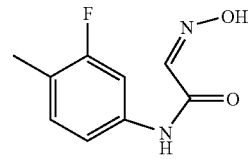

To a solution of chloral hydrate (2.97 g, 17.98 mmol) and anhydrous sodium sulfate (15.20 g, 107 mmol) in water (50 mL) add a mixture of hydroxylamine sulfate (13.67 g, 83.23 mmol), 3-Fluoro-4-methyl-phenylamine (2 g, 15.98 mmol), concentrated hydrochloric acid (1.67 mL) in water (17 mL). Heat the mixture at 45° C. for 2 h and at 75° C. for 1 hr. Cool the mixture to room temperature and filter the solid. Wash the solid with water and ethyl ether. Dry the solid under vacuum to yield the title compound (2.96 g, 94%). $^1$H NMR (DMSO-$d_6$, 300 MHz) δ 2.08 (d, J=1.0 Hz, 3H), 7.12 (t, J=8.8 Hz, 1H), 7.25 (dd, J=2.1, 8.2 Hz, 1H), 7.36 (dd, J=1.6, 12.4 Hz, 1H), 10.18 (s, 1H), 12.11 (s, 1H). MS (ES−): 195 (M−H).

Step 2. Preparation of 6-Amino-2-fluoro-3-methyl-benzoic acid methyl ester

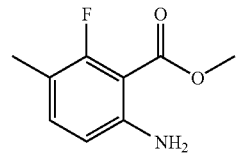

Add of N-(3-Fluoro-4-methyl-phenyl)-2-hydroxyimino-acetamide (2.96 g, 15.10 mmol) in small portions at 65° C. to concentrated sulfuric acid (15 mL) and heat the mixture at 80° C. for 10 minutes. Cool to room temperature, pour into ice water (100 mL) and filter the precipitate and wash with water. Dry the solid to yield 4-Fluoro-5-methyl-1H-indole-2,3-dione and 6-Fluoro-5-methyl-1H-indole-2,3-dione.

Add 30% aqueous hydrogen peroxide solution (4 mL) to a solution of the isatin mixture (2.70 g, 15.10 mmol) in 2 N sodium hydroxide (30 mL) over a period of 5 minutes, stir the mixture at room temperature for 1 h. Add 1N hydrochloric acid to pH=5 and extract with ethyl acetate (3×20 mL). Wash with brine, dry the organic layer over anhydrous sodium sulfate, filter and remove the solvent under reduced pressure. Chromatograph the residue over silica gel, eluting with hexanes/ethyl acetate (3:1), to afford 6-Amino-2-fluoro-3-methyl-benzoic acid and 2-Amino-4-fluoro-5-methyl-benzoic acid (1.91 g, 75%).

Dissolve in ethylacetate (1 mL) and ethanol (1 mL) 6-Amino-2-fluoro-3-methyl-benzoic acid and 2-Amino-4-fluoro-5-methyl-benzoic acid (240 mg, 1.42 mmol) and add (trimethylsilyl) diazomethane (0.7 mL, 1.4 mmol, 2M in hexane) at room temperature and stir the solution for 16 h. Remove the solvent under reduced pressure. Chromatograph the residue over silica gel, eluting with hexanes/ethyl acetate (10:1), to afford the titled compound (50 mg). $^1$H NMR (CDCl$_3$, 300 MHz) δ 2.13 (d, J=2.4 Hz, 3H), 3.9 (s, 3H), 6.39 (dd, J=0.8, 8.5 Hz, 1H), 7.04 (t, J=8.1 Hz, 1H). MS (ES+): 184 (M+H).

Step 3. Preparation of Methyl 6-fluoro-5-methyl-2-isopropoxycarbonyl aminobenzoate

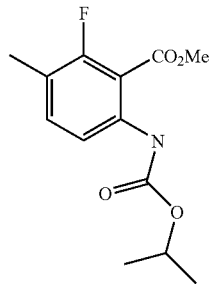

Add isopropyl chloroformate (0.27 mL, 0.27 mmol, 1.0 M in toluene) dropwise to a solution of methyl 2-amino-6-fluoro-5-methylbenzoate (50 mg, 0.27 mmol) and pyridine (0.055 mL, 0.68 mmol) in dichloromethane (1 mL) at 0° C. under an atmosphere of nitrogen and stir at room temperature for 24 h. Add 1N HCl and separate the layers. Extract the aqueous layer with dichloromethane (3×10 mL). Dry the organic layer over anhydrous sodium sulfate, filter, and remove the solvent under reduced pressure. Filter through silica cartridge eluting with hexanes/ethyl acetate (8:1), to afford the title compound (65 mg, 90%): $^1$H NMR (CDCl$_3$) δ 1.30 (d, J=6.5 Hz, 6H), 2.21 (d, J=2.4 Hz, 3H), 3.95 (s, 3H), 4.99 (septet, J=6.5 Hz, 1H), 7.29 (t, J=8.5 Hz, 1H), 8.05 (d, J=8.5 Hz, 1H), 9.56 (br s, 1H); MS (ES+): 270 (M+H)

Step 4. Preparation of Methyl 6-fluoro-5-methyl-2-[isopropoxycarbonyl-(3-methoxycarbonylpropyl) amino]benzoate

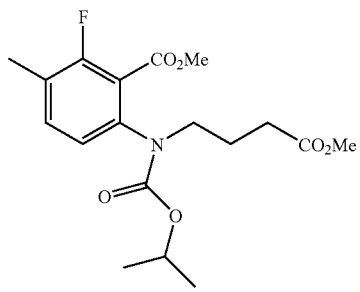

Heat a suspension of Methyl 6-fluoro-5-methyl-2-isopropoxycarbonyl aminobenzoate (65 mg, 0.24 mmol), methyl 4-bromobutyrate (174 mg, 0.96 mmol) and cesium carbonate (313 mg, 0.96 mmol) in N,N-dimethylformamide (1.2 mL) under nitrogen at 80° C. for 3 h. Cool the mixture to room temperature and pour into water (5 mL). Extract with ethyl acetate (3×10 mL). Dry the organic layer over anhydrous sodium sulfate, filter and remove the solvent under reduced pressure. Chromatograph the residue over silica cartridge, eluting with hexanes/ethyl acetate (6:1), to provide the title compound (66 mg, 75%): $^1$H NMR (CDCl$_3$, 300 MHz) δ 1.11-1.28 (m, 6H), 1.85-2.04 (m, 2H), 2.29-2.46 (m, 2H), 3.41 (m, 1H), 3.66 (s, 3H), 3.78 (m, 1H), 3.87 (s, 3H), 4.87 (m, 1H), 6.90 (br d, 1H), 7.26 (t, J=6.5 Hz, 1H). MS (ES+): 370 (M+H)

Step 5. Preparation of Isopropyl 6-fluoro-7-methyl-5-oxo-2,3,4,5-tetrahydrobenzo[b]azepine-1-carboxylate

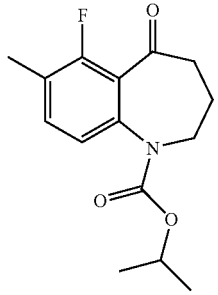

Add a solution of Methyl 6-fluoro-5-methyl-2-[isopropoxycarbonyl-(3-methoxycarbonylpropyl)amino]benzoate (66 mg, 0.18 mmol) in THF (3 mL) to a solution of potassium tert-butoxide (0.36 mL, 0.36 mmol, 1M in THF) in THF (2.5 mL) at room temperature under an atmosphere of nitrogen. After 15 min, add a saturated solution of ammonium chloride and extract with ethyl acetate (3×10 mL). Dry the organic layer over anhydrous sodium sulfate, filter, and remove the solvent under reduced pressure to provide 1-isopropyl-4-methyl-6-fluoro-7-methyl-5-oxo-2,3,4,5-tetrahydrobenzo[b]azepine-1,4-dicarboxylate (61 mg, 100% crude). Dissolve the dicarboxylate (61 mg, 0.18 mmol) in DMSO (1.5 mL) and add water (1 drop) followed by addition of lithium chloride (19 mg, 0.45 mmol) and heat the resulting solution at 160° C. for 45 minutes. Cool the mixture to room temperature and pour into brine. Extract the mixture with ethyl acetate (3×10 mL). Chromatograph the residue over silica cartridge eluting with hexanes/ethyl acetate (8:1), to afford the title compound (24 mg, 48% over two steps): MS (ES+): 280 (M+H)

Step 6. Preparation of (+/−)-Isopropyl 5-[acetyl-(3,5-bistrifluoromethylbenzyl)amino]-6-fluoro-7-methyl-2,3,4,5-tetrahydrobenzo[b]azepine-1-carboxylate

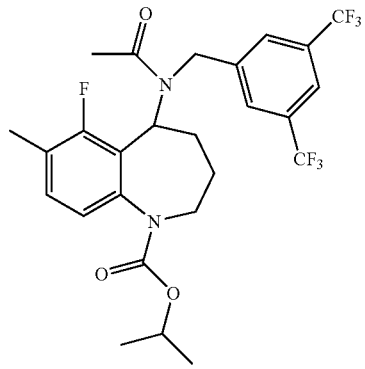

Add 3,5-bis(trifluoromethyl)benzylamine (23 mg, 0.095 mmol) followed by titanium isopropoxide (0.035 mL, 0.12 mmol) to isopropyl 6-fluoro-7-methyl-5-oxo-2,3,4,5-tetrahydro benzo[b]azepine-1-carboxylate (24 mg, 0.086 mmol) at room temperature under an atmosphere of nitrogen and stir the solution for 2 days. Filter the residue over silica cartridge, eluting with hexanes/ethyl acetate (8:1) to afford 5-(3,5-Bis-trifluoromethyl-benzylamino)-6-fluoro-7-methyl-2,3-dihydro-benzo[b]azepine-1-carboxylic (34 mg, 79%). Add methanol (1 mL) and platinum oxide (2 mg, 0.007 mmol) and hydrogenate the mixture at 1 atmosphere and room temperature for 7 h. Filter through celite and remove the solvent under reduced pressure to afford 5-(3,5-Bis-trifluoromethyl-benzylamino)-6-fluoro-7-methyl-2,3,4,5-tetrahydro-benzo[b]azepine-1-carboxylic acid isopropyl ester (36 mg, quantitative). Add acetic anhydride (0.1 mL, 1.07 mmol) dropwise to a suspension of the amine (36 mg, 0.071 mmol) and pyridine (0.1 mL g, 1.07 mmol) in dichloromethane (0.5 mL) under nitrogen cooled to 0° C. After the addition is complete, remove the cooling bath and warm the reaction to room temperature and stir for 12 h. Add 1 N hydrochloric acid and extract with dichloromethane (3×10 mL). Dry the organic layer over anhydrous sodium sulfate, filter and remove the solvent under reduced pressure. Chromatograph the residue over silica cartridge, eluting with hexanes/ethyl:acetate (6:1), to afford the title compound (18 mg, 46%); MS (ES+): 549 (M+H)

Example 126

Synthesis of (+/−)-9-[Acetyl-(3,5-bis-trifluoromethyl-benzyl)-amino]-2,3,6,7,8,9-hexahydro-1H-5-aza-cyclohepta[f]indene-5-carboxylic acid isopropyl ester

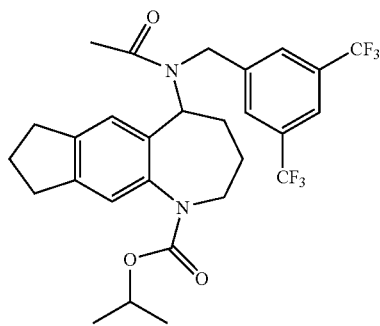

Step 1. Preparation of 2-Hydroxyimino-N-indan-5-yl-acetamide

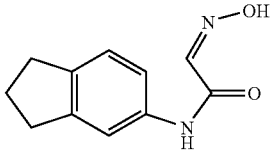

To a solution of chloral hydrate (5.56 g, 33.63 mmol) and anhydrous sodium sulfate (28.58 g, 201.20 mmol) in water (90 mL) add a mixture of hydroxylamine sulfate (25.63 g, 156.16 mmol), 5-aminoindane (4 g, 30.03 mmol), concentrated hydrochloric acid (3.14 mL) in water (30 mL). Heat the mixture at 45° C. for 1 h and at 75° C. for 2 hr. Cool the mixture to room temperature and filter the solid. Wash the solid with water and ethyl ether. Dry the solid under vacuum to yield the title compound (4.98 g, 81%). $^1$H NMR (DMSO-$d_6$, 300 MHz) δ 1.90 (quintuplet, J=7.8 Hz, 2H), 2.72 (q, J=7.8 Hz, 4H), 7.06 (d, J=8.2 Hz, 1H), 7.28 (dd, J=1.5, 8.2 Hz, 1H), 7.49 (bs, 1H), 9.94 (s, 1H), 12.02 (s, 1H). MS (ES−): 203 (M−H).

Step 2. Preparation of 1,5,6,7-Tetrahydro-1-aza-s-indacene-2,3-dione

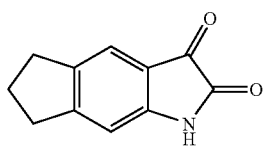

Add 2-Hydroxyimino-N-indan-5-yl-acetamide (4.66 g, 22.84 mmol) in small portions at 65° C. to concentrated sulfuric acid (22 mL) and heat the mixture at 80° C. for 15 minutes. Cool to room temperature, pour into ice water (200 mL) and filter the precipitate. Dissolve the solid in warmed ethanol and leave to cool overnight. Filter the precipitate and wash with ethyl ether. Dry the solid to yield the title compound (3.3 g, 77%). $^1$H NMR (DMSO-$d_6$, 300 MHz) δ 1.98 (quintuplet, J=7.7 Hz, 2H), 2.76 (t, J=7.7 Hz, 2H), 2.85 (t, J=7.7 Hz, 2H), 6.74 (s, 1H), 7.28 (s, 1H). MS (ES−): 186 (M−H).

Step 3. Preparation of 6-Amino-indan-5-carboxylic acid methyl ester

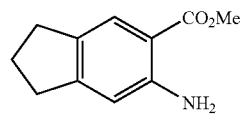

Add 30% aqueous hydrogen peroxide solution (3 mL) to a solution of 1,5,6,7-Tetrahydro-1-aza-s-indacene-2,3-dione (2.18 g, 11.66 mmol) in 2 N sodium hydroxide (23 mL) over a period of 5 minutes, stir the mixture at room temperature for 3 h. Add 1N hydrochloric acid to pH=5 and extract with ethyl acetate (3×20 mL). Wash with brine, dry the organic layer over anhydrous sodium sulfate, filter and remove the solvent under reduced pressure to afford 6-Amino-indan-5-carboxylic acid (1.7 g, 86%). Dissolve in ethylacetate (2 mL) and ethanol (2 mL) and add (trimethylsilyl) diazomethane (9.6 mL, 19.2 mmol, 2M in hexane) at room temperature and stir the solution for 16 h. Remove the solvent under reduced pressure. Chromatograph the residue over silica gel, eluting with hexanes/ethyl acetate (9:1), to afford the title compound (1.19 g, 66%). $^1$H NMR (CDCl$_3$, 300 MHz) δ 2.05 (quintuplet, J=7.3 Hz, 2H), 2.80 (q, J=7.7 Hz, 4H), 6.59 (s, 1H), 7.69 (s, 1H). MS (ES+): 192 (M+H).

Step 4. Preparation of 9-Oxo-2,3,6,7,8,9-hexahydro-1H-5-aza-cyclohepta[f]indene-5-carboxylic acid isopropyl ester

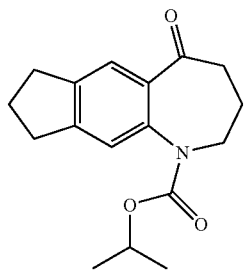

The titled compound was prepared following the procedure described for the preparation of isopropyl 6-fluoro-7-methyl-5-oxo-2,3,4,5-tetrahydrobenzo[b]azepine-1-carboxylate (example 132, from step 3 to 5) by replacing methyl 2-amino-6-fluoro-5-methylbenzoate with 6-Amino-indan-5-carboxylic acid methyl ester in example 132 step 3. MS (ES+): 288 (M+H).

Step 5. Preparation of (+/−)-9-[Acetyl-(3,5-bis-trifluoromethyl-benzyl)-amino]-2,3,6,7,8,9-hexahydro-1H-5-aza-cyclohepta[f]indene-5-carboxylic acid isopropyl ester

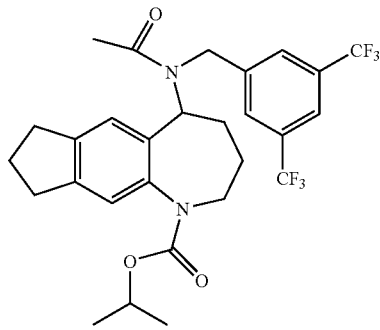

Add 3,5-bis(trifluoromethyl)benzylamine (187 mg, 0.77 mmol) followed by titanium isopropoxide (835 mg, 2.94 mmol) to 9-Oxo-2,3,6,7,8,9-hexahydro-1H-5-aza-cyclohepta[f]indene-5-carboxylic acid isopropyl ester (200 mg, 0.7 mmol) at room temperature under an atmosphere of nitrogen and stir the solution for 3 days. Add methanol (3 mL) and sodium borohydride (40 mg, 1.05 mmol) and stir the mixture under nitrogen at room temperature for 16 hours. Add sodium bicarbonate saturated solution. Filter through celite and wash the residue with AcOEt. Separate organic layer, extract aqueous with AcOEt. Wash organic layer with brine and dry the organic layers over anhydrous sodium sulfate. Filter and remove the solvent under reduced pressure. Purify the residue by silica cartridge, eluting with hexanes/ethyl acetate 9:1, to afford of (+/−)-9-(3,5-bis-trifluoromethyl-benzylamino)-2,3,6,7,8,9-hexahydro-1H-5-aza-cyclohepta[f]indene-5-carboxylic acid isopropyl ester (220 mg). Add acetic anhydride (0.22 mL, 2.33 mmol) dropwise to a solution of the amine (80 mg, 0.155 mmol) and pyridine (0.18 mL, 2.33 mmol) in dichloromethane (1 mL). Stir under nitrogen at room temperature for 14 h. Add 1 M hydrochloric acid and extract with dichloromethane. Dry the organic layer over anhydrous sodium sulfate, filter and remove the solvent under reduced pressure. Purify the residue by silica gel cartridge, eluting with hexanes/ethyl acetate 4:1, to afford the title compound (64 mg, 74%); MS (ES+): 579 (M+H+Na).

Example 127

Synthesis of (+/−)-5-[(3,5-Bis-trifluoromethyl-benzyl)-formyl-amino]-8-chloro-2,3,4,5-tetrahydro-benzo[b]azepine-1-carboxylic acid isopropyl ester

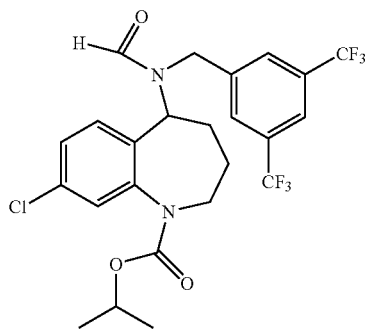

Add acetic anhydride (0.22 mL, 2.34 mmol) and sodium formate (26 mg, 0.39 mmol) to a solution of 5-(3,5-Bis-trifluoromethyl-benzylamino)-8-chloro-2,3,4,5-tetrahydro-benzo[b]azepine-1-carboxylic acid isopropyl ester (see example 3) (40 mg, 0.078 mmol) in formic acid (0.5 mL) and stir at room temperature for 16 h. Chromatograph the residue over silica cartridge, eluting with hexanes/ethyl acetate (5:1), to afford the title compound (27 mg, 64%). $^1$H NMR (DMSO-$d_6$, 300 MHz, 100° C.) δ 1.14 (d, J=6.5 Hz, 6H), 1.63-2.05 (m, 2H), 3.43 (m, 1H), 3.63 (m, 1H), 4.56-4.61 (m, 1H), 4.70-4.72 (m, 1H), 4.77-4.89 (m, 2H) 7.09 (d, J=8.3 Hz, 1H), 7.23-7.26 (m, 2H), 7.80-7.86 (m, 3H), 8.46 (s, 1H). MS (ES+): 537 (M+H).

Example 128

Synthesis of (+/−)-5-[(3,5-Bis-trifluoromethyl-benzyl)-ethyl-amino]-8-chloro-2,3,4,5-tetrahydro-benzo[b]azepine-1-carboxylic acid isopropyl ester

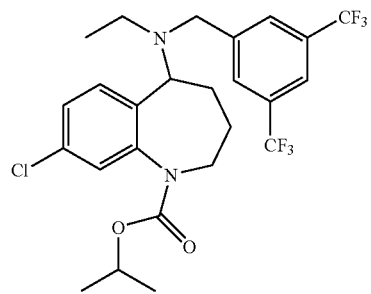

Add acetic acid (0.05 mL, 0.078 mmol) and acetaldehyde (34 mg, 0.78 mmol) to a solution of 5-(3,5-Bis-trifluoromethyl-benzylamino)-8-chloro-2,3,4,5-tetrahydro-benzo[b]azepine-1-carboxylic acid isopropyl ester (see example 3) (40 mg, 0.078 mmol) in dimethylformamide (1 mL). Stir at room temperature for 2 h. Add sodium triacetoxyborohydride (33 mg, 0.16 mmol) and stir the mixture at room temperature for 2 h. Add saturated solution of sodium bicarbonate and extract with ethyl acetate (3×10 mL). Dry the organic layer over anhydrous sodium sulfate, filter and remove the solvent under reduced pressure. Chromatograph the residue over silica cartridge, eluting with hexanes/ethyl acetate (10:1), to afford the title compound (11 mg, 26%). MS (ES+): 537 (M+H).

Example 129

Synthesis of (+/−)-6-[Acetyl-(3,5-bis-trifluoromethyl-benzyl)-amino]-2,3,6,7,8,9-hexahydro-1H-10-aza-cyclohepta[e]indene-10-carboxylic acid isopropyl ester

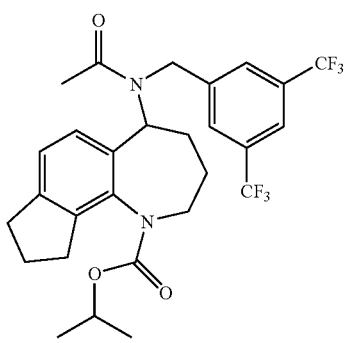

Step 1. Preparation of 2-Hydroxyimino-N-indan-4-yl-acetamide

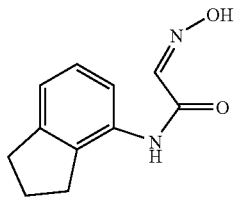

To a solution of chloral hydrate (5.46 g, 33 mmol) and anhydrous sodium sulfate (25.6 g, 180 mmol) in water (92 mL) add a mixture of hydroxylamine sulfate (25.6 g, 156 mmol), 4-aminoindane (4 g, 30 mmol), concentrated hydrochloric acid (3.1 mL) in water (30.8 mL). Heat the mixture up to 45° C. for 90 min, to 52° C. over 45 min and to 75° C. for 60 min. Cool the mixture to room temperature and filter the solid. Wash the solid with water and hexane. Dry the solid under vacuum to yield the title compound (5.54 g, 90%). MS (ES−): 203 (M−H).

Step 2. Preparation of 1,6,7,8-Tetrahydro-1-aza-as-indacene-2,3-dione

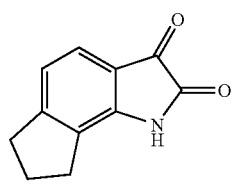

Add 2-Hydroxyimino-N-indan-4-yl-acetamide (5.54 g, 27.1 mmol) in small portions at 80° C. to methanesulfonic acid (21 mL). Stir the mixture at this temperature for 25 min. Cool to room temperature, pour into ice water and filter the precipitate. Dissolve the solid in warmed 1N NaOH, and neutralize with acetic acid. Filter the resulting solid and acidify the filtrate with concentrated HCl. Filter the precipitate and wash with water. Dry the solid to yield the title compound (3.80 g, 72%). MS (ES−): 186 (M−H).

Step 3. Preparation of 4-Amino-indan-5-carboxylic acid methyl ester

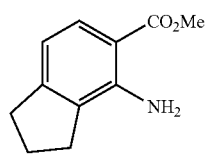

Add 30% aqueous hydrogen peroxide solution (5 mL) in water (44 mL) to a solution of 1,6,7,8-Tetrahydro-1-aza-as-indacene-2,3-dione (3.80 mg, 20.3 mmol) and sodium hydroxide (5.03 g, 126 mmol) in water (97 µL) over a period of 30 minutes, stir the mixture at room temperature for 1 h. Acidulate with 1N hydrochloric acid, filter the solid, wash with water and dry to afford 4-Amino-indan-5-carboxylic acid (3.13 g, 87%). Dissolve 4-Amino-indan-5-carboxylic acid (3.07 g, 17.3 mmol) in ethyl acetate (87 mL) and ethanol (87 mL) and add (trimethylsilyl) diazomethane (17.3 mL, 34.6 mmol, 2M in hexanes) at room temperature and stir the solution for 1 hour. Remove the solvent under reduced pressure. Purify the residue by flash chromatography, eluting with hexanes/ethyl acetate, to afford the title compound (2.50 g, 76%). $^1$H NMR (MeOD, 300 MHz) δ 2.12 (quintuplet, J=7.6 Hz, 2H), 2.75 (t, J=7.5 Hz, 2H), 2.89 (t, J=7.5 Hz, 2H), 3.83 (s, 3H), 6.53 (d, J=8.1 Hz, 1H), 7.66 (d, J=8.1 Hz, 1H). MS (ES+): 192 (M+H).

Step 4. Preparation of 4-Isopropoxycarbonylamino-indan-5-carboxylic acid methyl ester

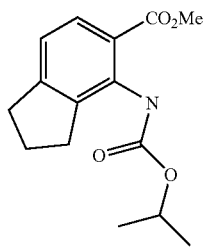

Add isopropyl chloroformate (2.22 mL, 2.22 mmol, 1.0 M in toluene) dropwise to a solution of 4-Amino-indan-5-carboxylic acid methyl ester (425 mg, 2.22 mmol) and pyridine (0.44 mL, 5.5 mmol) in dichloromethane (4.4 mL) at 0° C. under an atmosphere of nitrogen and stir at room temperature for 24 h. Add 1M HCl and separate the layers. Extract the aqueous layer with dichloromethane. Dry the organic layers over anhydrous sodium sulfate, filter, and remove the solvent under reduced pressure, to afford the title compound (576 mg, 93%): $^1$H NMR (MeOD) δ 1.37 (d, J=6.5 Hz, 6H), 2.16 (quintuplet, J=7.7 Hz, 2H), 2.97 (t, J=7.3 Hz, 2H), 3.05 (t, J=7.3 Hz, 2H), 3.94 (s, 3H), 4.97 (m, 1H), 7.22 (d, J=8.1 Hz, 1H), 7.80 (d, J=8.1 Hz, 1H). MS (ES+): 278 (M+H).

Step 5. Preparation of 4-[(3-Ethoxycarbonyl-propyl)-isopropoxycarbonyl-amino]-indan-5-carboxylic acid methyl ester

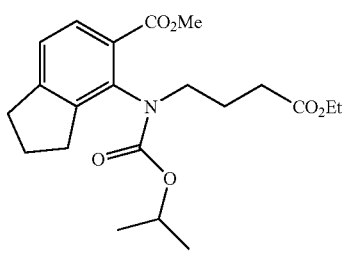

Add a solution of 4-Isopropoxycarbonylamino-indan-5-carboxylic acid methyl ester (570 mg, 2.1 mmol) in DMF (8.2 mL) to a suspension of sodium hydride 60% dispersion mineral oil (82 mg, 2.1 mmol) in DMF (8.2 mL) at 0° C. under an atmosphere of nitrogen and allow to reach room temperature over 1 h. Add ethyl 4-bromobutyrate (0.44 mL, 3.09 mmol) and stir at room temperature for 14 h, then heat at 65° C. for 2 h. Cool the mixture to room temperature, dilute with ethyl acetate, wash with 1M HCl, water and brine. Dry the organic layer over anhydrous sodium sulfate, filter and remove the solvent under reduced pressure. Purify the residue by flash chromatography, eluting with hexanes/ethyl acetate, to provide the title compound (651 mg, 81%): $^1$H NMR (MeOD, 300 MHz) δ 1.03-1.34 (m, 9H), 1.85 (m, 2H), 2.10 (m, 2H), 2.30 (m, 2H), 2.82-3.01 (m, 4H), 3.32 (m, 1H), 3.68 (m, 1H), 3.86 (s, 3H), 4.08 (m, 2H), 4.91 (m, 1H), 7.19 (d, J=7.7 Hz, 1H), 7.77 (d, J=7.7 Hz, 1H). MS (ES+): 392 (M+H).

Step 6. Preparation of 6-Oxo-2,3,6,7,8,9-hexahydro-1H-10-aza-cyclohepta[e]indene-10-carboxylic acid isopropyl ester

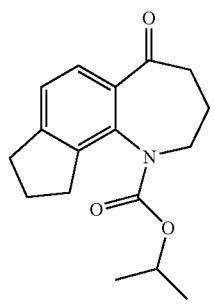

Add a solution of 4-[(3-Ethoxycarbonyl-propyl)-isopropoxycarbonyl-amino]-indan-5-carboxylic acid methyl ester (510 mg, 1.30 mmol) in THF (20.4 mL) to a solution of potassium tert-butoxide (2.60 μL, 2.60 mmol, 1 M in THF) in THF (18 mL) at room temperature under an atmosphere of nitrogen. After 30 min, pour the mixture into ice/water. Treat aqueous phase with 1M HCl to pH neutral and extract with dichloromethane. Dry the organic layer over anhydrous sodium sulfate, filter, and remove the solvent under reduced pressure. Dissolve the former crude in DMSO (11 mL) and add water (2 drops) followed by addition of lithium chloride (134 mg, 3.2 mmol) and heat the resulting solution at 160° C. for 30 minutes. Cool the mixture to room temperature and pour into brine. Extract the mixture with ethyl acetate. Dry the organic layers over anhydrous sodium sulfate, filter and remove the solvent under reduced pressure. Purify the residue by flash chromatography, eluting with hexanes/ethyl acetate, to afford the title compound (302 mg, 81% over two steps): MS (ES+): 288 (M+H).

Step 7. Preparation of (+/−)-6-[Acetyl-(3,5-bis-trifluoromethyl-benzyl)-amino]-2,3,6,7,8,9-hexahydro-1H-10-aza-cyclohepta[e]indene-10-carboxylic acid isopropyl ester

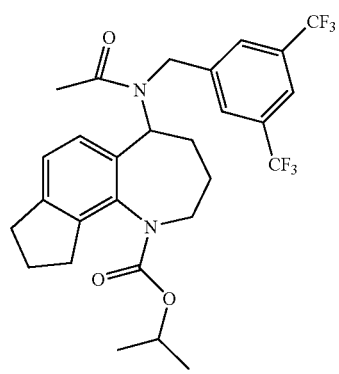

Add 3,5-bis(trifluoromethyl)benzylamine (349 mg, 1.15 mmol) followed by titanium isopropoxide (414 mg, 1.46 mmol) to 6-Oxo-2,3,6,7,8,9-hexahydro-1H-10-aza-cyclohepta[e]indene-10-carboxylic acid isopropyl ester (300 mg, 1.04 mmol) at room temperature under an atmosphere of nitrogen and stir the solution for 14 h. Add methanol (4.3 mL) and sodium borohydride (59 mg, 1.56 mmol) and stir the mixture under nitrogen at room temperature for 45 min. Add 0.1M NaOH, stir for 30 min. Filter through celite and wash the residue with AcOEt. Separate organic layer, extract aqueous with AcOEt. Wash organic layer with brine and dry the organic layers over anhydrous sodium sulfate. Filter and remove the solvent under reduced pressure. Purify the residue by flash chromatography, eluting with hexanes/ethyl acetate, to afford (+/−)-6-(3,5-Bis-trifluoromethyl-benzylamino)-2,3,6,7,8,9-hexahydro-1H-10-aza-cyclohepta[e]indene-10-carboxylic acid isopropyl ester (443 mg, 83%). Add acetic anhydride (0.24 mL, 2.52 mmol) dropwise to a solution of the amine (184 mg, 0.36 mmol) and pyridine (0.25 mL, 3.06 mmol) in dichloromethane (3.1 mL). Stir under nitrogen at room temperature for 14 h. Add 1 M hydrochloric acid and extract with dichloromethane. Dry the organic layer over anhydrous sodium sulfate, filter and remove the solvent under reduced pressure. Purify the residue by flash chromatography, eluting with hexanes/ethyl acetate, to afford the title compound (149 mg, 74%); MS (ES+): 557 (M+H).

Example 130

Synthesis of (+/−)-Isopropyl 5-[acetyl-(3,5-bistrifluoromethylbenzyl)amino]-6-methyl-tetrahydrobenzo[b]azepine-1-carboxylate

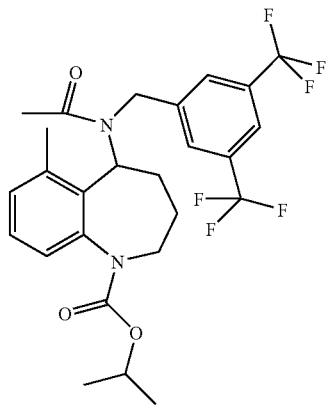

Step 1. Preparation of 2-Amino-6-methyl-benzoic acid methyl ester

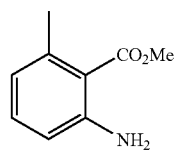

Dissolve 2-Amino-6-methyl-benzoic acid (3.00 g, 19.8 mmol) in ethylacetate (100 mL) and ethanol (100 mL) and add (trimethylsilyl) diazomethane (19.8 mL, 39.7 mmol, 2M in hexane) at room temperature and stir the solution for 1 h 30 min. Remove the solvent under reduced pressure to afford the title compound (3.30 g, quantitative). $^1$H NMR (CDCl$_3$, 300 MHz) δ 2.43 (s, 3H), 3.89 (s, 3H), 5.11 (brs, 2H), 6.52 (m, 2H), 7.08 (t, J=7.7 Hz, 1H). MS (ES+): 166 (M+H).

Step 2. Preparation of 2-Isopropoxycarbonylamino-6-methyl-benzoic acid methyl ester

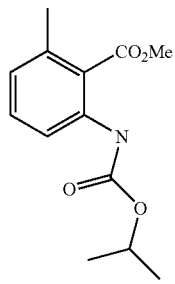

Add isopropyl chloroformate (19.8 mL, 19.8 mmol, 1.0 M in toluene) dropwise to a solution of 2-Amino-6-methyl-benzoic acid methyl ester (3.27 g, 19.8 mmol) and pyridine (4.0 mL, 50 mmol) in dichloromethane (39 mL) at 0° C. under an atmosphere of nitrogen and stir at room temperature for 14 h. Add 1M HCl and separate the layers. Extract the aqueous layer with dichloromethane. Dry the organic layer over anhydrous sodium sulfate, filter, and remove the solvent under reduced pressure. Purify the residue by flash chromatography, eluting with hexanes/ethyl acetate, to afford the title compound (3.80 g, 76%): $^1$H NMR (CDCl$_3$) δ 1.29 (d, J=6.5 Hz, 6H), 2.43 (s, 3H), 3.94 (s, 3H), 5.00 (septuplet, J=6.5 Hz, 1H), 6.90 (d, J=8.1 Hz, 1H), 7.32 (t, J=8.1 Hz, 1H), 8.07 (d, J=8.1 Hz, 1H), 8.86 (brs, 1H). MS (ES+): 252 (M+H).

Step 3. Preparation of 2-[(3-Ethoxycarbonyl-propyl)-isopropoxycarbonyl-amino]-6-methyl-benzoic acid methyl ester

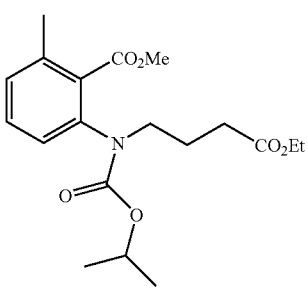

Add a solution of 2-isopropoxycarbonylamino-6-methyl-benzoic acid methyl ester (3.77 g, 15.0 mmol) in DMF (60 mL) to a suspension of sodium hydride 60% dispersion mineral oil (600 mg, 15.0 mmol) in DMF (60 mL) at 0° C. under an atmosphere of nitrogen and allow to reach room temperature over 1 h. Add ethyl 4-bromobutyrate (3.2 mL, 22 mmol) and stir at room temperature for 14 h. Dilute with ethyl acetate, wash with 1M HCl, water and brine. Dry the organic layer over anhydrous sodium sulfate, filter and remove the solvent under reduced pressure. Purify the residue by flash chromatography, eluting with hexanes/ethyl acetate, to provide the title compound (4.60 mg, 84%): $^1$H NMR (CDCl$_3$, 300 MHz) δ 1.05-1.30 (m, 9H), 1.90 (m, 2H), 2.32 (m, 2H), 2.36 (s, 3H), 3.85 (s, 3H), 4.11 (q, J=7.3 Hz, 2H), 4.88 (m, 1H), 7.02 (m, 1H), 7.16 (d, J=7.7 Hz, 1H), 7.31 (t, J=7.9 Hz, 1H). MS (ES+): 366 (M+H).

Step 4. Preparation of 6-Methyl-5-oxo-2,3,4,5-tetrahydro-benzo[b]azepine-1-carboxylic acid isopropyl ester

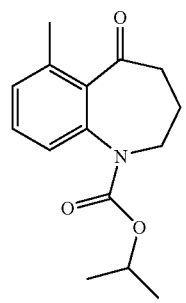

Add a solution of 2-[(3-Ethoxycarbonyl-propyl)-isopropoxycarbonyl-amino]-6-methyl-benzoic acid methyl ester (4.60 g, 12.6 mmol) in THF (197 mL) to a solution of potassium tert-butoxide (25.2 mL, 25.2 mmol, 1 M in THF) in THF (175 mL) at room temperature under an atmosphere of nitrogen. After 30 min, pour the mixture into ice/water. Treat aqueous phase with 1M HCl to pH neutral and extract with dichloromethane. Dry the organic layer over anhydrous sodium sulfate, filter, and remove the solvent under reduced pressure. Dissolve the former crude in DMSO (101 mL) and add water (8 drops) followed by addition of lithium chloride (1.32 g, 31.5 mmol) and heat the resulting solution at 160° C. for 45 minutes. Cool the mixture to room temperature and pour into brine. Extract the mixture with ethyl acetate. Dry the organic layers over anhydrous sodium sulfate, filter and remove the solvent under reduced pressure. Purify the residue by flash chromatography, eluting with hexanes/ethyl acetate, to afford the title compound (903 mg, 27% over two steps): MS (ES+): 262 (M+H).

Step 5. Preparation of (+/−)-Isopropyl 5-[acetyl-(3,5-bistrifluoromethylbenzyl)amino]-6-methyl-tetrahydrobenzo[b]azepine-1-carboxylate

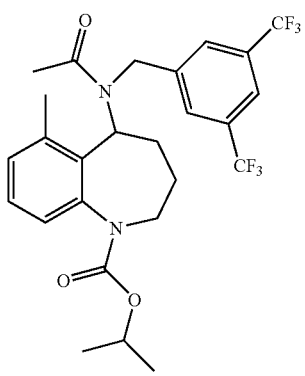

Add 3,5-bis(trifluoromethyl)benzylamine (423 mg, 1.62 mmol) followed by titanium isopropoxide (645 mg, 2.27 mmol) to 6-Methyl-5-oxo-2,3,4,5-tetrahydro-benzo[b] azepine-1-carboxylic acid isopropyl ester (423 mg, 1.62 mmol) at room temperature under an atmosphere of nitrogen and stir the solution for 14 h. Add methanol (6.7 mL) and sodium borohydride (92 mg, 2.43 mmol) and stir the mixture under nitrogen at room temperature for 45 min. Add 0.1M NaOH, stir for 30 min. Filter through celite and wash the residue with AcOEt. Separate organic layer, extract aqueous with AcOEt. Wash organic layer with brine and dry the organic layers over anhydrous sodium sulfate. Filter and remove the solvent under reduced pressure. Purify the residue by flash chromatography, eluting with hexanes/ethyl acetate, to afford (+/−)-5-(3,5-Bis-trifluoromethyl-benzylamino)-6-methyl-2,3,4,5-tetrahydro-benzo[b]azepine-1-carboxylic acid isopropyl ester (27 mg, 3%). Add acetic anhydride (0.037 mL, 0.39 mmol) dropwise to a solution of the amine (27 mg, 0.055 mmol) and pyridine (0.038 mL, 0.43 mmol) in dichloromethane (0.5 mL). Stir under nitrogen at room temperature for 14 h. Add 1 M hydrochloric acid and extract with dichloromethane. Dry the organic layer over anhydrous sodium sulfate, filter and remove the solvent under reduced pressure. Purify the residue by flash chromatography, eluting with hexanes/ethyl acetate, to afford the title compound (28 mg, 96%); MS (ES+): 531 (M+H).

Example 131

Synthesis of (+/−)-Isopropyl 5-[acetyl-(3,5-bistrifluoromethylbenzyl)amino]-8-bromo-9-methyl-tetrahydrobenzo[b]azepine-1-carboxylate

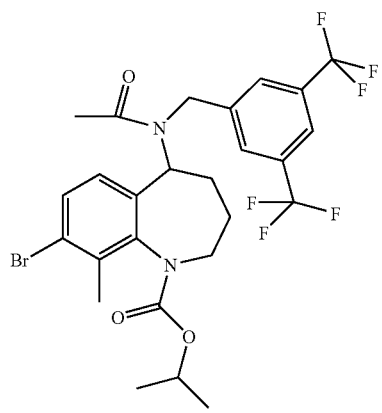

Step 1. Preparation of 2-Amino-4-bromo-3-methyl-benzoic acid methyl ester

Prepare the title compound in a manner analogous to the procedure set forth in the preparation of 4-Amino-indan-5-carboxylic acid methyl ester (see Example 129, step 3) by replacing 4-bromoindane with 3-bromo-2-methyl-phenylamine in Example 129 step 1 and replacing methanesulfonic acid by concentrated sulfuric acid in Example 129, step 2. MS (ES+): 245 (M+H).

Step 2. Preparation of 2-Isopropoxycarbonylamino-4-bromo-3-methyl-benzoic acid methyl ester Add isopropyl chloroformate (14.5 mL, 14.5 mmol, 1.0 M in toluene) dropwise to a solution of 2-Amino-8-bromo-9-methyl-benzoic acid methyl ester (3.54 g, 14.5 mmol) and pyridine (2.9 mL, 36.25 mmol) in dichloromethane (29 mL) at 0° C. under an atmosphere of nitrogen and stir at room temperature for 14 h. Add 1M HCl and separate the layers. Extract the aqueous layer with dichloromethane. Dry the organic layer over anhydrous magnesium sulfate, filter, and remove the solvent under reduced pressure. Purify the residue by flash chromatography, eluting with hexanes/ethyl acetate, to afford the titled compound (3.36 g, 70%): MS (ES+): 331 (M+H).

Step 3. Preparation of 2-[(3-Ethoxycarbonyl-propyl)-isopropoxycarbonyl-amino]-4-bromo-3-methyl-benzoic acid methyl ester Add a solution of 2-Isopropoxycarbonylamino-4-bromo-3-methyl-benzoic acid methyl ester (3.36 g, 10.18 mmol) in DMF (37 mL) to a suspension of sodium hydride 60% dispersion mineral oil (407 mg, 10.18 mmol) in DMF (37 mL) at 0° C. under an atmosphere of nitrogen and allow to reach room temperature over 1 h. Add ethyl 4-bromobutyrate (2.2 mL, 15.27 mmol) and stir at room temperature for 14 h. Dilute with ethyl acetate, wash with 1M HCl, water and brine. Dry the organic layer over anhydrous magnesium sulfate, filter and remove the solvent under reduced pressure. Purify the residue by flash chromatography, eluting with hexanes/ethyl acetate, to provide the titled compound (3.47 g, 77%): MS (ES+): 445 (M+H).

Step 4. Preparation of 8-Bromo-9-methyl-5-oxo-2,3,4,5-tetrahydro-benzo[b]azepine-1-carboxylic acid isopropyl ester Add a solution of 2-[(3-Ethoxycarbonyl-propyl)-isopropoxycarbonyl-amino]-4-bromo-3-methyl-benzoic acid methyl ester (3.47 g, 7.81 mmol) in THF (120 mL) to a solution of potassium tert-butoxide (15.6 mL, 15.62 mmol, 1 M in THF) in THF (120 mL) at room temperature under an atmosphere of nitrogen. After 2 h, pour the mixture into ice/water. Treat aqueous phase with 1M HCl to pH neutral and extract with dichloromethane. Dry the organic layer over anhydrous magnesium sulfate, filter, and remove the solvent under reduced pressure. Dissolve the former crude in DMSO (66 mL) and add water (4 drops) followed by addition of lithium chloride (0.882 g, 20.8 mmol) and heat the resulting solution at 160° C. for 2 h. Cool the mixture to room temperature and pour into brine. Extract the mixture with ethyl acetate. Dry the organic layers over anhydrous magnesium sulfate, filter and remove the solvent under reduced pressure. Purify the residue by flash chromatography, eluting with hexanes/ethyl acetate, to afford the title compound (2.0 g, 72% over two steps): MS (ES+): 341 (M+H).

Step 5. Preparation of (+/−)-5-[Acetyl-(3,5-bis-trifluoromethyl-benzyl)-amino]-8-bromo-9-methyl-2,3,4,5-tetrahydro-benzo[b]azepine-1-carboxylic acid isopropyl ester Inject titanium isopropoxide (1.1 mL, 3.89 mmol) to a mixture of 8-bromo-9-methyl-5-oxo-2,3,4,5-tetrahydro-benzo[b]azepine-1-carboxylic acid isopropyl ester (882 mg, 2.59 mmol) and 3,5-bis(trifluoromethyl)benzylamine (866 mg, 2.85 mmol) at room temperature under an atmosphere of nitrogen and stir the solution for 14 h. Add methanol (11.3 mL) and sodium borohydride (245 mg, 6.47 mmol) and stir the mixture under nitrogen at room temperature for 2 h. Add 0.1M NaOH (61 mL), stir for 30 min. Filter through celite and wash the residue with AcOEt. Separate organic layer, extract aqueous with AcOEt. Wash organic layer with brine and dry the organic layers over anhydrous magnesium sulfate. Filter and remove the solvent under reduced pressure. To the former crude in dichloromethane (9.8 mL), add acetic anhydride (0.980 mL, 10.36 mmol) dropwise and pyridine (0.980 mL, 10.36 mmol), stir under nitrogen at room temperature for 14 h. Add 1 M hydrochloric acid and extract with dichloromethane. Dry the organic layer over anhydrous sodium sulfate, filter and remove the solvent under reduced pressure. Purify the residue by flash chromatography, eluting with hexanes/ethyl acetate, to afford the title compound (162 mg, 10% over two steps); MS (ES+): 610 (M+H).

Example 132

Synthesis of (+/−)-Isopropyl 5-[acetyl-(3,5-bistrifluoromethylbenzyl)amino]-8-chloro-9-methyl-tetrahydrobenzo[b]azepine-1-carboxylate

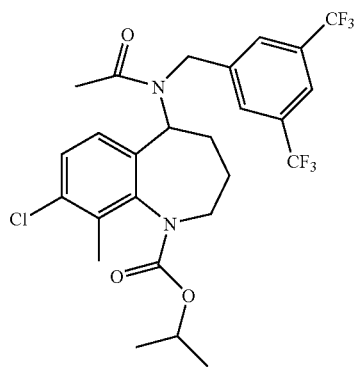

Step 1. Preparation of 8-Chloro-9-methyl-5-oxo-2,3,4,5-tetrahydro-benzo[b]azepine-1-carboxylic acid isopropyl ester In a 10 mL glass tube, 8-Bromo-9-methyl-5-oxo-2,3,4,5-tetrahydro-benzo[b]azepine-1-carboxylic acid isopropyl ester (162 mg, 0.47 mmol), dry DMF (1 mL), NiCl$_2$ (247 mg, 1.9 mmol) and a magnetic stirring bar were placed. The vessel was sealed with a septum and placed into the microwave cavity. Microwave irradiation of 100 W was used, the temperature being ramped from RT to 170° C. Once this temperature was reached, the reaction mixture was held at this temperature for 15 min. After allowing the mixture to cool to room temperature, the reaction vessel was opened and the contents poured into a separating funnel and the tube washed with water and then ether. The organic phase was separated and dried over magnesium sulfate, filtered and removed the solvent under reduced pressure. Purify the residue by flash chromatography, eluting with hexanes/ethyl acetate, to afford the title compound (94 mg, 68%); MS (ES+): 296 (M+H).

Step 2. Preparation of (+/−)-5-[Acetyl-(3,5-bis-trifluoromethyl-benzyl)-amino]-8-chloro-9-methyl-2,3,4,5-tetrahydro-benzo[b]azepine-1-carboxylic acid isopropyl ester Inject titanium isopropoxide (0.176 mL, 0.60 mmol) to a mixture of 8-chloro-9-methyl-5-oxo-2,3,4,5-tetrahydrobenzo[b]azepine-1-carboxylic acid isopropyl ester (90 mg, 0.30 mmol) and 3,5-bis(trifluoromethyl)benzylamine (137 mg, 0.45 mmol) at room temperature under an atmosphere of nitrogen and stir the solution for 14 h. Add methanol (1.3 mL) and sodium borohydride (28 mg, 0.75 mmol) and stir the mixture under nitrogen at room temperature for 2 h. Add 0.1M NaOH, stir for 30 min. Filter through celite and wash the residue with AcOEt. Separate organic layer, extract aqueous with AcOEt. Wash organic layer with brine and dry the organic layers over anhydrous sodium sulfate. Filter and remove the solvent under reduced pressure. Purify the residue by flash chromatography, eluting with hexanes/ethyl acetate, to afford (+/−)-5-(3,5-Bis-trifluoromethyl-benzylamino)-8-chloro-9-methyl-2,3,4,5-tetrahydro-benzo[b]azepine-1-carboxylic acid isopropyl ester (90 mg, 57%). Add acetyl chloride (0.025 mL, 0.34 mmol) dropwise to a solution of the amine (90 mg, 0.17 mmol) and pyridine (0.025 mL, 0.34 mmol) in dichloromethane (1.2 mL) at 0° C. Stir under nitrogen at room temperature for 1 h 30 min. Add water and extract with dichloromethane. Dry the organic layer over anhydrous magnesium sulfate, filter and remove the solvent under reduced pressure. Purify the residue by flash chromatography, eluting with hexanes/ethyl acetate, to afford the title compound (40 mg, 42%); MS (ES+): 565 (M+H).

Example 133

Synthesis of (+/−)-Isopropyl 5-[acetyl-(3,5-bistrifluoromethylbenzyl)amino]-8,9-dimethyl-tetrahydrobenzo[b]azepine-1-carboxylate

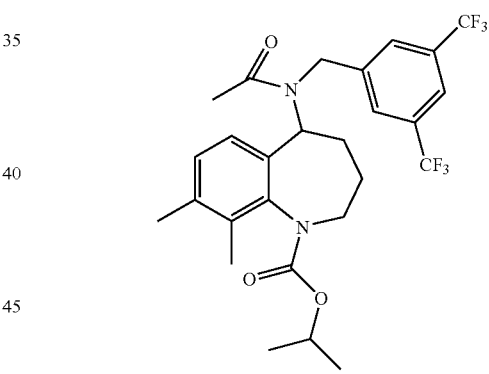

Mix in a 10 mL glass tube provided with a magnetic stirring bar (+/−)-5-[Acetyl-(3,5-bis-trifluoromethyl-benzyl)-amino]-8-bromo-9-methyl-2,3,4,5-tetrahydro-benzo[b]azepine-1-carboxylic acid isopropyl ester (46 mg, 0.075 mmol), trimethylboroxine (0.011 mL, 0.075 mmol), K$_2$CO$_3$ (31 mg, 0.225 mmol) and DMF (0.6 mL). Purge the suspension with nitrogen. Add tetrakis(triphenylphosphine) palladium (0) (9 mg, 0.0075 mmol). Place the vessel into the microwave cavity. Irradiate with 50 W, with a temperature ramp from RT to 150° C. Maintain the temperature at 150° C. for 20 min. Cool the mixture to room temperature, open the reaction vessel and pour the contents into a separating funnel and wash the tube with water and then ethyl acetate. Separate the layers, wash the organic phase with brine and dry over magnesium sulfate, filter and remove the solvent under reduced pressure. Purify the residue by flash chromatography, eluting with hexanes/ethyl acetate, to afford the title compound (7 mg, 17%); MS (ES+): 545 (M+H).

Example 134

Synthesis of (+/−)-Isopropyl 5-[acetyl-(3,5-bistrifluoromethylbenzyl)amino]-6-fluor-tetrahydrobenzo[b]azepine-1-carboxylate

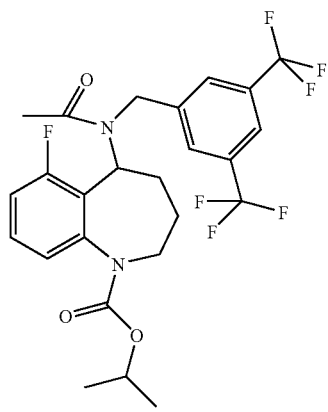

Step 1. Preparation of 2-Amino-6-fluor-benzoic acid methyl ester

Dissolve 2-Amino-6-fluoro-benzoic acid (3.00 g, 19.3 mmol) in ethylacetate (59 mL) and ethanol (59 mL) and add (trimethylsilyl) diazomethane (19.3 mL, 38.68 mmol, 2M in hexane) at room temperature and stir the solution for 1 h 30 min. Remove the solvent under reduced pressure to afford the title compound (3.26 g, quantitative). MS (ES+): 170 (M+H).

Step 2. Preparation of 2-Isopropoxycarbonylamino-6-fluor-benzoic acid methyl ester Add isopropyl chloroformate (20.7 mL, 20.7 mmol, 1.0 M in toluene) dropwise to a solution of 2-Amino-6-fluor-benzoic acid methyl ester (3.5 g, 20.7 mmol) and pyridine (4.2 mL, 51.75 mmol) in dichloromethane (41 mL) at 0° C. under an atmosphere of nitrogen and stir at room temperature for 14 h. Add 1M HCl and separate the layers. Extract the aqueous layer with dichloromethane. Dry the organic layer over anhydrous sodium sulfate, filter, and remove the solvent under reduced pressure. Purify the residue by flash chromatography, eluting with hexanes/ethyl acetate, to afford the title compound (3.00 g, 63%). MS (ES+): 256 (M+H).

Step 3. Preparation of 2-[(3-Ethoxycarbonyl-propyl)-isopropoxycarbonyl-amino]-6-fluor-benzoic acid methyl ester Add a solution of 2-Isopropoxycarbonylamino-6-fluor-benzoic acid methyl ester (3.0 g, 11.76 mmol) in DMF (43 mL) to a suspension of sodium hydride 60% dispersion mineral oil (471 mg, 11.76 mmol) in DMF (43 mL) at 0° C. under an atmosphere of nitrogen and allow to reach room temperature over 1 h. Add ethyl 4-bromobutyrate (2.5 mL, 17.64 mmol) and stir at room temperature for 14 h. Dilute with ethyl acetate, wash with 1M HCl, water and brine. Dry the organic layer over anhydrous magnesium sulfate, filter and remove the solvent under reduced pressure. Purify the residue by flash chromatography, eluting with hexanes/ethyl acetate, to provide the title compound (2.96, 68%). MS (ES+): 370 (M+H).

Step 4. Preparation of 6-Fluor-5-oxo-2,3,4,5-tetrahydro-benzo[b]azepine-1-carboxylic acid isopropyl ester Add a solution of 2-[(3-Ethoxycarbonyl-propyl)-isopropoxycarbonyl-amino]-6-fluor-benzoic acid methyl ester (2.96 g, 8.01 mmol) in THF (123 mL) to a solution of potassium tert-butoxide (16 mL, 16 mmol, 1 M in THF) in THF (123 mL) at room temperature under an atmosphere of nitrogen. After 2 h, pour the mixture into ice/water. Treat aqueous phase with 1M HCl to pH neutral and extract with dichloromethane. Dry the organic layer over anhydrous magnesium sulfate, filter, and remove the solvent under reduced pressure. Dissolve the former crude in DMSO (58 mL) and add water (4 drops) followed by addition of lithium chloride (773 mg, 18.23 mmol) and heat the resulting solution at 160° C. for 2 h. Cool the mixture to room temperature and pour into brine. Extract the mixture with ethyl acetate. Dry the organic layers over anhydrous magnesium sulfate, filter the mixture and evaporate the solvent under reduced pressure. Purify the residue by flash chromatography, eluting with hexanes/ethyl acetate, to afford the title compound (1.0 g, 47% over two steps): MS (ES+): 266 (M+H).

Step 5. Preparation of (+/−)-5-[Acetyl-(3,5-bis-trifluoromethyl-benzyl)-amino]-6-fluor-2,3,4,5-tetrahydro-benzo[b]azepine-1-carboxylic acid isopropyl ester Inject titanium isopropoxide (1.3 mL, 4.32 mmol) to a mixture of 6-fluor-5-oxo-2,3,4,5-tetrahydro-benzo[b]azepine-1-carboxylic acid isopropyl ester (572 mg, 2.16 mmol) and 3,5-bis(trifluoromethyl)benzylamine (972 mg, 3.2 mmol) at room temperature under an atmosphere of nitrogen and stir the solution for 14 h. Purify the residue by flash chromatography, eluting with hexanes/ethyl acetate, to afford 5-(3,5-Bis-trifluoromethyl-benzylamino)-6-fluoro-2,3-dihydro-benzo[b]azepine-1-carboxylic isopropyl ester (820 mg, 77%). Add methanol (9.3 mL) and platinum oxide (37 mg, 0.16 mmol) to 5-(3,5-Bis-trifluoromethyl-benzylamino)-6-fluoro-2,3-dihydro-benzo[b]azepine-1-carboxylic isopropyl ester (742 mg, 1.5 mmol) and hydrogenate the mixture at 1 atmosphere and room temperature for 2 h. Filter through celite and remove the solvent under reduced pressure to afford 5-(3,5-Bis-trifluoromethyl-benzylamino)-6-fluoro-2,3,4,5-tetrahydro-benzo[b]azepine-1-carboxylic acid isopropyl ester (730 mg, quantitative). Add acetic anhydride (0.5 mL, 5.78 mmol) dropwise to a suspension of the amine (190 mg, 0.385 mmol) and pyridine (0.5 mL, 5.78 mmol) in dichloromethane (1.5 mL), stir under nitrogen at room temperature for 14 h. Add 1 M hydrochloric acid and extract with dichloromethane. Dry the organic layer over anhydrous sodium sulfate, filter and remove the solvent under reduced pressure. Purify the residue by flash chromatography, eluting with hexanes/ethyl acetate, to afford the title compound (141 mg, 68%); MS (ES+): 535 (M+H).

Example 135

Synthesis of (+/−)-Isopropyl 5-[acetyl-(3,5-bistrifluoromethylbenzyl)amino]-9-methyl-8-trifluoromethyl-tetrahydrobenzo[b]azepine-1-carboxylate

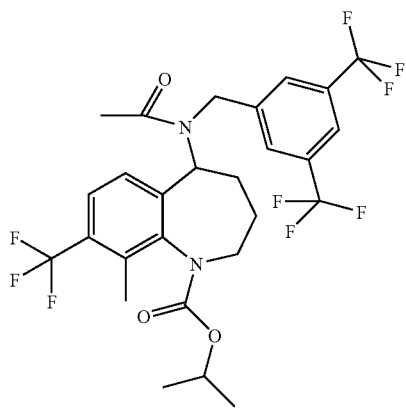

Step 1. Preparation of 7-methyl-6-trifluoromethyl-1H-indole,2,3-dione

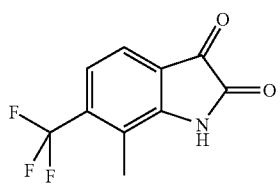

To a solution of chloral hydrate (6.08 g, 36.74 mmol) and anhydrous sodium sulfate (28.5 g, 200.4 mmol) in water (102 mL) add a mixture of hydroxylamine sulfate (28.5 g, 173.68 mmol), 2-methyl-3-trifluoromethyl-phenylamine (5.85 g, 33.4 mmol), concentrated hydrochloric acid (3.5 mL) in water (34 mL). Heat the mixture at 35° C. for 1 h, then heat up to 52° C. for 90 min and at 75° C. for 1 hr. Cool the mixture to room temperature and filter the solid. Wash the solid with water and hexane. Dry the solid under vacuum to afford 2-hydroxyimino-N-(2-methyl-3-trifluoromethyl-phenyl)-acetamide. MS (ES+): 245 (M−H). Add the former crude in small portions at 60° C. to concentrated sulfuric acid (44 mL) and heat the mixture at 80° C. for 1 h. Cool to room temperature, pour into ice water (100 mL) and filter the precipitate. Wash the solid with cool water twice. Dry the solid to afford the title compound (3.54 g, 46% two steps). MS (ES−): 228 (M−H).

Step 2. Preparation of 2-Amino-3-methyl-4-trifluoromethyl-benzoic acid

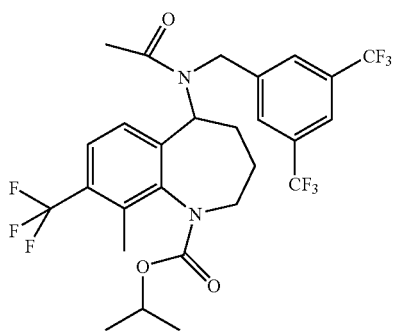

Add 30% aqueous hydrogen peroxide solution (3.8 mL) in water (33 mL) to solution of 7-methyl-6-trifluoromethyl-1H-indole,2,3-dione (3.54 g, 15.46 mmol) and sodium hydroxide (3.83 g, 95.84 mmol) in water (74 mL) slowly. Then stir the mixture at room temperature for 1 h. Add 1N hydrochloric acid to acidulate the mixture. Filter the resulting solid and wash with water. Dry the solid to afford the title compound (1.7 g, 50%). MS (ES+): 218 (M−H).

Step 3. Preparation of (+/−)-Isopropyl 5-[acetyl-(3,5-bistrifluoromethylbenzyl)amino]-9-methyl-8-trifluoromethyl-tetrahydrobenzo[b]azepine-1-carboxylate The titled compound was prepared following the procedures described for the preparation of (+/−)-Isopropyl 5-[acetyl-(3,5-bistrifluoromethylbenzyl)amino]-6-methyl-tetrahydrobenzo[b]azepine-1-carboxylate (Example 130, from step 1 to step 5) by replacing 2-Amino-6-methyl-benzoic acid with 2-Amino-3-methyl-4-trifluoromethyl-benzoic acid in Example 130, step 1. MS (ES+): 599 (M+H).

Example 136

Synthesis of (+/−)-6-[Acetyl-(3,5-bis-trifluoromethyl-benzyl)-amino]-4-bromo-2,3,6,7,8,9-hexahydro-1H-10-aza-cyclohepta[e]indene-10-carboxylic acid isopropyl ester

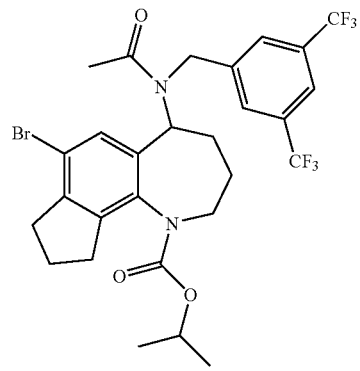

Step 1. Preparation of 4-Amino-7-bromo-indan-5-carboxylic acid methyl ester

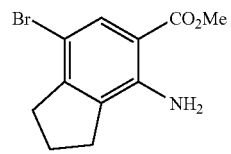

Add N-bromosuccinimide (1.99 g, 11.2 mmol) to 4-Amino-indan-5-carboxylic acid methyl ester (2.15 g, 11.2 mmol) in acetic acid (13 mL). Stir the mixture at room temperature for 48 h. Pour the mixture into ice-water and add ethyl acetate. Separate the layers and wash the organic phase with sat NaHCO$_3$ and brine and dry over sodium sulfate. Remove the solvent under reduced pressure to afford the title compound (3.10, quantitative). MS (ES+): 271 (M+H).

Step 2. (+/−)-6-[Acetyl-(3,5-bis-trifluoromethyl-benzyl)-amino]-4-bromo-2,3,6,7,8,9-hexahydro-1H-10-aza-cyclohepta[e]indene-10-carboxylic acid isopropyl ester

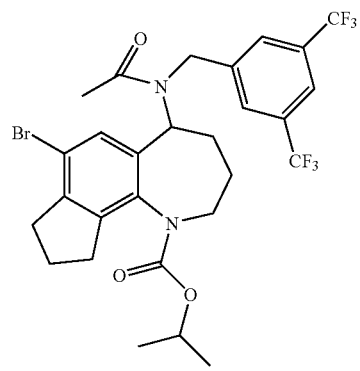

The titled compound was prepared following the procedure described for the preparation of (+/−)-Isopropyl 5-[acetyl-(3,5-bistrifluoromethylbenzyl)amino]-6-fluoro-7- methyl-2,3,4,5-tetrahydrobenzo[b]azepine-1-carboxylate (example 132, from step 3 to 6) by replacing methyl 2-amino-6-fluoro-5-methylbenzoate with 4-Amino-7-bromo-indan-5-carboxylic acid methyl ester in example 132 step 3. MS (ES+): 635.64 (M+H).

Example 137

Synthesis of (+/−)-6-[Acetyl-(3,5-bis-trifluoromethyl-benzyl)-amino]-4-methyl-2,3,6,7,8,9-hexahydro-1H-10-aza-cyclohepta[e]indene-10-carboxylic acid isopropyl ester

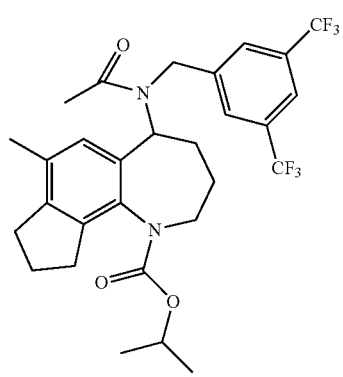

The titled compound was prepared in a manner analogous to the procedure for the preparation of N-(3,5-Bis-trifluoromethyl-benzyl)-N-(9-methyl-7-trifluoromethyl-2,3,4,5-tetrahydro-1H-benzo[b]azepin-5-yl)-acetamide (example 123, step 3) by replacing N-(3,5-Bis-trifluoromethyl-benzyl)-N-(9-bromo-7-trifluoromethyl-2,3,4,5-tetrahydro-1H-benzo[b]azepin-5-yl)-acetamide with (+/−)-6-[Acetyl-(3,5-bis-trifluoromethyl-benzyl)-amino]-4-bromo-2,3,6,7,8,9-hexahydro-1H-10-aza-cyclohepta[e]indene-10-carboxylic acid isopropyl ester (example 144, step 2)

MS (ES+): 570 (M+H).

Example 138

Synthesis of (+/−)-9-[Acetyl-(3,5-bis-trifluoromethyl-benzyl)-amino]-4-methyl-2,3,6,7,8,9-hexahydro-1H-5-aza-cyclohepta[f]indene-5-carboxylic acid isopropyl ester

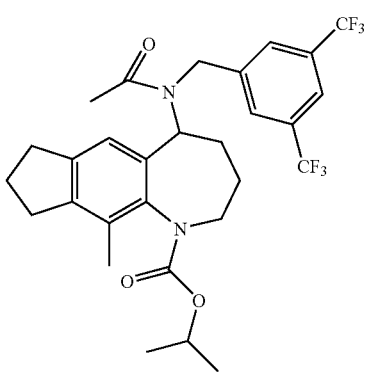

The titled compound was prepared following the procedures described for the preparation of (+/−)-6-[Acetyl-(3,5-bis-trifluoromethyl-benzyl)-amino]-4-methyl-2,3,6,7,8,9-hexahydro-1H-10-aza-cyclohepta[e]indene-10-carboxylic acid isopropyl ester (example 137) by replacing 4-amino-indan-5-carboxylic acid methyl ester by 6-amino-indan-5-carboxylic acid methyl ester in example 136 step 1.

Example 139

Synthesis of 5-[Acetyl-(3,5-bis-trifluoromethyl-benzyl)-amino]-7-trifluoromethyl-2,3,4,5-tetrahydro-benzo[b]azepine-1-carboxylic acid tert-butyl ester

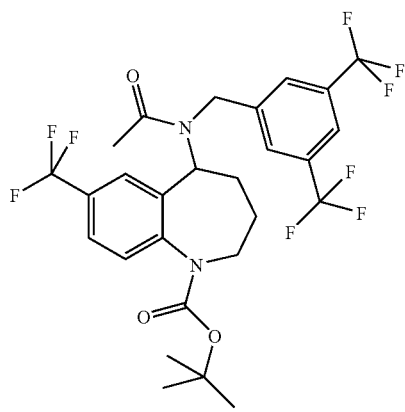

Step 1. Preparation of Methyl-3-trifluoromethyl-2-aminobenzoate

Add palladium (II) acetate (1.89 g, 8.4 mmol), 1,1-bis(diphenylphosphino)ferrocene (6.83 g, 12.3 mmol), and triethyl amine (32 mL, 44.0 mmol) to a solution of 2-bromo-4-trifluoromethylanaline (10.0 g, 42.0 mmol) in dimethylsulfoxide (283 mL) and methanol (187 mL). At 100 psi of carbon monoxide, heat the mixture to 80° C. After heating for 14-16 h cool the reaction to room temperature and filter. Dilute the organics with ethyl acetate (500 mL), wash with water (3×200 mL) and brine (200 mL). Dry the organics over sodium sulfate and filter. Remove solvent under vacuum and chromatograph the crude product using ethyl acetate/hexane (10%) to elute. This provides the title compound (8.0 g, 88%) as an off white solid: H NMR (CDCl$_3$, 400 MHz) δ 3.93 (s, 3H), 6.11 (bs, 2H), 6.73 (d, J=8.4 Hz, 1H), 7.49 (dd, J=2.0, 8.4 Hz, 1H), 8.17 (d, J=2.0 Hz, 1H).

Step 2. Preparation of Methyl-3-trifluoromethyl-2-t-butoxycarbonylaminobenzoate

Add di-t-butyl dicarbonate (2.0 g, 9.1 mmol) to a solution of methyl-3-trifluoromethyl-2-aminobenzoate (2.0 g, 9.1 mmol) in dichloromethane (20 mL). To this mixture, add triethylamine (9.1 mmol) and stir at room temperature under an atmosphere of nitrogen for 72 h. Dilute the reaction with dichloromethane (100 mL) and wash with water (100 mL×2). Dry the separated organic phase over sodium sulfate, filter, and remove solvent under vacuum. Chromatograph the product on silica gel using hexane/ethyl acetate (gradient, 2-10% ethyl acetate/hexane) to elute. This provides the title compound as a colorless solid (1.43 g, 49%): H NMR (CDCl$_3$, 400 MHz) δ 1.54 (s, 9H), 3.99 (s, 3H), 7.75 (dd, J=2.0, 9.2 Hz, 1H), 8.30 (d, J=1.6 Hz, 1H), 8.64 (d, J=9.2 Hz, 1H), 10.48 (s, 1H).

Step 3. Preparation of 2-[tert-Butoxycarbonyl-(3-methoxycarbonyl-propyl)-amino]-5-trifluoromethyl-benzoic acid methyl ester Add 50 mL of DMF to a mixture of methyl-3-trifluoromethyl-2-t-butoxycarbonylaminobenzoate (3.0 g, 9.4 mmol) and methyl 4-bromobutyrate (2.6 g, 14.1 mmol) under an atmosphere of nitrogen. To this, add cesium carbonate (9.2 g, 28.2 mmol) and heat the suspension to 60° C. for 6 h then cool to room temperature. Dilute the reaction with water (200 mL) and ethyl acetate (300 mL). Separate the organic phase and wash with water (100 mL) followed by brine (100 mL). Dry the organics over sodium sulfate, filter, and remove solvent under vacuum. Chromatograph the reaction over silica gel using ethyl acetate/hexane (0-10%) to elute. This provides the title compound as an oil (3.8 g, 97%): H NMR (CDCl$_3$, 400 MHz) δ 1.33 (s, 6H), 1.54 (s, 3H), 1.97 (bm, 2H), 2.41 (bt, J=7.2 Hz, 2H), 3.56-3.85 (m, 5H), 3.94 (bs, 3H), 7.40 (bt, J=8.0 Hz, 1H), 7.78 (dd, J=2.0, 8.0 Hz, 1H), 8.19 (bs, 1H).

Step 4. Preparation of 7-Trifluoromethyl-1,2,3,4-tetrahydro-benzo[b]azepin-5-one Add a solution of methyl 2-[tert-Butoxycarbonyl-(3-methoxycarbonyl-propyl)-amino]-5-trifluoromethyl-benzoic acid methyl ester (0.5 g, 1.3 mmol) in toluene (25 mL) to a suspension of potassium tert-butoxide (0.3 g, 2.6 mmol) in toluene (75 mL) at 70° C., under an atmosphere of nitrogen, over a period of 30 min. After 2 h, cool the reaction to room temperature and quench the reaction with acetic acid (2.6 mmol). Dilute the reaction with water (100 mL) and dichloromethane (100 mL). Separate the organic phase, dry over sodium sulfate, and filter. Remove the solvent under vacuum then dissolve the crude intermediate in acetic acid (20 mL). Dilute with conc. HCl (20 mL) and water (10 mL) and heat the mixture to 100° C. for 4 h. After cooling to room temperature neutralize the reaction with 5N NaOH while cooling in an ice bath. Extract the organics with ethyl acetate (3×100 mL), dry over sodium sulfate, and filter. Remove the solvent under vacuum and chromatograph the product over silica gel using ethyl acetate/hexane (5-20%) to elute. This provides the title compound as an off white solid (0.13 g, 45%): H NMR (CDCl$_3$, 400 MHz) δ 2.22-2.29 (m, 2H), 2.88 (t, J=6.4 Hz), 3.35 (t, J=6.8 Hz), 4.96 (bs, 1H), 6.84 (d, J=8.8 Hz, 1H), 7.46 (dd, J=2.0, 8.8 Hz, 1H), 8.02 (s, 1H).

Step 5. Preparation of 5-Oxo-7-trifluoromethyl-2,3,4,5-tetrahydro-benzo[b]azepine-1-carboxylic acid tert-butyl ester Add di-t-butyldicarbonate (0.68 mmol) to a solution of 7-trifluoromethyl-1,2,3,4-tetrahydro-benzo[b]azepin-5-one (0.1 g, 0.44 mmol) in dichloromethane (10 mL). To this solution add dimethylaminopyridine (0.22 mmol) and diisopropyl ethylamine (0.68 mmol). Stir the resulting mixture at room temperature overnight. Remove solvent under vacuum and chromatograph the product over silica gel using ethyl acetate/hexane (5-20%) to elute. This provides the title compound as an oil (0.13 g, 90%): MS (ES+): 330 (M+H).

Step 6. Preparation of 5-[Acetyl-(3,5-bis-trifluoromethyl-benzyl)-amino]-7-trifluoromethyl-2,3,4,5-tetrahydro-benzo[b]azepine-1-carboxylic acid tert-butyl ester Add 3,5-bis(trifluoromethyl)benzylamine (0.1 g, 0.4 mmol) followed by titanium isopropoxide (1.0 mL) to 5-Oxo-7-trifluoromethyl-2,3,4,5-tetrahydro-benzo[b]azepine-1-carboxylic acid tert-butyl ester (0.13 g, 0.4 mmol) and stir at room temperature overnight. Dilute the mixture with 5 mL of Methanol and add sodium borohydride (0.8 mmol). Stir the suspension at room temperature for 30 min then dilute with water (20 mL) and ethyl acetate (20 mL). Filter the resulting emulsion through celite and wash with ethyl acetate (3×20 mL). Separate the organics, dry over sodium sulfate, and filter. Remove the solvent under vacuum to afford (+/−)-t-butyl-5-(3,5-bistrifluoromethylbenzylamino)-7-trifluoromethyl-2,3,4,5-tetrahydrobenzo[b]azepine-1-carboxylate crude (0.2 g, MS (ES+): 557 (M+H)). Without further purification, add acetyl chloride (0.8 mmol) and pyridine (0.8 mmol) to a solution of (+/−)-t-butyl-5-(3,5-bistrifluoromethylbenzylamino)-7-trifluoromethyl-2,3,4,5-tetrahydrobenzo[b]azepine-1-carboxylate in dichloromethane. After stirring for 2 h remove solvent under vacuum and chromatograph over silica gel using ethyl acetate/hexane (5-40%) to elute. This affords the title compound as an oil (0.2 g, 83%) which foams under vacuum: MS (ES−): 597 (M−H).

Example 140

Synthesis of 5-[Acetyl-(3,5-bis-trifluoromethyl-benzyl)-amino]-8-chloro-2,3,4,5-tetrahydro-benzo[b]azepine-1-carboxylic acid tert-butyl ester

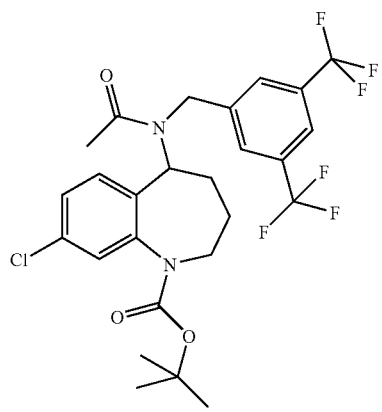

Step 1. Preparation of 2-tert-Butoxycarbonylamino-4-chloro-benzoic acid methyl ester Heat a mixture of methyl 4-chloro-2-aminobenzoate (124.8 g, 0.672 mol) and di-tert-butyl dicarbonate (161.4 g, 0.740 mol) at 70° C. After 48 h, add additional di-t-butyl dicarbonate (21.5 g, 0.0985 mol) and continue heating for 5 days. Concentrate the contents in vacuo. Recrystallize the title compound from Methanol to give a colorless solid (86.2 g, 45%). Remove solvent from the filtrate, under vacuum, and chromatograph over silica gel using ethyl acetate/hexane (0-10%) to elute. This affords an additional 13.5 g (7%) of the title compound: H NMR (CDCl$_3$, 300 MHz) δ 1.53 (s, 9H), 3.91 (s, 3H), 6.96 (dd, J=1.8, 8.7 Hz, 1H), 7.92 (d, J=8.7 Hz, 1H), 8.54 (d, J=2.4 Hz, 1H).

Step 2. Preparation of 2-[tert-Butoxycarbonyl-(3-methoxycarbonyl-propyl)-amino]-4-chloro-benzoic acid methyl ester Add methyl 4-bromobutyrate (54.4 mL, 0.437 mol) to a mixture of 2-tert-butoxycarbonylamino-4-chloro-benzoic acid methyl ester (96.15 g, 0.337 mol) and Cs$_2$CO$_3$ (274.10 g, 0.841 mol) in DMF (1.3 L). Heat the suspension at 55° C. overnight. Remove DMF under vacuum. Dilute the organics with ethyl acetate (1.5 L) and water (1.5 L). Separate the organic layer and extract the aqueous with ethyl acetate (2×0.5 L). Combine the organics and wash with half saturated potassium bicarbonate (1 L), water (2×0.5 L) and brine (0.5 L). Dry the organics over sodium sulfate, filter, and remove solvent under vacuum. This provides the title compound as a yellow oil crude (141.8 g):

H NMR (CDCl$_3$, 300 MHz) δ 1.28 (s, 6H), 1.48 (s, 3H), 1.87-1.98 (m, 2h), 2.33-2.43 (m, 2H), 3.41-3.80 (m, 5H), 3.86 (s, 3H), 7.22-7.31 (m, 2H), 7.85 (d, J=8.1 Hz, 1H).

Step 3. Preparation of 8-Chloro-1,2,3,4-tetrahydro-benzo[b]azepin-5-one

Add a mixture of crude 2-[tert-Butoxycarbonyl-(3-methoxycarbonyl-propyl)-amino]-4-chloro-benzoic acid methyl ester (141.5 g, ~0.337 mol) in toluene to potassium t-butoxide (95%, 100 g, 0.847 mol) in anhydrous toluene (4.5 L) at 60° C. over 1 h. After heating of 24 h concentrate the mixture under vacuum. Partition the residue between ethyl acetate (1.5 L) and saturated KH$_2$PO$_4$ (1.5 L). Separate the aqueous layer and extract with ethyl acetate (2×0.5 L). Combine the organics and wash with water (2×0.5 L). Remove solvent under vacuum. Dissolve the residue in acetic acid (250 mL) and dilute with 5N HCl (1 L). After heating at 85° C. for 4 h, cool the mixture to room temperature. Basify (pH=10) with 5N sodium hydroxide (ca. 1.8 L) while cooling in an ice bath. Extract the organics with ethyl acetate (3×0.5 L) and wash with brine (0.75 L). Dry over sodium sulfate, filter and concentrate under vacuum. Pass the beige crude product through a pad of silica (8 cmD×3 cmH), eluting with DCM/hexanes (2/1, ca. 3.5 L). Concentrate the crude product under vacuum to give a yellow solid. Recrystallize from EtOAc/hexanes (1/4) to give the title compound (42.85 g, 65%) as an off white solid: H NMR (CDCl$_3$, 300 MHz) δ 4.20 (m, 2H), 4.85 (t, J=4.2 Hz, 2H), 5.29 (t, J=4.2 Hz, 2H), 6.71 (bs, 1H), 8.79-8.82 (m, 2H), 9.68 (d, J=5.1 Hz, 1H).

Step 4. Preparation of 8-Chloro-5-oxo-2,3,4,5-tetrahydro-benzo[b]azepine-1-carboxylic acid tert-butyl ester Add dichloromethane (DCM) (100 mL) to a mixture of 8-Chloro-1,2,3,4-tetrahydro-benzo[b]azepin-5-one (3.0 g, 15.4 mmol) and di-t-butyl dicarbonate (38.5 mmol). To this mixture add dimethylaminopyridine (7.7 mmol) and diisopropyl ethylamine (38.5 mmol) and stir at room temperature under an atmosphere of nitrogen for 24 h. Concentrate the reaction under vacuum and chromatograph the product over silica gel using ethyl acetate/hexane (0-20%) to elute. This provides the title compound (3.6 g, 79%) as an oil which crystallizes upon standing: H NMR (CDCl₃, 400 MHz) δ 1.53 (s, 9H), 2.15 (m, 2H), 2.75 (t, J=6.8 Hz, 2H), 3.73 (bt, J=6.8 Hz, 2H), 7.22 (dd, J=2.0, 8.8 Hz, 1H), 7.49 (bs, 1H), 7.80 (d, J=8.8 Hz, 1H). MS (ES+): 296 (M+H).

Step 5. Preparation of 5-(3,5-Bis-trifluoromethyl-benzylamino)-8-chloro-2,3,4,5-tetrahydro-benzo[b]azepine-1-carboxylic acid tert-butyl ester Add 3,5-bis(trifluoromethyl)benzylamine (3.2 g, 13.1 mmol) followed by titanium isopropoxide (5.0 mL) to 8-Chloro-5-oxo-2,3,4,5-tetrahydro-benzo[b]azepine-1-carboxylic acid tert-butyl ester (3.5 g, 11.9 mmol) and stir at room temperature overnight. Dilute the mixture with 20 mL of Methanol and add sodium borohydride (23.8 mmol). Stir the suspension at room temperature for 1 h then dilute with water (200 mL) and ethyl acetate (200 mL). Filter the resulting emulsion through celite and wash with ethyl acetate (3×100 mL). Separate the organics and dry over sodium sulfate. Remove the solvent under vacuum and chromatograph the product over silica gel using ethyl acetate/hexane (5-30%) to elute. This affords the title compound (5.7 g, 93%) as an off white solid: MS (ES+): 523 (M+H).

Step 6. Preparation of 5-[Acetyl-(3,5-bis-trifluoromethyl-benzyl)-amino]-8-chloro-2,3,4,5-tetrahydro-benzo[b]azepine-1-carboxylic acid tert-butyl ester Add acetyl chloride (0.3 mmol) followed by pyridine (0.3 mmol) to a solution of 5-(3,5-Bis-trifluoromethyl-benzylamino)-8-chloro-2,3,4,5-tetrahydro-benzo[b]azepine-1-carboxylic acid tert-butyl ester (0.05 g, 0.1 mmol) in dichloromethane (1 mL). After stirring at room temperature for 24 h remove solvent under vacuum. Chromatograph the product over silica gel using ethyl acetate/hexane (10-40%) to elute. This affords the title compound (0.04 g, 71%) as an oil which foams under vacuum: MS (ES+): 563 (M–H).

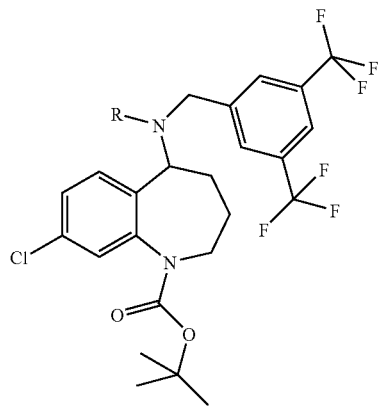

Additional compounds (Examples 141-147) were prepared using the methodology described in step 6 (5-[Acetyl-(3,5-bis-trifluoromethyl-benzyl)-amino]-8-chloro-2,3,4,5-tetrahydro-benzo[b]azepine-1-carboxylic acid tert-butyl ester) above. The R group is varied by replacing acetyl chloride with the appropriate Reagent.

| Example # | Reagent | R | MS (ES+) |
|---|---|---|---|
| 141 | Propionyl chloride | Propane-1-carbonyl | 577 (M – H) |
| 142 | Isovaleryl chloride | 3-methylbutyl-1-carbonyl | 605 (M – H) |
| 143 | Cyclopropanecarbonyl chloride | Cyclopropanecarbonyl | 589 (M – H) |
| 144 | Cyclopentanecarbonyl chloride | Cyclopentanecarbonyl | 617 (M – H) |
| 145 | Benzoyl chloride | Benzoyl | 625 (M – H) |
| 146 | Methoxyacetyl chloride | Methoxyacetyl | 593 (M – H) |
| 147 | 2-Furoyl chloride | Furan-2-carbonyl | 615 (M – H) |

Example 148

Synthesis of 5-[Acetyl-(3,5-bis-trifluoromethyl-benzyl)-amino]-8-chloro-2,3,4,5-tetrahydro-benzo[b]azepine-1-carboxylic acid cyclopentyl ester

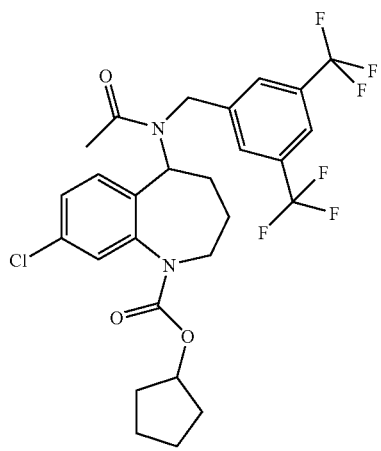

Step 1. Preparation of N-(3,5-Bis-trifluoromethyl-benzyl)-N-(8-chloro-2,3,4,5-tetrahydro-1H-benzo[b]azepin-5-yl)-acetamide

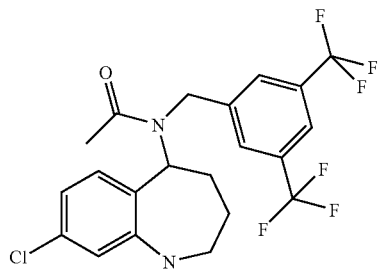

To a solution of 5-[Acetyl-(3,5-bis-trifluoromethyl-benzyl)-amino]-8-chloro-2,3,4,5-tetrahydro-benzo[b]azepine-1-carboxylic acid tert-butyl ester (7.9 g, 14.0 mmol) in dichloromethane (100 mL) add a solution of trifluoroacetic acid (50 mL) in dichloromethane (50 mL). After stirring at room temperature for 1 h, neutralize the reaction with concentrated sodium bicarbonate. Separate the organic phase and wash with water (100 mL) and brine (100 μL). Dry the organics over sodium sulfate, filter, and remove solvent under vacuum. Crystallize the compound from dichloromethane/hexane. This provides the title compound (5.3 g, 81%) as a colorless solid: MS (ES+): 465 (M+H).

Step 2. Preparation 5-[Acetyl-(3,5-bis-trifluoromethyl-benzyl)-amino]-8-chloro-2,3,4,5-tetrahydro-benzo[b]azepine-1-carboxylic acid cyclopentyl ester

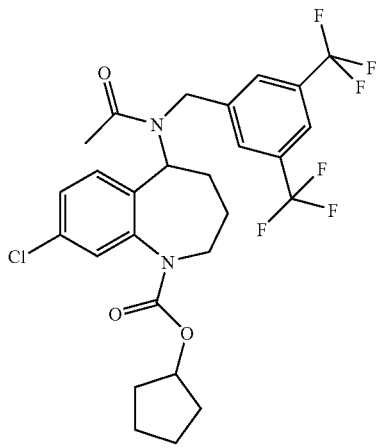

Add phosgene (0.5 mmol) to a solution of cyclopentanol (0.5 mmol) in DCM (1 mL) at 0° C. under nitrogen. To this cooled solution add diisopropyl ethylamine (0.5 mmol) dropwise. After stirring for 1 h with cooling, warm the mixture to room temperature and add N-(3,5-Bis-trifluoromethyl-benzyl)-N-(8-chloro-2,3,4,5-tetrahydro-1H-benzo[b]azepin-5-yl)-acetamide (0.05 g, 0.11 mmol) in dichloromethane (0.5 mL) and pyridine (0.5 mmol). After stirring at room temperature for 14-16 h dilute the reaction with dichloromethane (2 mL) and wash with 5% HCl (2 mL) followed by water (2 mL) and brine (2 mL). Dry the organics over sodium sulfate, filter, and remove solvent under vacuum. Chromatograph the crude mixture over silica gel using ethyl acetate/hexane (10-30%) to elute. This affords the title compound (0.06 g, 95%) as an oil which crystallizes upon standing: MS (ES+): 577 (M+H).

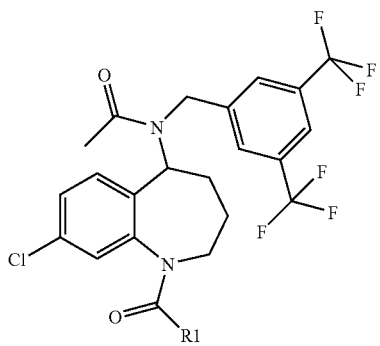

Additional compounds (examples 149-164) were prepared using the methodology described in step 2 (Preparation of 5-[Acetyl-(3,5-bis-trifluoromethyl-benzyl)-amino]-8-chloro-2,3,4,5-tetrahydro-benzo[b]azepine-1-carboxylic acid cyclopentyl ester) above. R1 is varied by replacing cyclopentanol with the appropriate reagent.

| Example # | Reagent | R1 | MS (ES+) |
|---|---|---|---|
| 149 | cyclobutanol | cyclobutyloxy | 563 (M + H) |
| 150 | Cyclohexanol | Cyclohexyloxy | 591 (M + H) |
| 151 | 3-pentanol | pentyloxy | 579 (M + H) |
| 152 | 2,4-dimethyl-3-pentanol | 2,4-dimethyl-3-pentyloxy | 607 (M + H) |
| 153 | 1,3-difluoro-2-butanol | 1,3-difluoro-2-butyloxy | 587 (M + H) |
| 154 | 3-methyl-2-butanol | 3-methyl-2-butyloxy | 579 (M + H) |
| 155 | 2-methyl-3-pentanol | 2-methyl-3-pentyloxy | 593 (M + H) |
| 156 | 1,1,1-trifluoro-2-propanol | 1,1,1-trifluoro-2-propyloxy | 605 (M + H) |
| 157 | 2-butanol | 2-butyloxy | 565 (M + H) |
| 158 | 3-methylcyclopentanol | 3-methylcyclopentyloxy | 591 (M + H) |
| 159 | 1-methoxy-2-butanol | 1-methoxy-2-butyloxy | 595 (M + H) |
| 160 | Tetrahydrothiophene-3-ol-1,1-dioxide | Tetrahydrothiophene-3-oxy-1,1-dioxide | 627 (M + H) |
| 161 | Tetrhydro-3-furanmethanol | Tetrhydro-3-furanmethyloxy | 593 (M + H) |
| 162 | (S)-(+)-3-hydroxytetrahydrofuran | (S)-(+)-3-tetrahydrofuranyloxy | 579 (M + H) |
| 163 | (R)-(−)-3-hydroxytetrahydrofuran | (R)-(−)-3-tetrahydrofuranyloxy | 579 (M + H) |
| 164 | 2-propanethiol | 2-propanethioxy | 567 (M + H) |

Example 165

Synthesis of N-(1-Acetyl-8-chloro-2,3,4,5-tetrahydro-1H-benzo[b]azepin-5-yl)-N-(3,5-bis-trifluoromethyl-benzyl)-acetamide

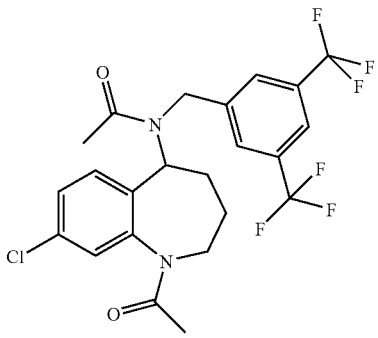

Add acetyl chloride (0.3 mmol) followed by dimethylaminopyridine (cat.) and pyridine (0.3 mmol) to a solution of N-(3,5-Bis-trifluoromethyl-benzyl)-N-(8-chloro-2,3,4,5-tetrahydro-1H-benzo[b]azepin-5-yl)-acetamide (0.05 g, 0.11 mmol) in dichloromethane (1 ml). After stirring for 14-16 h dilute with dichloromethane (2 mL) and wash with 5% HCl (2 mL), water (2 mL) and brine (2 mL). Dry the organics over sodium sulfate, filter, and remove solvent under vacuum. Chromatograph the crude product over silica gel using ethyl acetate/hexane (10-30%) to elute. This afford the title compound (0.04 g, 89%) as a colorless solid: MS (ES+): 507 (M+H).

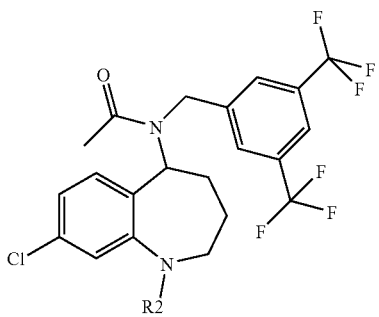

Additional compounds (examples 166-177) were prepared using the same methodology described for the (synthesis of N-(1-Acetyl-8-chloro-2,3,4,5-tetrahydro-1H-benzo[b]azepin-5-yl)-N-(3,5-bis-trifluoromethyl-benzyl)-acetamide. R2 is varied by replacing acetyl chloride with the appropriate reagent.

| Example # | Reagent | R2 | MS (ES+) |
|---|---|---|---|
| 166 | Isobutyryl chloride | isobutylcarbonyl | 535 (M + H) |
| 167 | Propionyl chloride | Propane-1-carbonyl | 521 (M + H) |
| 168 | DL-2-methylbutyryl chloride | DL-2-methylbutyl-1-carbonyl | 549 (M + H) |
| 169 | Isovaleryl chloride | 3-methylbutyl-1-carbonyl | 549 (M + H) |
| 170 | 2-ethylbutyryl chloride | 2-ethylbutyl-1-carbonyl | 563 (M + H) |
| 171 | Cyclopropanecarbonyl chloride | Cyclopropanecarbonyl | 533 (M + H) |
| 172 | Cyclopentanecarbonyl chloride | Cyclopentanecarbonyl | 561 (M + H) |
| 173 | Cyclohexanecarbonyl chloride | Cyclohexanecarbonyl | 575 (M + H) |
| 174 | Benzoyl chloride | Benzoyl | 569 (M + H) |
| 175 | Methoxyacetyl chloride | Methoxyacetyl | 537 (M + H) |
| 176 | 3,3-dimethylacryloyl chloride | 3,3-dimethylacryloyl-1-carbonyl | 547 (M + H) |
| 177 | 2-Furoyl chloride | Furan-2-carbonyl | 559 (M + H) |

Example 178

Synthesis of 5-[Acetyl-(3,5-bis-trifluoromethyl-benzyl)-amino]-8-chloro-2,3,4,5-tetrahydro-benzo[b]azepine-1-carboxylic acid isopropylamide

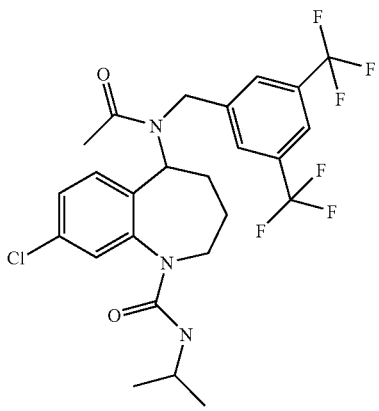

Step 1. Preparation of 5-[Acetyl-(3,5-bis-trifluoromethyl-benzyl)-amino]-8-chloro-2,3,4,5-tetrahydro-benzo[b]azepine-1-carbonyl chloride Add phosgene (1.1 mmol, 1.93 M solution in toluene) followed by diisopropyl ethylamine (1.1 mmol) to a toluene (15 mL) solution of N-(3,5-Bis-trifluoromethyl-benzyl)-N-(8-chloro-2,3,4,5-tetrahydro-1H-benzo[b]azepin-5-yl)-acetamide (0.50 g, 1.1 mmol) under nitrogen. After stirring at room temperature for 1 h, remove solvent under vacuum. Chromatograph the crude product over silica gel using ethyl acetate/hexane (10-30%) to elute. This provides the title compound (0.55 g, 96%) as an oil which solidifies upon standing: MS (ES+): 527 (M+H).

Step 2. Preparation of 5-[Acetyl-(3,5-bis-trifluoromethyl-benzyl)-amino]-8-chloro-2,3,4,5-tetrahydro-benzo[b]azepine-1-carboxylic acid isopropylamide Add isopropyl amine (0.3 mmol) to a dichloromethane solution of 5-[Acetyl-(3,5-bis-trifluoromethyl-benzyl)-amino]-8-chloro-2,3,4,5-tetrahydro-benzo[b]azepine-1-carbonyl chloride (0.050 g, 0.11 mmol) at room temperature under nitrogen. After stirring for 1 h remove solvent under vacuum and chromatograph the crude product over silica gel using ethyl acetate/hexane (30-40%) to elute. This provides the title compound (0.052 g, 87%) as a colorless solid: MS (ES+): 550 (M+H).

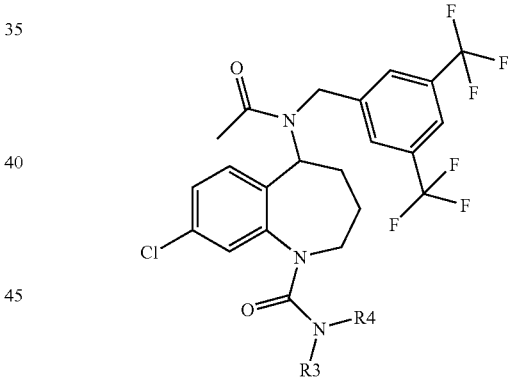

Additional compounds (examples 179-181) are prepared using the same methodology described in Example 178 above (Preparation of 5-[Acetyl-(3,5-bis-trifluoromethyl-benzyl)-amino]-8-chloro-2,3,4,5-tetrahydro-benzo[b]azepine-1-carboxylic acid isopropylamide). R3 and R4 is varied by replacing isopropyl amine with the appropriate reagent.

| Example # | Reagent | R3 | R4 | MS (ES+) |
|---|---|---|---|---|
| 179 | t-butylamine | H | t-butyl | 564 (M + H) |
| 180 | N,N-diethylamine | Ethyl | Ethyl | 564 (M + H) |
| 181 | pyrrolidine | — | — | 562 (M + H) |

Example 182

Synthesis of 5-[Acetyl-(3,5-bis-trifluoromethyl-benzyl)-amino]-7-methyl-8-trifluoromethoxy-2,3,4,5-tetrahydro-benzo[b]azepine-1-carboxylic acid cyclopentyl ester

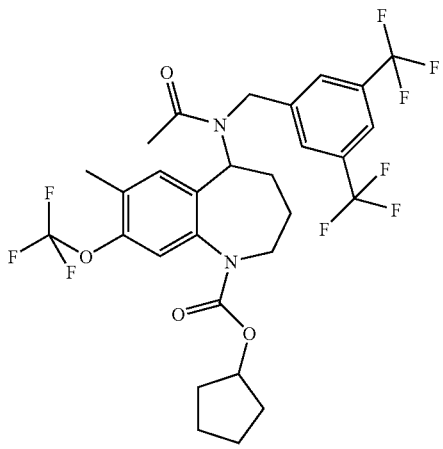

Step 1. Preparation of 4-iodo-3-trifluoromethoxyanaline

Add iodine monochlorinde (5.5 g, 33 mmol) in dichloromethane (10 mL) to a dichloromethane (40 mL) solution of 3-trifluoromethoxyanaline (5.0 g, 28 mmol) at room temperature under nitrogen. To this, add methanol (10 mL) followed by sodium bicarbonate (33 mmol) and stir for 2 h. Quench the reaction with concentrated sodium metabisulfite (100 mL). Separate the organics, wash with brine (50 mL), and dry over sodium sulfate. Chromatograph the crude product over silica gel using ethyl acetate/hexane (2-25%) to elute. This provides the title compound (5.8 g, 68%) as a tan oil: H NMR (CDCl$_3$, 400 MHz) δ 3.85 (bs, 2H), 6.38 (dd, J=2.8, 8.4 Hz, 1H), 6.61 (m, 1H), 7.51 (d, J=8.4 Hz, 1H).

Step 2. Preparation of 4-methyl-3-trifluoromethoxyanaline

Add 1,1-bis(diphenylphosphino)ferrocene palladium (II) chloride (0.8 g, 0.1 mmol), methyl boronic acid (1.8 g, 29.7 mmol) and cesium fluoride (5.2 g, 34.6 mmol) to a solution of 4-iodo-3-trifluoromethoxyanaline (3.0 g, 9.9 mmol) in dioxane under nitrogen. After heating at 80° C. for 3 h, cool the reaction to room temperature and dilute with ethyl acetate (100 mL) and water (100 mL). Separate the organics, wash with brine, dry over sodium sulfate, and filter. Remove the solvent under vacuum and chromatograph the crude product over silica gel using ethyl acetate/hexane (5-20%) to elute. This provides the title compound (1.5 g, 79%) as a tan oil: MS (ES+): 192 (M+H).

Step 3. Preparation of 2-iodo-4-methyl-5-trifluoromethoxyanaline

Add iodine monochloride (1.3 g, 7.8 mmol) in dichloromethane (10 mL) to a dichloromethane (40 mL) solution of 4-methyl-3-trifluoromethoxyanaline (1.5 g, 7.8 mmol) at room temperature under nitrogen. To this add methanol (10 mL) followed by sodium bicarbonate (8.0 mmol) and stir for 2 h. Quench the reaction with concentrated sodium metabisulfite (100 mL). Separate the organics, wash with brine (50 mL), dry over sodium sulfate, and filter. Remove solvent under vacuum and the crude material (2.5 g) crystallizes upon standing. The title compound is used without further purification: H NMR (CDCl$_3$, 400 MHz) δ 2.15 (s, 3H), 4.10 (bs, 2H), 6.61 (m, 1H), 7.51 (s, 1H).

Step 4. Preparation of 2-Amino-5-methyl-4-trifluoromethoxy-benzoic acid methyl ester Add 1,1-bis(diphenylphosphino)ferrocene palladium (II) chloride (0.92 g, 1.1 mmol), potassium carbonate (23.4 mmol), and triethyl amine (1.1 mL, 7.8 mmol) to a solution of 2-iodo-4-methyl-5-trifluoromethoxyanaline (2.5 g, 7.8 mmol) in dimethylsulfoxide (30 mL) and methanol (18 mL). Using a balloon of carbon monoxide, vacuum purge the reaction mixture several times. After heating at 70° C. under carbon monoxide for 1.5 h cool the reaction to room temperature. Dilute the reaction with ethyl acetate (300 mL), wash with water (3×100 mL) followed by brine. Dry the organics over sodium sulfate, filter, and remove solvent under vacuum. This provides the title compound (1.34 g, 69%) as an oil: MS (ES+): 250 (M+H).

Step 5. Preparation of 2-[tert-Butoxycarbonyl-(3-methoxycarbonyl-propyl)-amino]-5-methyl-4-trifluoromethoxy-benzoic acid methyl ester Add methyl 2-Amino-5-methyl-4-trifluoromethoxy-benzoic acid methyl ester (1.3 g, 5.2 mmol) in dichloromethane (10 mL) to a solution of di-tert-butyl dicarbonate (21 mmol) in dichloromethane (10 mL), pyridine (10.4 mmol), and dimethylaminopyridine (catalytic). After stirring at room temperature for 2 h concentrate the mixture under vacuum. Chromatograph the crude intermediate, 2-bis(tert-butoxycarbonyl)amino-5-methyl-4-trifluoromethoxy-benzoic acid methyl ester (bis-Boc), over silica gel using ethyl acetate/hexane to elute. Add 1% TFA in dichloromethane (40 mL) to the bis-Boc intermediate. After stirring at room temperature for 0.5 h, quench the reaction with sodium bicarbonate. Separate the organics and wash with water (50 mL) followed by brine (50 mL). Dry the organics over sodium sulfate, filter, and remove solvent under vacuum. This provides 2-(tert-butoxycarbonylamino)-5-methyl-4-trifluoromethoxy-benzoic acid methyl ester (1.4 g) as a colorless solid.

Add methyl 4-bromobutyrate (1.1 g, 6.0 mmol) and cesium carbonate (3.9 g, 12.0 mmol) to a DMF solution of 2-(tert-butoxycarbonylamino)-5-methyl-4-trifluoromethoxy-benzoic acid methyl ester (1.4 g, 4.0 mmol) under nitrogen. After stirring at 60° C. for 5 hours, the reaction mixture is cooled to room temperature and diluted with ethyl acetate (150 mL). Wash the organics with water (2×150 mL) followed by brine (100 mL), dry over sodium sulfate, and filter. Remove the solvent under vacuum and chromatograph the crude product over silica gel using ethyl acetate/hexane (5-30%) to elute. This provides the title compound (1.1 g, 61%) as an oil: H NMR (CDCl$_3$, 400 MHz) δ 1.28 (s, 6H), 1.49 (s, 3H), 1.91 (m, 2H), 2.33 (m, 5H), 3.39 (m, 1H), 3.63 (s, 3H), 3.77 (m, 1H), 3.86 (bs, 3H), 7.06 (m, 1H), 7.80 (m, 1H). MS (ES+): 350 (M+H-100).

Step 6. Preparation of 7-Methyl-8-trifluoromethoxy-1,2,3,4-tetrahydro-benzo[b]azepin-5-one Add a solution of 2-[tert-Butoxycarbonyl-(3-methoxycarbonyl-propyl)-amino]-5-methyl-4-trifluoromethoxy-benzoic acid methyl ester (1.1 g, 2.4 mmol), in toluene (25 mL) to a solution of potassium t-butoxide (0.51 g, 4.9 mmol) in toluene (75 mL) at 100° C. over 30 min. After heating for 1 h cool the reaction to room temperature and quench the reaction with acetic acid (5.0 mmol). Dilute the reaction with ethyl acetate (100 mL) and wash with water (2×200 mL) followed by brine (200 mL). Dry the organics over sodium sulfate and remove solvent under vacuum. Dissolve the residue in acetic acid (25 mL) and dilute with concentrated HCl (15 mL) and water (10 mL). Heat the mixture at 100° C. for 2 h then cool to room temperature. While cooling in an ice bath neutralize the reaction with 5 N NaOH. Extract the organics with ethyl acetate (200 mL) and wash the organic with brine (100 mL). Remove solvent under vacuum and chromatograph the crude product over silica gel using ethyl acetate/hexane (5-20%) to elute. This provides the title compound (0.28 g, 44%) as an oil that crystallizes upon standing: H NMR (CDCl₃, 400 MHz) δ 2.11-2.18 (m, 5H), 2.81 (t, J=6.8 Hz, 2H), 3.24 (t, J=6.8 Hz, 2H), 6.61 (m, 1H), 7.59 (s, 1H). MS (ES+): 260 (M+H).

Step 7. Preparation of 5-[Acetyl-(3,5-bis-trifluoromethyl-benzyl)-amino]-7-methyl-8-trifluoromethoxy-2,3,4,5-tetrahydro-benzo[b]azepine-1-carboxylic acid cyclopentyl ester Add phosgene (1.5 mmol, 1.93 M solution in toluene) to a solution of cyclopentanol (0.17 g, 1.9 mmol) in DCM (3 mL) at 0° C. under nitrogen. To this cooled solution add diisopropyl ethylamine (0.26 mL, 1.5 mmol) dropwise. After stirring for 1 h with cooling, warm the mixture to room temperature and add 7-Methyl-8-trifluoromethoxy-1,2,3,4-tetrahydro-benzo[b]azepin-5-one (0.10 g, 0.38 mmol) in dichloromethane (2 mL). After stirring for 1 h at room temperature, dilute with dichloromethane (5 mL) and wash with 5% HCl (5 mL) followed by water (5 mL) and brine (5 mL). Dry the organics over sodium sulfate, filter, and remove solvent under vacuum. To this residue, add titanium isopropoxide (1 mL) and 3,5-bis(trifluoromethyl)benzylamine (0.18 g, 0.76 mmol). After stirring at room temperature over night dilute with methanol (3 mL) and add sodium borohydride (3.0 mmol). After 1 h of stirring at room temperature dilute the reaction with water (5 mL) and ethyl acetate (10 mL). Filter the resulting emulsion through a pad of celite and rinse with ethyl acetate (3×5 mL). Separate the organics and wash with water (10 mL) followed by brine (10 mL). Dry the organics over sodium sulfate, filter, and concentrate under vacuum. To This residue in dichloromethane (5 mL), add acetyl chloride (2.3 mmol) followed by pyridine (2.3 mmol). After stirring for 0.5 h dilute with dichloromethane (5 mL), wash with 5% HCl (5 mL), water (5 mL) and brine (5 mL). Dry the organics over sodium sulfate and concentrate under vacuum. Chromatograph the crude product over silica gel using ethyl acetate/hexane (10-30%) to elute. This provides the title compound (0.14 g, 60%) as an oil that solidifies upon standing: MS (ES+): 641 (M+H).

Example 185

Synthesis of (S)-9-[Acetyl-(3,5-bis-trifluoromethyl-benzyl)-amino]-2,2-difluoro-6,7,8,9-tetrahydro-1,3-dioxa-5-aza-cyclohepta[f]indene-5-carboxylic acid tert-butyl ester

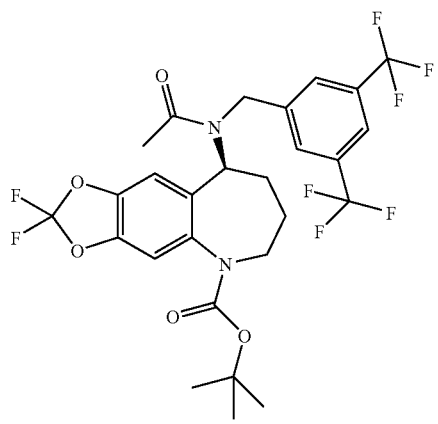

Step 1. Preparation of 2,2-Difluoro-9-oxo-6,7,8,9-tetrahydro-1,3-dioxa-5-aza-cyclohepta[f]indene-5-carboxylic acid tert-butyl ester The title compound was prepared using procedures analogous to Example 182 (Synthesis of 5-[Acetyl-(3,5-bis-trifluoromethyl-benzyl)-amino]-7-methyl-8-trifluoromethoxy-2,3,4,5-tetrahydro-benzo[b]azepine-1-carboxylic acid cyclopentyl ester, steps 3-7), starting with 2,2-difluoro-benzo[1,3]dioxol-5-ylamine in step 3 and replacing phosgene/cyclopropanol with di-t-butyl dicarbonate in step 7.

Step 2. Preparation of (R)-2,2-Difluoro-9-hydroxy-6,7,8,9-tetrahydro-1,3-dioxa-5-aza-cyclohepta[f]indene-5-carboxylic acid tert-butyl ester Add a solution of 2,2-Difluoro-9-oxo-6,7,8,9-tetrahydro-1,3-dioxa-5-aza-cyclohepta[f]indene-5-carboxylic acid tert-butyl ester (2.2 mmol) in THF (20 mL), to a cooled (−78° C.) solution of Borane-methyl sulfide (2.6 mmol) and (R)-2-methyl-CBS-oxazaborolidine (3.3 mmol) in THF (20 mL). After warming slowly to 0° C. for 1 h, quench the reaction with methanol (2 mL). Remove solvent under vacuum and chromatograph using ethyl acetate/hexane (2-35%) to elute. This gives the title compound as a colorless solid.

Step 3. Preparation of (S)-9-Amino-2,2-difluoro-6,7,8,9-tetrahydro-1,3-dioxa-5-aza-cyclohepta[f]indene-5-carboxylic acid tert-butyl ester To a solution of (R)-2,2-Difluoro-9-hydroxy-6,7,8,9-tetrahydro-1,3-dioxa-5-aza-cyclohepta[f]indene-5-carboxylic acid tert-butyl ester (1.9 mmol) in Toluene, add DPPA (2.5 mmol) and DBU (2.5 mmol). After heating the mixture at 65° C. for 14 h, remove solvent under vacuum and chromatograph the intermediate using ethyl acetate/hexane (5-20%) to elute. This provides (S)-9-Azido-2,2-difluoro-6,7,8,9-tetrahydro-1,3-dioxa-5-aza-cyclohepta[f]indene-5-carboxylic acid tert-butyl ester as a colorless oil. To a solution of (S)-9-Azido-2,2-difluoro-6,7,8,9-tetrahydro-1,3-dioxa-5-aza-cyclohepta[f]indene-5-carboxylic acid tert-butyl ester (1.8 mmol) in methanol (20 mL) add a catalytic amount of Pd/C after purging the solution with nitrogen. Place a balloon of hydrogen on the reaction and purge the solution several times. After stirring for 1 h, purge the solution with nitrogen then filter through celite. Collect the filtrate and remove solvent under vacuum to provide the title compound as a colorless oil.

Step 4. Preparation of (S)-9-[Acetyl-(3,5-bis-trifluoromethyl-benzyl)-amino]-2,2-difluoro-6,7,8,9-tetrahydro-1,3-dioxa-5-aza-cyclohepta[f]indene-5-carboxylic acid tert-butyl ester To a solution of (S)-9-Amino-2,2-difluoro-6,7,8,9-tetrahydro-1,3-dioxa-5-aza-cyclohepta[f]indene-5-carboxylic acid tert-butyl ester (1.8 mmol) in DCE (20 mL), add 3,5-bis(trifluoromethyl)benzylaldehyde (2.8 mmol), acetic acid (cat.), and Sodium triacetoxyborohydride (5.7 mmol). After stirring for 14 h, dilute with DCM (100 mL) and quench with concentrated sodium carbonate (50 mL). Separate the organics, dry over sodium sulfate, and remove solvent under vacuum. Chromatograph using ethyl acetate/hexane (5-25%)

to elute. This provides (S)-9-(3,5-Bis-trifluoromethyl-benzylamino)-2,2-difluoro-6,7,8,9-tetrahydro-1,3-dioxa-5-aza-cyclohepta[f]indene-5-carboxylic acid tert-butyl ester as an oil. MS (ES+): 569 (M+H). To a solution of (S)-9-(3,5-Bis-trifluoromethyl-benzylamino)-2,2-difluoro-6,7,8,9-tetrahydro-1,3-dioxa-5-aza-cyclohepta[f]indene-5-carboxylic acid tert-butyl ester (0.35 mmol) in DCM (5 mL), add pyridine (1.06 mmol) and acetyl chloride (1.06 mmol). After stirring for 1.5 h remove solvent under vacuum and chromatograph using ethyl acetate/hexane (5-25%) to elute. This provides the title compound as a foam. MS (ES+): 609 (M–H).

Example 186

(R)-6-[Acetyl-(3,5-bis-trifluoromethyl-benzyl)-amino]-2,3,6,7,8,9-hexahydro-1H-10-aza-cyclohepta[e]indene-10-carboxylic acid isopropyl ester

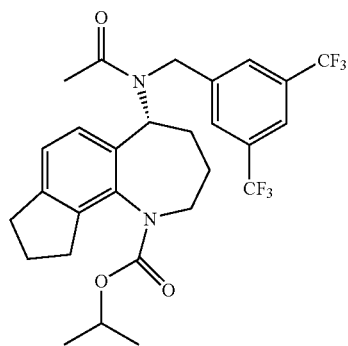

The title compound is obtained by chiral resolution of Example 129 on a Chiralpak AD (4.6×250 mm), flow rate 1 mL/min, solvents: 5% propan-2-ol in hexane 0.05% TFA, $R_f$=12.1 min, wavelength: 215.16. EE>95%. MS (ES+): 557 (M+H).

Example 187

(S)-6-[Acetyl-(3,5-bis-trifluoromethyl-benzyl)-amino]-2,3,6,7,8,9-hexahydro-1H-10-aza-cyclohepta[e]indene-10-carboxylic acid isopropyl ester

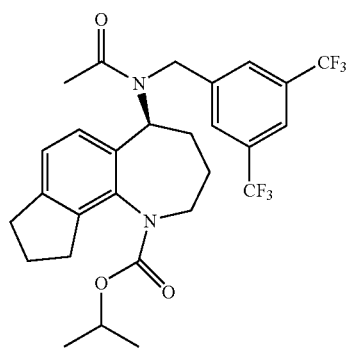

The title compound is obtained by chiral resolution of Example 129 on a Chiralpak AD (4.6×250 mm), flow rate 1 mL/min, solvents: 5% propan-2-ol in hexane 0.05% TFA, $R_f$=13.8 min, wavelength: 215.16. EE>90%. MS (ES+): 557 (M+H).

Example 188

Synthesis of (+/–)5-[Acetyl-(3,5-bis-trifluoromethyl-benzyl)-amino]-7-trifluoromethyl-2,3,4,5-tetrahydro-benzo[b]azepine-1-carboxylic acid isopropyl ester

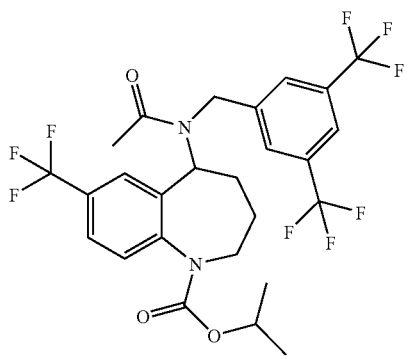

Step 1. Preparation of N-(2-Bromo-4-trifluoromethyl-phenyl)-4-methyl-benzenesulfonamide To a solution of 4-amino-3-bromobenzotrifluoride (20.0 g, 83.3 mmol) in pyridine at room temperature is added p-toluenesulfonyl chloride (19.8 g, 104.1 mmol) in portions over 3 minutes, and the resulting mixture stirred for 52 hours. The suspension is poured into an ice-water mix (300 ml), filtered; and the filtered solid is washed with water (250 ml). The solid is dissolved in dichloromethane (200 ml) and the resulting solution is washed with 1N HCl (2×150 ml), water (2×200 ml), dried ($Na_2SO_4$), and concentrated to a solid. The solid is suspended in ethanol (700 ml) and heated at reflux for 10 minutes, filtered while hot to remove insolubles, and the filtered solids washed with ethanol (250 ml). After concentration of the filtrate, the resulting solid is suspended in methanol (500 ml), treated with $K_2CO_3$ (2.0 g, 14.4 mmol), and the mixture is stirred at room temperature for 46 hours. After filtration of the suspension, the filtered solid is washed with methanol (150 ml), and the filtrate is concentrated to give the title compound as a foam. Mass spectrum (ES+): 394 (M+).

Step 2. Preparation of 2-(Toluene-4-sulfonylamino)-5-trifluoromethyl-benzoic acid methyl ester To a solution of N-(2-Bromo-4-trifluoromethyl-phenyl)-4-methyl-benzenesulfonamide (1.0 g, 2.53 mmol) in $CH_3OH$ (11 ml) and DMSO (17 ml) is added triethylamine (2.0 ml, 14.3 mmol), palladium (II) acetate (115 mg, 0.5 mmol) and 1,1'-Bis(diphenylphosphino)ferrocene (416 mg, 0.75 mmol). The mixture is heated at 80° C. for 24 hours under an atmosphere of carbon monoxide (100 psi). After cooling to room temperature the mixture is partially concentrated in vacuo to remove $CH_3OH$. The residual mixture is cooled to 0° C. and diluted with water (120 ml) and 1N HCl (300 ml), then extracted with ethyl acetate (3×70 ml). The combined ethyl acetate extracts are washed with water, brine, dried ($Na_2SO_4$), and concentrated to an oil. The oil is purified by silica gel column chromatography (eluent, 15% ethyl acetate in hexanes) to give the title compound as a white solid. Mass spectrum (ES–): 372 (M–H).

131

The titled compound was subsequently prepared following the procedures described in Example 1, Steps 2-8, by replacing 2-(Toluene-4-sulfonylamino)-benzoic acid methyl ester with 2-(Toluene-4-sulfonylamino)-5-trifluoromethyl-benzoic acid methyl ester. MS (ES+): 585 (M+H).

Example 189

Synthesis of (+/−) 6-[Acetyl-(3,5-bis-trifluoromethyl-benzyl)-amino]-8-bromo-3,4,5,6-tetrahydro-2H-benzo[b]azocine-1-carboxylic acid isopropyl ester

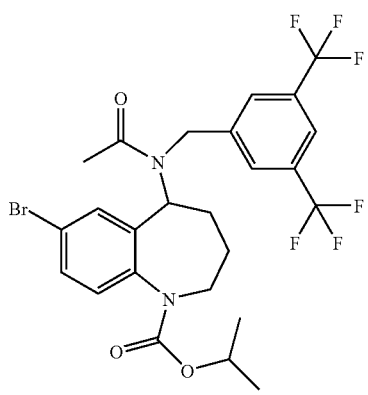

The titled compound may be prepared following the procedures described for the synthesis of (+/−)-5-[Acetyl-(3,5-bis-trifluoromethyl-benzyl)-amino]-6-fluoro-7-methyl-2,3,4,5-tetrahydro-benzo[b]azepine-1-carboxylic acid isopropyl ester (example 125 Steps 1-4) and replacing 3-fluoro-4-methylphanylamine with 4-methylaniline and also replacing methyl 4-bromobutyrate with methyl 5-bromovalerate. The reaction is worked up analogously or by methods known to one of skill in the art to afford the title compound. MS (ES+): 609(M+).

Example 190

Synthesis of (+/−)5-[(3,5-Bis-trifluoromethyl-benzyl)-methanesulfonyl-amino]-2,3,4,5-tetrahydro-benzo[b]azepine-1-carboxylic acid isopropyl ester

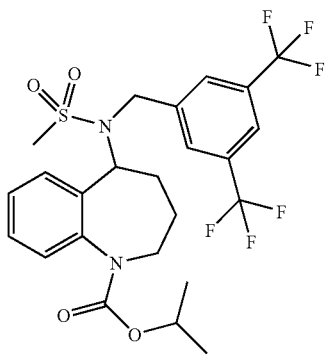

The titled compound was prepared following the procedures described in Example 1 for the synthesis of 5-[Acetyl-(3,5-bis-trifluoromethyl-benzyl)-amino]-2,3,4,5-tetrahydro-benzo[b]azepine-1-carboxylic acid isopropyl ester in step 8, by replacing acetic anhydride with methanesulfonyl chloride. MS (ES+): 553(M+).

132

Example 191

Synthesis of (+/−)N-(3,5-Bis-trifluoromethyl-benzyl)-N-[1-(toluene-4-sulfonyl)-2,3,4,5-tetrahydro-1H-benzo[b]azepin-5-yl]-acetamide

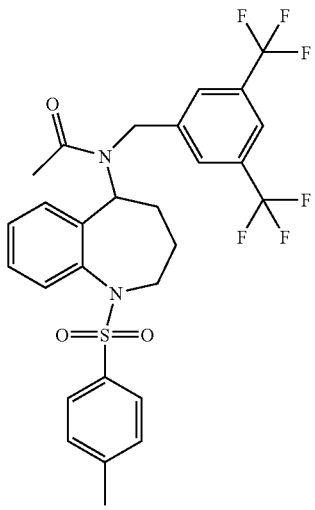

Step 1. Preparation of (+/−)1-(Toluene-4-sulfonyl)-1,2,3,4-tetrahydro-benzo[b]azepin-5-one To a solution of 1,2,3,4-Tetrahydro-benzo[b]azepin-5-one (500 mg, 3.1 mmol) in pyridine (2 ml) is added p-toluenesulfonyl chloride (650 mg, 3.4 mmol), and the mixture is heated at 50° C. for 1 hour. The reaction mixture is poured into 1N HCl (100 ml) and extracted with ethyl acetate (3×20 ml). The combined organic extracts are washed with brine, dried (Na$_2$SO$_4$), and concentrated to a solid. The solid is purified by silica gel column chromatography (eluent, 30% ethyl acetate in hexanes) to give the title compound as a solid. Mass spectrum (ES+): 316 (M+H).

Step 2. Preparation of (+/−) (3,5-Bis-trifluoromethyl-benzyl)-[1-(toluene-4-sulfonyl)-2,3,4,5-tetrahydro-1H-benzo[b]azepin-5-yl]-amine A mixture of (+/−)1-(Toluene-4-sulfonyl)-1,2,3,4-tetrahydro-benzo[b]azepin-5-one (500 mg, 1.58 mmol), 3,5-Bis(trifluoromethyl)benzylamine (423 mg, 1.74 mmol) and titanium(IV) isopropoxide (0.59 ml, 1.97 mmol) in diglyme (2 ml) is stirred at room temperature for 22 hours. The mixture is diluted with methanol (7 ml) and treated with sodium borohydride (90 mg, 2.37 mmol), then stirred at room temperature for 6 hours. The mixture is treated with 0.1N aqueous NaOH (15 ml) and stirred for 10 minutes, then filtered. The filter cake is washed with 1:1 ethanol:diethyl ether. The filtrate is diluted with water (70 ml) and extracted with ethyl acetate (2×30 ml). The combined organic extracts are washed with brine, dried (Na$_2$SO$_4$) and concentrated to an oil. The oil is purified by silica gel column chromatography (eluent, 15% ethyl acetate in hexanes) to give the title compound as a solid. Mass spectrum (ES+): 543 (M+H).

Step 3. Preparation of (+/−)N-(3,5-Bis-trifluoromethyl-benzyl)-N-[1-(toluene-4-sulfonyl)-2,3,4,5-tetrahydro-1H-benzo[b]azepin-5-yl]-acetamide To a solution of (+/−) (3,5-Bis-trifluoromethyl-benzyl)-[1-(toluene-4-sulfonyl)-2,3,4,5-tetrahydro-1H-benzo[b]azepin-5-yl]-amine (149 mg, 0.27 mmol) and pyridine (0.33 ml, 4 mmol) in dichloromethane (1.5 ml) at room temperature is added acetic anhydride (0.38 ml, 4.1 mmol) via dropwise addition over 2 minutes. The mixture is stirred at room temperature for 20 hours. The mixture is treated with 1N aqueous NaOH (4 ml) and stirred for 10 minutes, then diluted with 1N HCl (15 ml) and dichloromethane (15 ml). The organic layer is washed with water, dried (Na$_2$SO$_4$), and concentrated to a solid. Purification by silica gel column chromatography (eluent, 35% ethyl acetate in hexanes) gives the title compound as a solid. Mass spectrum (ES+): 585 (M+H).

Example 192

Synthesis of (+/−) (3,5-Bis-trifluoromethyl-benzyl)-[1-(toluene-4-sulfonyl)-2,3,4,5-tetrahydro-1H-benzo[b]azepin-5-yl]-carbamic acid methyl ester

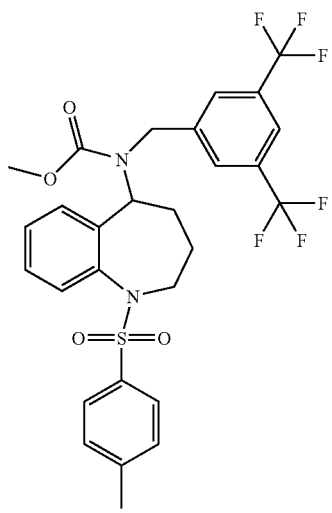

The titled compound was prepared following the procedures described for the preparation of (+/−) N-(3,5-Bis-trifluoromethyl-benzyl)-N-[1-(toluene-4-sulfonyl)-2,3,4,5-tetrahydro-1H-benzo[b]azepin-5-yl]-acetamide (example 191, step 3) by replacing acetic anhydride with methyl chloroformate. MS (ES+): 601(M+H).

Example 193

N-(3,5-Bis-trifluoromethyl-benzyl)-N-[8-chloro-1-(5-ethoxy-[1,3,4]oxadiazol-2-yl)-2,3,4,5-tetrahydro-1H-benzo[b]azepin-5-yl]-acetamide

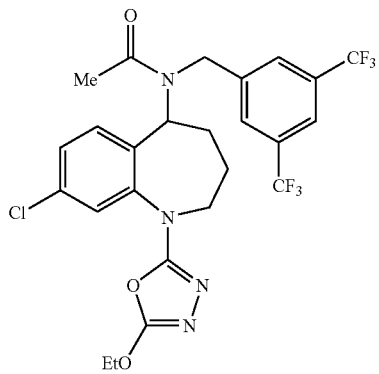

Step 1. Preparation of N-(3,5-Bistrifluoromethyl-benzyl)-N-(8-chloro-1-hydrazinocarbonyl-2,3,4,5-tetrahydro-1H-benzo[b]azepin-5-yl)-acetamide A mixture of 5-[Acetyl-(3,5-bis-trifluoromethyl-benzyl)-amino]-8-chloro-2,3,4,5-tetrahydro-benzo[b]azepine-1-carbonyl chloride (1.0 mmol, 0.52 g) and hydrazine hydrate (50.0 mmol, 1.56 mL) in MeOH (5 mL) was refluxed at 70° C. for 12 h with vigorous stirring. The solvent was removed in vacuo and the crude product was purified by crystallization using EtOAc. The product was obtained as white solid; R$_f$ 0.2 (EtOAc); MS (ES+): 523 (M+H$^+$).

Step 2. Preparation of N-(3,5-Bistrifluoromethyl-benzyl)-N-(8-chloro-1-(5-ethoxy-[1,3,4]oxadiazol-2-yl)-2,3,4,5-tetrahydro-1H-benzo[b]azepin-5-yl)-acetamide To a stirring solution of N-(3,5-Bistrifluoromethyl-benzyl)-N-(8-chloro-1-hydrazinocarbonyl-2,3,4,5-tetrahydro-1H-benzo[b]azepin-5-yl)-acetamide (0.13 mmol, 73 mg) in MeOH (1 mL) was added ethyl chloroformate (0.41 mmol, 45.0 µL) and the reaction mixture was refluxed for 12 h. After completion (by TLC), the mixture was cooled, diluted with EtOAc (20 mL), washed with water and brine. The organic layer was dried over Na$_2$SO$_4$ and concentrated in vacuo to afford the crude product as viscous oil. Purification by flash silica gel column chromatography gave the title compound as colorless foam; R$_f$ 0.40 (EtOAc/Hexane, 1:1, v/v); MS (ES+): 599 (M+Na$^+$).

Example 194

N-(3,5-Bis-trifluoromethyl-benzyl)-N-[8-chloro-1-(5-phenyl-[1,3,4]oxadiazol-2-yl)-2,3,4,5-tetrahydro-1H-benzo[b]azepin-5-yl]-acetamide

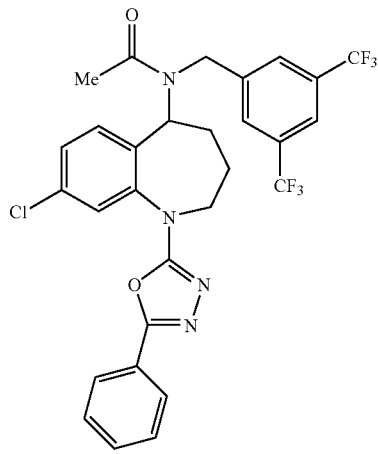

To a solution of N-(3,5-Bistrifluoromethyl-benzyl)-N-(8-chloro-1-hydrazinocarbonyl-2,3,4,5-tetrahydro-1H-benzo[b]azepin-5-yl)-acetamide (0.23 mmol, 0.12 g) in CH$_2$Cl$_2$ (3 mL) was added pyridine (0.5 mL) and catalytic amount of DMAP (2 mg). The reaction mixture was cooled to 0° C. and treated with benzoyl chloride (0.34 mmol, 40.0 µL). The resulting solution was warmed to room temperature and kept at that temperature for 12 h. After completion, the reaction mixture was diluted with CH$_2$Cl$_2$ (20 mL), washed with water, and brine. The organic layer was dried over Na$_2$SO$_4$, filtered, and concentrated in vacuo. The crude product was stirred with Con. H$_2$SO$_4$ at room temperature for 12 h. The reaction mixture was basified with aqueous NaHCO$_3$, extracted with EtOAc (3×30 mL). The combined organic layers were washed with water and brine. Removal of the solvent and purification by flash column chromatography gave the pure compound as a white solid; R$_f$ 0.21 (EtOAc-Hexane, 1:3, v/v); MS (ES+): 610 (M+H$^+$).

Example 195

N-(3,5-Bis-trifluoromethyl-benzyl)-N-[8-chloro-1-(4-isopropyl-4H-[1,2,4]triazol-3-yl)-2,3,4,5-tetrahydro-1H-benzo[b]azepin-5-yl]-acetamide

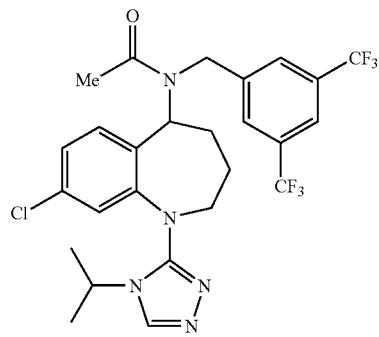

The title compound could be prepared as described for the synthesis of Example 194 for N-3,5-Bis-trifluoromethyl-benzyl)-N-[8-chloro-1-(5-phenyl-[1,3,4]oxadiazol-2-yl)-2,3,4,5-tetrahydro-1H-benzo[b]azepin-5-yl]-acetamide, using, N-(3,5-Bistrifluoromethyl-benzyl)-N-(8-chloro-1-hydrazinocarbonyl-2,3,4,5-tetrahydro-1H-benzo[b]azepin-5-yl)-acetamide, dimethylacetamide dimethyl acetal, and isopropylamine.

Example 196

N-(3,5-Bis-trifluoromethyl-benzyl)-N-[8-chloro-1-(5-methyl-1H-pyrazol-3-yl)-2,3,4,5-tetrahydro-1H-benzo[b]azepin-5-yl]-acetamide

Step 1. Preparation of N-(3,5-Bis-trifluoromethyl-benzyl)-N-[8-chloro-1-(3-oxo-butyryl)-2,3,4,5-tetrahydro-1H-benzo[b]azepin-5-yl]-acetamide To a solution of N-(3,5-Bis-trifluoromethyl-benzyl)-N-(8-chloro-2,3,4,5-tetrahydro-1H-benzo[b]azepin-5-yl)-acetamide (1.0 mmol, 465 mg) and DMAP (0.1 mmol, 12 mg) in THF (5 mL) was added diketene (1.1 mmol, 86.0 µL) at 0° C. The reaction mixture was stirred vigorously at that temperature for 1 h. After completion, the reaction mixture was diluted with EtOAc (50 mL), washed with water and brine. The organic phase was separated and dried over $Na_2SO_4$. Removal of the solvent and purification on flash column chromatography provided the pure compound as a colorless foam; $R_f$ 0.20 (EtOAc-Hexane, 1:1, v/v); MS (ES+): 549 (M+H$^+$).

Step 2. N-(3,5-Bis-trifluoromethyl-benzyl)-N-[8-chloro-1-(5-methyl-1H-pyrazol-3-yl)-2,3,4,5-tetrahydro-1H-benzo[b]azepin-5-yl]-acetamide To a mixture of N-(3,5-Bis-trifluoromethyl-benzyl)-N-[8-chloro-1-(3-oxo-butyryl)-2,3,4,5-tetrahydro-1H-benzo[b]azepin-5-yl]-acetamide (0.13 mmol, 72 mg), hydrazine hydrate (1.3 mmol, 40.0 µL) in MeOH (2 mL) was added $P_4O_{10}$ (0.5 g) at room temperature. The resulting suspension was stirred vigorously at 70° C. for 12 h. After completion, the mixture was diluted with water (20 mL), and extracted with EtOAc (3×20 mL). The combined organic layers were washed with water and brine, dried over $Na_2SO_4$ and evaporated to dryness. Flash chromatography (EtOAc-Hexane as eluent 1:1) afforded the title compound as viscous foam; $R_f$ 0.28 (EtOAc-Hexane, 1:1, v/v); MS (ES+): 545 (M+H$^+$).

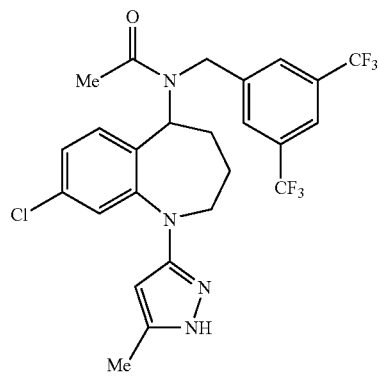

Example 197

N-(3,5-Bis-trifluoromethyl-benzyl)-N-[8-chloro-1-(3-methyl-isoxazol-5-yl)-2,3,4,5-tetrahydro-1H-benzo[b]azepin-5-yl]-acetamide

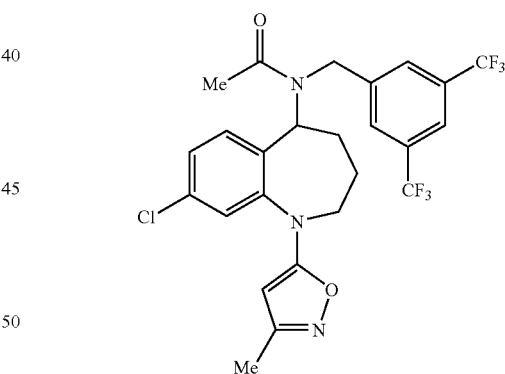

To a mixture of N-(3,5-Bis-trifluoromethyl-benzyl)-N-[8-chloro-1-(3-oxo-butyryl)-2,3,4,5-tetrahydro-1H-benzo[b]azepin-5-yl]-acetamide (0.13 mmol, 72 mg), hydroxylamine hydrochloride (1.3 mmol, 90 mg) in MeOH (2 mL) was added NaOAc (20 mg) at room temperature. The resulting suspension was stirred vigorously at 70° C. for 12 h. After completion, the mixture was diluted with water (20 mL), extracted with EtOAc (3×20 mL). The combined organic layers were washed with water and brine, dried over $Na_2SO_4$ and evaporated to dryness. Flash chromatography (EtOAc-Hexane as eluent 1:1) afforded the title compound as viscous foam; $R_f$ 0.35 (EtOAc-Hexane, 1:1, v/v); MS (ES+): 564 (M+H$_2$O).

Example 198

N-(3,5-Bis-trifluoromethyl-benzyl-N-[8-chloro-1-(2-methyl-2H-tetrazol-5-yl)-2,3,4,5-tetrahydro-1H-benzo[b]azepin-5-yl]-acetamide

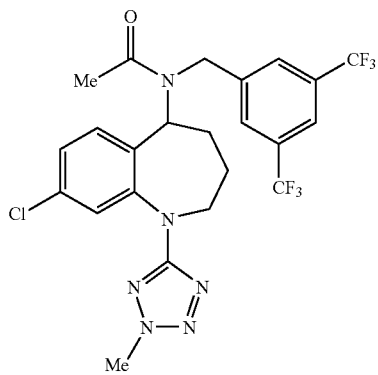

Step 1. Preparation of N-(3,5-Bis-trifluoromethyl-benzyl)-N-(8-chloro-1-cyano-2,3,4,5-tetrahydro-1H-benzo[b]azepin-5-yl)-acetamide To a solution of N-(3,5-Bis-trifluoromethyl-benzyl)-N-(8-chloro-2,3,4,5-tetrahydro-1H-benzo[b]azepin-5-yl)-acetamide (1.0 mmol, 465 mg) in THF (5 mL) was added n-BuLi (1.0 mmol, 0.62 mL, 1.6 M in THF) at −78° C. and stirred for 20 min. The above dark brown solution was treated with a solution of cyanogens bromide (2.0 mmol, 0.21 g) in THF (1 mL). The reaction mixture was stirred vigorously at that temperature for 1 h and slowly warmed to room temperature for 12 h. After completion, the reaction mixture was diluted with EtOAc (50 mL), washed with water and brine. The organic phase was separated and dried over $Na_2SO_4$. Removal of the solvent and purification on flash column chromatography provided the pure title compound as a colorless foam; $R_f$ 0.20 (EtOAc-Hexane, 4:1, v/v); MS (ES+): 490 (M+H$^+$).

Step 2. Preparation of N-(3,5-Bis-trifluoromethyl-benzyl-N-[8-chloro-1-(1H-tetrazol-5-yl)-2,3,4,5-tetrahydro-1H-benzo[b]azepin-5-yl]-acetamide A solution of N-(3,5-Bis-trifluoromethyl-benzyl)-N-(8-chloro-1-cyano-2,3,4,5-tetrahydro-1H-benzo[b]azepin-5-yl)-acetamide (0.92 mmol, 0.45 g) in toluene (5 mL) was treated with tributyltin azide (1.8 mmol, 0.49 mL) at room temperature. The reaction mixture was kept at reflux temperature for 12 h. After completion, the mixture was diluted with water (20 mL), extracted with EtOAC (3×25 mL) and the combined organic layers were washed with water and brine. The organic phase was dried ($Na_2SO_4$) and concentrated in vacuo. The crude compound was purified by flash column chromatography to afford the title compound as colorless foam; $R_f$ 0.40 (EtOAc-Hexane, 1:1, v/v); MS (ES+): 533 (M+H$^+$).

Step 3. Preparation of N-(3,5-Bis-trifluoromethyl-benzyl-N-[8-chloro-1-(2-methyl-2H-tetrazol-5-yl)-2,3,4,5-tetrahydro-1H-benzo[b]azepin-5-yl]-acetamide To a solution of N-(3,5-Bis-trifluoromethyl-benzyl-N-[8-chloro-1-(1H-tetrazol-5-yl)-2,3,4,5-tetrahydro-1H-benzo[b]azepin-5-yl]-acetamide (0.55 mmol, 0.29 g) in $CH_2Cl_2$ (5 mL) was added triphenyl phosphine (0.55 mmol, 0.14 g) and diethylazo dicarboxylate (0.55 mmol, 90.0 μL) at 0° C. To the above mixture, MeOH (2.75 mmol, 0.11 μL) was added and warmed to room temperature for 48 h. After completion, the reaction mixture was diluted with water (20 mL), extracted with EtOAC (3×25 mL) and the combined organic layers were washed with water and brine. The organic phase was dried ($Na_2SO_4$) and concentrated in vacuo. The crude compound was purified by flash column chromatography to afford the title compound as colorless foam; $R_f$ 0.60 (EtOAc-Hexane, 1:1, v/v); MS (ES+): 547 (M+H$^+$).

Example 199

N-(3,5-Bis-trifluoromethyl-benzyl-N-[8-chloro-1-(3-methyl-[1,2,4]oxadiazol-5-yl)-2,3,4,5-tetrahydro-1H-benzo[b]azepin-5-yl]-acetamide

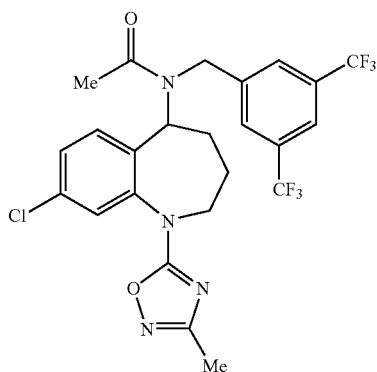

Step 1. Preparation of 5-[Acetyl-(3,5-bis-trifluoromethyl-benzyl)-amino]-8-chloro-2,3,4,5-tetrahydro-benzo[b]azepine-1-carboxylic acid amide A mixture of 5-[Acetyl-(3,5-bis-trifluoromethyl-benzyl)-amino]-8-chloro-2,3,4,5-tetrahydro-benzo[b]azepine-1-carbonyl chloride (0.1 mmol, 50.0 mg) and ammonia (1.0 mmol, 1.0 mL, 1M in MeOH) was refluxed at 70° C. for 6 h with vigorous stirring. The solvent was removed in vacuo and the crude product was purified by crystallization using EtOAc. The product was obtained as a white solid; $R_f$ 0.1 (EtOAc); MS (ES+): 508 (M+H$^+$).

Step 2. Preparation of N-(3,5-Bis-trifluoromethyl-benzyl-N-[8-chloro-1-(3-methyl-[1,2,4]oxadiazol-5-yl)-2,3,4,5-tetrahydro-1H-benzo[b]azepin-5-yl]-acetamide A mixture of 5-[Acetyl-(3,5-bis-trifluoromethyl-benzyl)-amino]-8-chloro-2,3,4,5-tetrahydro-benzo[b]azepine-1-carboxylic acid amide (0.1 mmol, 51 mg) and 85% dimethyl acetamide dimethylacetal (1.5 mmol, 0.22 mL) was heated at reflux for 1 h and then evaporated in vacuo. Dioxane (1 mL), hydroxylamine hydrochloride (0.2 mmol, 14 mg), acetic acid (0.4 mL), and a 2N NaOH (0.2 ml) solution were added and the mixture was stirred at room temperature for 2 h. Then the reaction mixture was refluxed for 1 h, cooled to room temperature and poured into ice water (10 mL). After the pH of the solution had been adjusted to 7-8 using 1 N NaOH, it was extracted with EtOAc (2×20 mL). The combined organic layers were dried over $Na_2SO_4$ and the solvent evaporated in vacuo. The pure compound was obtained by flash column chromatography (EtOAc-Hexane 1:1) to afford the title compound as colorless oil. $R_f$ 0.6 (EtOAc-Hexane, 1:1, v/v); MS (ES+): 547 (M+H$^+$).

Example 200

N-(3,5-Bis-trifluoromethyl-benzyl-N-[8-chloro-1-methanesulfonylaminocarbonyl-2,3,4,5-tetrahydro-1H-benzo[b]azepin-5-yl]-acetamide

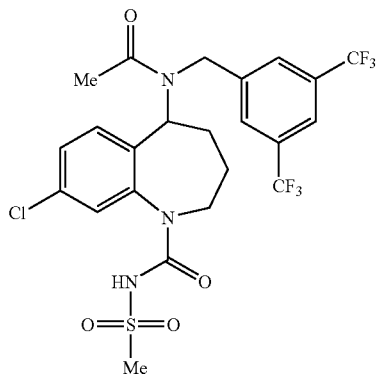

To a solution of 5-[Acetyl-(3,5-bis-trifluoromethyl-benzyl)-amino]-8-chloro-2,3,4,5-tetrahydro-benzo[b]azepine-1-carboxylic acid amide (0.1 mmol, 51.0 mg) in CH$_2$Cl$_2$ (1 mL) was added pyridine (0.5 mL) at room temperature. The reaction mixture was cooled to 0° C. and treated with methansulfonyl chloride (0.3 mmol, 25.0 µL). Stirring was continued at room temperature for 12 h. The reaction mixture was diluted with water (5 mL), and extracted with EtOAc (3×10 mL). The combined organic layers were washed with water and brine. The pure compound was obtained by flash column chromatography (EtOAc-Hexane 1:1) to provide the title compound as a white solid; R$_f$ 0.48 (EtOAc-Hexane, 1:1, v/v); MS (ES+): 586 (M+H$^+$).

Example 201

N-(3,5-Bis-trifluoromethyl-benzyl)-N-[8-chloro-1-(toluene-4-sulfonylaminocarbonyl)-2,3,4,5-tetrahydro-1H-benzo[b]azepin-5-yl]-acetamide

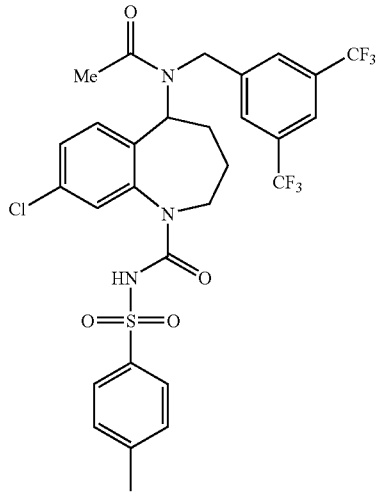

The title compound was prepared by similar procedure as described in Example 200 (0.1 mmol scale of 5-[Acetyl-(3,5-bis-trifluoromethyl-benzyl)-amino]-8-chloro-2,3,4,5-tetrahydro-benzo[b]azepine-1-carboxylic acid amide). The title compound was obtained as a white solid; R$_f$ 0.58 (EtOAc-Hexane, 1:1, v/v); MS (ES+): 662 (M+H$^+$).

Example 202

(S)-N-(3,5-bis-trifluoromethyl-benzyl)-N-(1-cyclopentyl-7-methyl-8-trifluoromethyl-2,3,4,5-tetrahydro-1H-benzo[b]azepin-5-yl]-acetamide

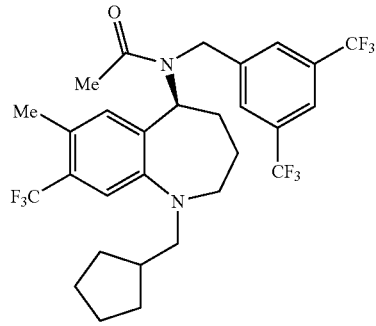

Method A: To a solution of (S)-N-(3,5-Bis-trifluoromethyl-benzyl)-N-(7-methyl-8-trifluoromethyl-2,3,4,5-tetrahydro-1H-benzo[b]azepin-5-yl)-acetamide (0.15 mmol, 80.0 mg) in CH$_2$Cl$_2$ (2 mL) was added cyclopentane carboxyaldehyde (0.23 mmol, 22 µL), followed by dropwise addition of TiCl$_4$ (0.23 mmol, 0.23 mL, 1M in CH$_2$Cl$_2$). The reaction mixture was stirred at room temperature for 12 h. After completion, the solvent was removed in vacuo. The resulting crude imine was dissolved in MeOH (2 mL) and treated with NaBH$_4$ (1.5 mmol, 60 mg) at 0° C. After, stirring for 1 at 0° C., the reaction was diluted with saturated NH$_4$Cl (10 mL) and extracted with EtOAc (3×10 mL). The combined organic layers were washed with water, brine and dried (Na$_2$SO$_4$). Removal of the solvent and further purification on flash column chromatography provided the title compound as a viscous oil; R$_f$ 0.58 (EtOAc-Hexane, 1:1, v/v); MS (ES+): 594 (M+H$^+$)

Method B: To a solution of (S)-N-(3,5-Bis-trifluoromethyl-benzyl)-N-(7-methyl-8-trifluoromethyl-2,3,4,5-tetrahydro-1H-benzo[b]azepin-5-yl)-acetamide (0.15 mmol, 80.0 mg) in CH$_2$Cl$_2$ (2 mL) was added cyclopentane carboxaldehyde (0.23 mmol, 22 µL), AcOH (10 µL), and NaBH(OAc)$_3$ (0.45 mmol, 95.0 mg). After stirring overnight at room temperature, the reaction mixture was poured in to saturated NaHCO$_3$ solution and extracted with CH$_2$Cl$_2$ (3×10 mL). The organic extracts were dried and concentrated. Flash chromatography on silica gel (EtOAc-Hexane) afforded the title compound as viscous oil; R$_f$ 0.58 (EtOAc-Hexane, 1:1, v/v); MS (ES+): 594 (M+H$^+$).

Example 203

(S)-2-{5-[Acetyl-(3,5-bis-trifluoromethyl-benzyl)-amino]-7-methyl-8-trifluoromethyl-2,3,4,5-tetrahydro-benzo[b]azepin-1-ylmethyl}-cyclopropanecarboxylic acid

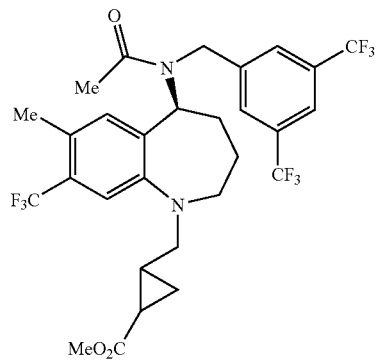

The title compound prepared by similar procedure (Method B) as described in Example 202 for (S)-N-(3,5-bis-trifluoromethyl-benzyl)-N-(1 cyclopentyl-7-methyl-8-trifluoromethyl-2,3,4,5-tetrahydro-1H-benzo[b]azepin-5-yl]-acetamide, using, (S)-N-(3,5-Bis-trifluoromethyl-benzyl)-N-(7-methyl-8-trifluoromethyl-2,3,4,5-tetrahydro-1H-benzo[b]azepin-5-yl)-acetamide and 2-formyl-cyclopropanecarboxylic acid methyl ester; $R_f$ 0.46 (EtOAc-Hexane, 1:1, v/v); MS (ES+): 639.3 (M+H$^+$).

Example 204

(S)-5-{5-[Acetyl-(3,5-bis-trifluoromethyl-benzyl)-amino]-7-methyl-8-trifluoromethyl-2,3,4,5-tetrahydro-benzo[b]azepin-1-yl}-3,3-dimethyl-pentanoic acid

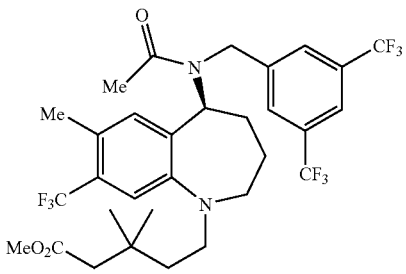

The title compound prepared by similar procedure (Method B) as described in Example 202 for (S)-N-(3,5-bis-trifluoromethyl-benzyl)-N-(1-cyclopentyl-7-methyl-8-trifluoromethyl-2,3,4,5-tetrahydro-1H-benzo[b]azepin-5-yl]-acetamide, using, N-(3,5-Bis-trifluoromethyl-benzyl)-N-(7-methyl-8-trifluoromethyl-2,3,4,5-tetrahydro-1H-benzo[b]azepin-5-yl)-acetamide and 3,3-dimethyl-5-oxo-pentanoic acid methyl ester; $R_f$ 0.41 (EtOAc-Hexane, 1:1, v/v); MS (ES+): 655.2 (M+H$^+$).

Example 205

Synthesis of 5-[Acetyl-(3,5-bis-trifluoromethyl-benzyl)-amino]-2,3,4,5,7,8,9,10-octahydro-naphtho[2,3-b]azepine-1-carboxylic acid isopropyl ester

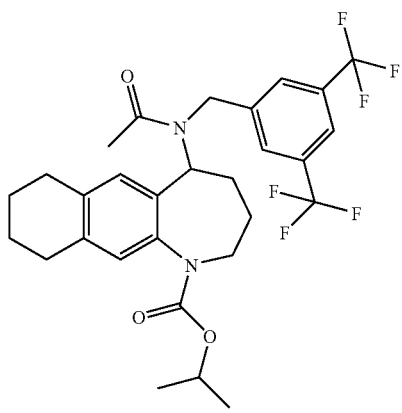

The title compound can be prepared using procedures analogous to the synthesis of 5-[Acetyl-(3,5-bis-trifluoromethyl-benzyl)-amino]-8-chloro-2,3,4,5-tetrahydro-benzo[b]azepine-1-carboxylic acid tert-butyl ester (Example 140), starting with 5,6,7,8-Tetrahydro-naphthalen-2-ylamine and isopropyl chloroformate.

Example 206

Synthesis of (S)-(3,5-Bis-trifluoromethyl-benzyl)-(5-cyclopentylmethyl-2,2-difluoro-6,7,8,9-tetrahydro-5H-1,3-dioxa-5-aza-cyclohepta[f]inden-9-yl)-amine

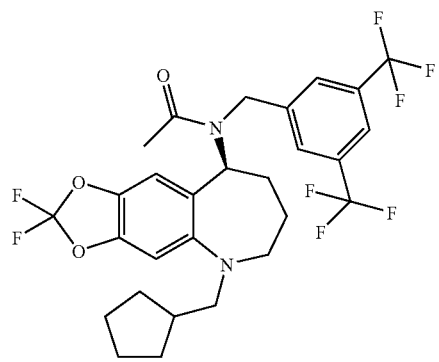

To a solution of (S)-9-[Acetyl-(3,5-bis-trifluoromethyl-benzyl)-amino]-2,2-difluoro-6,7,8,9-tetrahydro-1,3-dioxa-5-aza-cyclohepta[f]indene-5-carboxylic acid tert-butyl ester (0.26 mmol) in DCM (5 mL) add trifluoroacetic acid (1 mL). After stirring for 1 h, quench the reaction with sodium bicarbonate (5 mL) and dilute with DCM (20 mL). Separate and dry the organics over sodium sulfate. Remove the solvent and chromatograph the product using ethyl acetate/hexane (5-20%) to elute. This provides N-(3,5-Bis-trifluoromethyl-benzyl)-N-(2,2-difluoro-6,7,8,9-tetrahydro-5H-1,3-dioxa-5-aza-cyclohepta[f]inden-9-yl)-acetamide as an oil. To this crude intermediate in DCE (dichloroethane) (5 mL), add cyclopentylcarbaldehyde (1.3 mmol), acetic acid (cat.), and sodium triacetoxyborohydride (1.6 mmol). After stirring for 14 h, dilute the reaction with DCM (20 mL) and quench with concentrated sodium carbonate (5 mL). Separate the organics, dry over sodium sulfate, and remove solvent under vacuum. Chromatograph the product using ethyl acetate/hexane (5-20%) to elute. This provides the title compound as a foam. MS (ES+): 593 (M+H).

Example 207

Synthesis of N-(3,5-Bis-trifluoromethyl-benzyl)-N-(5-cyclopentylmethyl-3,5,6,7,8,9-hexahydro-1H-2-oxa-5-aza-cyclohepta[f]inden-9-yl)-acetamide

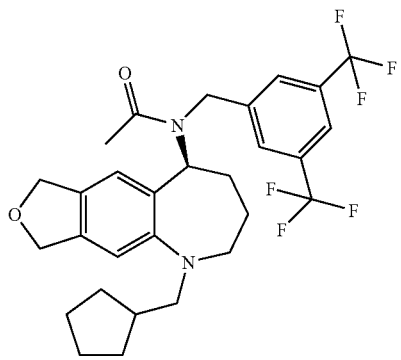

Step 1. Preparation of 1,3-Dihydro-isobenzofuran-5-ylamine

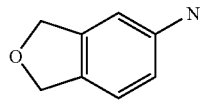

To a solution of 1,3-dihydro-isobenzofuran (83.2 mmol) in sulfuric acid (75 mL) cooled in an ice bath, add a solution of potassium nitrate (83.2 mmol) in sulfuric acid (25 mL) dropwise. After stirring for 30 min. pour the reaction mixture over ice and collect the resulting precipitate on a glass frit. Wash the precipitate with water (200 mL) and dry under vacuum. Dissolve the precipitate in ethanol (250 mL) and add tin chloride dihydrate (273.6 mmol). After heating at 70° C. for 2 h dilute with water (200 mL), cool to room temperature and neutralize the reaction with 5 N sodium hydroxide. Extract the mixture with ethyl acetate (3×200 mL) and dry the organics over sodium sulfate. Remove solvent to afford the title compound as a tan solid. H NMR (CDCl$_3$, 400 MHz) δ 3.50 (bs, 2H), 5.02 (s, 4H), 6.56 (d, J=2.4 Hz, 1H), 6.60 (dd, J=2.4, 8.0 Hz, 1H), 7.01 (d, J=8.0 Hz, 1H).

Step 2. Preparation of 9-Oxo-1,3,6,7,8,9-hexahydro-2-oxa-5-aza-cyclohepta[f]indene-5-carboxylic acid tert-butyl ester

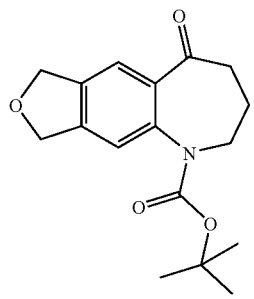

The title compound was prepared using procedures analogous to Example 182 (Synthesis of 5-[Acetyl-(3,5-bis-trifluoromethyl-benzyl)-amino]-7-methyl-8-trifluoromethoxy-2,3,4,5-tetrahydro-benzo[b]azepine-1-carboxylic acid cyclopentyl ester, steps 3-7), starting with 1,3-Dihydro-isobenzofuran-5-ylamine in step 3 and replacing phosgene/cyclopropanol with di-t-butyl dicarbonate in step 7.

Step 3. Preparation of N-(3,5-Bis-trifluoromethyl-benzyl)-N-(5-cyclopentylmethyl-3,5,6,7,8,9-hexahydro-1H-2-oxa-5-aza-cyclohepta[f]inden-9-yl)-acetamide

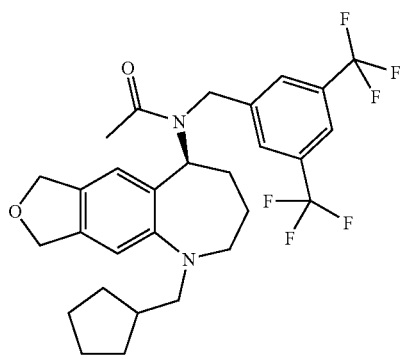

The title compound could be prepared using procedures described in Example 185 (Synthesis of 9-[Acetyl-(3,5-bis-trifluoromethyl-benzyl)-amino]-2,2-difluoro-6,7,8,9-tetrahydro-1,3-dioxa-5-aza-cyclohepta[f]indene-5-carboxylic acid tert-butyl ester) and Example 207 (Synthesis of (3,5-Bis-trifluoromethyl-benzyl)-(5-cyclopentylmethyl-2,2-difluoro-6,7,8,9-tetrahydro-5H-1,3-dioxa-5-aza-cyclohepta[f]inden-9-yl)-amine) starting with 9-Oxo-1,3,6,7,8,9-hexahydro-2-oxa-5-aza-cyclohepta[f]indene-5-carboxylic acid tert-butyl ester.

We claim:
1. A compound of a formula below:

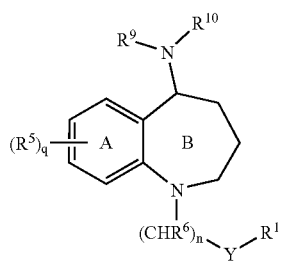

wherein
n is 0, 1, 2, or 3;
q is 0, 1, 2, or 3;
Y is a bond, C=O, or S(O)$_t$; wherein t is 0, 1, or 2;
R$^1$ is selected from a group consisting of C$_1$-C$_6$ alkyl, aryl, C$_2$-C$_6$ alkenyl, C$_1$-C$_6$ alkylheterocyclic, C$_3$-C$_8$ cycloalkyl, C$_1$-C$_6$ alkylcycloalkyl, C$_1$-C$_6$ alkylaryl, heterocyclyl, C$_1$-C$_6$ alkoxy, aryloxy, OC$_1$-C$_6$ haloalkyl, —OC$_3$-C$_8$ cycloalkyl, —OC$_1$-C$_6$ alkylcycloalkyl, —NR$^7$R$^8$, —OC$_1$-C$_6$ alkylaryl, —O-heterocyclic, and —OC$_1$-C$_6$ alkylheterocyclic; and wherein each of cycloalkyl, aryl and heterocyclic group is optionally substituted with 1 to 3 groups independently selected from oxo, halo, C$_1$-C$_6$ alkyl, C$_1$-C$_6$ alkoxy, C$_1$-C$_6$ haloalkyl, CONR$^{11}$R$^{12}$, C$_0$-C$_3$ alkylNR$^{11}$R$^{12}$, C$_0$-C$_6$ alkylCOOR$^{11}$, cyano, and phenyl;
each R$^5$ is selected from a group consisting of hydroxy, halogen, C$_1$-C$_6$ haloalkyl, aryl, heterocyclic, cyano, C$_1$-C$_6$ alkyl, C$_2$-C$_6$ alkenyl, C$_1$-C$_6$ alkoxy, —OC$_1$-C$_6$ haloalkyl, C$_0$-C$_6$ alkylNR$^7$R$^8$, C$_0$-C$_6$ alkylCOR$^7$, C$_0$-C$_6$ alkylCO$_2$R$^7$, NR$^7$SO$_2$R$^8$, NR$^7$COR$^8$, S(O)$_t$R$^7$, and —OC$_1$-C$_6$ alkylaryl wherein each of the aryl and heterocyclic groups is optionally substituted by oxo or alkyloxy;
R$^6$ is hydrogen or C$_1$-C$_6$ alkyl;
each R$^7$ is independently selected from a group consisting of hydrogen, C$_1$-C$_6$ alkyl, OC$_1$-C$_6$ alkyl, C$_1$-C$_6$ haloalkyl, —C$_3$-C$_8$ cycloalkyl, heterocyclic, and aryl, wherein each alkyl, is optionally substituted with 1-3 groups independently selected from C$_1$-C$_6$ alkoxy, SO$_2$R$^{11}$, and NR$^{11}$R$_{12}$,
each R$^8$ is independently selected from a group consisting of hydrogen, C$_1$-C$_6$ alkyl, and aryl;
R$^9$ is COR$^7$ wherein R$^7$ is as defined above;
R$^{10}$ is benzyl, optionally substituted with 1 or 2 groups selected from halo, C$_1$-C$_6$alkyl, haloalkyl, C$_1$-C$_6$alkoxy, and C$_1$-C$_6$ haloalkoxyalkyl;
R$^{11}$ and R$^{12}$ are independently selected from a group consisting of hydrogen, C$_1$-C$_6$ alkyl, and aryl;
or a pharmaceutically acceptable salt thereof.

2. The compound according to claim 1 wherein $R^1$ is selected from a group consisting of $C_1$-$C_6$ alkoxy, $C_1$-$C_6$ alkylcycloalkyl, $C_3$-$C_8$ cycloalkyl, $C_1$-$C_6$ alkylheterocyclic, aryloxy, —$OC_1$-$C_6$ haloalkyl, —$OC_3$-$C_8$ cycloalkyl, —$OC_1$-$C_6$ alkylaryl and —$OC_1$-$C_6$ alkylheterocyclic wherein each of cycloalkyl, aryl and heterocyclic group is optionally substituted with 1 to 3 groups independently selected from oxo, halo, $C_1$-$C_6$ alkyl, $C_1$-$C_6$ alkoxy, $C_1$-$C_6$ haloalkyl, $CONR^{11}R^{12}$ and $C_0$-$C_6$ alkyl$COOR^{11}$.

3. A compound according to claim 1 wherein $R^1$ is selected from a group consisting of aryloxy, —$OC_1$-$C_6$ haloalkyl, —$OC_3$-$C_8$ cycloalkyl, —$OC_1$-$C_6$ alkylaryl, -Oheterocyclic, and —$OC_1$-$C_6$ alkylheterocyclic; wherein each of cycloalkyl, aryl and heterocyclic group is optionally substituted with 1 to 3 groups independently selected from halo, $C_1$-$C_6$ alkyl, $C_1$-$C_6$ alkoxy, $C_1$-$C_6$ haloalkyl, and $C_0$-$C_6$ alkyl$COOR^{11}$.

4. The compound according to claim 1 wherein $R^1$ is selected from a group consisting of $C_1$-$C_6$ alkylcycloalkyl, $C_1$-$C_6$ alkylheterocyclic, $C_3$-$C_8$ cycloalkyl and aryloxy, wherein each of cycloalkyl, aryl and heterocyclic group is optionally substituted with 1 to 3 groups independently selected from halo, $C_1$-$C_6$ alkyl, $C_1$-$C_6$ alkoxy, $C_1$-$C_6$ haloalkyl, and $C_0$-$C_6$ alkyl$COOR^{11}$.

5. The compound according to claim 1 Y is a bond; and $R^1$ is alkylaryl, alkylheterocyclic, $C_1$-$C_6$ alkylcycloalkyl wherein the aryl, cycloalkyl and heterocyclic groups are each optionally substituted with 1, 2 or 3 groups independently selected from oxo, —COOH, $C_1$-$C_6$ alkyl, and $C_1$-$C_6$ alkoxy.

6. The compound of claim 1, wherein n is 0 or 1 and q is 1, 2, or 3.

7. The compound according to claim 1 wherein n is 0 or 1; and q is 2 or 3.

8. A compound selected from the group consisting of:
5-[Acetyl-(3,5-bis-trifluoromethyl-benzyl)-amino]-7-trifluoromethyl-2,3,4,5-tetrahydro-benzo[b]azepine-1-carboxylic acid isopropyl ester,
5-[(3,5-Bis-trifluoromethyl-benzyl)-methoxycarbonyl-amino]-7-trifluoromethyl-2,3,4,5-tetrahydro-benzo[b]azepine-1-carboxylic acid isopropyl ester,
5-[(3,5-Bis-trifluoromethyl-benzyl)-methoxycarbonyl-amino]-7-trifluoromethyl-2,3,4,5-tetrahydro-benzo[b]azepine-1-carboxylic acid ethyl ester,
5-[Acetyl-(3,5-bis-trifluoromethyl-benzyl)-amino]-7-trifluoromethyl-2,3,4,5-tetrahydro-benzo[b]azepine-1-carboxylic acid ethyl ester,
5-[Acetyl-(3,5-bis-trifluoromethyl-benzyl)-amino]-2,3,4,5-tetrahydro-benzo[b]azepine-1-carboxylic acid isopropyl ester,
5-[(3,5-Bis-trifluoromethyl-benzyl)-methoxycarbonyl-amino]-2,3,4,5-tetrahydro-benzo[b]azepine-1-carboxylic acid isopropyl ester,
5-[(3,5-Bis-trifluoromethyl-benzyl)-methoxycarbonyl-amino]-7-bromo-2,3,4,5-tetrahydro-benzo[b]azepine-1-carboxylic acid isopropyl ester,
5-[(3,5-Bis-trifluoromethyl-benzyl)-methoxycarbonyl-amino]-7-bromo-2,3,4,5-tetrahydro-benzo[b]azepine-1-carboxylic acid ethyl ester,
5-[Acetyl-(3,5-bis-trifluoromethyl-benzyl)-amino]-7-bromo-2,3,4,5-tetrahydro-benzo[b]azepine-1-carboxylic acid ethyl ester,
5-[Acetyl-(3,5-bis-trifluoromethyl-benzyl)-amino]-7-methoxy-2,3,4,5-tetrahydro-benzo[b]azepine-1-carboxylic acid ethyl ester,
5-[Acetyl-(3,5-bis-trifluoromethyl-benzyl)-amino]-8-trifluoromethyl-2,3,4,5-tetrahydro-benzo[b]azepine-1-carboxylic acid isopropyl ester,
5-[Acetyl-(3,5-bis-trifluoromethyl-benzyl)-amino]-8-fluoro-7-trifluoromethyl-2,3,4,5-tetrahydro-benzo[b]azepine-1-carboxylic acid isopropyl ester,
4-[Acetyl-(3,5-bis-trifluoromethyl-benzyl)-amino]-7-trifluoromethyl-2,3,4,5-tetrahydro-benzo[b]azepine-1-carboxylic acid isopropyl ester,
5-[Acetyl-(3,5-bis-trifluoromethyl-benzyl)-amino]-8-chloro-2,3,4,5-tetrahydro-benzo[b]azepine-1-carboxylic acid isopropyl ester, and
5-[(3,5-Bis-trifluoromethyl-benzyl)-methoxycarbonyl-amino]-8-chloro-2,3,4,5-tetrahydro-benzo[b]azepine-1-carboxylic acid isopropyl ester,
or a pharmaceutically acceptable salt thereof.

9. A method of treating dyslipidemia comprising administering a compound of claim 1, or a pharmaceutically acceptable salt thereof, to a patient in need thereof.

10. A method of treating artherosclerosis comprising administering a compound of claim 1, or a pharmaceutically acceptable salt thereof, to a patient.

11. A method of according to claim 9 comprising lowering plasma LDL-cholesterol in a mammal.

12. A method of treating pathological sequelae due to low levels of plasma HDL-cholesterol in a mammal comprising administering a pharmaceutically effective amount of a compound of claim 1, or a pharmaceutically acceptable salt thereof, to a patient in need thereof.

13. A pharmaceutical formulation comprising a compound according to claim 1 and at least one of: a carrier, a diluent and an excipient.

14. A method according to claim 9 comprising raising plasma HDL-cholesterol in a mammal.

\* \* \* \* \*

UNITED STATES PATENT AND TRADEMARK OFFICE
CERTIFICATE OF CORRECTION

PATENT NO. : 7,749,992 B2
APPLICATION NO. : 10/574649
DATED : March 30, 2006
INVENTOR(S) : Guoqing Cao et al.

It is certified that error appears in the above-identified patent and that said Letters Patent is hereby corrected as shown below:

In the issued patent, please note the following corrections:

| S. No. | P/A | Original Page | Line | Issued Patent Column | Line | Description of Error |
|---|---|---|---|---|---|---|
| 1 | P | Page 1 Specification (03/30/2006) | 1 | Title page Col. 1 (Title) | 2 | Delete "DISLIPIDEMIA" and insert -- DYSLIPIDEMIA --, therefor. |
| 2 | P | Page 1 Abstract (03/30/2006) | 1 (Approx.) (Structure) (Abstract) | Title page item 57 Col. 2 (Abstract) | 2 (Approx.) | Delete " [structure] " and insert -- [structure] --, therefor. |
| 3 | P | Page 1 Abstract (03/30/2006) | 2 (Abstract) | Title page item 57 Col. 2 (Abstract) | 3 | Delete "y, R¹" and insert -- Y, R¹, --, therefor. |
| 4 | A | Page 1 Abstract (03/30/2006) | 4 (Abstract) | Col. 2 | 5 | Delete "artherosclerosis" and insert -- atherosclerosis --, therefor. |

Signed and Sealed this

Seventh Day of September, 2010

David J. Kappos
*Director of the United States Patent and Trademark Office*

CERTIFICATE OF CORRECTION (continued)
U.S. Pat. No. 7,749,992 B2

| | | | | | | |
|---|---|---|---|---|---|---|
| 5 | P | Page 1 Specification (03/30/2006) | 1 | 1 | 2 | Delete "DISLIPIDEM1A" and insert -- DYSLIPIDEM1A --, therefor. |
| 6 | P | Page 2 Claims (02/10/2010) | Claim 1 Line 8 (Including Structure) | 144 | 32 | In Claim 1, delete "alkylbeterocyclic," and insert --alkylheterocyclic, --, therefor. |
| 7 | P | Page 2 Claims (02/10/2010) | Claim 1 Line 23 (Including Structure) | 144 | 58 | In Claim 1, delete "$NR^{11}R_{12}$," and insert -- $NR^{11}R^{12}$, --, therefor. |
| 8 | P | Page 3 Claims (02/10/2010) | Claim 2 Lines 3-4 | 145 | 5 | In Claim 2, delete "—$OC_1$-C $_6$" and insert -- —$OC_1$-$C_6$ --, therefor. |
| 9 | A | Page 3 Claims (02/10/2010) | Claim 3 Line 3 | 145 | 13 | In Claim 3, delete "-Oheterocyclic," and insert -- -O-heterocyclic, --, therefor. |
| 10 | A | Page 5 Claims (02/10/2010) | Claim 16 Line 1 | 146 | 35 | In Claim 10, delete "artherosclerosis" and insert -- atherosclerosis --, therefor. |
| 11 | A | Page 5 Claims (02/10/2010) | Claim 18 Line 1 | 146 | 38 | In Claim 11, after "method" delete "of". |